(12) United States Patent
Ruminski et al.

(10) Patent No.: US 11,306,084 B2
(45) Date of Patent: Apr. 19, 2022

(54) INTEGRIN ANTAGONISTS

(71) Applicants: Saint Louis University, St. Louis, MO (US); Indalo Therapeutics, Inc., St. Louis, MO (US)

(72) Inventors: Peter G. Ruminski, Wildwood, MO (US); David W. Griggs, Ballwin, MO (US); Scott Seiwert, Seattle, WA (US)

(73) Assignees: Saint Louis University, St. Louis, MO (US); Indalo Therapeutics, Inc., St. Louis, MO (US)

( * ) Notice: Subject to any disclaimer, the term of this patent is extended or adjusted under 35 U.S.C. 154(b) by 0 days.

(21) Appl. No.: 16/474,505

(22) PCT Filed: Dec. 28, 2017

(86) PCT No.: PCT/US2017/068801
§ 371 (c)(1),
(2) Date: Jun. 27, 2019

(87) PCT Pub. No.: WO2018/132268
PCT Pub. Date: Jul. 19, 2018

(65) Prior Publication Data
US 2019/0345155 A1    Nov. 14, 2019

Related U.S. Application Data

(60) Provisional application No. 62/440,253, filed on Dec. 29, 2016, provisional application No. 62/471,882, filed on Mar. 15, 2017.

(51) Int. Cl.
*C07D 471/04* (2006.01)
*A61K 9/00* (2006.01)

(52) U.S. Cl.
CPC .......... *C07D 471/04* (2013.01); *A61K 9/0014* (2013.01); *A61K 9/0019* (2013.01); *A61K 9/0048* (2013.01); *A61K 9/0053* (2013.01)

(58) Field of Classification Search
CPC .. C07D 471/04; A61K 9/0014; A61K 9/0019; A61K 9/0048; A61K 9/0053; A61P 17/02; A61P 11/00; A61P 9/00; A61P 17/00; A61P 13/12; A61P 43/00
USPC .......................................... 514/300; 546/122
See application file for complete search history.

(56) References Cited

U.S. PATENT DOCUMENTS

| | | | |
|---|---|---|---|
| 7,119,098 B2 | 10/2006 | Nagarajan et al. | |
| 2014/0051715 A1 | 2/2014 | Ruminski et al. | |

FOREIGN PATENT DOCUMENTS

| | | |
|---|---|---|
| JP | 2006-518333 | 8/2006 |
| JP | 2015-524412 | 8/2015 |
| WO | WO 2001/096334 | 12/2001 |
| WO | WO 2004-058254 | 7/2004 |
| WO | WO 2004/058760 | 7/2004 |
| WO | WO 2004/058761 | 7/2004 |
| WO | WO 2014-015054 | 1/2014 |
| WO | WO 2015/048819 | 4/2015 |
| WO | WO 2018/089353 | 5/2018 |
| WO | WO 2018/089355 | 5/2018 |
| WO | WO 2018/089357 | 5/2018 |
| WO | WO 2018/089358 | 5/2018 |
| WO | WO 2018/089360 | 5/2018 |
| WO | WO 2018/132268 | 7/2018 |
| WO | WO 2018/160522 | 9/2018 |
| WO | WO 2020/006315 | 1/2020 |
| WO | WO 2020/009889 | 1/2020 |

OTHER PUBLICATIONS

CAS RN: 791586-47-5, STN entry date Dec. 2, 2004, Chemical name: 4-Thiazolebutanoic acid, β-(3,4-difluorophenyl)-2-[3-(5,6,7,8-tetrahydro-1,8-naphthyridin-2-yl)propyl]-ethyl ester.
CAS RN: 794450-94-5, STN entry date Dec. 8, 2004, Chemical name: 4-Thiazolebutanoic acid, β-(3-fluorophenyl)-2-[3-(5,6,7,8-tetrahydro-1,8-naphthyridin-2-yl)propyl]-, ethyl ester.
Conroy et al., αv integrins: key regulators of tissue fibrosis, Cell and Tissue Research, 2016, vol. 365 (3), pp. 511-519, Abstract; Table 1; figure 1; and Concluding remarks.
Gerber et al., "Integrin-modulating therapy prevents fibrosis and autoimmunity in mouse models of scleroderma", Nature, 2013, vol. 503, pp. 126-132, abstract; p. 126, left column first paragraph, and paragraph bridging left and right column; Figure 2; and p. 130, left column.
Marinelli et al., "Ligand Binding Analysis for Human $α_5β_1$ Integrin: Strategies for Designing New 60 $_5β_1$ Integrin Antagonists", Journal of Medicinal Chemistry, 2005, vol. 48, pp. 4204-4207, abstract; and table 1, with 3 pages of supporting documentation.

(Continued)

Primary Examiner — Taylor V Oh
(74) Attorney, Agent, or Firm — Parker Highlander PLLC

(57) ABSTRACT

The present disclosure provides pharmaceutical agents, including those of the formula: (I) wherein the variables are defined herein. Also provided are pharmaceutical compositions, kits and articles of manufacture comprising such pharmaceutical agents. Methods of using the pharmaceutical agents are also provided. The compounds may be used for the inhibition or antagonism of integrins αvβι and/or α5βι. In some embodiments, the compounds provided herein exhibit reduced inhibitory or antagonistic activity of integrins αvβ3, αvβ5, αvβ6, αvβ8, and/or αIIbβ3.

(I)

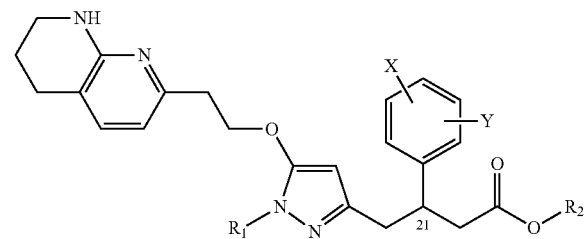

29 Claims, No Drawings

(56) References Cited

OTHER PUBLICATIONS

Pitts et al., Isoxazolines as Potent Antagonists of the Integrin $\alpha_v\beta_3$; Journal of Medicinal Chemistry, 2000, vol. 43, pp. 27-40, abstract; figures 1 and 2; and tables 1 and 2.
Reed, et al., "The $\alpha_v\beta_1$ integrin plays a critical in vivo role in tissue fibrosis", Science Translational Medicine, 2015, vol. 7 (288), 288ra79, pp. 1-8 abstract; figure 1; p. 5, right column.
Stragies et al., "Design and synthesis of a new class of selective integrin $\alpha_5\beta_1$ antagonists," J Med. Chem., 50(16):3786-3794, 2007.
Penning et al., Synthesis of Pyrazoles and Isoxazoles as Potent $\alpha v\beta_3$ Receptor Antagonists, Bioorg. Med. Chem. Letters., 16(12):3156-3161.
International Search Report and Written Opinion re PCT Application No. PCT/US2017/068801, dated Jun. 20, 2018.
International Preliminary Report on Patentability re PCT Application No. PCT/US2017/068801, dated Jul. 2, 2019.
International Search Report and Written Opinion re PCT Application No. PCT/US2019/039430, dated Sep. 10, 2019.
Office Action issued in Japanese Application No. 2019-534956, dated Nov. 10, 2021.

INTEGRIN ANTAGONISTS

INCORPORATION BY REFERENCE TO ANY PRIORITY APPLICATIONS

Any and all priority claims identified in the Application Data Sheet, or any correction thereto, are hereby incorporated by reference under 37 CFR 1.57.

BACKGROUND OF THE INVENTION

Field of the Invention

The present disclosure relates to the fields of pharmaceuticals, medicine and cell biology. More specifically, it relates to pharmaceutical agents (compounds) which are useful as integrin antagonists

Description of the Related Art

Integrins are a family of integral cytoplasmic membrane proteins that mediate cell interactions with other cells and with the extracellular matrix. Recently, integrin $\alpha v \beta \iota$ was identified to play a role in a variety of fibrotic conditions. Other integrins, such as $\alpha v \beta_3$ and $\alpha v \beta_5$, are also associated with fibrotic conditions and compounds which inhibit these two integrins may be useful in the treatment of these conditions.

Integrin $\alpha_5 \beta_1$ is believed to bind to fibronectin in a region that incorporates the ninth and tenth type III fibronectin repeats, the latter of which is believed to contain the RGD motif for integrin binding. In addition to fibronectin, $\alpha_5 \beta_1$ has been reported to interact with other RGD-containing extracellular matrix proteins including fibrinogen, denatured collagen, and fibrillin-1 (Bax et al., *J. Biol. Chem.*, 278(36): 34605-34616, 2003, 2003; Perdih, Curr. Med. Chem., 17(22):2371-2392, 2010; Suehiro et al., *J. Biochem.*, 128 (4):705-710, 2000). These ligands are generally classified as components of the provisional matrix that is laid down by cells as part of the wound healing response in tissues. Components of this response are angiogenesis and fibrosis.

In contrast, inhibition of some other integrins, such as $\alpha v \beta_6$ and $\alpha v \beta_8$, has been associated with a variety of undesired, inflammation-related side effects (Huang, et al., 1996; Lacy-Hulbert, et al., 2007; Travis, et al., 2007; Worthington, et al., 2015). Selective inhibition of $\alpha v \beta_1$, $\alpha v \beta_3$, $\alpha v \beta_5$, and/or $\alpha_5 \beta_1$ is desirable for some indications.

Integrin $\alpha_{IIb} \beta_{III}$ (also known as glycoprotein IIb/IIIa or GPIIb/IIIa) is an integrin complex found on platelets. Integrin $\alpha_{IIb} \beta_{III}$ inhibition is associated with disruption of platelet aggregation, which is associated with toxicity and/or contraindicated when treating certain disease or disorders (King et al., 2016; Bennet, 2005; Giordano et al., 2016; Cook et al., 1997).

SUMMARY

The present disclosure provides novel integrin receptor antagonists, pharmaceutical compositions, and methods for their manufacture, and methods for their use.

In some aspects, the present disclosure provides compounds of the formula:

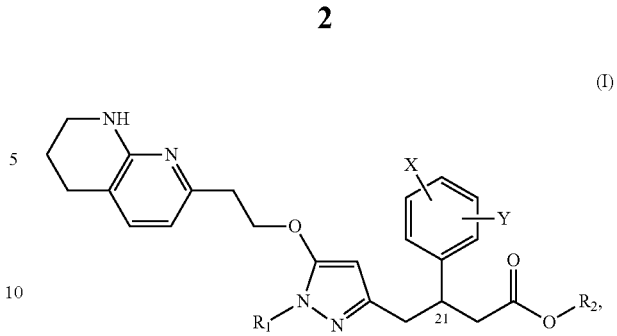

or a pharmaceutically acceptable salt, solvate or tautomer of the above formula, wherein: $R_1$, $R_2$, X, and Y have any of the values described herein.

In some embodiments, $R_1$ is hydrogen, $alkyl_{(C \leq 8)}$, $aryl_{(C \leq 12)}$, $aralkyl_{(C \leq 12)}$, substituted $alkyl_{(C \leq 8)}$, substituted $aryl_{(C \leq 8)}$, or substituted $aralkyl_{(C \leq 12)}$;

$R_2$ is hydrogen, $alkyl_{(C \leq 8)}$, substituted $alkyl_{(C \leq 8)}$, or a substituent convertible in vivo to hydrogen;

X is cyano, halo, $alkoxy_{(C \leq 8)}$, substituted $alkoxy_{(C \leq 8)}$, $alkyl_{(C \leq 8)}$, or substituted $alkyl_{(C \leq 8)}$; and Y is hydrogen, cyano, halo, $alkoxy_{(C \leq 8)}$, substituted $alkoxy_{(C \leq 8)}$, $alkyl_{(C \leq 8)}$, or substituted $alkyl_{(C \leq 8)}$.

In some other embodiments of Formula (I), $R_1$ may be hydrogen, unsubstituted $C_{1-8}$alkyl, substituted $C_{1-8}$alkyl, unsubstituted $C_{6 \, or \, 10}$aryl, substituted $C_{6 \, or \, 10}$aryl, unsubstituted $C_{7-12}$aralkyl, or substituted $C_{7-12}$aralkyl;

$R_2$ may be hydrogen, unsubstituted $C_{1-8}$alkyl, or substituted $C_{1-8}$alkyl;

X may be hydrogen, halo, cyano, unsubstituted $C_{1-12}$alkyl, substituted $C_{1-12}$alkyl, unsubstituted $C_{1-12}$alkoxy, substituted $C_{1-12}$alkoxy, unsubstituted $C_{6 \, or \, 10}$aryl, substituted $C_{6 \, or \, 10}$aryl, unsubstituted $C_{7-12}$aralkyl, substituted $C_{7-12}$aralkyl, unsubstituted 5-10 membered heteroaryl, substituted 5-10 membered heteroaryl, unsubstituted 3-10 membered heterocycloalkyl, substituted 3-10 membered heterocycloalkyl, unsubstituted $C_{6 \, or \, 10}$aryloxy, substituted $C_{6 \, or \, 10}$aryloxy, unsubstituted $C_{2-12}$acyloxy, substituted $C_{2-12}$acyloxy, or

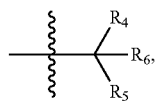

where $R_4$ and $R_5$ are each independently unsubstituted $C_{1-8}$alkyl or substituted $C_{1-8}$alkyl, and $R_6$ may be hydrogen, —OH, —CN, —NH$_2$, —CF$_3$, —CF$_2$H, —CH$_2$F, —CO$_2$H, —CO$_2$—$C_{1-8}$alkyl, —C(=O)NH$_2$, —CH$_2$OH, —CH$_2$O—$C_{1-8}$alkyl, or $C_{1-8}$alkoxy, or X is

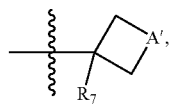

where A' is —CF$_2$—, —O—, $C_{1-6}$alkanediyl, $C_{1-8}$alkoxydiyl, or a covalent bond, thereby forming a cyclopropane ring, and $R_7$ may be —OH, —CN, —NH$_2$, —CO$_2$H, —CO$_2$—C$_{1-8}$alkyl, —C(=O)NH$_2$, —CF$_3$, —CF$_2$H, —CH$_2$F, —CH$_2$OH, —CH$_2$O—C$_{1-8}$alkyl, C$_{1-8}$alkyl or C$_{1-8}$alkoxy;

Y may be t-butyl, or

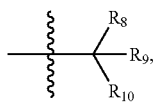

where $R_8$ and $R_9$ are each independently unsubstituted C$_{1-8}$alkyl or substituted C$_{1-8}$alkyl, and $R_{10}$ may be hydrogen, —OH, —CN, —NH$_2$, —CF$_3$, —CF$_2$H, —CFH$_2$, —CO$_2$H, —CO$_2$—C$_{1-8}$alkyl, —C(=O)NH$_2$, —CH$_2$OH, —CH$_2$O—C$_{1-8}$alkyl, or C$_{1-8}$alkoxy, or Y may be

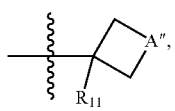

where A" is —CF$_2$—, —O—, C$_{1-6}$alkanediyl, C$_{1-8}$alkoxydiyl, or a covalent bond, thereby forming a cyclopropane ring; and $R_{11}$ is —OH, —CN, —NH$_2$, —CO$_2$H, —CO$_2$—C$_{1-8}$alkyl, —C(=O)NH$_2$, —CF$_3$, —CF$_2$H, —CH$_2$F, —CH$_2$OH, —CH$_2$O—C$_{1-8}$alkyl, C$_{1-8}$alkyl or C$_{1-8}$alkoxy.

In some other embodiments of Formula (I):

$R_1$ is hydrogen, alkyl$_{(C\leq 8)}$, aryl$_{(C\leq 12)}$, aralkyl$_{(C\leq 12)}$, substituted alkyl$_{(C\leq 8)}$, substituted aryl$_{(C\leq 8)}$, or substituted aralkyl$_{(C\leq 12)}$;

$R_2$ is hydrogen, alkyl$_{(C\leq 8)}$, substituted alkyl$_{(C\leq 8)}$, or a substituent convertible in vivo to hydrogen, and X and Y are each independently cyano, halo, alkoxy$_{(C\leq 8)}$, substituted alkoxy$_{(C\leq 8)}$, alkyl$_{(C\leq 8)}$, or substituted alkyl$_{(C\leq 8)}$;

or a pharmaceutically acceptable salt or tautomer of the above formula.

In some embodiments, the compounds are further defined as:

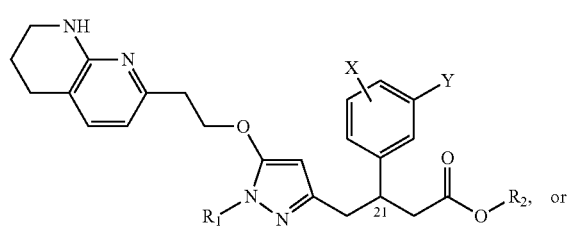

(Ia)

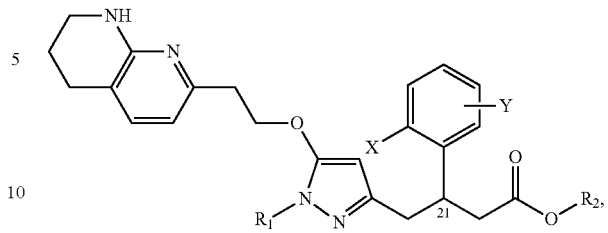

(Ib)

or a pharmaceutically acceptable salt, solvate or tautomer thereof, wherein: $R_1$, $R_2$, X, and Y have any of the values described herein.

In some embodiments, the compounds are further defined as:

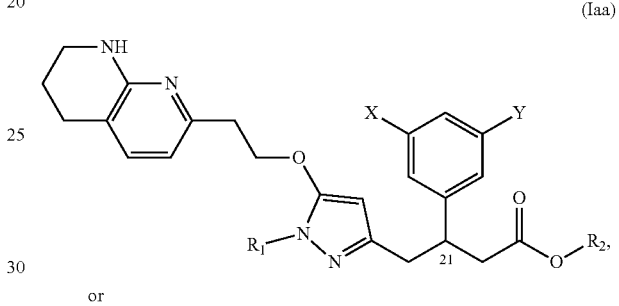

(Iaa)

or

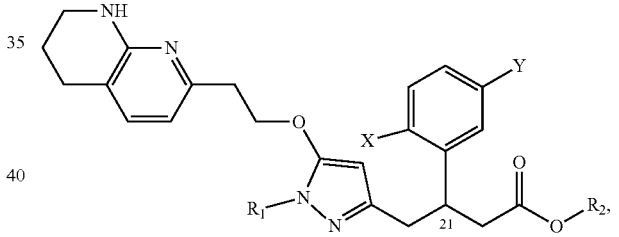

(Iba)

or a pharmaceutically acceptable salt, solvate or tautomer thereof, wherein: $R_1$, $R_2$, X, and Y have any of the values described herein. In some embodiments, $R_1$ may be unsubstituted C$_{1-8}$alkyl, substituted C$_{1-8}$alkyl, unsubstituted C$_{6\text{ or }10}$aryl, substituted C$_{6\text{ or }10}$aryl, unsubstituted C$_{7-10}$aralkyl, or substituted C$_{7-10}$aralkyl; $R_2$ may be hydrogen, unsubstituted C$_{1-6}$alkyl, or substituted C$_{1-6}$alkyl; X may be halo, cyano, unsubstituted C$_{1-12}$alkyl, substituted C$_{1-12}$alkyl, unsubstituted C$_{1-12}$alkoxy, substituted C$_{1-12}$alkoxy, unsubstituted C$_{6\text{ or }10}$aryl, substituted C$_{6\text{ or }10}$aryl, unsubstituted C$_{7-10}$aralkyl, substituted C$_{7-10}$aralkyl, unsubstituted 5-10 membered heteroaryl, substituted 5-10 membered heteroaryl, unsubstituted 3-10 membered heterocycloalkyl, substituted 3-10 membered heterocycloalkyl, unsubstituted C$_{6\text{ or }10}$aryloxy, substituted C$_{6\text{ or }10}$aryloxy, unsubstituted C$_{2-12}$acyloxy, substituted C$_{2-12}$acyloxy, or

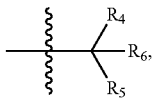

or X may be

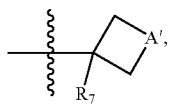

where A' is —CF$_2$—, —O—, C$_{1-6}$alkanediyl, C$_{1-8}$alkoxydiyl, or a covalent bond, thereby forming a cyclopropane ring; R$_8$ and R$_9$ are each independently are each independently unsubstituted C$_{1-6}$alkyl or substituted C$_{1-6}$alkyl; and R$_{10}$ may be hydrogen, —OH, —CN, —NH$_2$, —CF$_3$, —CF$_2$H, —CFH$_2$, —CO$_2$H, —CO$_2$—C$_{1-6}$alkyl, —C(=O)NH$_2$, —CH$_2$OH, CH$_2$O—C$_{1-6}$alkyl, or C$_{1-6}$alkoxy.

In some embodiments, the compounds are further defined as:

(Iaa)

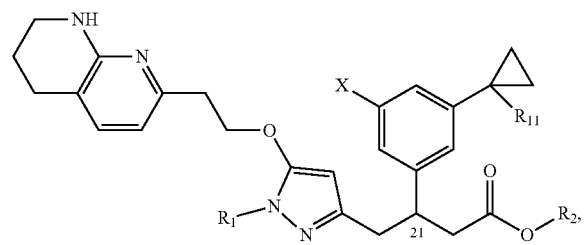

or (Iab)

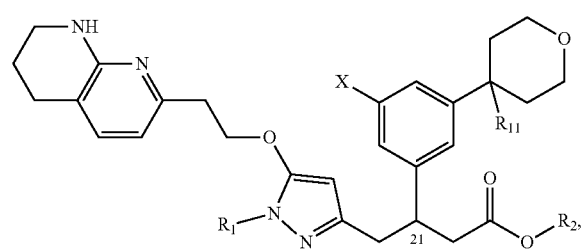

or a pharmaceutically acceptable salt, solvate or tautomer thereof, wherein: R$_1$, R$_2$, X, and Y have any of the values described herein.

In some embodiments, R$_1$ is alkyl$_{(C≤8)}$ such as methyl. In some embodiments, R$_2$ is hydrogen. In other embodiments, R$_2$ is a substituent convertible in vivo to hydrogen which results in a pro-drug.

In some embodiments, X is halo such as bromo, fluoro, or chloro. In other embodiments, X is cyano. In other embodiments, X is alkyl$_{(C≤8)}$. In some embodiments, X is alkyl$_{(C3-6)}$ such as t-butyl. In other embodiments, X is alkoxy$_{(C≤8)}$ such as methoxy.

In some embodiments, Y is hydrogen. In other embodiments, Y is halo such as bromo, fluoro, or chloro. In other embodiments, Y is cyano. In other embodiments, Y is alkyl$_{(C≤8)}$. In some embodiments, Y is alkyl$_{(C3-6)}$ such as t-butyl. In other embodiments, Y is alkoxy$_{(C≤8)}$ such as methoxy.

In some embodiments, the carbon atom 21 is in the S configuration. In some embodiments, X is in the 3 position. In some embodiments, Y is in the 4 or 5 position.

In some embodiments, R$_1$ may be unsubstituted C$_{1-8}$alkyl. In some embodiments, R$_1$ may be methyl. In some embodiments, R$_2$ may be hydrogen. In some embodiments, X may be hydrogen, halo, cyano, unsubstituted C$_{1-12}$alkyl, substituted C$_{1-12}$alkyl, unsubstituted C$_{1-12}$alkoxy, substituted C$_{1-12}$alkoxy, unsubstituted C$_{6\ or\ 10}$aryl, substituted C$_{6\ or\ 10}$aryl, unsubstituted C$_{1-12}$aralkyl, substituted C$_{7-12}$aralkyl, unsubstituted 5-10 membered heteroaryl, substituted 5-10 membered heteroaryl, unsubstituted 3-10 membered heterocycloalkyl, substituted 3-10 membered heterocycloalkyl, unsubstituted C$_{6\ or\ 10}$aryloxy, substituted C$_{6\ or\ 10}$aryloxy, unsubstituted C$_{2-12}$acyloxy, or substituted C$_{2-12}$acyloxy. In some embodiments, X is hydrogen, halo, cyano, unsubstituted C$_{1-12}$alkoxy, substituted C$_{1-12}$alkoxy, unsubstituted C$_{6\ or\ 10}$aryl, substituted C$_{6\ or\ 10}$aryl, unsubstituted C$_{7-12}$aralkyl, substituted C$_{7-12}$aralkyl, unsubstituted 5-10 membered heteroaryl, substituted 5-10 membered heteroaryl, unsubstituted 3-10 membered heterocycloalkyl, substituted 3-10 membered heterocycloalkyl, unsubstituted C$_{6\ or\ 10}$aryloxy, substituted C$_{6\ or\ 10}$aryloxy, unsubstituted C$_{2-12}$acyloxy, substituted C$_{2-12}$acyloxy or

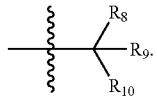

In some embodiments, X may be halo. In some embodiments, X may be bromo, fluoro, or chloro. In some embodiments, X may be —CF$_3$. In some embodiments, X may be —OH or cyano. In some embodiments, X may be unsubstituted C$_{1-8}$alkyl. In some embodiments, X may be unsubstituted C$_{3-6}$alkyl. In some embodiments, X may be t-butyl. In some embodiments, X may be unsubstituted C$_{1-8}$alkoxy. In some embodiments, X may be methoxy or isopropoxy. In some embodiments, Y may be t-butyl. In some embodiments, Y may be

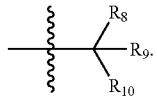

In some embodiments, R$_8$ and R$_9$ are each independently unsubstituted C$_{2-8}$alkyl. In some embodiments, R$_8$ may be methyl and R$_9$ may be unsubstituted C$_{2-8}$alkyl. In some embodiments, R$_8$ and R$_9$ are each —CH$_3$. In some embodiments, R$_{10}$ may be —CF$_3$, —CF$_2$H, or —CFH$_2$. In some embodiments, R$_{10}$ may be —CF$_3$. In some embodiments, R$_{10}$ may be hydrogen or —CH$_3$. In some embodiments, Y may be

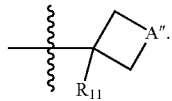

In some embodiments, A" may be C$_{1-3}$alkanediyl, C$_{1-4}$alkoxydiyl, or a covalent bond, thereby forming a cyclopropane ring. In some embodiments, A" may be a covalent bond, thereby forming a cyclopropane ring. In some embodiments, R$_{11}$ may be —CF$_3$, —CF$_2$H, —CH$_2$F, —CH$_2$O—C$_{1-6}$alkyl, C$_{1-6}$alkyl or C$_{1-8}$alkoxy. In some embodiments, $R_{11}$ may be —$CF_3$, —$CF_2H$, —$CH_2F$, $C_{1-6}$alkyl or $C_{1-6}$alkoxy. In some embodiments, $R_{11}$ may be —$CF_3$, —$CF_2H$ or methoxy. In some embodiments, $R_{11}$ may be —$CF_3$ or —$CF_2H$. In some embodiments, $R_{11}$ may be —$CH_2O$—$CH_3$. In some embodiments, X may be in the 3 position. In some embodiments, Y may be in the 4 or 5 position. In some embodiments, the compound may be an integrin antagonist. In some embodiments, the integrin may be an $\alpha_5\beta_1$ integrin antagonist. In some embodiments, the compound exhibits an $IC_{50}$ value for the $\alpha_5\beta_1$ integrin of less than 50 nM, 40 nM, 30 nM, 20 nM, 15 nm or 1 nM, or a range defined by any of the preceding as measured by a solid phase receptor assay for $\alpha_5\beta_1$ integrin function. In some embodiments, the integrin is an $\alpha v\beta_1$ integrin antagonist. In some embodiments, the compound exhibits an $IC_{50}$ value for the $\alpha v\beta_1$ integrin of less than 15 nM as measured by a solid phase receptor assay for $\alpha v\beta_1$ integrin function. In some embodiments, the compound exhibits an $IC_{50}$ value for an $\alpha v\beta_3$ integrin of less than 10 nM as measured by a solid phase receptor assay for $\alpha v\beta_3$ integrin function. In some embodiments, the compound exhibits an $IC_{50}$ value for an $\alpha v\beta_5$ integrin of less than 10 nM as measured by a solid phase receptor assay for $\alpha v\beta_5$ integrin function. In some embodiments, the compound exhibits an $IC_{50}$ value for the $\alpha v\beta_1$, $\alpha v\beta_3$, and $\alpha v\beta_5$ integrins of less than 10 nM as measured by a solid phase receptor assays for $\alpha v\beta_1$, $\alpha v\beta_3$, and $\alpha v\beta_5$ integrin function. In some embodiments, the compound exhibits an $IC_{50}$ value for an $\alpha v\beta_6$ integrin of greater than 10 nM as measured by a solid phase receptor assay for $\alpha v\beta_6$ integrin function. In some embodiments, the compound exhibits an $IC_{50}$ value for an $\alpha v\beta_8$ integrin of greater than 10 nM as measured by a solid phase receptor assay for $\alpha v\beta_8$ integrin function. In some embodiments, the compound exhibits an $IC_{50}$ value for the $\alpha v\beta_6$ and $\alpha v\beta_8$ integrins of greater than 10 nM as measured by solid phase receptor assays for $\alpha v\beta_6$ and $\alpha v\beta_8$ integrin function.

In some embodiments, the compound is an integrin antagonist such as an $\alpha v\beta_1$ integrin antagonist. In some embodiments, the compound exhibits an $IC_{50}$ value for the $\alpha v\beta_1$ integrin of less than 15 nM as measured by a solid phase receptor assay for $\alpha v\beta_1$ integrin function. In some embodiments, the compound exhibits an $IC_{50}$ value for an $\alpha v\beta_3$ integrin of less than 10 nM as measured by a solid phase receptor assay for $\alpha v\beta_6$ integrin function. In some embodiments, the compound exhibits an $IC_{50}$ value for an $\alpha v\beta_5$ integrin of less than 10 nM as measured by a solid phase receptor assay for $\alpha v\beta_5$ integrin function. In some embodiments, the compound exhibits an $IC_{50}$ value for the $\alpha v\beta_1$, $\alpha v\beta_3$, and $\alpha v\beta_5$ integrins of less than 10 nM as measured by a solid phase receptor assays for $\alpha v\beta_1$, $\alpha v\beta_3$, and $\alpha v\beta_5$ integrin function. In some embodiments, the compound exhibits an $IC_{50}$ value for an $\alpha v\beta_6$ integrin of greater than 10 nM as measured by a solid phase receptor assay for $\alpha v\beta_1$ integrin function. In some embodiments, the compound exhibits an $IC_{50}$ value for an $\alpha v\beta_8$ integrin of greater than 10 nM as measured by a solid phase receptor assay for $\alpha v\beta_1$ integrin function. In some embodiments, the compound exhibits an $IC_{50}$ value for the $\alpha v\beta_6$ and $\alpha v\beta_8$ integrins of greater than 10 nM as measured by solid phase receptor assays for $\alpha v\beta_6$ and $\alpha v\beta_8$ integrin function.

In some embodiments, the compounds are further defined as:

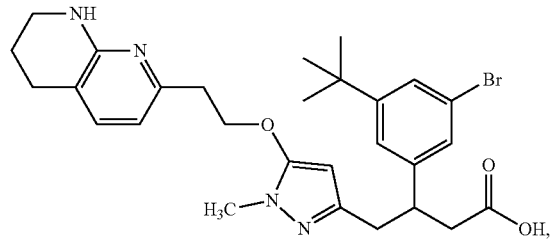

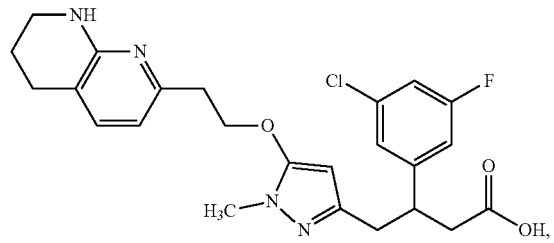

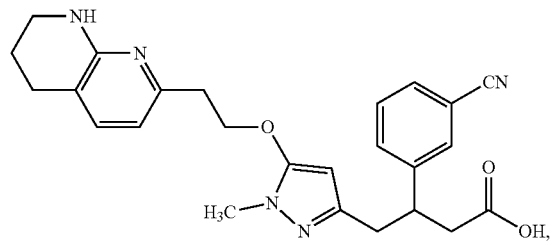

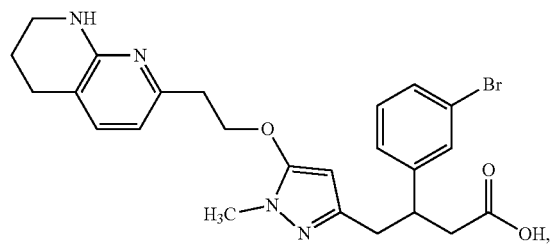

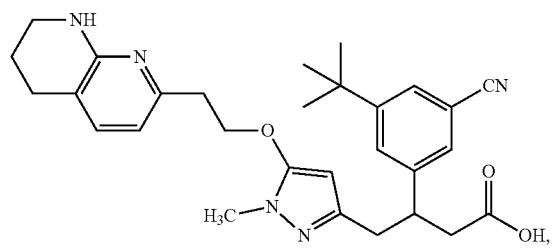

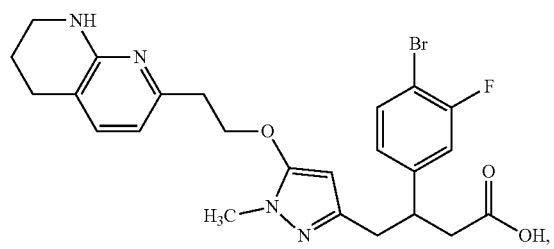

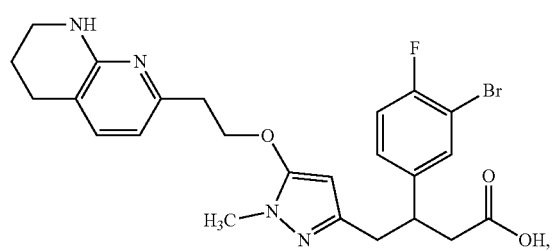

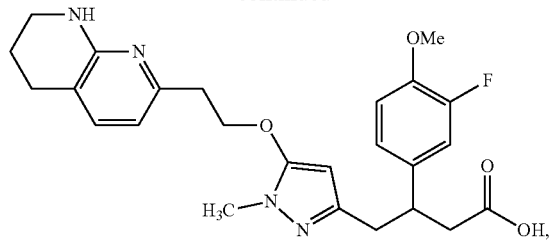
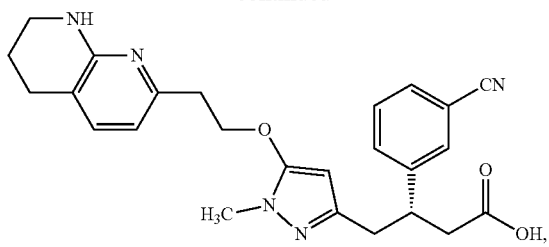
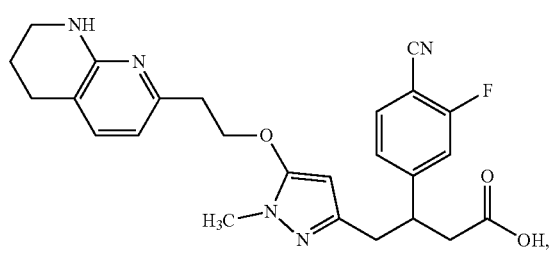
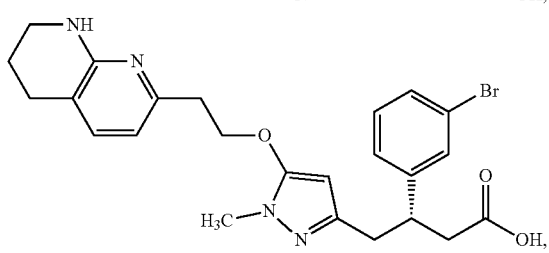
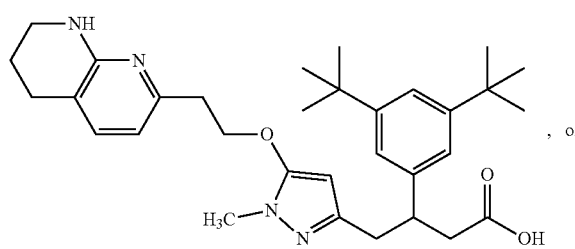
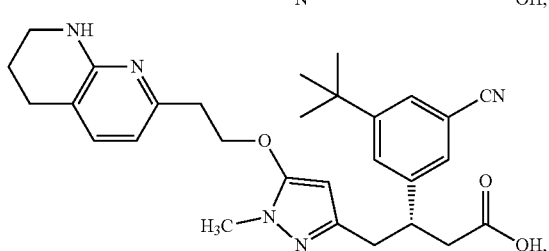
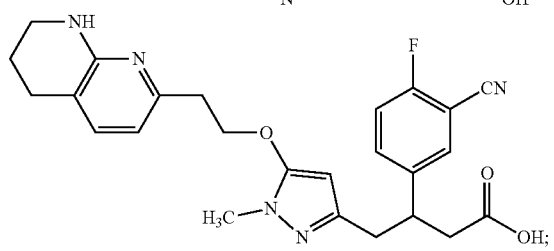
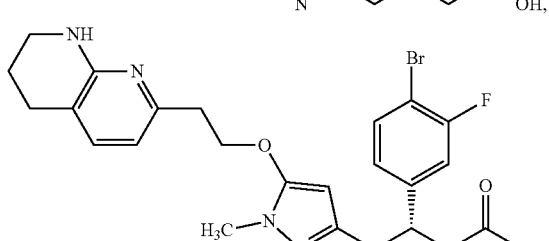
or a pharmaceutically acceptable salt thereof. In some embodiments, the compounds are further defined as:
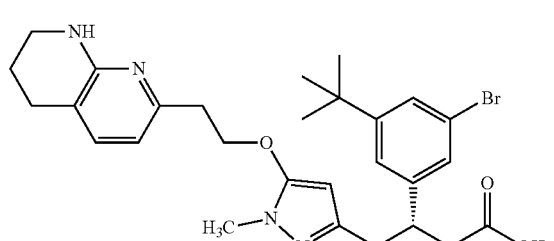
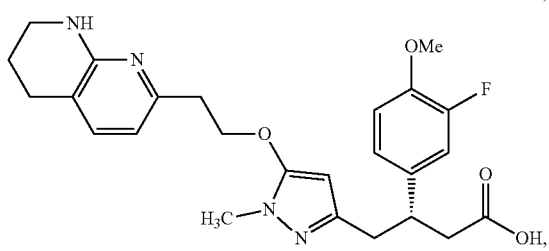
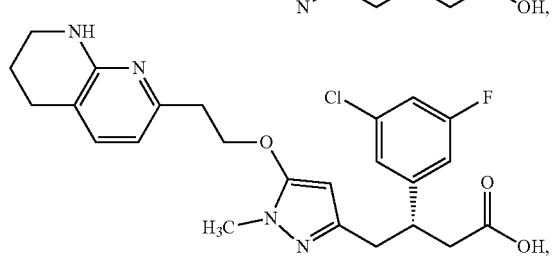

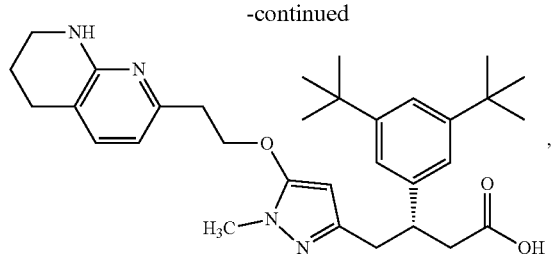
, or
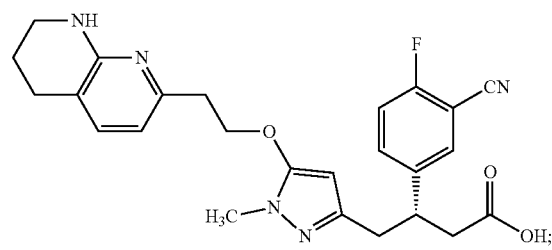
or a pharmaceutically acceptable salt thereof.
In some embodiments, the compounds are further defined as:
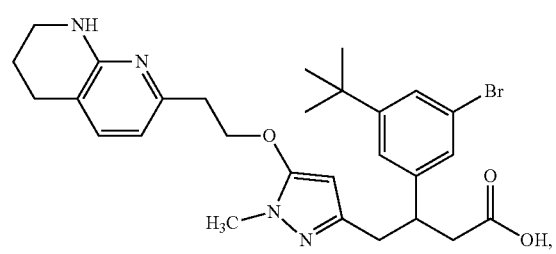
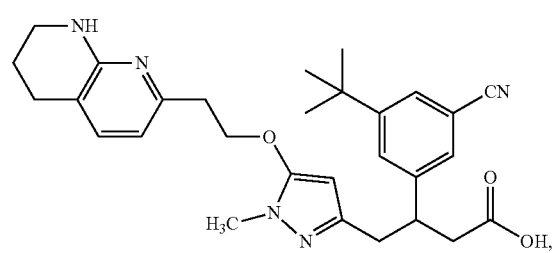
or
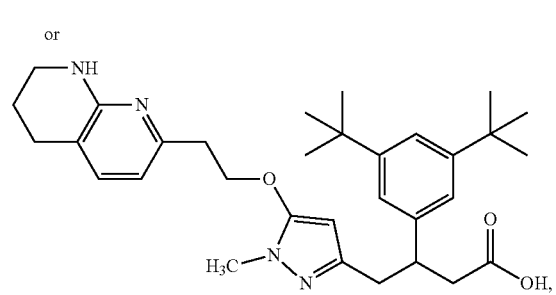
or a pharmaceutically acceptable salt, solvate or tautomer thereof.
In some embodiments, the compounds are further defined as:
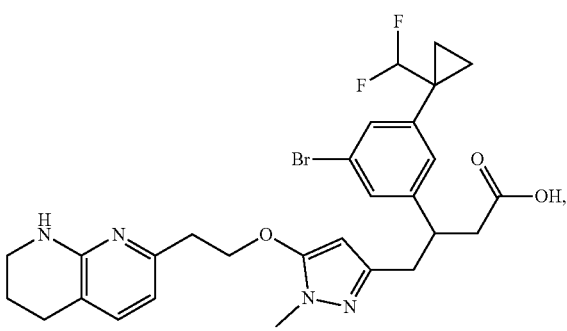
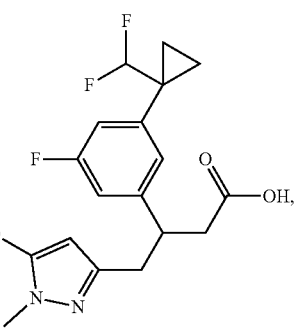
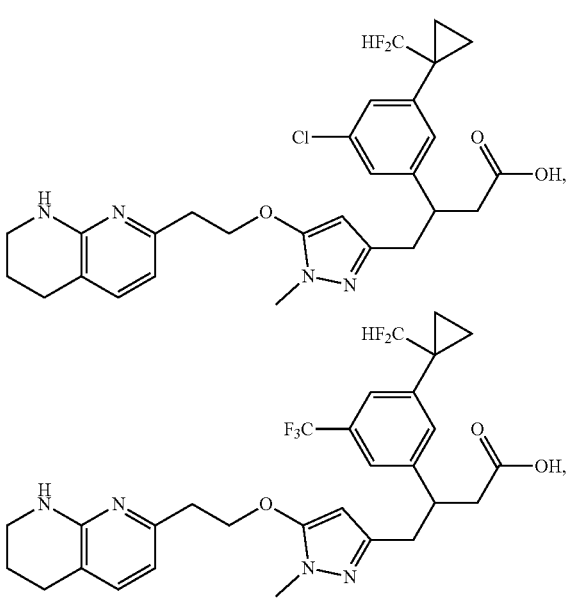

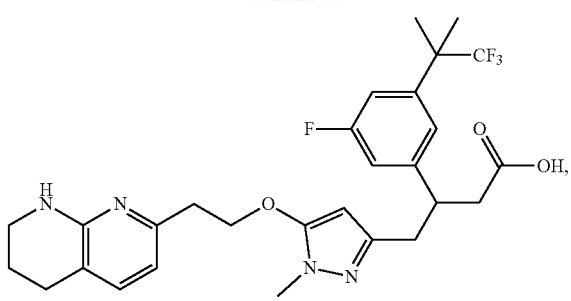
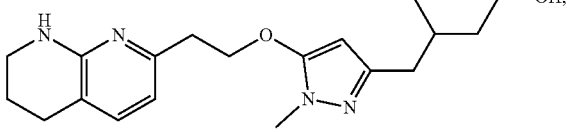
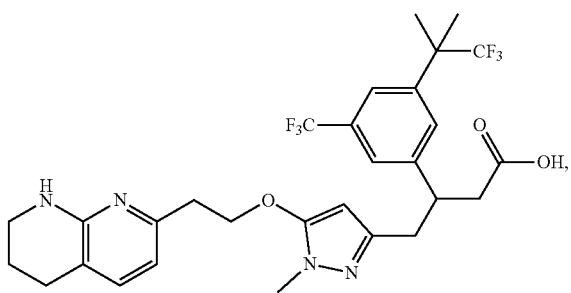
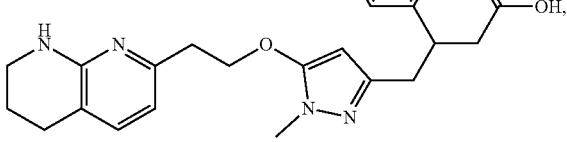
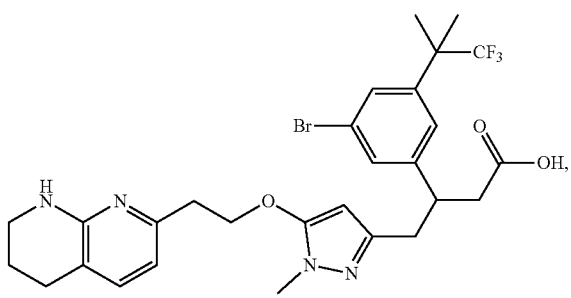
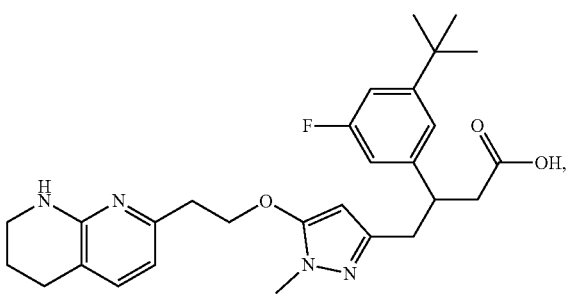
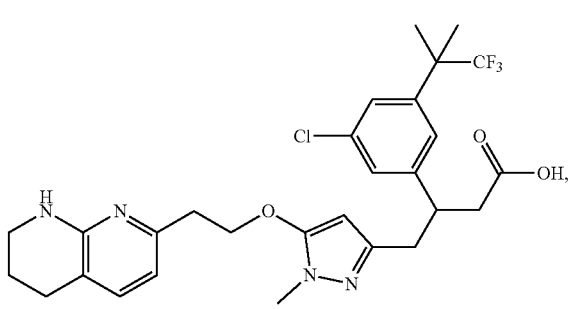
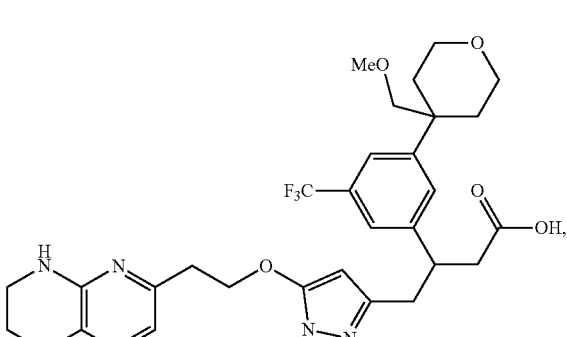
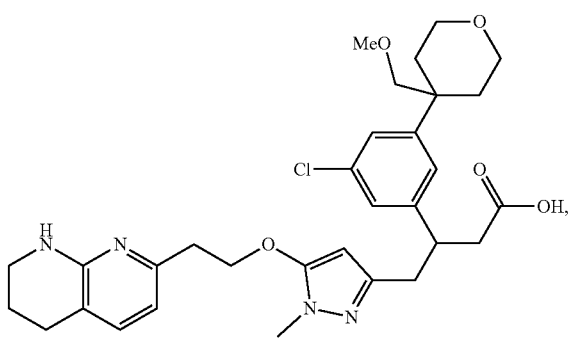
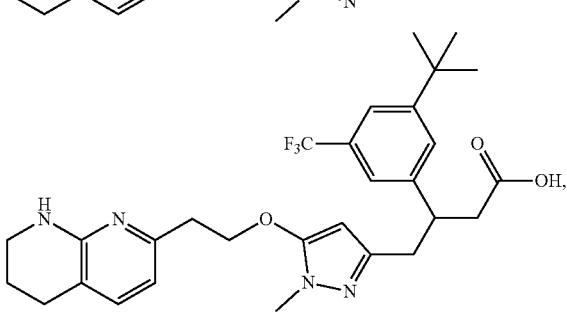

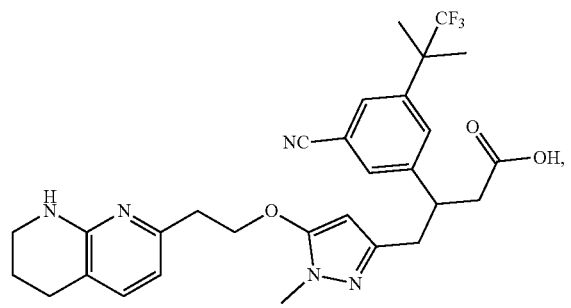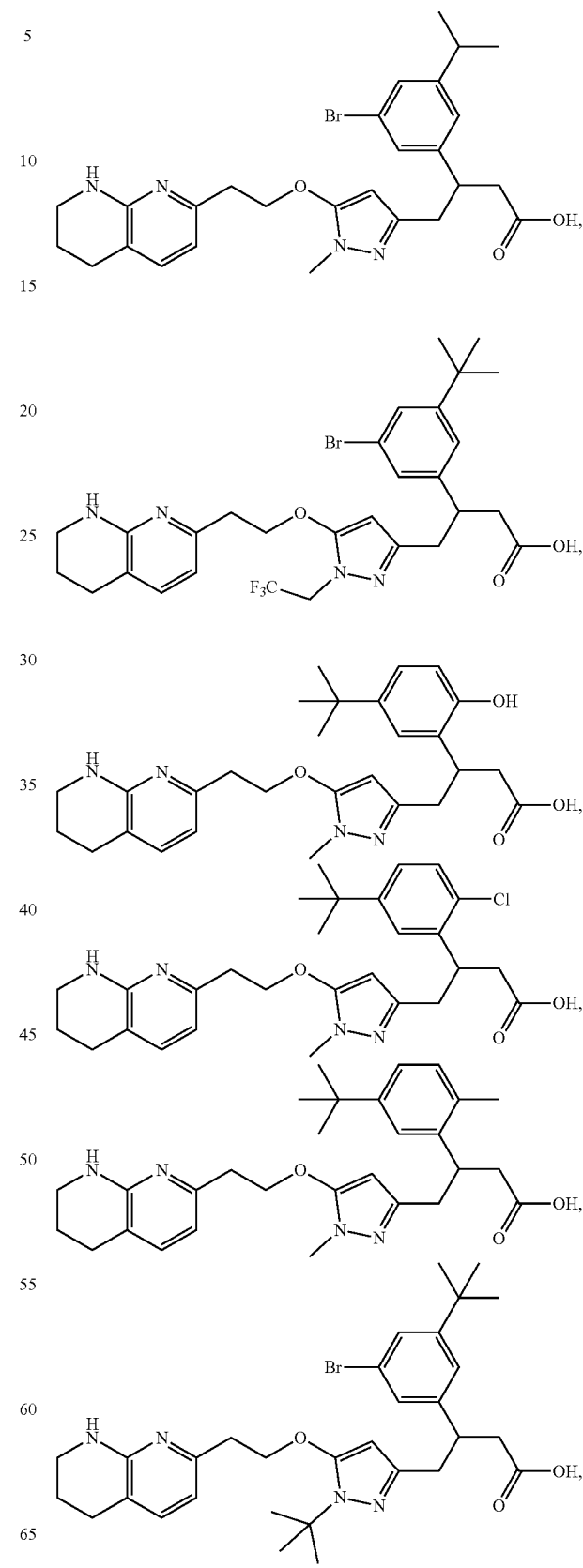

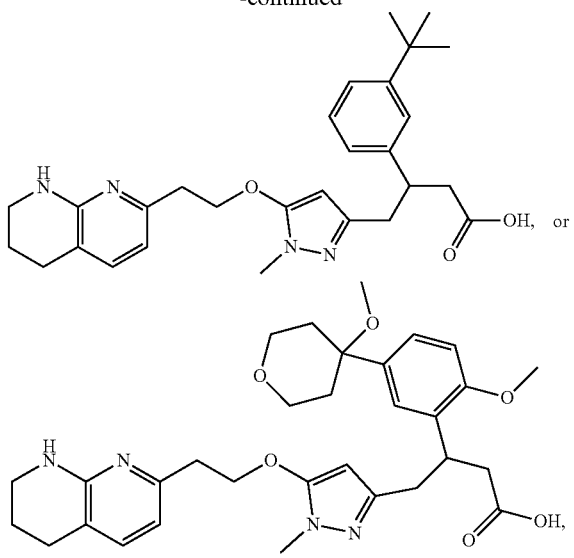

or a pharmaceutically acceptable salt, solvate or tautomer thereof.

In yet another aspect, the present disclosure provides compounds of the formula:

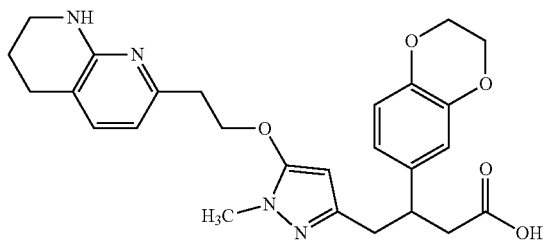 [SMILES: Cn1nc(CC(CC(=O)O)c2ccc3c(c2)OCCO3)cc1OCCc1ccc2c(n1)NCCC2]

or a pharmaceutically acceptable salt thereof. In some embodiments, the compounds are further defined as:

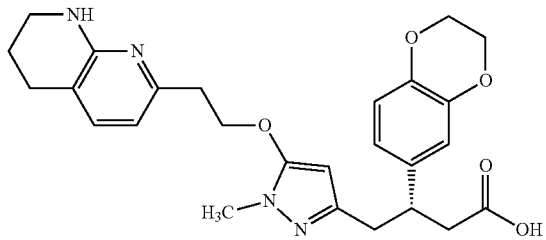 [SMILES: Cn1nc(C[C@@H](CC(=O)O)c2ccc3c(c2)OCCO3)cc1OCCc1ccc2c(n1)NCCC2]

or a pharmaceutically acceptable salt thereof.

In still yet another aspect, the present disclosure provides pharmaceutical compositions comprising:
a) a compound as disclosed and described herein; and
b) an excipient.

In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion. The pharmaceutical composition may be formulated for oral, topical, intravenous, or intravitreal administration. In some embodiments, the pharmaceutical composition is formulated as a unit dose.

In yet another aspect, the present disclosure provides methods of treating and/or preventing a disease or a disorder in a patient in need thereof, comprising administering to the patient a compound or composition described herein in an amount sufficient to treat and/or prevent the disease or disorder. In some embodiments, the disease or disorder is associated with fibrosis. The disease or disorder may be scleroderma or fibrosis of the lungs, liver, kidneys, heart, skin, or pancreas. In some embodiments, the disease or disorder is fibrosis of the lungs. In other embodiments, the disease or disorder is fibrosis of the liver. In other embodiments, the disease or disorder is fibrosis of the heart. In other embodiments, the disease or disorder is fibrosis of the kidneys. In other embodiments, the disease or disorder is fibrosis of the pancreas. In other embodiments, the disease or disorder is fibrosis of the skin. In some embodiments, the disease or disorder is scleroderma.

In some embodiments, the patient is a human, monkey, cow, horse, sheep, goat, dog, cat, mouse, rat, guinea pig, or transgenic species thereof. The patient may be a monkey, cow, horse, sheep, goat, dog, cat, mouse, rat, or guinea pig. Alternatively, the patient may be a human.

In still yet another aspect, the present disclosure provides methods of inhibiting the binding of an integrin comprising contacting the integrin with a compound or composition described herein. The integrin may be $\alpha_5\beta_1$, $\alpha v\beta_1$, $\alpha v\beta_3$, or $\alpha v\beta_5$. In some embodiments, the integrin is $\alpha_5\beta_1$. In some further embodiments, the integrin is $\alpha v\beta_1$. In some embodiments, the method is performed in vitro. In other embodiments, the method is performed ex vivo or in vivo. In some embodiments, the inhibition of binding is sufficient to treat or prevent a disease or disorder in a patient.

Some embodiments provide a method of treating and/or preventing a disease or a disorder in a patient in need thereof, comprising administering to the patient a compound or composition as disclosed and described herein in an amount sufficient to treat and/or prevent the disease or disorder. In some embodiments, the disease or disorder is associated with fibrosis. In some embodiments, the disease or disorder is scleroderma or fibrosis of the lungs, liver, kidneys, heart, skin, or pancreas. In some embodiments, the disease or disorder is fibrosis of the lungs. In some embodiments, the disease or disorder is fibrosis of the liver. In some embodiments, the disease or disorder is fibrosis of the heart. In some embodiments, the disease or disorder is fibrosis of the kidneys. In some embodiments, the disease or disorder is fibrosis of the pancreas. In some embodiments, the disease or disorder is fibrosis of the skin. In some embodiments, the disease or disorder is scleroderma. In some embodiments, the patient is a human, monkey, cow, horse, sheep, goat, dog, cat, mouse, rat, guinea pig, or transgenic species thereof. In some embodiments, the patient is a monkey, cow, horse, sheep, goat, dog, cat, mouse, rat, or guinea pig. In some embodiments, the patient is a human.

Some embodiments provide a method of inhibiting the binding of an integrin comprising contacting the integrin with a compound or composition as disclosed and described herein. In some embodiments, the integrin is α5β1, αVβ1, αVβ3, or αVβ5. In some embodiments, the integrin is αVβ1. In some embodiments, the integrin is α5β1. In some embodiments, the method is performed in vitro. In some embodiments, the method is performed ex vivo or in vivo. In some embodiments, the inhibition of binding is sufficient to treat or prevent a disease or disorder in a patient.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description. Note that simply because a particular compound is ascribed to one particular generic formula doesn't mean that it cannot also belong to another generic formula.

DETAILED DESCRIPTION

Disclosed herein are new compounds and compositions which may act as $α_5β_1$, or $α_vβ_1$ integrin antagonist, methods for their manufacture, and methods for their use, including for the treatment and/or prevention of diseases or disorders mediated by integrins. In some embodiments, the compounds provided herein may be used for the selective inhibition or antagonism of integrins $α_5β_1$, $αvβ_1$, $αvβ_3$, and/or $αvβ_5$. In some embodiments, the compounds provided herein exhibit reduced inhibitory or antagonistic activity of integrins $αvβ_6$, $αvβ_8$, and/or $α_{IIb}β_3$.

I. COMPOUNDS AND SYNTHETIC METHODS

The compounds provided by the present disclosure may be made using the methods outlined below and further described in the Examples section. Those with skill in the art will readily understand that known variations of the conditions and processes described in the Examples can be used to synthesize the compounds of the present disclosure. Starting materials and equipment employed were either commercially available prepared by methods previously reported and readily duplicated by those skilled in the art. Such principles and techniques are taught, for example, in *March's Advanced Organic Chemistry: Reactions, Mechanisms, and Structure* (2007), which is incorporated by reference herein.

In some embodiments, the compounds of the present disclosure include the compounds described in the Examples and claims listed below. Some embodiments include compounds active as inhibitors of integrin αvβ1, such as compounds listed in Table 1 below (which contain non-bulky X and Y substituent groups). Some embodiments include compounds active as inhibitors of integrin αvβ1, that also in general have increased activity as inhibitors of integrin $α_5β_1$ as compared with the compounds in Table 1, such as compounds listed in Table 2 below (which contain a bulky Y substituent).

TABLE 1

| Example Compounds of the Present Disclosure | |
|---|---|
| Example Number | Compound Structure |
| Example 1 | *(structure)* |
| Example 2 | *(structure)* |
| Example 3 | *(structure)* |

TABLE 1-continued
Example Compounds of the Present Disclosure
| Example Number | Compound Structure |
|---|---|
| Example 4 | 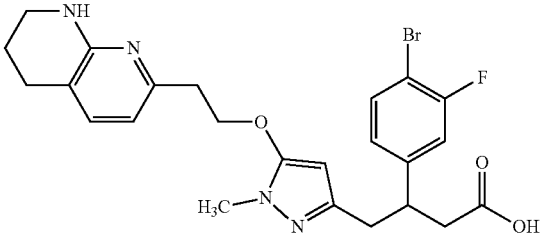 [SMILES: Cn1nc(CC(CC(=O)O)c2ccc(Br)c(F)c2)cc1OCCc1ccc2c(n1)NCCC2] |
| Example 5 | 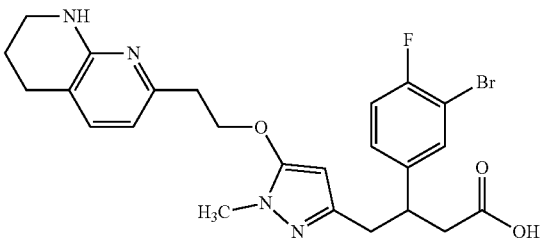 [SMILES: Cn1nc(CC(CC(=O)O)c2ccc(F)c(Br)c2)cc1OCCc1ccc2c(n1)NCCC2] |
| Example 6 | 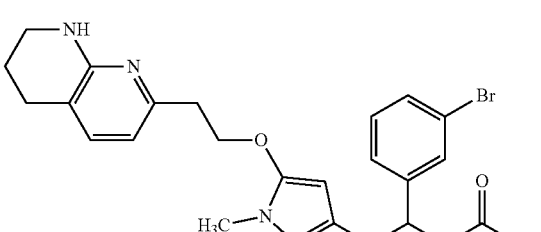 |
| Example 7 | 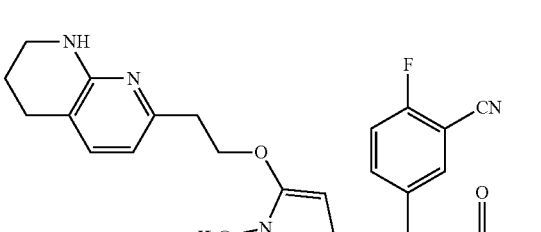 |
| Example 8 | 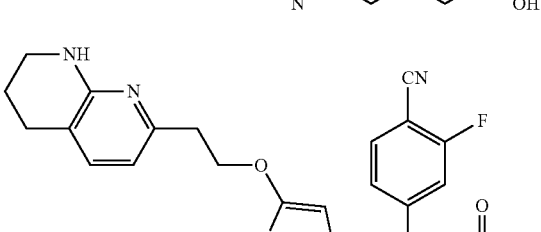 |
| Example 9 | 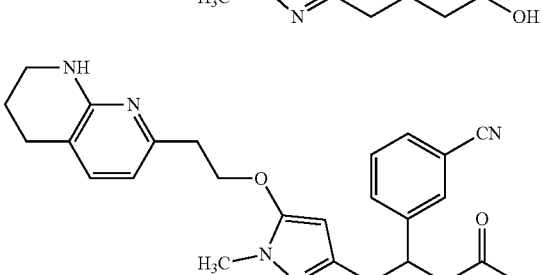 |

TABLE 1-continued
Example Compounds of the Present Disclosure
| Example Number | Compound Structure |
|---|---|
| Example 10 | 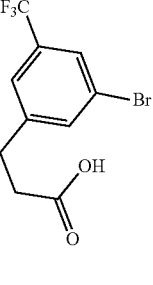 |
| Example 11 | 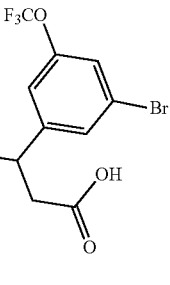 |
| Example 12 | 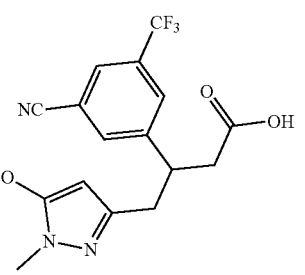 |
| Example 13 | 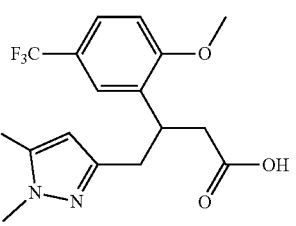 |
| Example 14 | 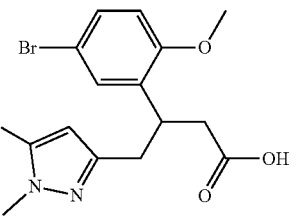 |
| Example 15 | 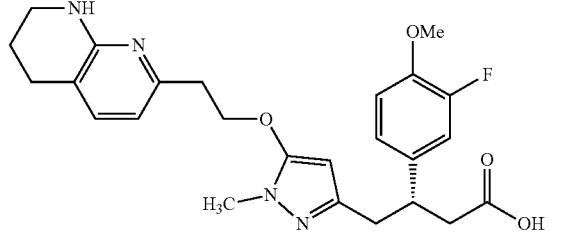 |

TABLE 1-continued
Example Compounds of the Present Disclosure
| Example Number | Compound Structure |
|---|---|
| Example 46 | 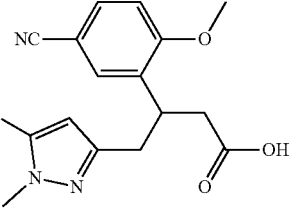 |
| Example 47 | 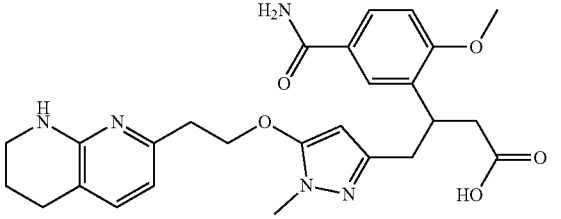 [SMILES: COc1ccc(C(N)=O)cc1C(CC(=O)O)Cc1cc(OCCc2ccc3c(n2)NCCC3)n(C)n1] |
| Example 48 | 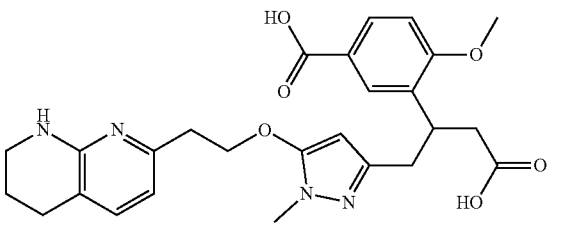 [SMILES: COc1ccc(C(=O)O)cc1C(CC(=O)O)Cc1cc(OCCc2ccc3c(n2)NCCC3)n(C)n1] |
TABLE 2
Example Compounds of the Present Disclosure
| Example Number | Compound Structure |
|---|---|
| Example 16 | 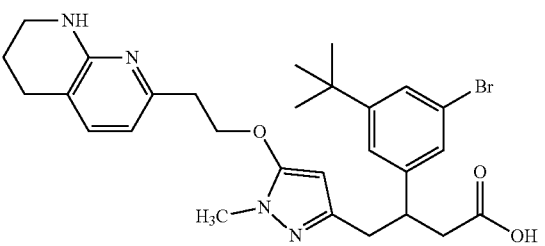 [SMILES: Cn1nc(CC(CC(=O)O)c2cc(Br)cc(C(C)(C)C)c2)cc1OCCc1ccc2c(n1)NCCC2] |
| Example 17 | 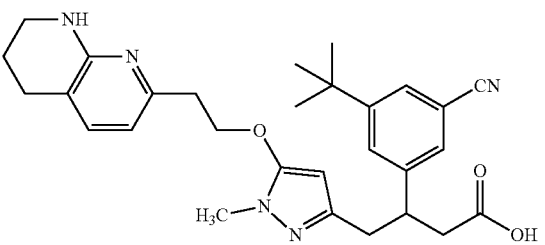 [SMILES: Cn1nc(CC(CC(=O)O)c2cc(C#N)cc(C(C)(C)C)c2)cc1OCCc1ccc2c(n1)NCCC2] |

TABLE 2-continued
Example Compounds of the Present Disclosure
| Example Number | Compound Structure |
|---|---|
| Example 18 | 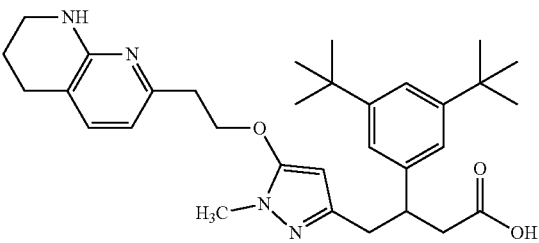 [SMILES: Cn1nc(CC(CC(=O)O)c2cc(C(C)(C)C)cc(C(C)(C)C)c2)cc1OCCc1ccc2c(n1)NCCC2] |
| Example 19 | 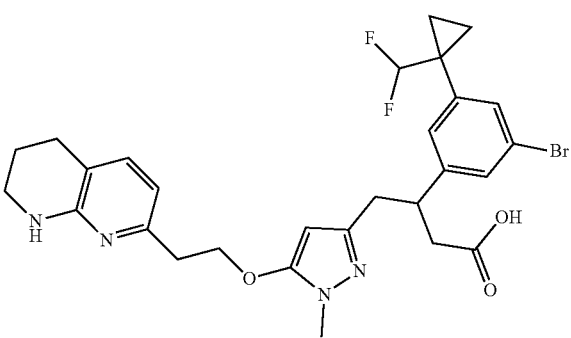 [SMILES: Cn1nc(CC(CC(=O)O)c2cc(Br)cc(C3(C(F)F)CC3)c2)cc1OCCc1ccc2c(n1)NCCC2] |
| Example 20 | 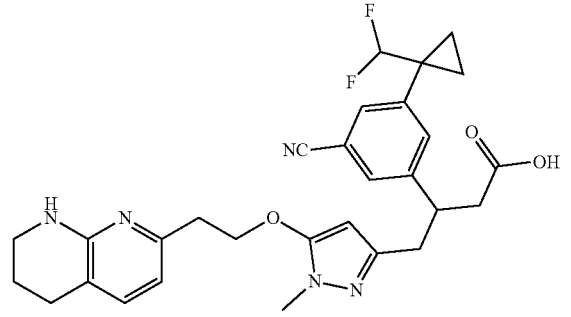 [SMILES: Cn1nc(CC(CC(=O)O)c2cc(C#N)cc(C3(C(F)F)CC3)c2)cc1OCCc1ccc2c(n1)NCCC2] |
| Example 21 | 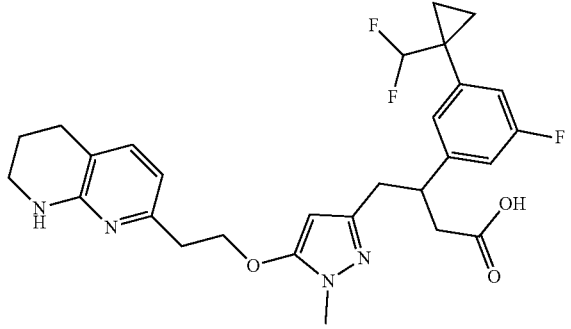 [SMILES: Cn1nc(CC(CC(=O)O)c2cc(F)cc(C3(C(F)F)CC3)c2)cc1OCCc1ccc2c(n1)NCCC2] |
| Example 22 | 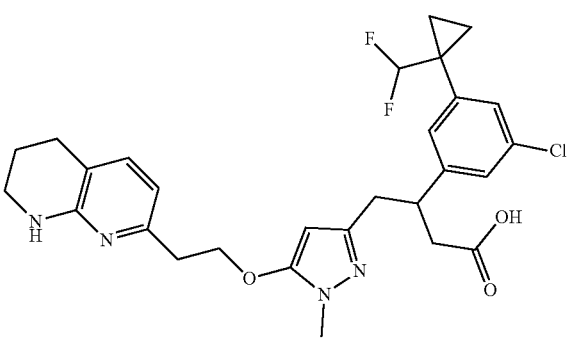 [SMILES: Cn1nc(CC(CC(=O)O)c2cc(Cl)cc(C3(C(F)F)CC3)c2)cc1OCCc1ccc2c(n1)NCCC2] |

TABLE 2-continued
Example Compounds of the Present Disclosure
| Example Number | Compound Structure |
| --- | --- |
| Example 23 | 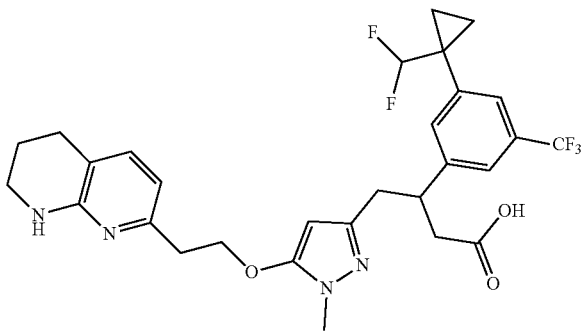 [SMILES: Cn1nc(CC(CC(=O)O)c2cc(C(F)(F)F)cc(C3(C(F)F)CC3)c2)cc1OCCc1ccc2c(n1)NCCC2] |
| Example 24 | 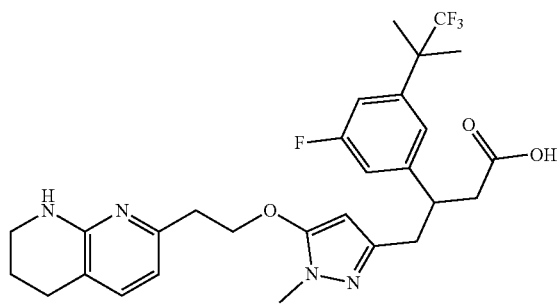 [SMILES: Cn1nc(CC(CC(=O)O)c2cc(F)cc(C(C)(C)C(F)(F)F)c2)cc1OCCc1ccc2c(n1)NCCC2] |
| Example 25 | 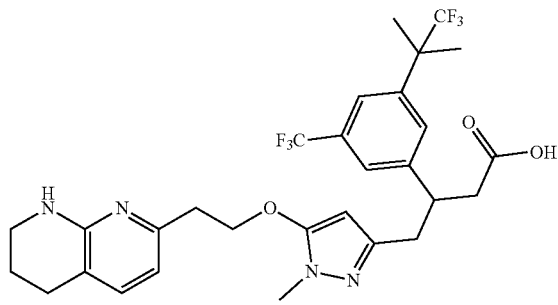 [SMILES: Cn1nc(CC(CC(=O)O)c2cc(C(F)(F)F)cc(C(C)(C)C(F)(F)F)c2)cc1OCCc1ccc2c(n1)NCCC2] |
| Example 26 | 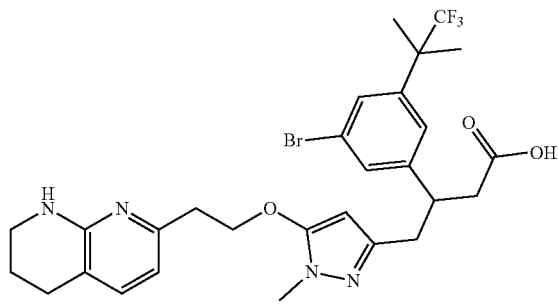 [SMILES: Cn1nc(CC(CC(=O)O)c2cc(Cl)cc(C(C)(C)C(F)(F)F)c2)cc1OCCc1ccc2c(n1)NCCC2] |

TABLE 2-continued
Example Compounds of the Present Disclosure
| Example Number | Compound Structure |
| --- | --- |
| Example 27 | 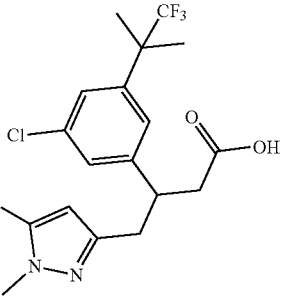 |
| Example 28 | 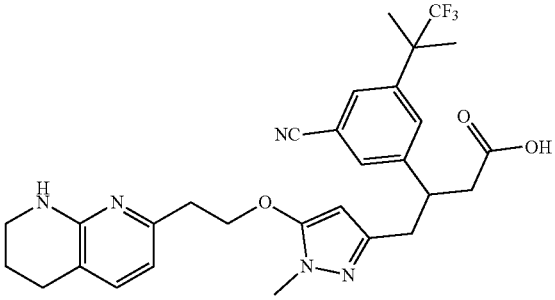 [SMILES: Cn1nc(CC(CC(=O)O)c2cc(C#N)cc(C(C)(C)C(F)(F)F)c2)cc1OCCc1ccc2c(n1)NCCC2] |
| Example 29 | 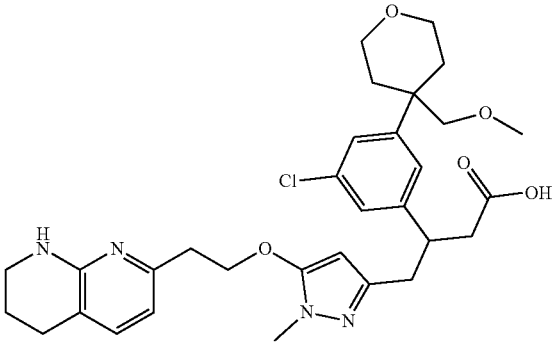 [SMILES: COCC1(c2cc(Cl)cc(C(CC(=O)O)Cc3cc(OCCc4ccc5c(n4)NCCC5)n(C)n3)c2)CCOCC1] |
| Example 30 | 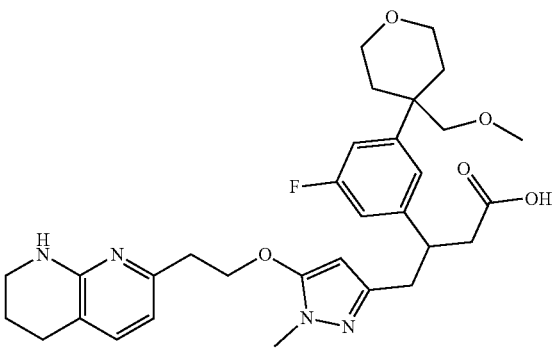 [SMILES: COCC1(c2cc(F)cc(C(CC(=O)O)Cc3cc(OCCc4ccc5c(n4)NCCC5)n(C)n3)c2)CCOCC1] |

TABLE 2-continued
Example Compounds of the Present Disclosure
| Example Number | Compound Structure |
|---|---|
| Example 31 | 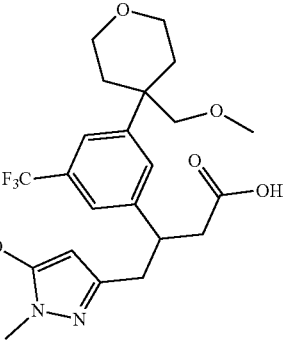 |
| Example 32 | 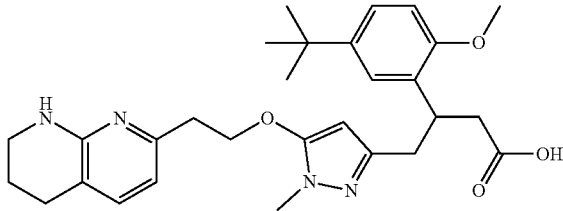 [SMILES: COc1ccc(C(C)(C)C)cc1C(CC(=O)O)Cc1cc(OCCc2ccc3c(n2)NCCC3)n(C)n1] |
| Example 33 | 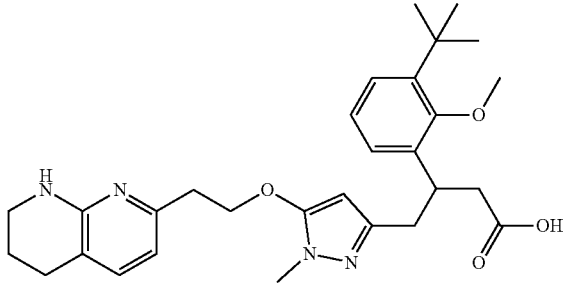 [SMILES: COc1c(C(CC(=O)O)Cc2cc(OCCc3ccc4c(n3)NCCC4)n(C)n2)cccc1C(C)(C)C] |
| Example 34 | 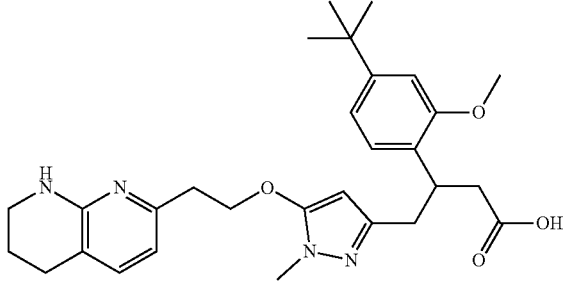 [SMILES: COc1cc(C(C)(C)C)ccc1C(CC(=O)O)Cc1cc(OCCc2ccc3c(n2)NCCC3)n(C)n1] |
| Example 35 | 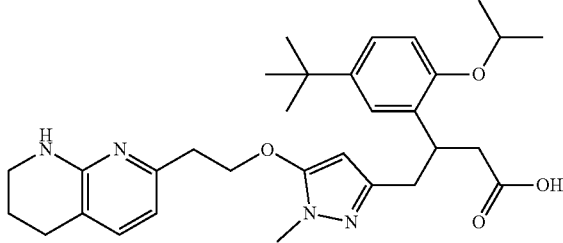 [SMILES: CC(C)Oc1ccc(C(C)(C)C)cc1C(CC(=O)O)Cc1cc(OCCc2ccc3c(n2)NCCC3)n(C)n1] |

TABLE 2-continued

Example Compounds of the Present Disclosure

| Example Number | Compound Structure |
|---|---|
| Example 36 | 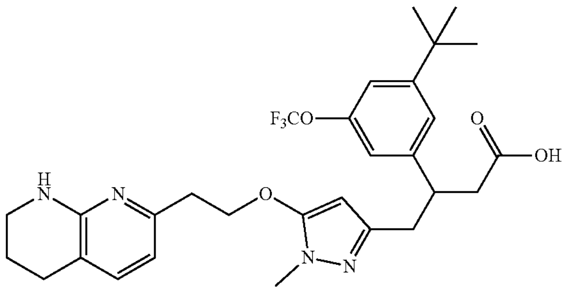 [SMILES: Cn1nc(CC(CC(=O)O)c2cc(OC(F)(F)F)cc(C(C)(C)C)c2)cc1OCCc1ccc2c(n1)NCCC2] |
| Example 37 | 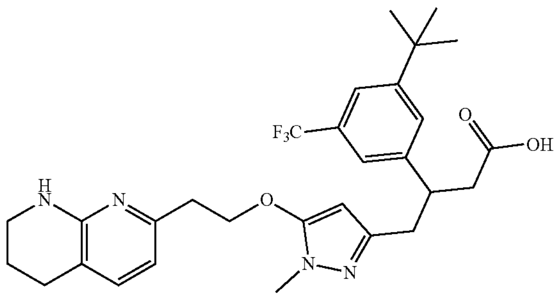 [SMILES: Cn1nc(CC(CC(=O)O)c2cc(C(C)(C)C)cc(C(F)(F)F)c2)cc1OCCc1ccc2c(n1)NCCC2] |
| Example 38 | 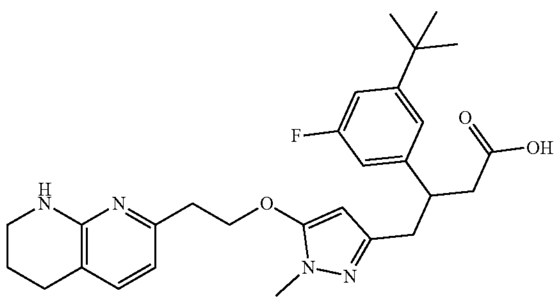 [SMILES: Cn1nc(CC(CC(=O)O)c2cc(F)cc(C(C)(C)C)c2)cc1OCCc1ccc2c(n1)NCCC2] |
| Example 39 | 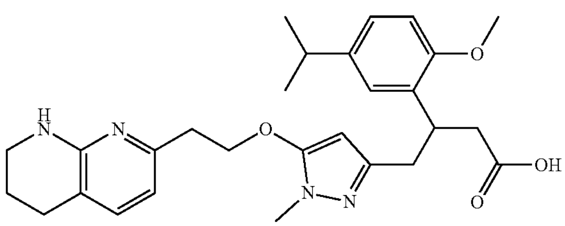 [SMILES: COc1ccc(C(C)C)cc1C(CC(=O)O)Cc1cc(OCCc2ccc3c(n2)NCCC3)n(C)n1] |
| Example 40 | 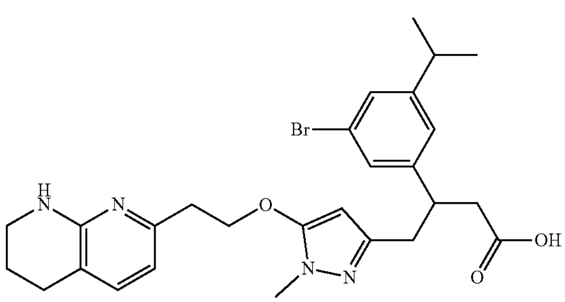 [SMILES: CC(C)c1cc(Br)cc(C(CC(=O)O)Cc2cc(OCCc3ccc4c(n3)NCCC4)n(C)n2)c1] |

TABLE 2-continued

Example Compounds of the Present Disclosure

| Example Number | Compound Structure |
|---|---|
| Example 41 | 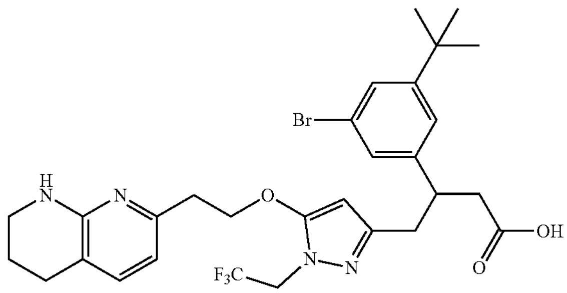 [SMILES: CC(C)(C)c1cc(Br)cc(C(CC(=O)O)Cc2cc(OCCc3ccc4c(n3)NCCC4)n(CC(F)(F)F)n2)c1] |
| Example 42 | 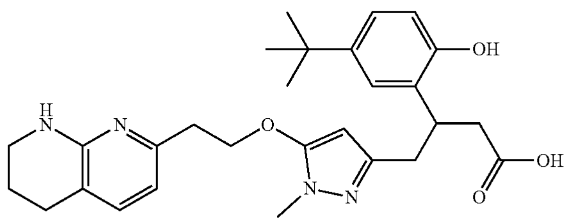 [SMILES: Cn1nc(CC(CC(=O)O)c2cc(C(C)(C)C)ccc2O)cc1OCCc1ccc2c(n1)NCCC2] |
| Example 43 | 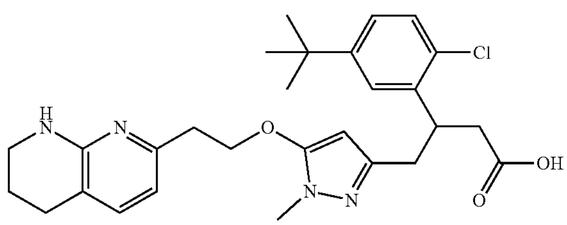 [SMILES: Cn1nc(CC(CC(=O)O)c2cc(C(C)(C)C)ccc2Cl)cc1OCCc1ccc2c(n1)NCCC2] |
| Example 44 | 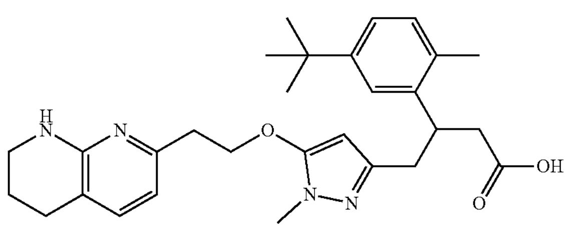 [SMILES: Cc1ccc(C(C)(C)C)cc1C(CC(=O)O)Cc1cc(OCCc2ccc3c(n2)NCCC3)n(C)n1] |
| Example 45 | 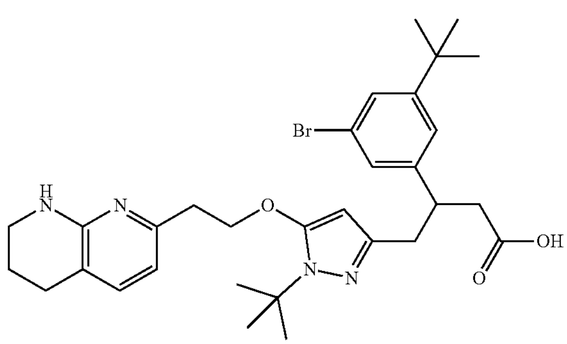 [SMILES: CC(C)(C)c1cc(Br)cc(C(CC(=O)O)Cc2cc(OCCc3ccc4c(n3)NCCC4)n(C(C)(C)C)n2)c1] |

TABLE 2-continued

Example Compounds of the Present Disclosure

| Example Number | Compound Structure |
| --- | --- |
| Example 49 | 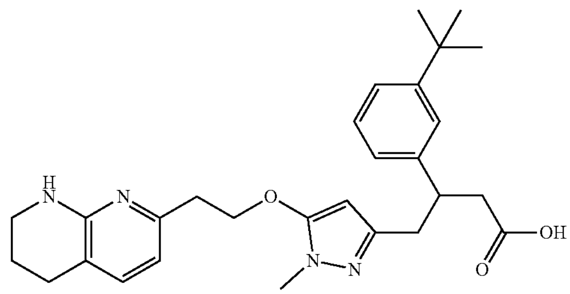 [SMILES: Cn1nc(CC(CC(=O)O)c2cccc(C(C)(C)C)c2)cc1OCCc1ccc2c(n1)NCCC2] |
| Example 50 | 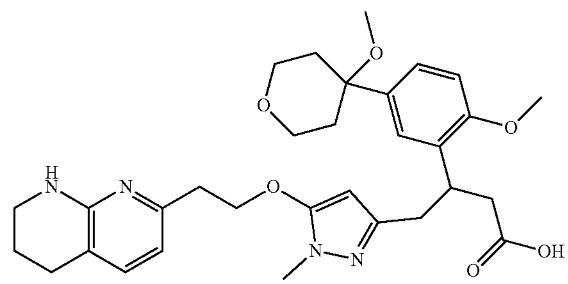 [SMILES: COc1ccc(C2(OC)CCOCC2)cc1C(CC(=O)O)Cc1cc(OCCc2ccc3c(n2)NCCC3)n(C)n1] |

All of the compounds of the present disclosure may be useful for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all of the compounds of the present invention are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present disclosure have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds employed in methods of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration, as defined by the IUPAC 1974 Recommendations. In some embodiments, the compounds of the present disclosure are in the S configuration. For example, mixtures of stereoisomers may be separated using the techniques taught in the Examples section below, as well as modifications thereof. Tautomeric forms are also included as well as pharmaceutically acceptable salts of such isomers and tautomers.

Atoms making up the compounds of the present disclosure are intended to include all isotopic forms of such atoms. Compounds of the present disclosure include those with one or more atoms that have been isotopically modified or enriched, in particular those with pharmaceutically acceptable isotopes or those useful for pharmaceutically research. Isotopes, as used herein, include those atoms having the same atomic number but different mass numbers. By way of general example and without limitation, isotopes of hydrogen include deuterium and tritium, and isotopes of carbon include $^{13}C$ and $^{14}C$. Similarly, it is contemplated that one or more carbon atom(s) of a compound of the present disclosure may be replaced by a silicon atom(s). Furthermore, it is contemplated that one or more oxygen atom(s) of a compound of the present disclosure may be replaced by a sulfur or selenium atom(s).

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It should be further recognized that the compounds of the present disclosure include those that have been further modified to comprise substituents that are convertible to hydrogen in vivo. This includes those groups that may be convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$, Boc), benzyloxycarbonyl, p-methoxy-benzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$, Boc), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

I. BIOLOGICAL ACTIVITY

It is another object of the disclosure to provide new compounds and compositions which may act as $\alpha_v\beta_1$ and/or $\alpha_5\beta_1$ integrin antagonist, methods for their manufacture, and methods for their use, including for the treatment and/or prevention of diseases or disorders mediated by integrins. In some embodiments, the compounds may be used for the selective inhibition or antagonism of integrins $\alpha_5\beta_3$, $\alpha v\beta_1$, $\alpha v\beta_1$, and/or $\alpha v\beta_5$. In some embodiments, the compounds provided herein exhibit reduced inhibitory or antagonistic activity of integrins $\alpha v\beta_3$, $\alpha v\beta_5$, $\alpha v\beta_6$, $\alpha v\beta_8$, and/or $\alpha_{IIb}\beta_3$. In some further embodiments, the compounds provided herein exhibit reduced inhibitory or antagonistic activity of integrins $\alpha v\beta_3$, and/or $\alpha v\beta_5$.

Such compounds and compositions are useful in inhibiting or antagonizing integrins, and therefore in another embodiment, the present disclosure provides methods for inhibiting or antagonizing the $\alpha_5\beta_1$, $\alpha v\beta 1$, $\alpha v\beta 3$, and/or $\alpha v\beta 5$ integrins.

While not being bound by any particular theory, it has been unexpectedly discovered that compounds of Formula (I) having at least one bulky substituent at substituent X and/or Y exhibit significantly increased activity against integrin α5β1. Examples of bulky substituents include unsubstituted alkyl groups, for example branched alkyl groups; substituted alkyl groups; cyclic groups, for example, cycloalkyl; and heterocycloalkyl groups. In some embodiments, at least one bulky substituent is at the meta position on the phenyl ring. Prior compounds lacking such a bulky substituents primarily acted on other integrin receptors, while activity against α5β1 was relatively low. In some embodiments, a compound of Formula (I) having a bulky group at X or Y exhibits increased activity against integrin α5β1 compared to a structurally related compound lacking such a bulky substituent, for example, comparing compounds of Table 2 (having a bulky Y group) with those of Table 1 (having no bulky X or Y groups) and with the comparator compounds of Table 3 below.

TABLE 3

Comparator Compounds

| Comparator Number | Compound Structure |
|---|---|
| Comparator 1 (CC1) | 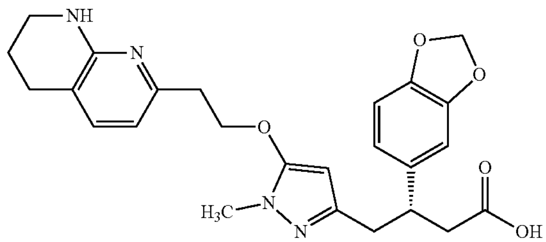 [SMILES: Cn1nc(C[C@@H](CC(=O)O)c2ccc3c(c2)OCO3)cc1OCCc1ccc2c(n1)NCCC2] |
| Comparator 2 (CC2) | 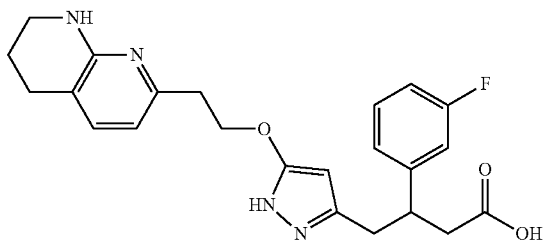 [SMILES: O=C(O)CC(Cc1cc(OCCc2ccc3c(n2)NCCC3)[nH]n1)c1cccc(F)c1] |

The difference in activity between related compounds of Formula (I) having at least one bulky group at substituent X and/or Y and those lacking such a bulky group is noteworthy. For instance, analogous compounds to Comparator 2 (CC2), but having a pyrazole ($R^1$) methyl and a bulky substituent at X and/or Y, provided increased activity against α5β1 compared to CC2. Specifically, CC2 gave a measured IC50 of 770 nM against α5β1, while Example 21

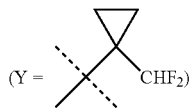

gave 12 nM, Example 24

gave 15 nM, Example 30

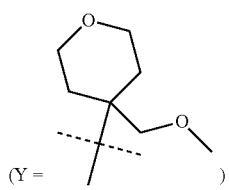

gave 12 nM, and Example 38 (Y=tert-butyl) gave 23 nM. Additionally, Example 6 (from Table 1) gave a measured IC50 of 158 nM against α5β1, while Example 16 (from Table 2), differing only by the addition of a tert-butyl group, gave a measured IC50 of 30 nM against α5β1, a several-fold increase in activity. Comparison of Example 17 (from Table 2) with Example 9 (from Table 1) indicates a similar increase in activity when at least one bulky group is included at X and/or Y of a compound of Formula (I). Specifically, Example 9 gave a measured IC50 of 110 nM against α5β1, while Example 17 gave a measured IC50 of 11 nM against α5β1.

Accordingly, compounds of Formula (I) having at least one bulky group at substituent X and/or Y may be used in treating conditions involving integrin α5β1 activity. Cells expressing α5β1 are believed to bind to fibronectin in a region that incorporates the ninth and tenth type III fibronectin repeats, the latter of which is believed to contain the RGD motif for integrin binding. In addition to fibronectin, α5β1 has been reported to interact with other RGD-containing extracellular matrix proteins including fibrinogen, denatured collagen, and fibrillin-1 (Bax et al., *J. Biol. Chem.*, 278(36): 34605-34616, 2003, 2003; Perdih, Curr. Med. Chem., 17(22):2371-2392, 2010; Suehiro et al., *J. Biochem.*, 128 (4):705-710, 2000). These ligands are generally classified as components of the provisional matrix that is laid down by cells as part of the wound healing response in tissues. Components of this response are angiogenesis (new blood vessel formation) and fibrosis (scar formation) which are beneficial for healing of acute injuries, but can be deleterious in many disease contexts. The important role of α5β1 in angiogenesis is supported by numerous studies. For example, mice lacking this integrin exhibit embryonic lethality at day 10-11 with a phenotype that includes defects in both the embryonic and extraembryonic vasculature (Yang et al., *Development*, 119(4):1093-1105, 1993). Angiogenic cytokines such as bFGF, IL-8, TGFβ, and TNFα are believed to upregulate α5β1 expression on endothelial cells in vitro and in vivo, and immunohistochemistry shows coordinated increases in both α5β1 and fibronectin staining in blood vessels from various types of human tumor biopsies and xenograft tumors in animals (Collo, *J. Cell Sci.*, 112(Pt 4):569-578, 1999; Kim et al., *Am. J. Pathol.*, 156(4):1345-1362, 2000). Monoclonal antibodies that specifically inhibit α5β1, and compounds that have been described as α5β1 inhibitors, have been observed to significantly reduce angiogenesis in some experimental models (Kim et al., Am. J.

Pathol., 156(4):1345-1362, 2000; Bhaskar et al., *J. Transl. Med.*, 5:61, 2007; Livant et al., *J. Clin. Invest.*, 105(11): 1537-1545, 2000; Zahn et al., *Arch. Ophthalmol.*, 127(10): 1329-1335, 2009).

α5β1 expression is not confined to the endothelium, and it may have other functional roles in addition to angiogenesis. α5β1 is expressed to varying degrees in many cell types including fibroblasts, hematopoietic and immune cells, smooth muscle cells, epithelial cells, and tumor cells. Expression on tumor cells has been implicated in the progression of tumor growth and metastasis (Adachi et al., *Clin. Cancer Res.*, 6(1):96-101, 2000, 2000; Blase et al., *Int. J. Cancer*, 60(6):860-866, 1995; Danen et al., *Histopathology*, 24(3):249-256, 1994; Edward, *Curr. Opin. Oncol.*, 7(2):185-191, 1995). In human fibroblasts, α5β1 was found to promote motility and survival (Lobert et al., *Dev. Cell*, 19(1): 148-159, 2010). In pancreatic stellate cells, α5β1 interacts with connective tissue growth factor to stimulate adhesion, migration, and fibrogenesis (Gao and Brigstock, *Gut*, 55:856-862, 2006). It has been shown that pharmacologic antagonism of α5β1 inhibits the attachment migration, and proliferation of human retinal epithelial cells in vitro, and reduces retinal cell proliferation and scarring when administered intravitreally to rabbits with retinal detachment (Li et al., *Invest. Ophthalmol. Vis. Sci.*, 50(12):5988-5996, 2009; Zahn et al., *Invest. Ophthalmol. Vis. Sci.*, 51(2):1028-1035, 2010).

In some embodiments, a compound of Formula (I) may be useful in the treatment of angiogenesis, and/or a related condition. Such related conditions include fibrosis, for example, fibroid growth, and/or a disease of cellular proliferation, for example, cancer. Some embodiments include using a compound of Formula (I) in the treatment or prevention of both fibrosis and angiogenesis. In some embodiments, a compound of Formula (I) is administered to a patient suffering from cancer. In further embodiments, a compound of Formula (I) is administered to a patient suffering from a fibrotic growth. In still further embodiments, a compound of Formula (I) slows the growth of a fibroid, halts the growth of a fibroid, or reverses the growth of a fibroid. In further embodiments, the fibroid is a tumor.

The term "tumor" is used broadly herein to mean any non-congenital, pathological, localized tissue growth. The tumor can be benign, for example, a hemangioma, glioma, teratoma, and the like, or can be malignant, for example, a carcinoma, sarcoma, glioblastoma, astrocytoma, neuroblastoma, retinoblastoma, and the like. The tumor may or may not be metastatic. The term "cancer" is used generally to refer to a disease that accompanies the appearance of a malignant tumor. The tumor can be a carcinoma of, for example, lung cancer, breast cancer, prostate cancer, cervical cancer, pancreatic cancer, colon cancer or ovarian cancer, or a sarcoma, for example, osteosarcoma or Kaposi's sarcoma.

In further embodiments, the fibroid is a fibroma. The fibroma may be, for example, a hard fibroma or a soft fibroma. The fibroma may be, for further example, an angiofibroma, a cystic fibroma, a myxofibroma, a cemento-ossifying fibroma, a chondromyxoid fibroma, a desmoplasmic fibroma, a nonossifying fibroma, an ossifying fibroma, a nuchal fibroma, a collagenous fibroma, a fibroma of tendon sheath, a perifollicular fibroma, a pleomorphic fibroma, a uterine fibroma, a neurofibroma, or an ovarian fibroma.

The integrin αvβ1 is expressed on the surface of the principal cellular mediators of organ fibrosis, activated myofibroblasts (Henderson, et al., 2013). Furthermore, a recent study showed cellular-expressed αvβ1 directly binds and activates the pro-fibrotic growth factor, transforming growth factor-β1 (TGFβ1), in vitro (Reed, et al., 2015). This same study also showed that therapeutic treatment with a selective small molecule inhibitor of αvβ1 could attenuate injury-induced fibrosis in the lungs or livers of mice. Altogether, these data provide evidence for a critical in vivo role for αvβ1 in tissue fibrosis.

Like αvβ1, the integrins αvβ3 and αvβ5 are also capable of binding and activating latent TGFβ in vitro (Tatler, et al., 2011; Wipff, et al, 2007). Specific blockade of $αvβ_{33}$ reduces TGFβ signaling and can normalize pro-fibrotic gene expression patterns in cells (Wipff, et al., 2007; Asano, et al., 2005a; Patsenker, et al., 2007). Mice that are deficient in beta-3 subunit expression, and thus lack αvβ3 expression, show attenuated CCL18-driven pulmonary collagen accumulation (Luzina, et al., 2009), and are protected in a mouse model of human "stiff skin syndrome", a form of scleroderma (Gerber, et al., 2013). Modulation of the level of integrin αvβ5 expression on cells affects the nuclear localization of components of the TGFβ signaling pathway, and alters expression of fibrosis markers such as alpha smooth muscle actin and collagen (Luzina, et al., 2009; Asano, et al., 2005b; Scotton, et al., 2009).

Integrins αvβ3 and αvβ5 have been implicated in promoting angiogenesis (Avraamides et al., 2008), so that their antagonism in addition to other integrins may be predicted to provide superior blockade of this process. Integrin αvβ3 is also known to play a role in tumor cell metastasis, and in the elevated bone resorption associated with osteoporosis and some cancers (Nakamura, et al., 2007; Schneider, et al., 2011).

Additionally, in some aspects, the antagonists of the present disclosure show reduced activity for other integrins such as αvβ6 and αvβ8. Loss or excessive inhibition of these specific integrins has been associated with inflammation-related side effects or development of autoimmunity in mice (Huang, et al., 1996; Lacy-Hulbert, et al., 2007; Travis, et al., 2007; Worthington, et al., 2015).

Additionally, in some embodiments, the compounds of the present disclosure show reduced inhibitory or antagonistic activity for integrin $α_{IIb}β_{III}$, which is an integrin complex found on platelets. Integrin $α_{IIb}β_{III}$ inhibition is associated with disruption of platelet aggregation, which is associated with toxicity and/or contraindicated when treating certain disease or disorders. In some embodiments, the compounds provided herein exhibit increased specificity for integrins $αvβ_1$ and $α_5β_1$ relative to an untargeted integrin, e.g., integrin $α_{IIb}β_{III}$. In some embodiments, the compounds provided herein may be used as anti-fibrotic agents that minimize the potential for toxicities associated with bleeding disorders.

While not being bound by any particular theory, it has been unexpectedly discovered that certain compounds of Formula (I) having a bulky X and/or Y substituent, wherein the X, Y substitution pattern is 2,5 di-substitution, exhibit inhibitory activity for $αvβ_1$ and $α_5β_1$ while sparing $αvβ_3$, $αvβ_5$, $αvβ_6$, and/or $αvβ_8$. For example, Example 32 exhibits high inhibitory activity at αvβ1 and $α_5β_1$ and low activity at $αvβ_3$, $αvβ_5$, $αvβ_6$, and $αvβ_8$. Accordingly, some embodiments include compounds according to Formula (Iba).

There are many types of integrin, and many cells have multiple types on their surface. Integrins are of vital importance to all animals and have been found in all animals investigated, from sponges to mammals. As such compounds, which target integrins have found numerous uses in different animals including companion animals, livestock animals, zoo animals as well as wild animals. Integrins have been extensively studied in humans. Integrins work along-side other proteins such as cadherins, immunoglobulin superfamily cell adhesion molecules, selectins and syndecans to mediate cell-cell and cell-matrix interaction and communication. Integrins bind cell surface and ECM components such as fibronectin, vitronectin, collagen, and laminin.

Each integrin is formed by the non-covalent heterodimerization of alpha and beta glycoprotein subunits, the combination of which conveys distinct biological activities such as cell attachment, migration, proliferation, differentiation, and survival. Currently, 24 integrins have been described in mammals that are formed by pairing of 18 α subunits and 8 β subunits and are listed in Table 4:

TABLE 4

| Integrins | | | |
|---|---|---|---|
| Gene | Protein | Synonym | Type |
| ITGA1 | CD49a | VLA1 | Alpha |
| ITGA2 | CD49b | VLA2 | Alpha |
| ITGA3 | CD49c | VLA3 | Alpha |
| ITGA4 | CD49d | VLA4 | Alpha |
| ITGA5 | CD49e | VLA5 | Alpha |
| ITGA6 | CD49f | VLA6 | Alpha |
| ITGA7 | ITGA7 | FLJ25220 | Alpha |
| ITGA8 | ITGA8 | | Alpha |
| ITGA9 | ITGA9 | RLC | Alpha |
| ITGA10 | ITGA10 | | Alpha |
| ITGA11 | ITGA11 | HsT18964 | Alpha |
| ITGAD | CD11D | FLJ39841 | Alpha |
| ITGAE | CD103 | HUMINAE | Alpha |
| ITGAL | CD11a | LFA1A | Alpha |
| ITGAM | CD11b | MAC-1 | Alpha |
| ITGAV | CD51 | VNRA, MSK8 | Alpha |
| ITGAW | ITGAW | | Alpha |
| ITGAX | CD11c | | Alpha |
| ITGB1 | CD29 | FNRB, MSK12, MDF2 | Beta |
| ITGB2 | CD18 | LFA-1, MAC-1, MFI7 | Beta |
| ITGB3 | CD61 | GP3A, GPIIIa | Beta |
| ITGB4 | CD104 | | Beta |
| ITGB5 | ITGB5 | FLJ26658 | Beta |
| ITGB6 | ITGB6 | | Beta |
| ITGB7 | ITGB7 | | Beta |
| ITGB8 | ITGB8 | | Beta |

In addition, variants of some of the subunits are formed by differential splicing; for example, four variants of the beta-1 subunit exist. Through different combinations of these α and β subunits, some 24 unique integrins are generated, although the number varies according to different studies.

In some embodiments, the compound is an integrin antagonist such as an $\alpha_5\beta_1$ integrin antagonist. In some embodiments, the compound exhibits an $IC_{50}$ value for the $\alpha_5\beta_1$ integrin of less than 20 nM, less than 15 nM, or less than 10 nM as measured by a solid phase receptor assay for $\alpha_5\beta_1$ integrin function. In some embodiments, the compound is an integrin antagonist such as an $\alpha v\beta_1$ integrin antagonist. In some embodiments, the compound exhibits an $IC_{50}$ value for the $\alpha v\beta_1$ integrin of less than 15 nM as measured by a solid phase receptor assay for $\alpha v\beta_1$ integrin function. In some embodiments, the compound exhibits an $IC_{50}$ value for an $\alpha v\beta_3$ integrin of less than 10 nM as measured by a solid phase receptor assay for $\alpha v\beta_3$ integrin function. In some embodiments, the compound exhibits an $IC_{50}$ value for an $\alpha v\beta_5$ integrin of less than 10 nM as measured by a solid phase receptor assay for $\alpha v\beta_5$ integrin function. In some embodiments, the compound exhibits an $IC_{50}$ value for the $\alpha v\beta_1$, $\alpha v\beta_3$, and $\alpha v\beta_5$ integrins of each less than 10 nM as measured by a solid phase receptor assays for $\alpha v\beta_1$, $\alpha v\beta_3$, and $\alpha v\beta_5$ integrin function, respectively. In some embodiments, the compound exhibits an $IC_{50}$ value for an $\alpha v\beta_6$ integrin of greater than 10 nM as measured by a solid phase receptor assay for $\alpha v\beta_6$ integrin function. In some embodiments, the compound exhibits an $IC_{50}$ value for an $\alpha v\beta_8$ integrin of greater than 10 nM as measured by a solid phase receptor assay for $\alpha v\beta_8$ integrin function. In some embodiments, the compound exhibits an $IC_{50}$ value for each of the $\alpha v\beta_6$ and $\alpha v\beta_8$ integrins of greater than 10 nM as measured by solid phase receptor assays for $\alpha v\beta_6$ and $\alpha v\beta_8$ integrin function, respectively. In some embodiments, the compound exhibits an $IC_{50}$ value for an $\alpha_{IIb}\beta_3$ integrin of greater than 2,000 nM as measured by a solid phase receptor assay for $\alpha_{IIb}\beta_3$ integrin function. In some embodiments, the compound exhibits an $IC_{50}$ value for an $\alpha_{IIb}\beta_3$ integrin of greater than 5,000 nM as measured by a solid phase receptor assay for $\alpha_{IIb}\beta_3$ integrin function.

II. THERAPEUTIC METHODS

The present disclosure relates to the fields of pharmaceuticals, medicine and cell biology. More specifically, it relates to pharmaceutical agents (compounds) and pharmaceutical compositions thereof which may be used as antagonists of one or more specific integrins, such as antagonist of the $\alpha_5\beta_1$, $\alpha v\beta 1$, $\alpha v\beta 3$, and/or $\alpha v\beta 5$ integrins. As such, these compounds may be used in pharmaceutical compositions and in methods for treating conditions mediated by one or more of such integrins, for example, by inhibiting or antagonizing one or more of these integrins. In several aspects of the present disclosure, the compounds provided herein may be used in a variety of biological, prophylactic or therapeutic areas which involves one of these integrins. In some aspects of the present disclosure, the compounds described herein may also show reduced activity in other integrins, such as $\alpha v\beta 6$ and $\alpha v\beta 8$, which have been implicated in inflammatory side effects (Huang, et al., 1996; Lacy-Hulbert, et al., 2007; Travis, et al., 2007; Worthington, et al., 2015).

In another aspect, this disclosure provides methods of inhibiting or antagonizing one or more of the $\alpha_5\beta_1$, $\alpha v\beta 1$, $\alpha v\beta 3$, and/or $\alpha v\beta 5$ integrins using one or more of the compounds disclosed herein, as well as pharmaceutical compositions thereof. Such pharmaceutical compositions further comprise one or more non-toxic, pharmaceutically acceptable carriers and/or diluents and/or adjuvants (collectively referred to herein as "carrier" materials) and if desired other active ingredients. In some embodiments, the compound is administered as part of a pharmaceutical composition further comprising a pharmaceutically acceptable carrier. In some embodiments, the compounds and/or pharmaceutical compositions thereof may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intravitreal, intramuscular, intrasternal, infusion techniques or intraperitoneally. In some embodiments, the compounds of the present disclosure are administered by any suitable route in the form of a pharmaceutical composition adapted to such a route, and in a dose effective for the treatment intended. Therapeutically effective doses of the compounds required to prevent or arrest the progress of or to treat a medical condition are readily ascertained by one of ordinary skill in the art using preclinical and clinical approaches familiar to the medicinal arts.

Based upon standard laboratory experimental techniques and procedures well known and appreciated by those skilled in the art, as well as comparisons with compounds of known usefulness, the compounds described above can be used in the treatment of patients suffering from the above pathological conditions. One skilled in the art will recognize that selection of the most appropriate compound of the disclosure is within the ability of one with ordinary skill in the art and will depend on a variety of factors including assessment of results obtained in standard assay and animal models.

In several aspects of the present disclosure, the compounds provided herein may be used in a variety of biological, prophylactic or therapeutic areas, including those in which one or more the $\alpha_5\beta_1$, $\alpha v\beta 1$, $\alpha v\beta 3$, and/or $\alpha v\beta 5$ integrins plays a role.

The disclosure further involves treating or inhibiting pathological conditions associated therewith fibrosis and fibrotic diseases such as pulmonary fibrosis, renal, cardiac, muscle, and liver fibrosis, scleroderma, scarring, such as retinal, corneal and dermal scarring. Additionally, such integrin antagonists may be useful for treatment of conditions characterized by increased or excessive bone loss including, but not limited to, osteoporosis, osteogenenesis imperfecta, Paget's disease, humoral hypercalcemia of malignancy, primary and metastatic cancer of bone, and arthritis including rheumatoid arthritis. Further, such pharmaceutical agents may be useful for reduction of pathological angiogenesis and fibrosis associated with diseases that such as cancer, macular degeneration, vitreoretinopathy, and diabetic retinopathy.

III. PHARMACEUTICAL FORMULATIONS AND ROUTES OF ADMINISTRATION

For administration to an animal especially a mammal in need of such treatment, the compounds in a therapeutically effective amount are ordinarily combined with one or more excipients appropriate to the indicated route of administration. The compounds of the present disclosure are contemplated to be formulated in a manner amenable to treatment of a veterinary patient as well as a human patient. In some embodiments, the veterinary patient may be a companion animal, livestock animals, zoo animals, and wild animals The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art and may be adapted to the type of animal being treated.

The pharmaceutical compositions useful in the present disclosure may be subjected to conventional pharmaceutical operations such as sterilization and/or may contain conventional pharmaceutical carriers and excipients such as preservatives, stabilizers, wetting agents, emulsifiers, buffers, etc.

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions may be suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it may be useful to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the methods of preparation include vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the disclosure are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically or by injection to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in a human or another animal, such as the model systems shown in the examples and drawings.

An effective dose range of a therapeutic can be extrapolated from effective doses determined in animal studies for a variety of different animals. In general, a human equivalent dose (HED) in mg/kg can be calculated in accordance with the following formula (see, e.g., Reagan-Shaw et al., *FASEB J.*, 22(3):659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milli-gram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 1% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the disclosure provides that the agent(s) may taken orally and that the timing of which is or is not dependent upon food intake. Thus, for example, the agent can be taken every morning and/or every evening, regardless of when the subject has eaten or will eat.

IV. COMBINATION THERAPY

In addition to being used as a monotherapy, the compounds of the present disclosure may also find use in combination therapies. Effective combination therapy may be achieved with a single composition or pharmacological formulation that includes both agents, or with two distinct compositions or formulations, administered at the same time, wherein one composition includes a compound of this disclosure, and the other includes the second agent(s). Alternatively, the therapy may precede or follow the other agent treatment by intervals ranging from minutes to months.

Non-limiting examples of such combination therapy include combination of one or more compounds of the disclosure with another agent, for example, an anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the disclosure may be combined with agents designed to improve a patient's immune response to cancer, including (but not limited to) cancer vaccines.

V. DEFINITIONS

When used in the context of a chemical group: "hydrogen" means —H; "hydroxy" means —OH; "oxo" means =O; "carboxy" means —C(=O)OH (also written as —COOH or —CO$_2$H); "halo" means independently —F, —Cl, —Br or —I; "amino" means —NH$_2$; "cyano" means —CN; "azido" means —N$_3$; "mercapto" means —SH; and "thio" means =S.

In the context of chemical formulas, the symbol "-" means a single bond, "=" means a double bond, and "-" means triple bond. The symbol "----" represents an optional bond, which if present is either single or double. The symbol " ===== " represents a single bond or a double bond. Thus, the formula

covers, for example,

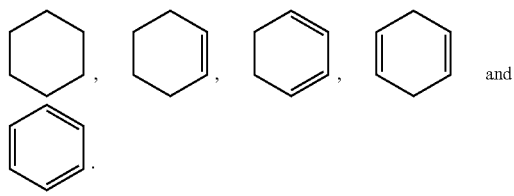

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol " ⌇ ", when drawn perpendicularly across a bond

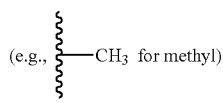

indicates a point of attachment of the group. It is noted that the point of attachment is typically only identified in this manner for larger groups in order to assist the reader in unambiguously identifying a point of attachment. The symbol " ◢ " means a single bond where the group attached to the thick end of the wedge is "out of the page." The symbol " ⫽ " means a single bond where the group attached to the thick end of the wedge is "into the page". The symbol " ⌇ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

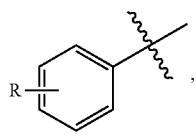

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

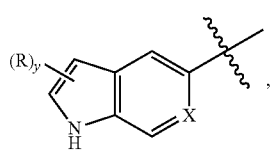

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$," is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C8)}$", and "olefin$_{C5}$" are all synonymous. When any of the chemical groups or compound classes defined herein is modified by the term "substituted", any carbon atom(s) in the moiety replacing a hydrogen atom is not counted. Thus methoxyhexyl, which has a total of seven carbon atoms, is an example of a substituted alkyl$_{(C1-6)}$.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$). (tert-butyl, t-butyl, t-Bu or Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl, cycloalkyl, and/or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl and/or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

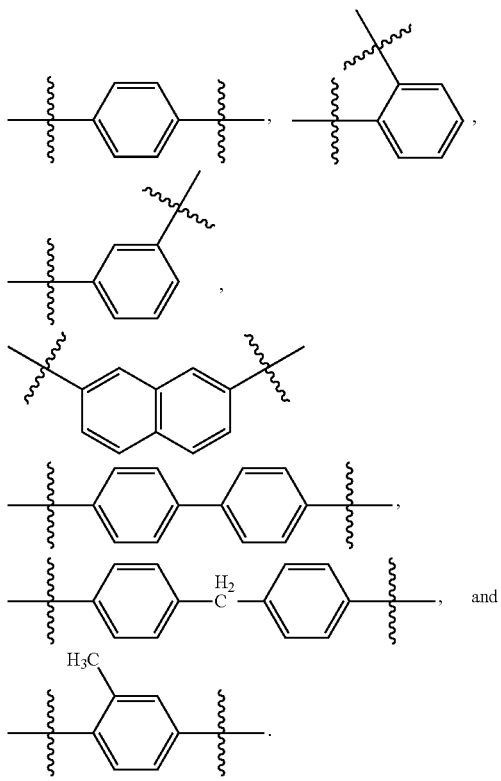

An "arene" refers to the class of compounds having the formula H—R, wherein R is aryl as that term is defined above. Benzene and toluene are non-limiting examples of arenes. When any of these terms are used with the "substituted" modifier one or more hydrogen atom on either the aromatic ring(s) or any alkyl, cycloalkyl, and/or aralkyl group attached thereto has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2] oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, trifluoroacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical agent, pharmaceutical preparation, pharmaceutical composition, pharmaceutical formulation, pharmaceutical product, medicinal product, medicine, medication, medicament, or simply a drug) is a drug used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%/o. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl ($-C(O)OC(CH_3)_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups ($-C(O)OC(CH_3)_3$), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups ($-C(O)OC(CH_3)_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: $^1$H NMR is proton nuclear magnetic resonance, AcOH is acetic acid, $Ac_2O$ is acetic anhydride, ACN or $CH_3CN$ is acetonitrile, br is broad, d is doublet, DCM is dichloromethane, DIAD is diisopropyl azodicarboxylate, DMA is N,N-dimethylacetamide, DMF is N,N-dimethylformamide, DMSO is dimethylsulfoxide, EtOAc or EA is ethyl acetate, EtOH is ethanol, FAB MS is fast atom bombardment mass spectroscopy, g is gram(s), GC-MS is gas chromatograph mass spectroscopy, HOBT is 1-hydroxybenzotriazole hydrate. HPLC is high performance liquid chromatography, L is liter, LAH is lithium aluminum hydride, LC-MS is liquid chromatograph mass spectroscopy, LDA is lithium diisopropylamide, LiHMDS is lithium bis(trimethylsilyl)amide, m is multiplet, MeOH is methanol, mg is milligram, ml is milliliter, mL is milliliter, MS is mass spectroscopy, N is normal, $N_2$ is nitrogen, $Na_2SO_4$ is sodium sulfate, NMR is nuclear magnetic resonance, PE is petroleum ether, q is quintet, rt is retention time, t is triplet, THF is tetrahydrofuran, TLC is thin layer chromatography, and Δ signifies heating the reaction mixture.

The above definitions supersede any conflicting definition in any of the reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

VII. INSTRUMENTATION AND GENERAL METHODS

Analytical HPLC analyses were performed on an Agilent 1100 system and LC-MS analyses were conducted on Agilent 1100 Series LC/MSD (G1946C) electrospray mass spectrometer system. Reverse-phase preparative HPLC purifications were performed either on a Biotage SP4 HPFC system or on a CombiFlashRf (Teledyne Isco) system using a variable dual wavelength UV detector on a Biotage KP-C18-HS 120 g SNAP column and on Redisep Rf Gold C18 cartridges using acetonitrile/water gradient containing 0.05% TFA. Normal phase preparative HPLC purifications were performed either on a Biotage SP4 HPFC system or on a CombiFlashRf (Teledyne Isco) system using a variable dual wavelength UV detector on Biotage KP-SIL SNAP cartridges and on Redisep Rf silica gel (Isco) cartridges.

All final compounds were analyzed by analytical HPLC using a C18 analytical column with a diode array detector and peaks were monitored at 210, 254 and 280 nm for their purity. $^1$H and $^{19}$F NMR spectra were recorded in deuterated solvents (DMSO-$d_6$, $CD_3OD$ and $CDCl_3$) on a Bruker Avance-III/400 MHz spectrometer equipped with a Broad Band NMR probe. The signal of the deuterated solvent was used as an internal reference. The chemical shifts are expressed in ppm (δ) and coupling constants (J) are reported in hertz (Hz). Reactions were performed under an atmosphere of dry nitrogen unless otherwise stated.

The starting materials were obtained from commercial sources and used without further purification after verifying their purities by LC-MS analysis. Solvents were analytical grade and used as supplied. Non commercially available starting materials were synthesized following the literature procedures and used after further purification and verifying their purities by $^1$H NMR and LC-MS analysis.

VIII. PREPARATION OF COMPOUNDS

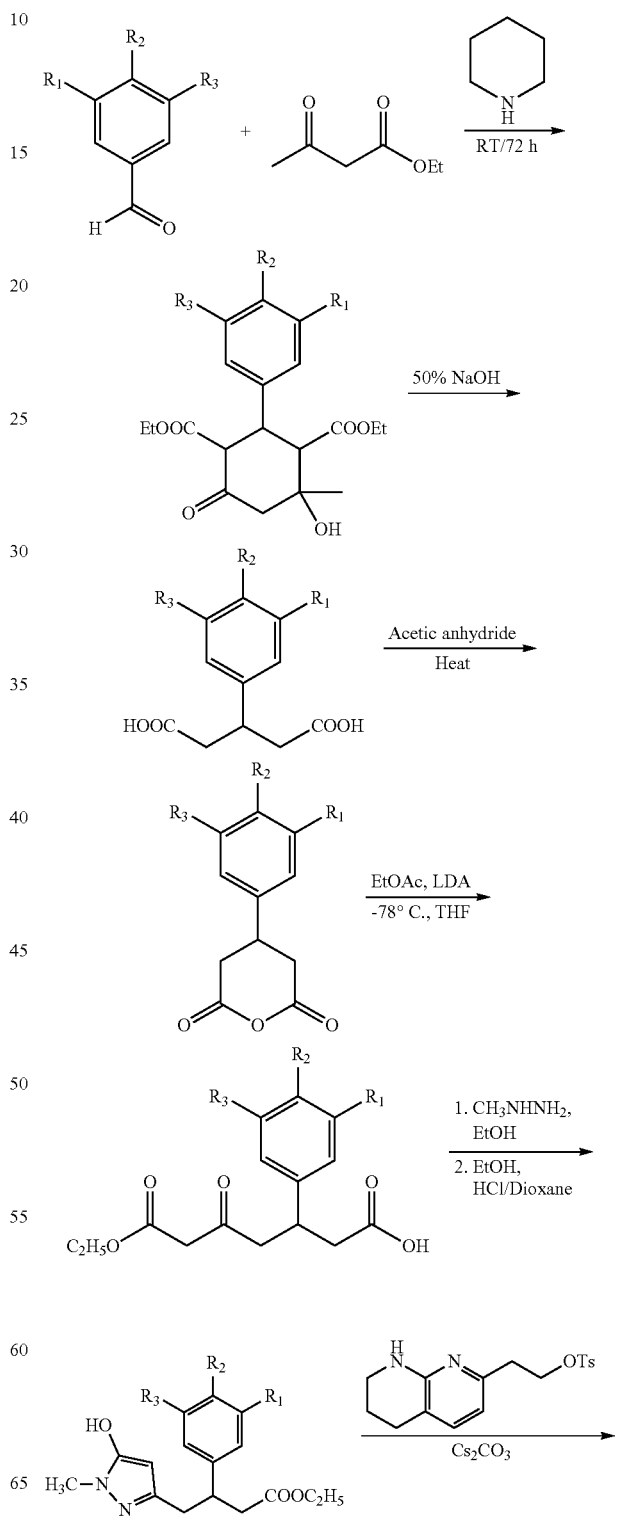

Scheme 1
General Procedure for preparation of 3-(mono and di-substituted-phenyl)-4-(1-methyl-5-(2-(5,6,7,8-tetrahydro-1,8-naphthyridin-2-yl)ethoxy)-1H-pyrazol-3-yl) butanoic acid -continued

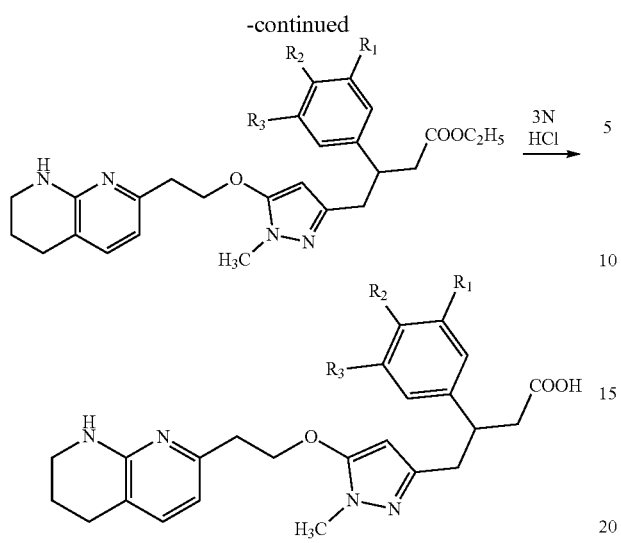

Scheme 2: Preparation of 2-(5,6,7,8-tetrahydro-1,8-naphthyridin-2-yl)ethanol

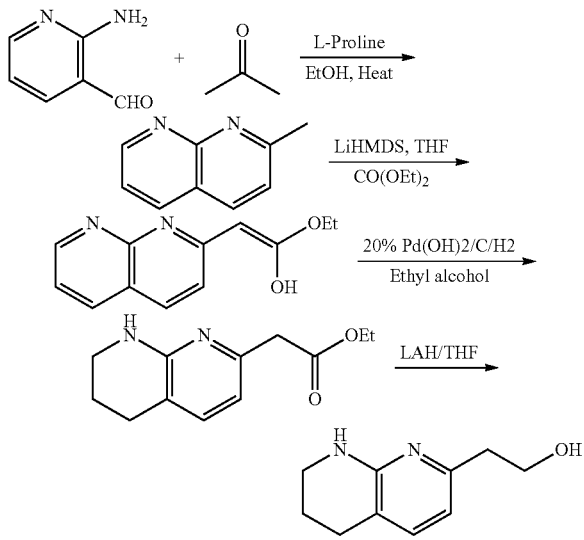

Step 1. Preparation of 2-methyl-1,8-naphthyridine

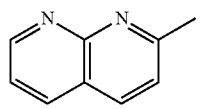

A mixture of 2-aminopyridine-3-carboxyaldehyde (5.125 g, 42.0 mmol), acetone (9.5 mL, 126.0 mmol) and L-proline (5.31 g, 46.2 mmol) in absolute ethyl alcohol (70 mL) was heated at reflux overnight (15 h) under nitrogen atmosphere. The solvent was evaporated in vacuo to afford a canary yellow solid. The solid was dissolved in dichloromethane (50 mL) to give a white precipitate, filtered, washed with dichloromethane and the combined filtrate was evaporated in vacuo to give a yellow-orange residue. The solid was redissolved in dichloromethane (50 mL), washed with water (1×50 mL), the organic layer was separated and the aqueous layer was extracted with dichloromethane (1×25 mL). The combined organic extract was washed with brine (1:50 mL), dried over anhydrous $Na_2SO_4$, filtered and evaporated in vacuo to afford a dirty yellow solid (6.04 g, yield 99%). GC-MS analysis of the solid shows the desired product's mass: m/z 144 ($M^+$); Calculated for $C_9H_8N_2$:144.17. $^1H$ NMR (400 MHz, $CDCl_3$): δ 2.83 (s, 3H), 7.38 (d, J=8.00 Hz, 1H), 7.45 (dd, 1H), 8.09 (d, J=8.00 Hz, 1H), 8.16 (d, J=8.00 Hz, 1H), 9.08 (s, 1H). $^1H$ NMR spectrum of the sample was consistent with the suggested structure of the product.

Step 2. Preparation of (E)-1-ethoxy-2-(1,8-naphthridin-2-yl)ethanol

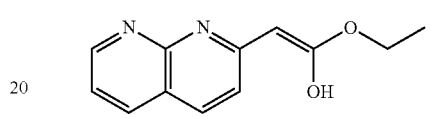

To a solution of 2-methyl-1,8-naphthyridine (6.024 g, 41.8 mmol) (from step 1) in anhydrous THF (140 mL) at −40° C. under nitrogen atmosphere was added a 1.0 M solution of lithium bis(trimethylsilyl)amide in THF (88.0 mL) and the reaction mixture was stirred at −40° C. for 30 min to give a blood-red solution. After stirring for 30 min at −40° C., neat diethyl carbonate (5.60 mL) was added drop wise to above solution in 5 min and the reaction mixture was warmed up to 0° C. (ice-bath) and stirred at that temperature for 2 h to give a dark reddish-orange solution. The reaction mixture was quenched with saturated aqueous ammonium chloride solution (60.0 mL) to give an orange-red solution and the THF was removed in vacuo to give an orange-red mixture. The resulting mixture was extracted with ethyl acetate (3×50 mL). The organic layers were combined, washed with brine, dried over anhydrous $Na_2SO_4/MgSO_4$, filtered and evaporated in vacuo to afford a dark orange-red crystalline solid (8.65 g). The crude residue was purified by Silica-gel flash chromatography using a Varian SF-40-120 g Super Flash silica gel column and elution with 10-100% ethyl acetate in n-heptane to afford the desired product as a yellow-orange crystalline solid (7.76 g, yield 85%). LC-MS analysis of the solid shows the desired product's mass: m/z 217 (M+H) and m/z 239 (M+Na); Calculated for $C_{12}H_{12}N_2O_2$: 216.23. $^1H$ NMR (400 MHz, DMSO-$d_6$): δ 1.21 (t, J=7.0 Hz, 3H), 4.10 (q, 2H), 4.89 (s, 1H), 6.77 (d, J=9.38 Hz, 1H), 7.14 (m, 1H), 7.46 (d, J=9.36 Hz, 1H), 7.89 (d, 1H), 8.36 (d, 1H), 11.80 (brs, 1H, —OH). $^1H$ NMR of the isolated product was superimposable with that of an authentic sample of the product.

Step 3. Preparation of Ethyl 5,6,7,8-tetrahydro-1,8-naphthyridin-2-ylacetate

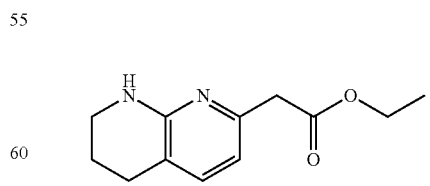

To a degassed solution of (E)-1-ethoxy-2-(1,8-naphthyridin-2-yl)ethanol (5.18 g, 23.98 mmol) (from step 2) in absolute ethanol (100 mL) was added palladium hydroxide on activated charcoal (1.44 g) and the reaction mixture was stirred at room temperature under a balloon of hydrogen gas overnight (16 h). The reaction mixture was filtered through a pad of Celite® to remove the Pd(OH)$_2$/C. The residue was washed with absolute ethanol (2×25 mL) and the filtrate was evaporated in vacuo to afford a yellow viscous liquid, crystallized slowly to a pale yellow solid (5.30 g, yield 98%). LC-MS analysis of the product shows the desired product's mass: min 221 (M+H); Calculated for C$_{12}$H$_{16}$N$_2$O$_2$: 220.26. The product will be used such for the next step.

Step 4. Preparation of 2-(5,6,7,8-tetrahydro-1,8-naphthyridin-2-yl)ethanol

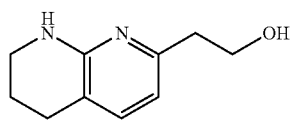 [SMILES: OCCc1ccc2c(n1)NCCC2]

To anhydrous THF (95.0 mL) under nitrogen gas atmosphere at room temperature was added a 1.0 M solution of lithium aluminum hydride in THF (95.0 mL) with stirring. The temperature of the reaction mixture was lowered to 15° C. (water-ice bath) and a solution of ethyl 2-(5,6,7,8-tetrahydro-1,8-naphthyridin-2-yl)acetate (from step 3) in anhydrous THF (50.0 mL) was added drop wise over 30 min to give a yellow solution. The resulting reaction mixture was stirred at room temperature for 4 h. The reaction mixture was cooled to 0° C. (salt-ice bath) and the reaction was quenched slowly with brine (25.0 mL). Additional THF (30.0 mL) was added during the quench to break-up the emulsions. After complete addition of brine, the reaction mixture was stirred at room temperature overnight. Anhydrous sodium sulfate (25.0 g) was added to above reaction mixture and the mixture was stirred at room temperature for another 30 min and filtered. The solid salts residue was washed with ethyl acetate (3×30 mL). The filtrates were combined and concentrated to about 150 mL, dried again with anhydrous sodium sulfate, filtered and evaporated in vacuo to afford an orange viscous liquid (4.8063 g). The crude product was purified by Silica-gel flash chromatography on a SF-40-120 g Super Flash silica gel column and elution with 0-5% methanol in ethyl acetate to afford the desired product as a yellow viscous liquid (3.504 g. yield 82%). LC-MS analysis of the purified liquid shows the desired product's mass: m/z 179 (M+H); Calculated for C$_{10}$H$_{14}$N$_2$O: 178.23. The liquid solidified to a pale yellow waxy/crystalline solid on storing in a refrigerator overnight.

Example 1

Scheme 3 Preparation of 3-(2,3-dihydrobenzo[b][1,4]dioxin-6-yl)-4-(1-methyl-5-(2-(5,6,7,8-tetrahydro-1,8-naphthyridin-2-yl)ethoxy)-1H-pyrazol-3-yl)butanoic acid

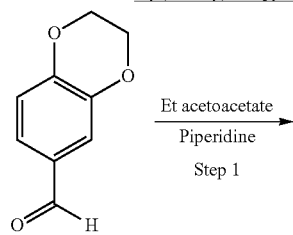

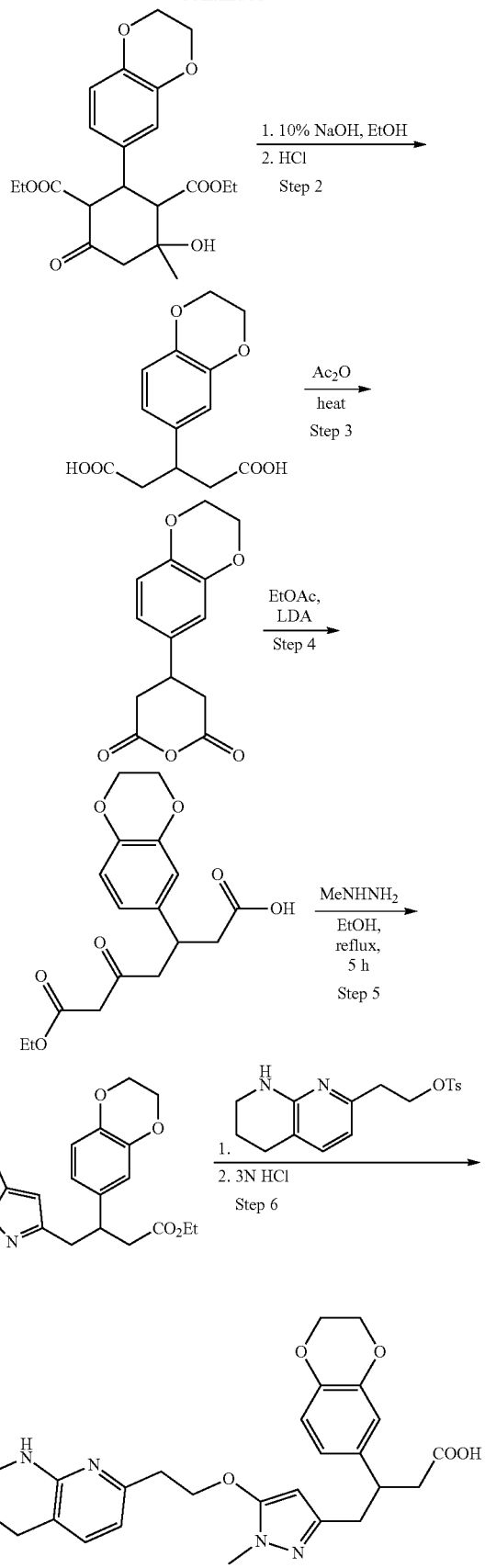

Step 1. Preparation of Diethyl 2-(2,3-dihydrobenzo[b][1,4]dioxin-6-yl)-4-hydroxy-4-methyl-6-oxocyclohexane-1,3-dicarboxylate

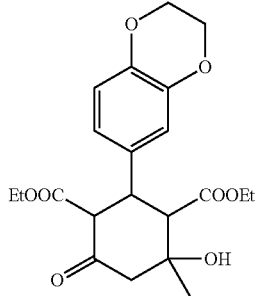 [SMILES: CCOC(=O)C1C(=O)CC(C)(O)C(C(=O)OCC)C1c1ccc2c(c1)OCCO2]

To a solution of a mixture of 2,3-dihydrobenzo[b][1,4]dioxine-6-carbaldehyde (15 g, 91.44 mmol) and ethyl acetoacetate (41.6 g, 320.04 mmol) was added piperidine (2.73 g, 32 mmol) in one portion at 25° C. Then the mixture was stirred at 25° C. for 72 hrs. The reaction mixture was diluted with EtOH (200 mL) and cooled to −20° C. and filtered to give the desired product as a white crystalline solid (21.1 g yield 57%).

Step 2. Preparation of 3-(2,3-dihydrobenzo[b][1,4]dioxin-6-yl)pentanedioic acid

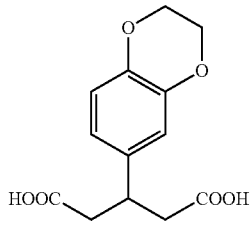 [SMILES: O=C(O)CC(CC(=O)O)c1ccc2c(c1)OCCO2]

To a solution of diethyl 2-(2,3-dihydrobenzo[b][1,4]dioxin-6-yl)-4-hydroxy-4-methyl-6-oxocyclohexane-1,3-dicarboxylate (20.00 g, 49.24 mmol) (from step 1) in EtOH (200 mL) was added NaOH (3.94 g, 98.48 mmol) in one portion. The mixture was heated to 100° C. with stirring for 1.5 h. The reaction mixture was cooled to 25° C. and concentrated under reduced pressure at 60° C. To the above residue conc. HCl was added until pH 1, and then the mixture was poured into water (50 mL) and stirred for 20 minutes. The aqueous phase was extracted with ethyl acetate (3×100 mL). The combined organic phase was washed with brine solution (2×100 mL), dried with anhydrous Na$_2$SO$_4$, filtered and evaporated in vacuo to afford the acid as a brown solid (10.00 g, yield 76.92%).

Step 3. Preparation of 4-(2,3-dihydrobenzo[b][1,4]dioxin-6-yl)dihydro-2H-pyran-2,6(3H)-dione

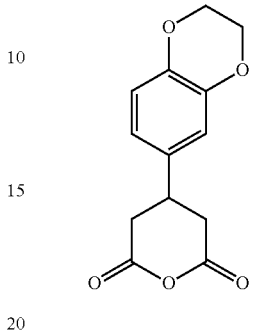

A solution of 3-(2,3-dihydrobenzo[b][1,4]dioxin-6-yl)pentanedioic acid (8 g, 30.06 mmol) (from step 2) in acetic anhydride (217.4 g, 2.12 mol) was heated with stirring at 140° C. for 2.5 h. The mixture was cooled to 25° C., and then evaporated in vacuo to afford the desired product as a brown oil (6.02 g, yield 80.04%/).

Step 4. Preparation of 3-(2,3-dihydrobenzo[b][1,4]dioxin-6-yl)-7-ethoxy-5,7-dioxoheptanoic Acid

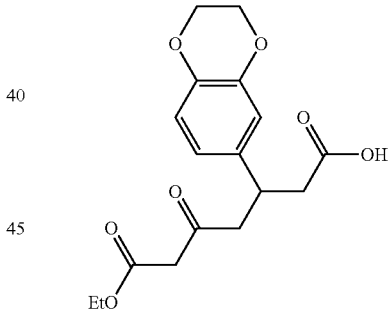

To a solution of 4-(2,3-dihydrobenzo[b][1,4]dioxin-6-yl)dihydro-2H-pyran-2,6(3H)-dione (6.00 g, 24.19 mmol) (from step 3) in THF (50 mL) was added LDA (5.18 g, 48.38 mmol) drop-wise at −78° C. over a period of 2 min under N$_2$. After stirring for 1 h at −60° C., dry EtOAc (4.25 g, 48.38 mmol) was added drop-wise at −78° C. over a period of 2 min under N$_2$. The reaction mixture was stirred at −78° C. for another 5 h. TLC (PE:EtOAc=20:1) showed the starting material was consumed completely. The reaction was quenched with 2 N HCl until pH=1 and then the reaction mixture was extracted with EtOAc (3'80 mL). The combined organic phase was washed with saturated brine solution, dried over anhydrous Na$_2$SO$_4$, filtered and concentrated in vacuum give the product to give the desired product (6.50 g, yield 80.0%) as a yellow liquid, which was purified by column chromatography on silica gel (PE:EA=3:1).

Step 5. Preparation of ethyl 3-(2,3-dihydrobenzo[b][1,4]dioxin-6-yl)-4-(5-hydroxy-1-methyl-1H-pyrazol-3-yl)butanoate

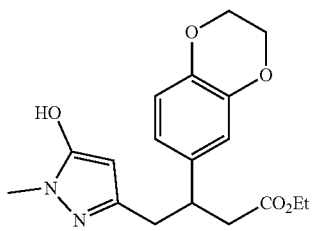 [SMILES: CCOC(=O)CC(Cc1cc(O)n(C)n1)c1ccc2c(c1)OCCO2]

To a solution of 3-(2,3-dihydrobenzo[b][1,4]dioxin-6-yl)-7-ethoxy-5,7-dioxoheptanoic acid (3 g, 8.9 mmol) (from step 4) in EtOH (120 mL), methyl hydrazine (450.34 mg, 9.79 mmol) was added in portions at 40° C. under $N_2$. Then the mixture was stirred at 100° C. for 5 hr. TLC showed the reaction was complete. The mixture was cooled to 25° C. and the reaction mixture was concentrated in vacuo. To the above residue was added EtOH (20 mL) and dioxane/HCl (20 mL), and the resulting suspension was allowed to stir at room temperature for 12 h, then it was concentrated under reduced vacuum to give the desired product (2.2 g, yield 71.45%) as a yellow oil, which was purified by column chromatography on silica gel (DCM:EtOH=8:1). $^1$H NMR (400 MHz, $CDCl_3$): δ 1.10-1.19 (m, 3H), 2.02-2.08 (m, 1H), 2.53-2.73 (m, 2H), 2.89-3.05 (m, 2H), 3.24 (s, 1H), 3.38-3.50 (m, 1H), 3.52-3.66 (m, 1H), 3.74 (br. s, 2H), 3.95-4.07 (m, 2H), 4.16-4.23 (m, 4H), 5.78 (br, s, 1H), 6.62-6.80 (m, 3H).

Step 6. Preparation of 3-(2,3-dihydrobenzo[b][1,4]dioxin-6-yl)-4-(1-methyl-5-(2-(5,6,7,8-tetrahydro-1,8-naphthyridin-2-yl)ethoxy)-1H-pyrazol-3-yl)butanoic Acid Example 1

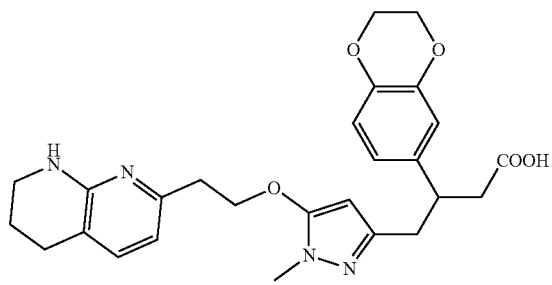 [SMILES: Cn1nc(CC(CC(=O)O)c2ccc3c(c2)OCCO3)cc1OCCc1ccc2c(n1)NCCC2]

To a solution of ethyl 3-(2,3-dihydrobenzo[b][1,4]dioxin-6-yl)-4-(5-hydroxy-1-methyl-1H-pyrazole-3-yl)butanoate (1.0 g, 2.89 mmol, 1.00 eq) (from step 5) in $CH_3CN$ (10 mL), 2-(5,6,7,8-tetrahydro-1,8-naphthyridin-2-yl)ethyl 4-methylbenzenesulfonate (960 mg, 2.89 mmol, 1.00 eq; made by reacting 2-(5,6,7,8-tetrahydro-1,8-naphthyridin-2-yl)ethanol (from Example A, Step 4) with tosyl chloride and base in THF), and $Cs_2CO_3$ (1.88 g, 5.78 mmol, 2.00 eq) were added, and then the reaction mixture was allowed to stir for 8 h at 80° C., The reaction mixture was filtered to remove insoluble and the filtrate was concentrated in vacuo. The residue was suspended in 3 N HCl (10 mL) and then it was allowed to stir for another 8 h at 100° C. to afford the desired product. The crude product was purified by reverse-phase preparative HPLC to give Example 1 as yellow oil (48 mg, yield 3.6%). The second purification of the liquid by reverse-phase preparative HPLC and lyophilization of the fractions afforded Example 1 as a colorless powder (23.2 mg). LC-MS analysis of the solid showed the desired product's mass: m/z 479 (M+H) and m/z 501 (M+Na); Calculated for $C_{26}H_{30}N_4O_5$: 478.54. $^1$H NMR (400 MHz, DMSO-$d_6$): δ 1.75-1.86 (m, 2H), 2.35-2.45 (m, 1H), 2.62 (d, J=7.53 Hz, 2H), 2.73 (t, J=5.77 Hz, 2H), 3.11 (t, J=6.02 Hz, 3H), 3.15-3.23 (m, 2H), 4.18 (s, 4H), 4.32 (t, J=6.15 Hz, 2H), 5.49 (s, 1H), 6.64-6.69 (m, 2H), 6.69-6.74 (m, 2H) 7.61 (d, J=7.28 Hz, 1H), 8.15 (br s, 1H), 14.34-14.55 (m, 1H).

Example 2

Preparation of 3-(3-chloro-5-fluorophenyl)-4-(1-methyl-5-(2-(5,6,7,8-tetrahydro-1,8-naphthyridin-2-yl)ethoxy)-1H-pyrazol-3-yl)butanoic Acid

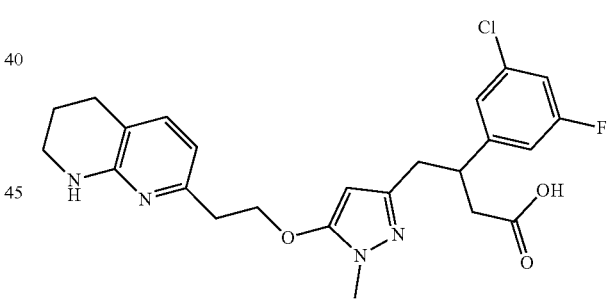

Example 2 was prepared in analogous manner to Example 1, using 3-chloro-5-fluorobenzaldehyde as the required benzaldehyde in the reaction Scheme 3. The crude product was purified by reverse-phase preparative HPLC and after lyophilization of the fractions afforded the title compound as a colorless powder (39.4 mg). LC-MS analysis of the solid showed the desired product at rt 1.92 min with a purity >98% and the desired product's mass: m/z 473 ($^{35Cl}$M+H), m/z 475 ($^{37Cl}$M+H), m/z 495 ($^{35Cl}$M+Na) and m/z 497 ($^{37Cl}$M+Na); Calculated for $C_{24}H_{26}ClFN_4O_3$: 472.94. $^1$H NMR (400 MHz, DMSO-$d_6$): δ 1.81 (brs, 2H), 2.54-2.64 (m, 2H), 2.65-2.77 (m, 5H), 3.11 (brs, 3H), 3.39 (brs, 6H), 4.31 (brs, 2H), 5.52 (s, 1H), 6.66 (d, J=6.78 Hz, 1H), 7.13 (d, J=9.91 Hz, 1H), 7.16-7.22 (m, 2H), 7.61 (d, J=6.15 Hz, 1H), 8.13 (brs, 1H), 14.32-14.57 (m, 1H).

Example 3

Preparation of 3-(3-fluoro-4-methoxyphenyl)-4-(1-methyl-5-(2-(5,6,7,8-tetrahydro-1,8-naphthyridin-2-yl)-ethoxy)-1H-pyrazol-3-yl)butanoic Acid

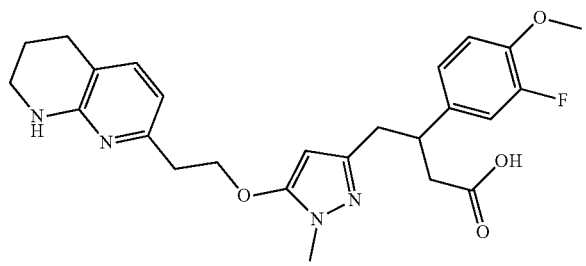 [SMILES: COc1ccc(C(CC(=O)O)Cc2cc(OCCc3ccc4c(n3)NCCC4)n(C)n2)cc1F]

Example 3 was prepared in analogous manner to Example 1, using 3-fluoro-4-methoxybenzaldehyde as the required benzaldehyde in the reaction Scheme 3. The crude product was purified by reverse-phase preparative HPLC and after lyophilization of the fractions afforded the title compound as a cream powder (26.6 mg). LC-MS analysis of the solid showed the desired product at rt 1.76 min and the desired product's mass: m/z 469 (M+H), and m/z 491 (M+Na); Calculated for $C_{25}H_{29}FN_4O_4$: 468.52. $^1$H NMR (400 MHz, DMSO-$d_6$): δ 1.77-1.87 (m, 2H), 2.54-2.69 (m, 3H), 2.70-2.78 (m, 2H), 3.09 (t, J=6.09 Hz, 2H), 3.17-3.29 (m, 1H), 3.39-3.47 (m, 3H), 3.78 (s, 4H), 4.25 (t, J=6.09 Hz, 2H), 5.43 (s, 1H), 6.69 (d, J=7.28 Hz, 1H), 6.95-7.06 (m, 2H), 7.09 (dd, J=12.86, 1.82 Hz, 1H), 7.58-7.70 (m, 1H), 8.26 (brs, 1H).

Example 4

Preparation of 3-(4-bromo-3-fluorophenyl)-4-(1-methyl-5-(2-(5,6,7,8-tetrahydro-1,8-naphthyridin-2-yl)ethoxy)-1H-pyrazol-3-yl)butanoic Acid

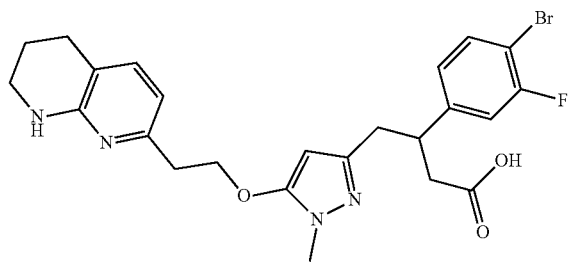 [SMILES: Cn1nc(CC(CC(=O)O)c2ccc(Br)c(F)c2)cc1OCCc1ccc2c(n1)NCCC2]

Example 4 was prepared in analogous manner to Example 1, using 3-fluoro-4-bromobenzaldehyde as the required benzaldehyde in the reaction Scheme 3. The crude product was purified by reverse-phase preparative HPLC and after lyophilization of the fractions afforded Example 5 as a cream powder (84.7 mg). LC-MS analysis of the solid showed the desired product at rt 1.93 min and the desired product's mass: m/z 517 ($^{79Br}$M+H), m/z 519 ($^{81Br}$M+H), m/z 539 ($^{79Br}$M+Na) and m/z 541 ($^{81Br}$Ma+Na); Calculated for $C_{24}H_{26}BrFN_4O_3$: 517.39. $^1$H NMR (300 MHz, CDCl$_3$): δ 1.88-2.02 (m, 2H), 2.46-2.72 (m, 2H), 2.78 (d, J=5.84 Hz, 2H), 2.86-3.02 (m, 2H), 3.15 (brs, 2H), 3.51 (brs, 2H), 3.60 (s, 3H), 4.39 (brs, 2H), 5.66 (s, 1H), 6.43 (d, J=6.97 Hz, 1H), 6.95 (dd, J=18.65, 8.29 Hz, 2H), 7.34-7.50 (m, 2H), 9.13 (brs, 3H), 9.59-9.94 (m, 1H), 15.27 (brs, 1H).

Example 5

Preparation of 3-(3-bromo-4-fluorophenyl)-4-(1-methyl-5-(2-(5,6,7,8-tetrahydro-1,8-naphthyridin-2-yl)ethoxy)-1H-pyrazol-3-yl)butanoic Acid

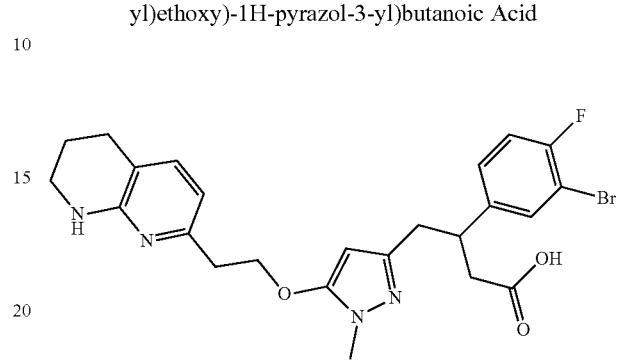

Example 5 was prepared in analogous manner to Example 1, using 3-bromo-4-fluorobenzaldehyde as the required benzaldehyde in the reaction Scheme 3. The crude product was purified by reverse-phase preparative HPLC and after lyophilization of the fractions afforded the title compound as a cream powder (93.2 mg). LC-MS analysis of the solid showed the desired product at rt 1.91 min and the desired product's mass: m/z 517 ($^{79Br}$M+H), m/z 519 ($^{81Br}$M+H), m/z 539 ($^{79Br}$M+Na) and m/z 541 ($^{81Br}$M+Na); Calculated for $C_{24}H_{26}BrFN_4O_3$: 517.39. $^1$H NMR (400 MHz, CDCl$_3$): δ 1.87-1.99 (m, 2H), 2.55-2.72 (m, 2H), 2.77 (t, J=5.83 Hz, 2H), 2.86-3.06 (m, 2H), 3.13 (t, J=5.90 Hz, 2H), 3.38-3.45 (m, 1H), 3.49 (brs, 2H), 3.59 (s, 3H), 4.37 (t, J=6.02 Hz, 2H), 5.68 (s, 1H), 6.43 (d, J=7.15 Hz, 1H), 6.97-7.04 (m, 1H), 7.13 (brs, 1H), 7.27 (s, 1H), 7.37 (d, J=7.15 Hz, 2H), 9.67 (brs, 1H), 15.03 (brs, 1H).

Example 6

Preparation of 3-(3-bromophenyl)-4-(1-methyl-5-(2-(5,6,7,8-tetrahydro-1,8-naphthyridin-2-yl)ethoxy)-1H-pyrazol-3-yl)butanoic Acid

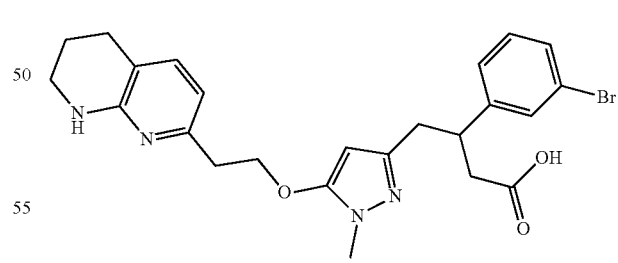

Example 6 was prepared in analogous manner to Example 1, using 3-bromo benzaldehyde as the required benzaldehyde in the reaction Scheme 3. The crude product was purified by reverse-phase preparative HPLC and after lyophilization of the fractions afforded the title compound as a cream powder (64.9 mg). LC-MS analysis of the solid showed the desired product at rt 1.89 min and the desired product's mass: m/z 499 ($^{79Br}$M+H), m/z 501 ($^{81Br}$M+H), m/z 521 ($^{79Br}$M+Na) and m/z 523 ($^{81Br}$M+Na); Calculated for $C_{24}H_{27}BrN_4O_3$: 499.40. $^1$H NMR (300 MHz, CD$_3$OD): δ 1.96 (brs, 2H), 2.61-2.79 (m, 2H), 2.84 (brs, 2H), 2.93-3.09 (m, 1H), 3.11-3.27 (m, 3H), 3.52 (brs, 3H), 3.61-3.78 (m, 3H), 4.58 (brs, 2H), 6.14 (brs, 1H), 6.73 (d, J=6.40 Hz, 1H), 7.26 (brs, 2H), 7.39 (d, J=6.41 Hz, 1H), 7.45 (s, 1H), 7.63 (d, J=5.65 Hz, 1H).

The following Examples 7, 8, 9 and 12 were synthesized by the displacement reaction with zinc cyanide in N,N-dimethylacetamide. Examples 5, 4, 11, and 6 were used as the precursors for the reactions respectively.

Example 7

Preparation of 3-(3-cyano-4-fluorophenyl)-4-(1-methyl-5-(2-(5,6,7,8-tetrahydro-1,8-naphthyridin-2-yl)ethoxy)-1H-pyrazol-3-yl)butanoic Acid

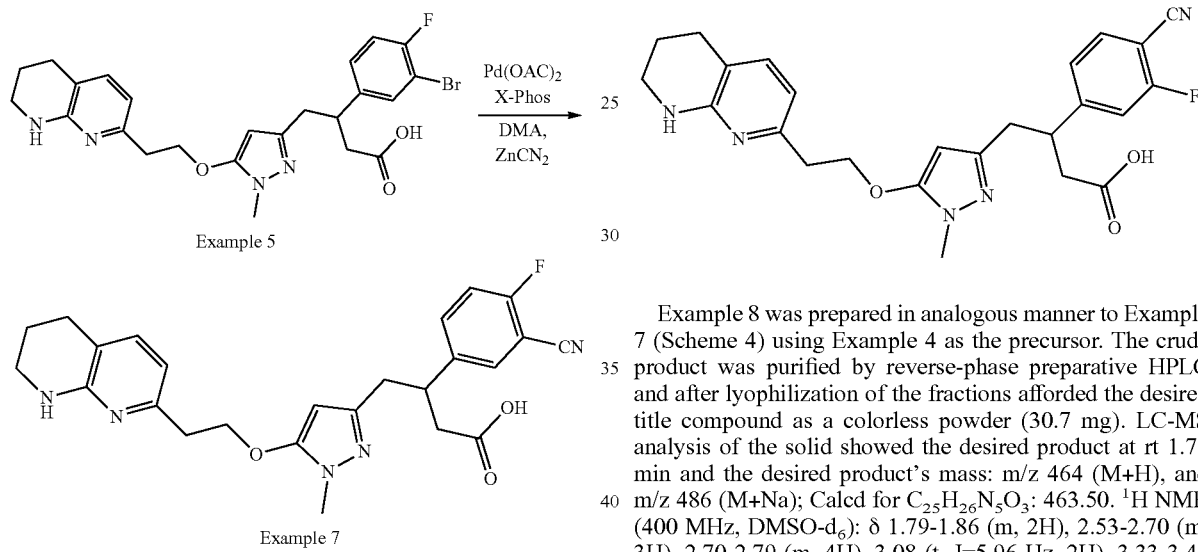

Anhydrous N,N-Dimethylacetamide (DMA) (50 mL) was degassed under high vacuum and alternated by N$_2$ for 30 min prior to use. A round bottom flask was charged with Pd(OAc)$_2$ (1.5 g, 6.8 mmol) and X-phos (6.38 g 0.439 mmol) under N$_2$ atmosphere followed by degassed DMA. Then the mixture was heated at 80° C. for 60 min to give a dark color solution. A second round bottom flask was charged with Example 5 (500 mg, 0.919 m mol), Zn(CN)$_2$ (118 mg, 1.01 m mol) and Zn (5 mg, cat.) under N$_2$ atmosphere and followed by degassed DMA (5 mL). The catalyst solution was added to the above solution at 25° C. and the resulting mixture was heated at 90° C. for 1 h. The reaction mixture was cooled to 25° C. and the solvent was removed by evaporation in vacuum. The residue was partitioned between water (20 mL) and ethyl acetate (20 mL). The mixture was first filtered through Celite®, and then the layers were separated. The aqueous layer was extracted with ethyl acetate (3×20 mL), the combined organic layer was washed with water, brine, dried over Na$_2$SO$_4$ and then solvent was evaporated in vacuo. To crude residue was wadded 3 N aqueous LiOH solution (10 mL) and the reaction mixture was allowed to stir at 100° C. for 8 h. The crude residue was purified by reverse-phase preparative HPLC and after lyophilization afforded Example 7 as yellow oil (100.0 mg). The second purification of the liquid by reverse-phase preparative HPLC and lyophilization of the fractions afforded the title compound as a cream powder. LC-MS analysis of the solid showed the desired product at rt 1.80 min and the desired product's mass: m/z 464 (M+H), and m/z 486 (M+Na); Calculated for $C_{25}H_{26}N_5O_3$: 463.50. $^1$H NMR (400 MHz, DMSO-d$_6$): δ 1.78-1.86 (m, 2H), 2.33 (brs, 1H), 2.55-2.70 (m, 3H), 2.71-2.78 (m, 3H), 3.10 (t, J=6.15 Hz, 2H), 3.37 (brs, 5H), 4.28 (t, J=6.27 Hz, 2H), 5.44 (s, 1H), 6.67 (d, J=7.40 Hz, 1H), 7.41 (t, J=9.16 Hz, 1H), 7.61-7.67 (m, 2H), 7.81-7.87 (m, 1H), 7.98 (brs, 1H) 13.95-14.07 (m, 1H).

Example 8

Preparation of 3-(4-cyano-3-fluorophenyl)-4-(1-methyl-5-(2-(5,6,7,8-tetrahydro-1,8-naphthyridin-2-yl)ethoxy-1H-pyrazol-3-yl)butanoic Acid

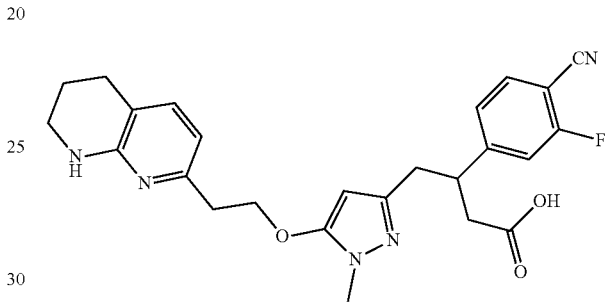

Example 8 was prepared in analogous manner to Example 7 (Scheme 4) using Example 4 as the precursor. The crude product was purified by reverse-phase preparative HPLC and after lyophilization of the fractions afforded the desired title compound as a colorless powder (30.7 mg). LC-MS analysis of the solid showed the desired product at rt 1.79 min and the desired product's mass: m/z 464 (M+H), and m/z 486 (M+Na); Calcd for $C_{25}H_{26}N_5O_3$: 463.50. $^1$H NMR (400 MHz, DMSO-d$_6$): δ 1.79-1.86 (m, 2H), 2.53-2.70 (m, 3H), 2.70-2.79 (m, 4H), 3.08 (t, J=5.96 Hz, 2H), 3.33-3.45 (m, 8H), 4.23 (t, J=6.09 Hz, 2H), 5.43 (s, 1H), 6.68 (d, J=7.28 Hz, 1H), 7.28 (dd, J=8.09 and 1.32 Hz, 1H), 7.46 (d, J=10.16 Hz, 1H), 7.63 (d, J=7.40 Hz, 1H), 7.80 (t, J=7.53 Hz, 1H) 8.08 (brs, 1H).

Example 9

Preparation of 3-(3-cyanophenyl)-4-(1-methyl-5-(2-(5,6,7,8-tetrahydro-1,8-naphthyridin-2-yl)ethoxy)-1H-pyrazol-3-yl)butanoic Acid

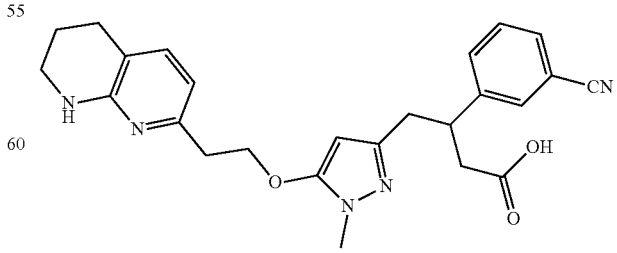

Example 9 was prepared in analogous manner to Example 7 (Scheme 4) using Example 6 as the precursor. The crude product was purified by reverse-phase preparative HPLC and after lyophilization of the fractions afforded the desired title compound as a colorless powder (65.5 mg). LC-MS analysis of the solid showed the desired product at rt 1.72 min and the desired product's mass: m: 446 (M+H), and m/z 468 (M+Na); Calculated for $C_{25}H_{27}N_5O_3$: 445.51. $^1$H NMR (400 MHz, DMSO-$d_6$): δ 1.78-1.86 (m, 2H), 2.52-2.62 (m, 3H), 2.63-2.78 (m, 6H), 3.08 (t, J=6.09 Hz, 2H), 3.31-3.38 (m, 4H), 3.39-3.47 (m, 3H), 4.24 (t, J=6.15 Hz, 4H), 5.42 (s, 1H), 6.68 (d, J=7.28 Hz, 1H), 7.43-7.49 (m, 1H), 7.58 (d, 0.1=8.03 Hz, 1H), 7.63 (d, 0.1=7.40 Hz, 2H), 7.72 (s, 1H), 8.17 (brs, 1H).

Example 10

Preparation of 3-(3-bromo-5-(trifluoromethyl)phenyl)-4-(1-methyl-5-(2-(5,6,7,8-tetrahydro-1,8-naphthyridin-2-yl)ethoxy)-1H-pyrazol-3-yl)butanoic Acid

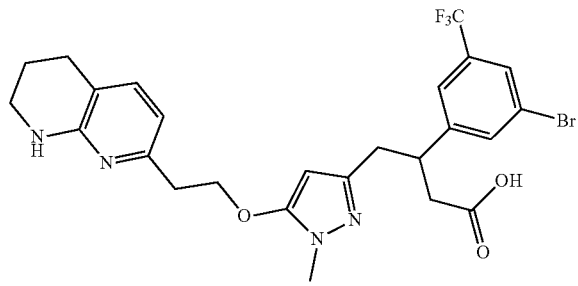 [SMILES: Cn1nc(CC(CC(=O)O)c2cc(Br)cc(C(F)(F)F)c2)cc1OCCc1ccc2c(n1)NCCC2]

Example 10 was prepared in analogous manner to Example 1, using 3-bromo-5-(trifluoromethyl)benzaldehyde as the required benzaldehyde in the reaction Scheme 3. The crude product was purified by was purified by Prep-HPLC (column: Phenomenex Gemini C18 250*50 10µ; mobile phase: [water (0.225% FA)-ACN]; B %: 15%-45%, 11.2 min). The HPLC effluent was lyophilized to give the title compound as a white solid (29 mg) and the recovered starting ester (115 mg). 3-[3-bromo-5-(trifluoromethyl)phenyl]-4-[1-methyl-5-[2-(5,6,7,8-tetrahydro-1,8-naphthyridin-2-yl)ethoxy]pyrazol-3-yl]butanoic acid (29 mg, 51 µmol, 12% yield, 99.5% purity) was obtained as a white solid. $^1$H NMR (400 MHz, CD$_3$OD) δ ppm 1.84-1.92 (m, 2H) 2.53-2.63 (m, 1H) 2.64-2.87 (m, 5H) 2.94-3.09 (m, 2H) 3.36-3.42 (m, 5H) 3.46-3.56 (m, 1H) 4.30 (t, J=6.39 Hz, 2H) 5.48 (s, 1H) 6.50 (d, J=7.28 Hz, 1H) 7.31 (d, J=7.28 Hz, 1H) 7.48 (s, 1H) 7.62 (s, 1H) 7.67 (s, 1H).

Example 11

Preparation of 3-(3-bromo-5-(trifluoromethoxy)phenyl)-4-(1-methyl-5-(2-(5,6,7,8-tetrahydro-1,8-naphthyridin-2-yl)ethoxy)-1H-pyrazol-3-yl)butanoic Acid

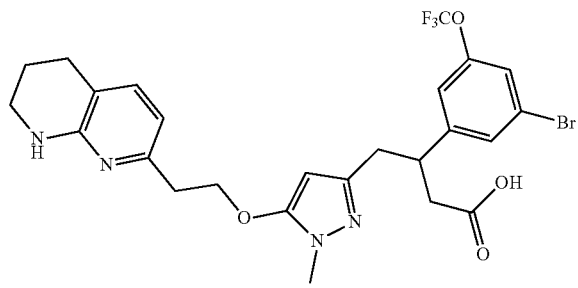 [SMILES: Cn1nc(CC(CC(=O)O)c2cc(Br)cc(OC(F)(F)F)c2)cc1OCCc1ccc2c(n1)NCCC2]

Example 11 was prepared in analogous manner to Example 1, using 3-bromo-5-(trifluoromethoxy)benzaldehyde as the required benzaldehyde in the reaction Scheme 3 with ethyl 3-[3-bromo-5-(trifluoromethoxy)phenyl]-4-[1-methyl-5-[2-(5,6,7,8-tetrahydro-1,8-naphthyridin-2-yl)ethoxy]pyrazol-3-yl]butanoate as the direct precursor of the title compound. The crude product was purified by Prep-HPLC (TFA condition: Column: Boston pH-lex 150*25 10 µm; Water (0.1% TFA)-ACN from 22-52; Gradient Time (min): 8; FlowRate (mL/min) 2). The title compound was obtained as a yellow solid [LC-MS (ES7911-26-P1E), $^1$H NMR (ES7911-26-P1A_01), $^{19}$F NMR (ES7911-26-P1A_02), COSY (ES7911-26-P1C)]. LC-MS analysis of the solid showed the desired product's mass: m/z 583.0 (M+H); $^1$H NMR (400 MHz, CD$_3$OD) 7.60 (d, J=7.6 Hz, 1H), 7.41 (t, J=1.6 Hz, 1H), 7.29 (s, 1H), 7.09 (s, 1H), 6.68 (d, J=7.2 Hz, 1H), 5.44 (s, 1H), 4.36-4.26 (m, 2H), 3.54-3.42 (m, 6H), 3.16 (t, J=6.0 Hz, 2H), 2.90-2.79 (m, 3H), 2.79-2.69 (m, 2H), 2.68-2.60 (m, 1H), 2.00-1.90 (m, 2H).

Example 12

Preparation of 3-(3-cyano-5-(trifluoromethyl)phenyl)-4-(1-methyl-5-(2-(5,6,7,8-tetrahydro-1,8-naphthyridin-2-yl)ethoxy)-1H-pyrazol-3-yl)butanoic Acid Scheme 5

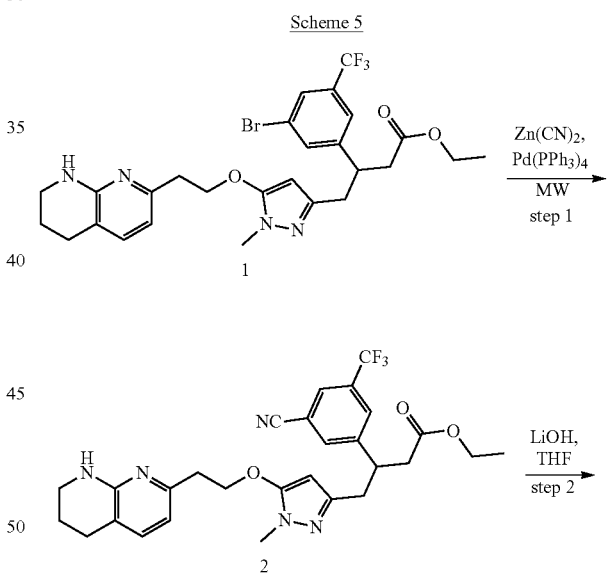

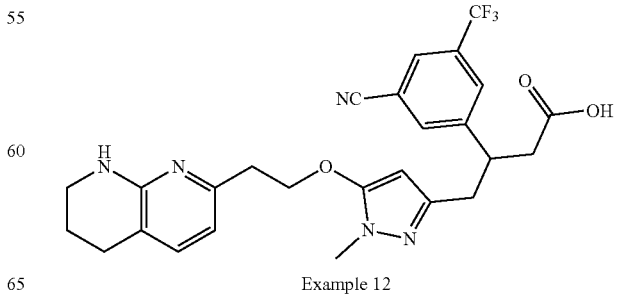

Example 12

Step 1. Preparation of ethyl 3-(3-cyano-5-(trifluoromethyl)phenyl)-4-(1-methyl-5(2-(5,6,7,8-tetrahydro-1,8-naphthyridin-2-yl)ethoxy)-1H-pyrazol-3-yl)butanoate

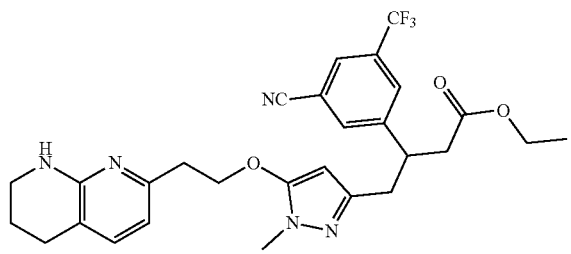 [SMILES: CCOC(=O)CC(Cc1cc(OCCc2ccc3c(n2)NCCC3)n(C)n1)c1cc(C#N)cc(C(F)(F)F)c1]

A mixture of ethyl 3-[3-bromo-5-(trifluoromethyl)phenyl]-4-[1-methyl-5-[2-(5,6,7,8-tetrahydro-1,8-naphthyridin-2-yl)ethoxy]pyrazol-3-yl]butanoate (343 mg, 576 µmol, 1 eq. the direct precursor of the title compound of Example 10) and dicyanozinc (203 mg, 1.73 mmol, 110 µL, 3 eq) in DMF (8 mL) in a 25 mL microwave vial was evacuated and back-filled with $N_2$ (3×). Palladium triphenylphosphane (67 mg, 58 µmol, 0.1 eq) was added. The reaction vial was sealed, and the reaction mixture was again degassed and back-filled with $N_2$ (3×), and then stirred at 120° C. for 90 min under micro-wave irradiation. The solvent was removed under vacuum to give a gray gum. The residue was purified by flash silica gel chromatography (ISCO®; 12 g Sepa-Flash® Silica Flash Column, Eluent of 0~80% Ethyl acetate/Petroleum ether gradient @ 35 mL/min) to give the desired substance as brown gum (181 mg). LCMS showed the purity was 77.5%. LC-MS analysis of the solid shows the desired product's mass: m/z 542 (M+H); Calcd for $C_{25}H_{30}F_3N_5O_3$: 541.23.

Step 2. Preparation of 3-(3-cyano-5-(trifluoromethyl)phenyl)-4-(1-methyl-5-(2-(5,6,7,8-tetrahydro-1,8-naphthyridin-2-yl)ethoxy)-1H-pyrazol-3-yl)butanoic Acid

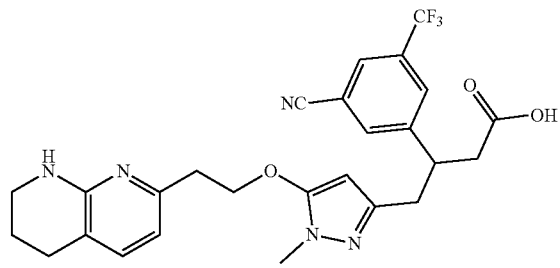 [SMILES: Cn1nc(CC(CC(=O)O)c2cc(C#N)cc(C(F)(F)F)c2)cc1OCCc1ccc2c(n1)NCCC2]

To a stirred solution of ethyl 3-[3-cyano-5-(trifluoromethyl)phenyl]-4-[1-methyl-5-[2-(5,6,7,8-tetrahydro-1,8-naphthyridin-2-yl)ethoxy]pyrazol-3-yl]butanoate (90 mg, 166 µmol, 1 eq) in a mixture of THF (3 mL) and MeOH (1 mL) was added a solution of $LiOH.H_2O$ (50 mg, 1.19 mmol, 7.17 eq) in $H_2O$ (2 mL), stirring maintained at 25° C. for 3 hr. The organic solvent was removed under vacuum and the residual aqueous was acidified with 1 mL of AcOH to pH<7. The solvent was evaporated to dryness under vacuum, then re-suspended in MeOH (5 mL) and stirred for 2 min. The un-dissolved sediment was filtered off and the filtrate was purified by Prep-HPLC (column: Boston Green ODS 150*30 5µ; mobile phase: [water (0.1% TFA)-ACN]; B %: 28%-38%, 8 min). The HPLC effluent was lyophilized to give the title compound as a white solid (43 mg, 69 µmol, 41% yield, 100% purity, TFA). LC-MS analysis of the solid shows the desired product's mass: m/z 514 (M+H); Calcd for $C_{26}H_{26}F_3N_5O_3$: 513.20. $^1$H NMR (400 MHz, $CD_3OD$) δ ppm 1.95 (dd, J=6.50, 5.18 Hz, 2H) 2.68-2.86 (m, 5H) 2.90 (d, J=6.61 Hz, 1H) 3.15 (t, J=5.95 Hz, 2H) 3.43 (s, 3H) 3.45-3.52 (m, 2H) 3.52-3.63 (m, 1H) 4.31 (t, J=6.06 Hz, 2H) 5.48 (s, 1H) 6.69 (d, J=7.28 Hz, 1H) 7.60 (d. J=7.50 Hz, 1H) 7.77 (s, 1H) 7.89 (d, J=13.23 Hz, 2H); $^{19}$FNMR (400 MHz, $CD_3OD$) δ ppm –64.44, –77.33.

Example 13

Preparation of 3-(2-methoxy-5-(trifluoromethyl)phenyl)-4-(1-methyl-5-(2-(5,6,7,8-tetrahydro-1,8-naphthyridin-2-yl)ethoxy)-1H-pyrazol-3-yl)butanoic Acid Trifluoroacetate

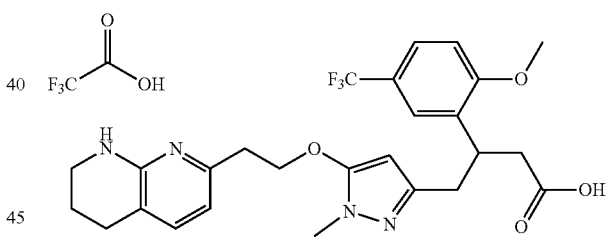

Example 13 was prepared in analogous manner to Example 1, using 2-methoxy-5-(trifluoromethyl) benzaldehyde as the required benzaldehyde in the reaction Scheme 3. The crude product was purified by Prep-HPLC (column Boston Green ODS 150*30 5µ; mobile phase: [water (0.1% TFA)-ACN]; B %: 20%-50%, 8 min). The title compound (120 mg, 189 µmol, 55% yield, 99.6% purity, TFA salt) was obtained as a white solid, which was confirmed by LCMS, HPLC, $^1$H NMR and, $^{19}$F NMR. LC-MS analysis of the solid showed the desired mass: m/z 519.0 (M+H); Calcd for $C_{26}H_{29}N_4O_4F_3$: 518.53. $^1$H NMR ($CD_3OD$, 400 MHz) 7.58 (d, J=7.2 Hz, 1H), 7.49 (br d, J=8.8 Hz, 1H). 7.36 (d, J=16 Hz, 1H), 7.08 (d, J=8.8 Hz, 1H), 6.66 (d, J=7.6 Hz, 1H), 5.55 (s, 1H), 4.35 (t, J=6.0 Hz, 2H), 3.91 (s, 3H), 3.81 (quin, J=7.6 Hz, 1H), 3.47–3.53 (m, 5H), 3.16 (t, J=6.0 Hz, 2H), 2.86-2.97 (m, 2H), 2.82 (br t, J=6.0 Hz, 2H), 2.65-2.78 (m, 2H), 1.95 (quin, J=6.0 Hz. 2H). $^{19}$F NMR ($CD_3OD$, 376 MHz) –62.86 (s, 1F), –77.37 (s, 1F).

Example 14

Preparation of 3-(5-bromo-2-methoxyphenyl)-4-(1-methyl-5-(2-(5,6,7,8-tetrahydro-1,8-naphthyridin-2-yl)ethoxy)-1H-pyrazol-3-yl)butanoic acid trifluoroacetate

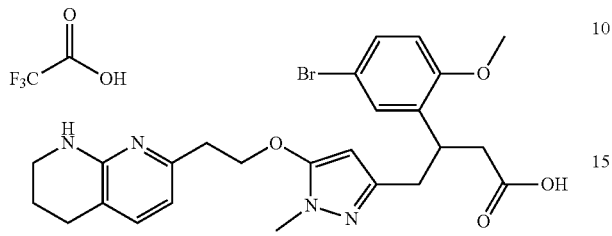

Example 14 was prepared in analogous manner to Example 1, using 5-bromo-2-methoxy-benzaldehyde as the required benzaldehyde in the reaction Scheme 3. The crude product was purified by Prep-HPLC (column: Boston Green ODS 150*30 5μ; mobile phase: [water (0.1% TFA)-ACN]; B %: 20%-50%, 8 min). The title compound (190 mg, 293 μmol, 84% yield, 99.4% purity, TFA) was obtained as a white solid, which was confirmed by LCMS (m/z 529.0 (M+H)), HPLC, $^1$H NMR and $^{19}$F NMR. $^1$H NMR (CD$_3$OD, 400 MHz) 7.59 (d, J=7.2 Hz, 1H), 7.29 (dd, J=8.8, 2.4 Hz, 1H), 7.22 (d, J=2.4 Hz, 1H), 6.86 (d, J=8.8 Hz, 1H), 6.66 (d, J=7.2 Hz, 1H), 5.55 (s, 1H), 4.37 (t, J=6.0 Hz, 2H), 3.82 (s, 3H), 3.73 (quin, J=7.6 Hz, 1H), 3.47-3.53 (m, 5H), 3.16 (t, J=6.0 Hz, 2H), 2.85-2.94 (m, 2H), 2.82 (t, J=6.4 Hz, 2H), 2.61-2.73 (m, 2H), 1.95 (quin, J=6.0 Hz, 2H), $^{19}$F NMR (CD$_3$OD, 376 MHz) −77.32 (br s, 1F).

Example 15

Preparation of (3S)-3-(3-fluoro-4-methoxyphenyl)-4-(1-methyl-5-(2-(5,6,7,8-tetrahydro-1,8-naphthyridin-2-yl)ethoxy)-1H-pyrazol-3-yl)butanoic Acid

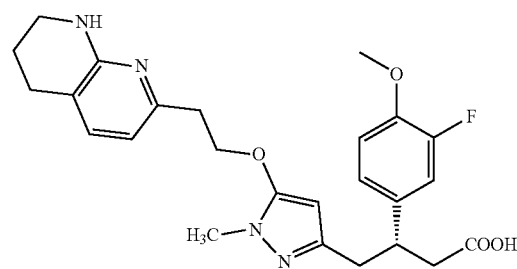 [SMILES: COc1ccc([C@H](CC(=O)O)Cc2cc(OCCc3ccc4c(n3)NCCC4)n(C)n2)cc1F]

Scheme 6

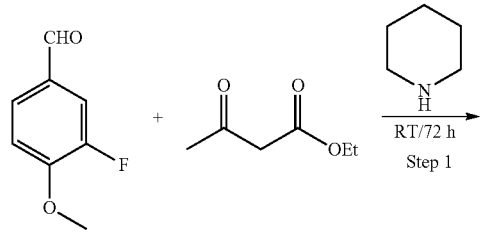

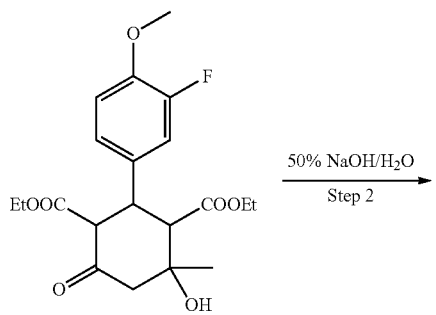

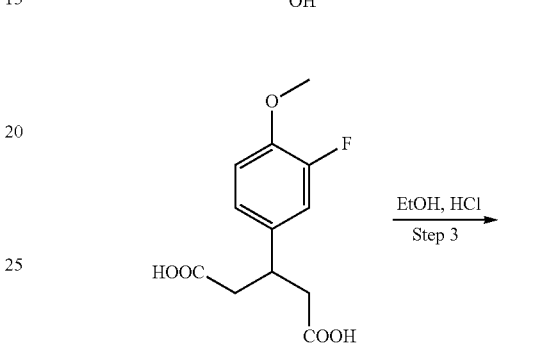

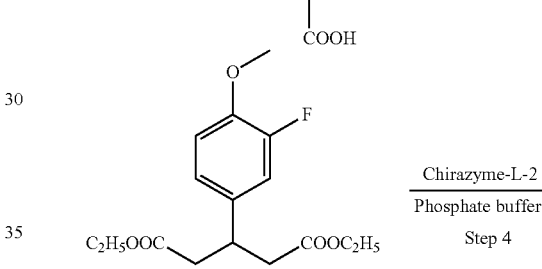

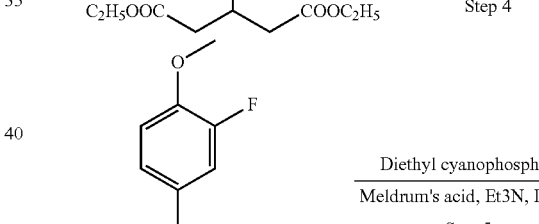

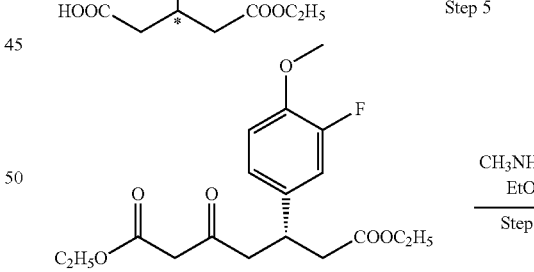

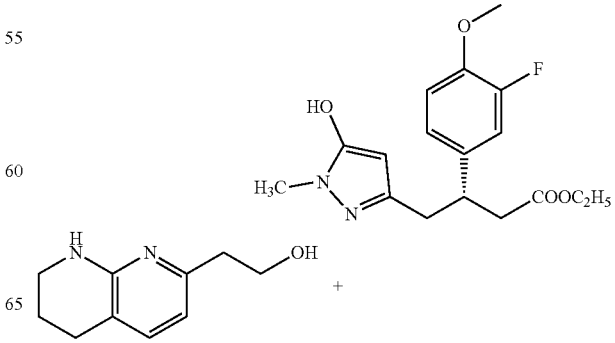

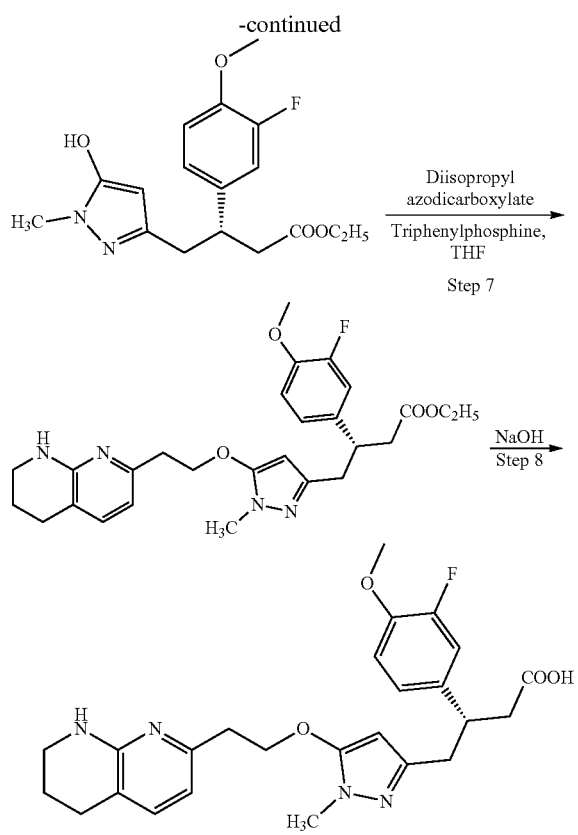

Step 1. Preparation of diethyl 2-(3-fluoro-4-methoxy-phenyl)-4-hydroxy-4-methyl-6-oxo-cyclohexane-1,3-dicarboxylate

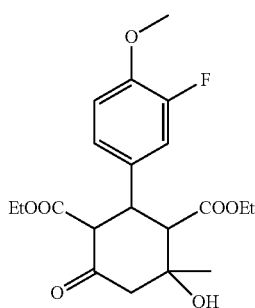 [SMILES: CCOC(=O)C1C(=O)CC(C)(O)C(C(=O)OCC)C1c1ccc(OC)c(F)c1]

Piperidine (310 µL, 3.13 mmol) was added to a solution of a mixture of 3-fluoro-4-methoxybenzaldehyde (5.0 g, 31.14 mmol) and ethyl acetoacetate (8.75 g, 67.21 mmol). The reaction mixture was stirred at room temperature for 72 h to give a pale yellow microcrystalline solid. The crude product was recrystallized by dissolving the solid in boiling abs. ethyl alcohol (70 mL) and cooling the yellow solution to room temperature to afford a pale yellow crystalline solid. The solid was filtered, washed with abs. ethyl alcohol (2×100 mL) and dried in vacuo to afford a colorless crystalline solid (9.59 g yield 78%). LC-MS analysis of the solid showed the desired product's mass: m/z 397 (M+H), m/z 419 (M+Na) and m/z 815 (2M+Na); Calculated for $C_{20}H_{25}FO_7$: 396.41. $^1$H NMR (400 MHz, DMSO-d$_6$): δ 0.89 (t, J=7.09 Hz, 3H, $CH_3$—$CH_2$—), 0.98 (t, J=7.09 Hz, 3H, $CH_3$—$CH_2$—), 1.24 (s, 3H, $CH_3$—), 2.33 (d, J=3.45 Hz, 1H, —CH—), 2.88 (d, J=13.45 Hz, 1H, —CH—), 3.27 (d, J=11.98 Hz, 1H, —CH—) 3.78 (s, 3H, —O—$CH_3$), 3.79-3.97 (m, 6H, 2×—$CH_2$—$CH_3$+—$CH_2$—C($CH_3$)OH), 4.94 (s, 1H, —OH), 6.99-7.11 (m, 2H, H-5, H-6), 7.16-7.22 (m, 1H, H-2). $^1$H NMR spectrum of the product was consistent with the suggested structure of the product.

Step 2. Preparation of 3-(3-fluoro-4-methoxy-phenyl)pentanedioic Acid

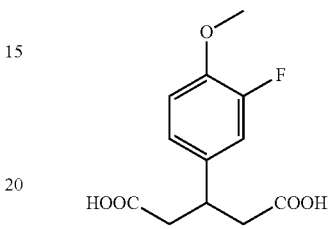

To a suspension of diethyl 2-(3-fluoro-4-methoxy-phenyl)-4-hydroxy-4-methyl-6-oxo-cyclohexane-1,3-dicarboxylate (4.05 g, 10.22 mmol) from step 1 in abs. ethyl alcohol (50.0 mL) was added 50% sodium hydroxide solution (20 mL) and the reaction mixture was heated under refluxing conditions for 1 h to give a beige suspension. After 1.5 h, the reaction mixture was cooled to room temperature, and ethanol was evaporated in vacuo to give a brown precipitate suspended in water. Ethyl acetate (75 mL) was added to above solution and stirred at room temperature for 30 min. The aqueous layer and the organic layers were separated. The aqueous layer was washed with ethyl acetate (1×25 mL) to remove residual byproduct. The aqueous layer was acidified with conc. HCl until pH=1. The solvent was evaporated in vacuo to afford a colorless to cream solid. The solid was filtered, washed with water (2×10 mL) and dried in vacuo to afford a cream-yellow crystalline solid (2.08 g, 79%). LC-MS analysis of the solid showed the desired product at rt 1.51 min and the desired product's mass: m/z 239 (M+H–$H_2O$), m/z 257 (M+H) and m/z 279 (M+Na); Calculated for $C_{12}H_{13}FO_5$: 256.23. $^1$H NMR (400 MHz, DMSO-d$_6$): δ 2.48 (dd, J=15.90 Hz and 8.80 Hz, 2H, —CH—$CH_2$—COOH, partially hidden under DMSO peak), 2.61 (dd, J=15.90 Hz and 8.80 Hz, 2H, HOOC—$CH_2$—CH—), 3.34-3.39 (m, 1H, partially hidden under water peak, —CH—$CH_2$—COOH), 3.79 (s, 3H, $CH_3O$—), 6.98-7.08 (dd/m, 2H, H-5 and H-6), 7.13 (dd, J=12.84 and 1.83 Hz, Hz, 1H, H-2), 12.07 (s, 2H, 2×—COOH); $^1$H NMR spectrum of the product was consistent with the suggested structure of the product.

Step 3. Preparation of diethyl 3-(3-fluoro-4-methoxy-phenyl)pentanedioate

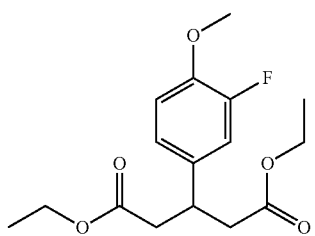 [SMILES: CCOC(=O)CC(CC(=O)OCC)c1ccc(OC)c(F)c1]

To a solution of 3-(3-fluoro-4-methoxy-phenyl)pentanedioic acid (2.04 g, 794 mmol) from step 2 in absolute ethanol (25 mL) and was added a 2.0 M HCl solution in diethyl ether (20 mL) and the reaction mixture was stirred at room temperature overnight to give a yellow-orange solution. Evaporation of the solvent in vacuo gave a yellow viscous liquid. The residue was partitioned between water (50 mL) and ethyl acetate (50 mL). The aqueous and organic layers were separated. The organic layer was washed with a saturated solution of NaHCO₃ (1×10 mL), brine (1×25 mL), dried over anhydrous sulfate, filtered and evaporated in vacuo to afford a yellow-orange viscous liquid (2.382 g, yield 96%). LC-MS analysis of the liquid showed the desired product at rt 2.42 min and the desired product's mass: m/z 267 (M+H—$C_2H_5O$—), m/z 313 (M+H), m/z 335 (M+Na); Calculated for $C_{16}H_{21}FO_5$: 312.34. ¹H NMR (400 MHz, CDCl₃): δ 1.17 (t, J=7.1 Hz, 6H, 2×CH₃—CH₂—), 2.53-2.74 (m, 4H, 2x—CH₂—C=O—), 3.59 (t, J=7.58 Hz, 1H, —CH₂—CH—CH₂—), 3.86 (s, 3H, —OCH₃), 3.99-4.12 (m, 4H, 2×CH₃—CH₂—O—), 6.85-6.91 (m, 1H), 6.92-7.00 (m, 2H). ¹H NMR spectrum of the compound was consistent with the suggested structure of the product.

Step 4. Preparation of (S)-5-ethoxy-3-(3-fluoro-4-methoxyphenyl)-5-oxopentanoic Acid

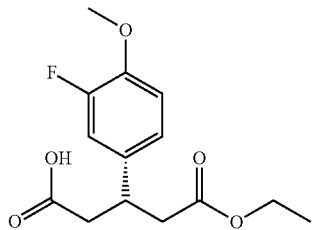

A suspension of diethyl 3-(3-fluoro-4-methoxy-phenyl) pentanedioate (2.356 g, 7.52 mmol) from step 3 in 28 mM KH₂PO₄ solution was stirred at room temperature. The pH of the aqueous phase was adjusted to pH 7.30 by the addition of 1 N NaOH solution and 50 mM KH₂PO₄ solution. Lipase acrylic resin from *Candida antartica* (203.0 mg) was added and the reaction mixture was stirred at room temperature overnight. A cream-yellow suspension, LC-MS analysis of the reaction mixture after overnight stirring (17 h) showed the desired product at rt 1.98 min (48%) and the unreacted starting material at rt 2.42 min (52%). After 46 h, another portion of Lipase acrylic resin beads (142.0 mg) was added and the pH of the reaction mixture was adjusted to 7.30 by 1N NaOH solution and the reaction mixture was stirred at room temperature. LC-MS analysis of the reaction mixture after stirring for 6 days (138 h) showed the desired product at rt 1.97 min (>98%) and the unreacted starting material at rt 2.41 min (<2%). After 144 h the reaction mixture was filtered on a Whatman #1 filter paper to remove Lipase acrylic resin. The LC-MS analysis of the filtrate showed the desired product at rt 1.97 min (>99%) and a baseline trace of the unreacted starting material at rt 2.41 min (<1%). LC-MS analysis also showed the desired product's mass: m/z 267 (M+H–H₂O), m/z 285 (M+H) and m/z 307 (M+Na); a fairly pure reaction mixture. The filtrate was acidified with 3N HCl (5 mL) to give a colorless suspension. The suspension was saturated with solid sodium chloride to give a colorless gummy suspension. The sodium chloride was filtered off and the filtrate was extracted with ethyl acetate (2×50 mL). The ethyl acetate layer was washed with brine (2×50 mL), dried with anhydrous Na₂SO₄, filtered and evaporated in vacuo to give a pale yellow viscous oil, started to solidify slowly to a pale yellow crystalline solid (2.14 g, yield 99%). LC-MS analysis of the solid showed the desired product at rt 1.97 min and the desired product's mass: m/z 267 (M+H–H₂O), m/z 285 (M+H) and m/z 307 (M+Na); Calculated for $C_{14}H_{17}FO_5$: 284.28. ¹H NMR (400 MHz, CDCl₃): δ 1.18 (t, J=7.09 Hz, 3H, CH₃—CH₂—CO—), 2.53-2.82 (m, 4H, 2×—CH₂—), 3.59 (quin/m, 1H, —CH₂—CH—CH₂—), 3.87 (s, 3H, —O—CH₃), 4.06 (qd, J=7.09 and 1.22 Hz, 2H), 6.86-6.92 (m, 1H), 6.94-7.00 (m, 2H), —COOH peak was hidden under baseline. ¹H NMR spectrum of the product was consistent with the suggested structure of the product.

Step 5. Preparation of diethyl (3S)-3-(3-fluoro-4-methoxy-phenyl)-5-oxo-heptanedioate

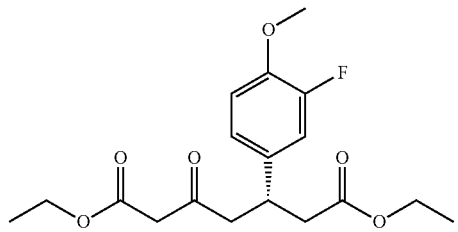 [SMILES: CCOC(=O)CC(=O)C[C@@H](CC(=O)OCC)c1ccc(OC)c(F)c1]

To a solution of (S)-5-ethoxy-3-(3-fluoro-4-methoxy-phenyl)-5-oxo-pentanoic acid (2.06 g, 7.246 mmol) from step 4 and Meldrum's acid (1.23 g, 114.13 mmol) in anhydrous DMF (15.0 mL) under nitrogen atmosphere and at 0° C. (ice-bath) was slowly added diethyl cyanophosphonate (1.61 g, 163.11 mmol), followed by triethylamine (3.5 mL, 25.11 mmol). The reaction mixture was stirred at 0° C. for 30 min to give an orange solution. After 30 min, the reaction mixture was warmed to room temperature and stirred at room temperature overnight under nitrogen atmosphere. The reaction mixture was quenched into an ice cold 2N HCl (20 mL) and stirred for 5 min to give a brown oily residue. The mixture was diluted with water (20 mL) and extracted with ethyl acetate (4×25 mL). The organic layer were combined, washed with water (1×50 mL), brine (1×50 mL), dried over anhydrous Na₂SO₄, filtered and evaporated in vacuo to give an orange-brown oil (6.21 g). The oil was dissolved in absolute ethanol (80.0 mL) and the reaction mixture was refluxed for 3 h to give an orange solution. The solvent was evaporated in vacuo to afford an orange-brown oil (3.34 g). LC-MS analysis of the crude product showed the desired product at rt 2.36 min and a byproduct at rt 2.46 min. LC-MS also showed the desired product's mass: m/z 309 (M+H—C₂H₅O—), m/z 355 (M+H), m/z 377 (M+Na) and the byproduct's mass: m/z 430 (M+H), m/z 452 (M+Na) and m/z 881 (2M+Na). The crude product was dissolved in dichloromethane and applied to 80 g RediSep Silica column and was purified by silica-gel flash chromatography using 0 to 60% EtOAc in hexanes. The pure fractions were mixed together and the mixture was evaporated in vacuo to afford a colorless to a very pale yellow viscous liquid (1.767 g, yield 690%). LC-MS analysis of the liquid showed the desired product at rt 2.35 min and the desired product's mass: m/z 309 (M+H—C₂H₅O—), m/z 355 (M+H), m/z 377 (M+Na); Calculated for $C_{18}H_{23}FO_6$: 354.37. ¹H NMR (400 MHz, CDCl₃): δ 1.17 (t, J=7.21 Hz, 3H, CH₃—CH₂—CO—), 1.25 (t, J=7.21 Hz, 3H, CH₃—CH₂—CO—), 2.48-2.72 (m, 4H), 2.83-3.00 (m, 2H), 3.86 (s, 3H, —O—CH₃), 4.05 (qd, J=7.13 and 1.83 Hz, 2H), 4.12-4.22 (m, 2H), 4.28 (q, J=7.25 Hz, 1H), 6.89 (d, J=8.31 Hz, 1H), 6.92-6.94 (m, 2H), 6.96 (t, J=2.20 Hz, 1H, —OH). ¹H NMR spectrum of the product was consistent with the suggested structure of the product.

Step 6: Preparation of ethyl (3S)-3-(3-fluoro-4-methoxy-phenyl)-4-(5-hydroxy-1-methyl-pyrazol-3-yl)butanoate

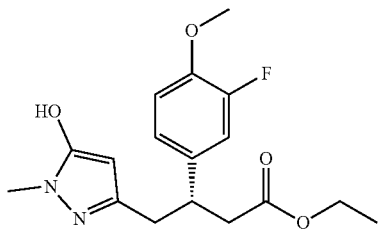 [SMILES: CCOC(=O)C[C@H](Cc1cc(O)n(C)n1)c1ccc(OC)c(F)c1]

To a solution of diethyl (3S)-3-(3-fluoro-4-methoxy-phenyl)-5-oxo-heptanedioate (1.756 g, 4.955 mmol) from step 5 in absolute ethyl alcohol was added methylhydrazine (300 µL, 5.697 nmmol) at room temperature to give a pale yellow solution. The reaction mixture was heated under refluxing conditions for 1.5 h to give a bright yellow solution. The reaction mixture was cooled to room temperature and evaporated in vacuo to afford a yellow gummy residue (1.82 g). The crude product was dissolved in ethyl acetate containing a trace of ethanol and applied to 40 g RediSep Silica column and was purified by silica-gel flash chromatography using 0 to 20% methanol in EtOAc to afford a very pale yellow viscous liquid, dried on a vacuum pump to afford a pale yellow foamy solid (1.347 g, yield 81%). LC-MS analysis of the solid showed the desired product at rt 1.84 min and the desired product's mass: m/z 337 (M+H), m/z 359 (M+Na), and m/z 695 (2M+Na); Calculated for $C_{17}H_{21}FN_2O_4$: 336.36. ¹H NMR (400 MHz, CDCl₃): δ 1.18 (t, J=7.21 Hz, 3H, CH₃—CH₂—CO—), 2.55-2.62 (m, 1H, —CHH—CH—CH₂—), 2.63-2.71 (m, 2H, —CHH—CH—CHH—), 2.74-2.82 (m, 1H, —CHH—CH—CH₂—), 3.23 (s, 3H, N—CH₃), 3.34-3.46 (m, 1H, —CH₂—CH—CH₂—), 3.88 (s, 3H, —OCH₃), 4.06 (q, J=7.09 Hz, 2H, CH₃—CH₂—CO—), 6.85-6.92 (m, 3H, Ph-H-2, H-5, H-6), 6.92-6.94 (m, 1H, Py-H-4), 6.96 (s, 1H, —OH). ¹H NMR spectrum of the product was consistent with the suggested structure of the product.

Step 7: Preparation of ethyl (3S)-3-(3-fluoro-4-methoxy-phenyl)₄-[1-methyl-5-[2-(5,6,7,8-tetrahydro-1,8-naphthyridin-2-yl)ethoxyl]pyrazol-3-yl]butanoate

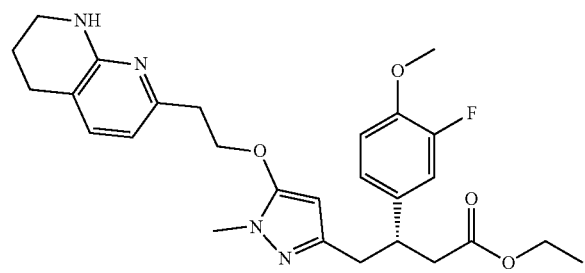 [SMILES: CCOC(=O)C[C@H](Cc1cc(OCCc2ccc3c(n2)NCCC3)n(C)n1)c1ccc(OC)c(F)c1]

To a solution of triphenylphosphine (1.15 g, 4.388 mmol) in anhydrous THF (15 mL) at −10° C. (salt-ice bath) was added DIAD (900 µL, 4.57 mmol) drop wise to give a yellow suspension within 5-10 min. The reaction mixture was stirred at −10° C. for another 20 min. To the above reaction mixture was added drop wise a solution of 2-(5,6,7,8-tetrahydro-1,8-naphthyridin-2-yl)ethanol (711.0 mg, 3.987 mmol) (from Scheme 2) in THF (5.0 mL). The reaction mixture was stirred at −10° C. for 20 min and a solution of ethyl (3S)-3-(3-fluoro-4-methoxy-phenyl)-4-(5-hydroxy-1-methyl-pyrazol-3-yl)butanoate (1.341 g, 3.987 mmol) from step 6 in anhydrous THF (5.0 mL) was added in one portion to give an orange solution. The reaction mixture was warmed up to room temperature after stirring for 10 min at −10° C. and stirred overnight at room temperature. The reaction mixture was quenched with a saturated NH₄Cl solution (50 mL) and extracted with ethyl acetate (2×50 mL). The combined organic layer was washed with brine (1×50 mL), dried over anhydrous Na₂SO₄, filtered and evaporated in vacuo to afford a yellow foamy/gummy residue. The crude product was purified by silica-gel flash chromatography on a RediSep 80 g silica column and elution with 0-2% methanol in ethyl acetate to give a cream crystalline solid (858.0 mg, yield 44%). LC-MS analysis of the solid showed the desired product at rt 2.04 min and the desired product's mass: m/z 497 (M+H) and m/z 519 (M+Na); Calculated for $C_{27}H_{33}FN_4O_4$: 496.58. ¹H NMR (400 MHz, CDCl₃): δ 1.12 (t, J=7.21 Hz, 3H), 1.92 (dt, J=11.68, 6.02 Hz, 1H), 2.52 (dd, J=15.41, 10.03 Hz, 1H), 2.65-2.84 (m, 5H), 2.97 (t, J=6.85 Hz, 2H), 3.32-3.39 (m, 1H), 3.40-3.46 (m, 2H), 3.50 (s, 3H), 3.85 (s, 3H), 3.93-4.04 (m, 2H), 4.26 (t, J=6.85 Hz, 2H), 4.89-5.03 (m, 1H), 4.96 (br s, 1H), 5.22 (s, 1H) 6.39 (d, J=7.09 Hz, 1H), 6.83-6.89 (m, 1H), 6.91-6.98 (m, 2H), 7.09 (d, J=7.34 Hz, 1H). ¹H NMR spectrum of the product was consistent with the suggested structure of the product.

Step 8: Preparation of (3S)-3-(3-fluoro-4-methoxy-phenyl)-4-(1-methyl-5-(2-(5,6,7,8-tetrahydro-1,8-naphthyridin-2-yl)ethoxy)-1H-pyrazol-3-yl)butanoic Acid

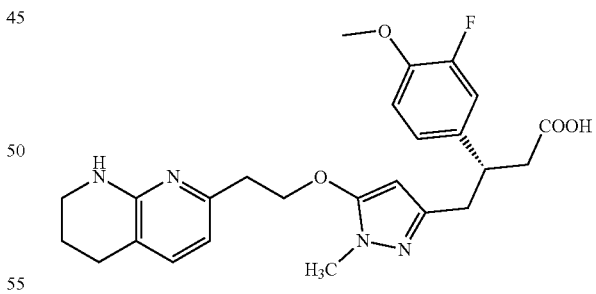

To a solution of ethyl (3S)-3-(3-fluoro-4-methoxy-phenyl)-4-[1-methyl-5-[2-(5,6,7,8-tetrahydro-1,8-naphthyridin-2-yl)ethoxy]pyrazol-3-yl]butanoate (806 mg, 1.623 mmol) from step 7 in anhydrous THF (5 mL) was added 1.0 N aqueous NaOH solution (8.0 mL) and the resulting suspension was stirred at 50° C. to give a yellow suspension. LC-MS analysis of the reaction mixture after stirring for 8 h showed the desired product at rt 1.78 min; no trace of the starting material was present at rt 2.04 min. The solvent was evaporated in vacuo to afford a yellow gummy residue. The crude residue was purified by reverse-phase preparative HPLC on a Biotage KP-C18-HS (120 g) column and using a gradient 10-50% acetonitrile in water containing 0.05% TFA to afford the desired title compound (Example 15) as a pale yellow gummy residue. LC-MS analysis of the residue showed the desired product at rt 1.77 min and the desired product's mass: m/z 469 (M+H) and m/z 491 (M+Na); Calculated for $C_{25}H_{29}FN_4O_4$: 468.53. The above residue was dissolved in water containing a few drops of acetonitrile and lyophilized to afford a cream to pale yellow lyophilized powder (708.0 mg, yield 93%). $^1$H NMR (400 MHz, DMSO-$d_6$): δ 1.77-1.87 (m, 2H), 2.40-2.48 (m, 1H), 2.54-2.62 (m, 1H), 2.65 (t, J=6.97 Hz, 2H), 2.74 (t, J=6.11 Hz, 2H), 3.09 (t, J=6.11 Hz, 2H), 3.19-3.29 (m, 1H), 3.38 (s, 3H), 3.41 (t, J=5.38 Hz, 1H), 3.78 (s, 3H), 4.25 (t, J=6.11 Hz, 2H), 5.43 (s, 1H), 6.68 (d, J=7.34 Hz, 1H), 6.94-7.05 (m, 2H), 7.09 (dd, J=12.96 and 1.71 Hz, 1H), 7.62 (d, J=7.34 Hz, 1H), 8.44 (brs, 1H), 13.92 (brs, 1H). $^{19}$F NMR (376 MHz, DMSO-$d_6$): δ− 135.81 (dd, J=12.95 and 8.86 Hz, 1F, 3-F); also showed TFA at δ −74.35 (s, 3F, $CF_3COOH$).

Example 16

Preparation of 3-(3-bromo-5-tert-butyl-phenyl)-4-(1-methyl-5-(2-(5,6,7,8-tetrahydro-1,8-naphthyridin-2-yl)ethoxy)-1H-pyrazol-3-yl)butanoic Acid

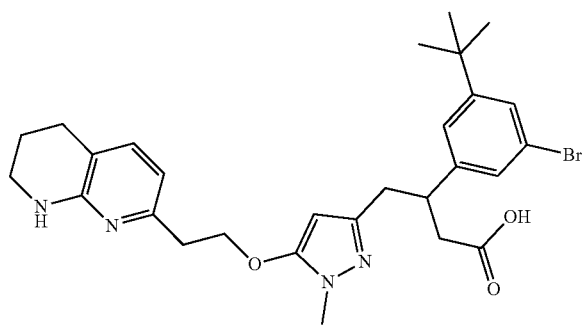 [SMILES: Cn1nc(CC(CC(=O)O)c2cc(Br)cc(C(C)(C)C)c2)cc1OCCc1ccc2c(n1)NCCC2]

Example 16 was prepared in analogous manner to Example 1, using 3-bromo-5-tert-butylbenzaldehyde as the required benzaldehyde in the reaction Scheme 3. The crude product was purified by reverse-phase preparative HPLC and after lyophilization of the fractions afforded the title compound as a colorless powder (75.2 mg). LC-MS analysis of the solid showed the desired product at rt 2.20 min with a purity >95% and the desired product's mass: m/z 555 ($^{79Br}$M+H), m/z 557 ($^{81Br}$M+H), m/z 577 ($^{79Br}$M+Na) and m/z 579 ($^{81Br}$M+Na); Calculated for $C_{30}H_{36}BrN_4O_3$: 555.51. $^1$H NMR (400 MHz, $CD_3OD$): δ 1.24-1.31 (m, 9H), 1.92-2.01 (m, 2H), 2.65-2.78 (m, 2H), 2.78-2.88 (m, 2H), 2.95 (dd, J=14.62, 8.97 Hz, 1H), 3.12 (dd, J=14.62, 6.59 Hz, 1H), 3.24 (t, J=5.90 Hz, 2H) 3.43-3.55 (m, 3H), 3.66 (s, 3H), 4.54 (t, J=5.77 Hz, 2H), 6.06 (s, 1H), 6.73 (d, J=7.28 Hz, 1H), 7.21 (s, 1H), 7.26 (s, 1H), 7.39 (s, 1H), 7.63 (d, J=7.40 Hz, 1H).

Example 17

Preparation of 3-(3-tert-butyl-5-cyanophenyl)-4-(1-methyl-5-(2-(5,6,7,8-tetrahydro-1,8-naphthyridin-2-ylethoxy)-H-pyrazol-3-yl)butanoic Acid

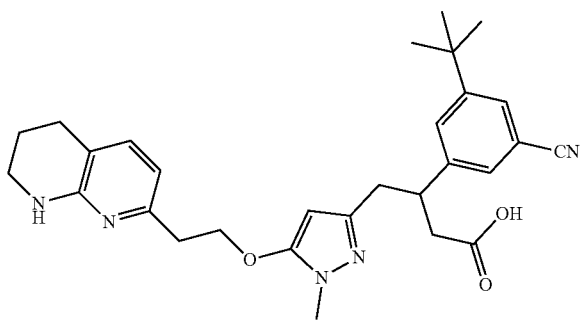 [SMILES: Cn1nc(CC(CC(=O)O)c2cc(C#N)cc(C(C)(C)C)c2)cc1OCCc1ccc2c(n1)NCCC2]

Example 17 was prepared in analogous manner to Example 7 (Scheme 4) using example 16 as the precursor. The crude product was purified by reverse-phase preparative HPLC and after lyophilization of the fractions afforded the title compound as a colorless powder (38.2 mg). LC-MS analysis of the solid showed the desired product at rt 2.04 min and the desired product's mass: m/z 502 (M+H), and m/z 524 (M+Na); Calculated for $C_{29}H_{35}N_5O_3$: 501.62. $^1$H NMR (400 MHz, DMSO-$d_6$): δ 1.19-1.25 (m, 9H), 1.78-1.88 (m, 2H), 2.54-2.69 (m, 3H), 2.70-2.80 (m, 3H), 3.08 (t, J=6.02 Hz, 2H), 3.37 (s, 4 H), 3.39-3.45 (m, 4H), 4.22 (t, J=6.02 Hz, 2H), 5.41 (s, 1H), 6.68 (d, J=7.40 Hz, 1H), 7.50 (s, 1H), 7.54 (s, 1H), 7.59 (s, 1H), 7.63 (d, J=7.40 Hz, 1H), 8.18 (brs, 1H).

Example 18

Preparation of 3-(3,5-di-tert-butylphenyl)-4-[1-methyl-5-[2-(5,6,7,8-tetrahydro-1,8-naphthyridin-2-yl)ethoxyl]pyrazol-3-yl]butanoic Acid

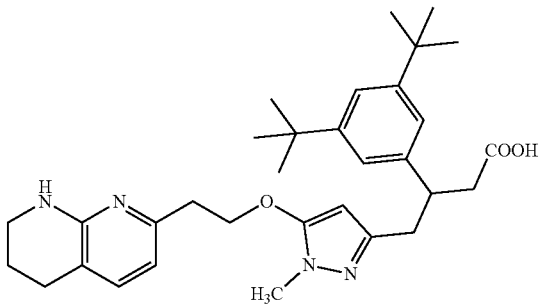 [SMILES: Cn1nc(CC(CC(=O)O)c2cc(C(C)(C)C)cc(C(C)(C)C)c2)cc1OCCc1ccc2c(n1)NCCC2]

Scheme 7

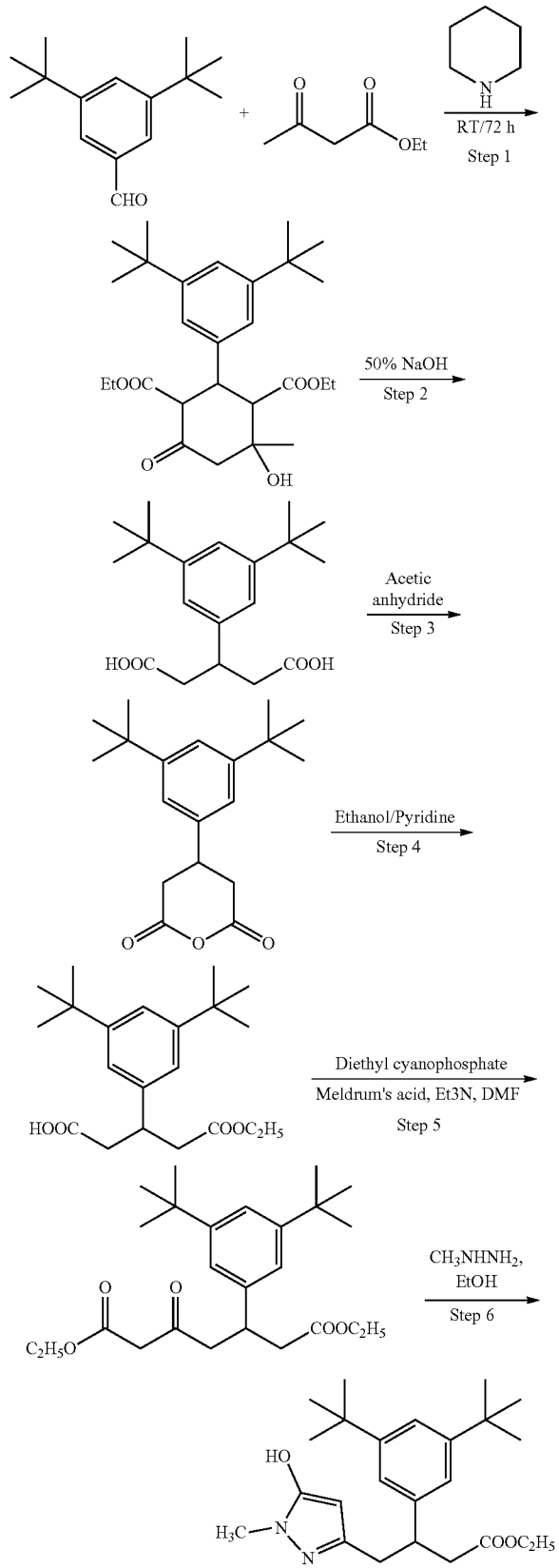
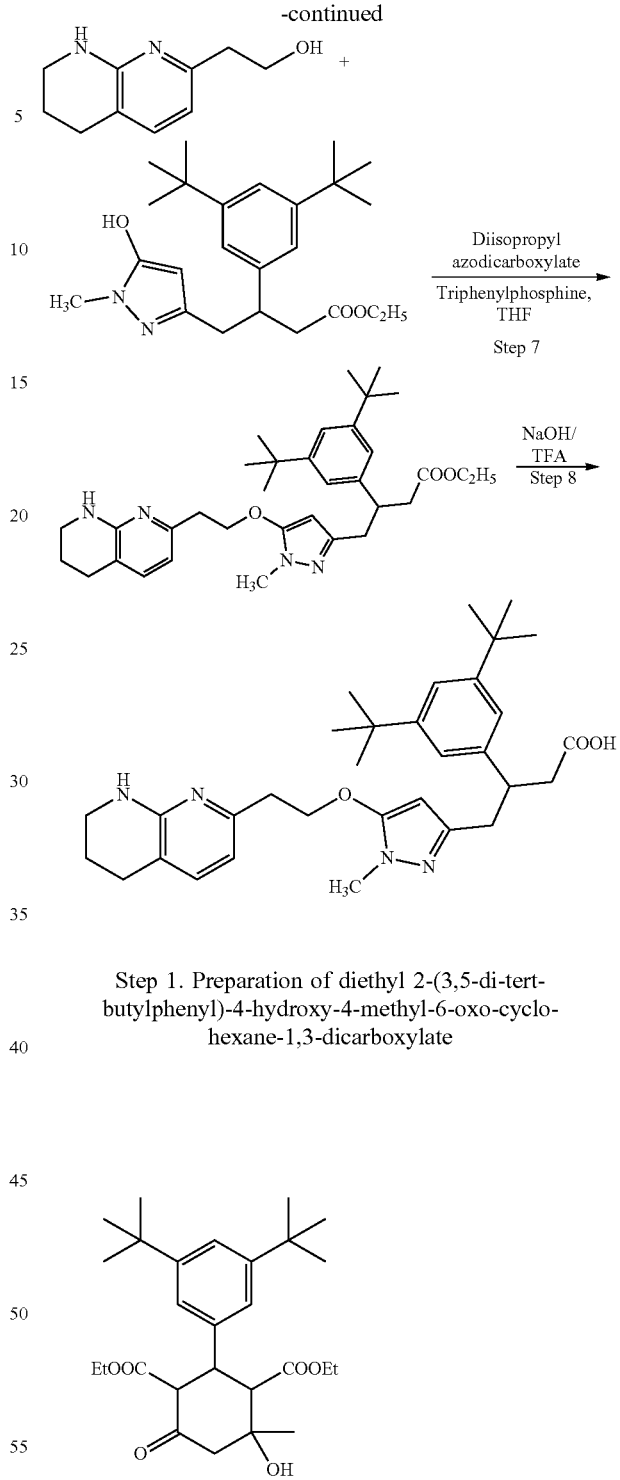

Step 1. Preparation of diethyl 2-(3,5-di-tert-butylphenyl)-4-hydroxy-4-methyl-6-oxo-cyclohexane-1,3-dicarboxylate Piperidine (90 μL, 0.91 mmol) was added to a solution of a mixture of 3,5-di-tert-butylbenzaldehyde (1.774 g, 7.88 mmol) and ethyl acetoacetate (2.57 g, 19.76 mmol). The reaction mixture was stirred at room temperature for 92 h to give a canary yellow microcrystalline solid. The crude product was recrystallized by dissolving the solid in boiling hexanes (30 mL) and cooling the yellow solution to room temperature to afford a colorless crystalline solid. The solid was filtered, washed with hexanes (3×10 mL) and dried in vacuo to afford a colorless crystalline solid (2.70 g, yield 74%). LC-MS analysis of the solid showed the desired product's mass: m/z 443 (M+H–H$_2$O), m/z 461 (M+H), m/z 483 (M+Na) and m/z 943 (2M+Na); Calculated for C$_{27}$H$_{40}$O$_6$: 460.61. $^1$H NMR (400 MHz, CDCl$_3$): δ 0.72 (t, J=7.21 Hz, 3H, CH$_3$—CH$_2$—), 1.01 (t, J=7.09 Hz, 3H, CH$_3$—CH$_2$—), 1.29 (s, 18H, 2×t-C$_4$H$_9$—), 1.36 (s, 3H, CH$_3$—), 2.51 (dd, J=14.18 Hz and 2.69 Hz, 1H, —CH— at C-2), 2.72 (d, J=14.18 Hz, 1H, —CH— at C-1), 3.03 (d, J=12.23 Hz, 1H, —CH—, at C-3), 3.70 (d, J=12.47 Hz, 1H, —OH), 3.73-3.89 (m, 3H, —CH$_2$—CH$_3$+—CHH—), 3.94-3.99 (s, 1H, —CHH—), 4.01 (q, 2H, —CH$_2$—CH$_3$), 7.03 (d, J=1.71 Hz, 1H, Ar—H-4), 7.19-7.32 (m, 2H, Ar—H-2, H-6). $^1$H NMR spectrum of the product was consistent with the suggested structure of the product.

Step 2. Preparation of
3-(3-di-tert-butylphenyl)pentanedioic Acid

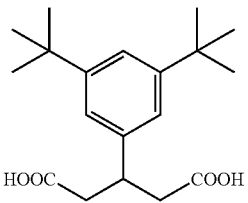

To a solution of diethyl 2-(3,5-di-tert-butyl-phenyl)-4-hydroxy-4-methyl-6-oxo-cyclohexane-1,3-dicarboxylate (2.70 g, 5.86 mmol) from step 1 in abs. ethyl alcohol (15.0 mL) was added 50% sodium hydroxide solution (20 mL) and the reaction mixture was heated under refluxing conditions for 1 h to give a beige suspension. After 1.5 h, the reaction mixture was cooled to room temperature, and ethanol was evaporated in vacuo to give a cream-beige precipitate. The precipitate was dissolved in water (50 mL) and diluted with ethyl acetate (50 mL) and stirred at room temperature for 15 min. The aqueous layer and the organic layers were separated. The aqueous layer was washed with ethyl acetate (1×25 mL) to remove residual byproduct. The aqueous layer was acidified with conc. HCl until pH=1 to afford a cream crystalline solid. The solid was filtered, washed with water (3×25 mL) and dried in-vacuo to afford a cream-yellow crystalline solid (1.767 g, yield 94%). LC-MS analysis of the solid showed the desired product's mass: m/z 303 (M+H–H$_2$O), m/z 321 (M+H) and m/z 343 (M+Na); Calculated for C$_{19}$H$_{28}$O$_4$: 320.43. $^1$H NMR (400 MHz, DMSO-d$_6$): δ 1.26 (s, 18H, 2×t-C$_4$H$_9$—), 2.50 (dd J=15.75 Hz and 7.0 Hz, 2H, —CH—CH$_2$—COOH, partially hidden under DMSO peak), 2.62 (dd, J=15.75 Hz and 7.0 Hz, 2H, HOOC—CH$_2$—CH—), 3.43 (quin, J=7.52 Hz, 1H, —CH$_2$—CH—CH$_2$—COOH), 7.08 (d, J=1.71 Hz, 2H, H-2 and H-6), 7.20 (t, J=1.71 Hz, 1H, H-4), 12.04 (s, 2H, 2×—COOH); 1H NMR spectrum of the product was consistent with the suggested structure of the product.

Step 3. Preparation of 4-(3,5-di-tert-butylphenyl) tetrahydropyran-2,6-dione

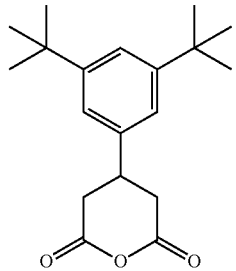 [SMILES: CC(C)(C)c1cc(C2CC(=O)OC(=O)C2)cc(C(C)(C)C)c1]

A suspension of 3-(3,5-di-tert-butylphenyl)pentanedioic acid (2.13 g, 6.647 mmol) from step 2 in acetic anhydride (40.0 mL) was heated under refluxing conditions to give a yellow-orange solution within 10 min. The heating was discontinued after 4 h and the reaction mixture was cooled to room temperature. The solvent was evaporated in vacuo to afford a light brown viscous liquid which solidified to a light brown crystalline solid at room temperature. The crude product was crystallized from hexanes containing dichloromethane to afford an almost colorless crystalline solid, the solid was filtered, washed with hexanes and dried in vacuo to afford an almost colorless crystalline solid (1.90 g, yield 95%). LC-MS analysis of the crystallized solid showed the desired product's mass: m/z 303 (M+H) and m/z 325 (M+Na); Calculated for C$_{19}$H$_{26}$O$_3$: 302.41. $^1$H NMR (400 MHz, CDCl$_3$): δ 1.33 (s, 18H, 2×tert-C$_4$H$_9$—), 2.89 (dd, J=17.36, 11.49 Hz, 2H, —CH$_2$—), 3.14 (dd, J=17.36, 4.40 Hz, 2H, —CH$_2$—), 3.42 (tt, J=11.55, 4.34 Hz, 1H, —CH$_2$—CH—CH$_2$—), 7.02 (d, J=1.47 Hz, 2H, H-2, H-6), 7.40 (t, J=1.71 Hz, 1H, H-3). $^1$H NMR spectrum of the product was consistent with the suggested structure of the product.

Step 4. Preparation of 3-(3,5-di-tert-butylphenyl)-5-ethoxy-5-oxo-pentanoic Acid

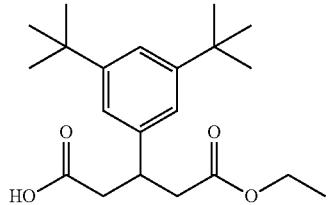 [SMILES: CCOC(=O)CC(CC(=O)O)c1cc(C(C)(C)C)cc(C(C)(C)C)c1]

A solution of 4-(3,5-di-tert-butylphenyl)tetrahydropyran-2,6-dione from step 3 in a mixture of anhydrous pyridine and abs. ethyl alcohol was heated under reflux for 1.5 h to give a light tan solution. The solvent was evaporated in vacuo to afford a light tan viscous residue. The residue was dissolved in ethyl acetate (25 mL). The ethyl acetate layer washed first with 1N HCl (25 mL) and then with water (1×25 mL) and finally with brine (1×10 mL). The ethyl acetate layer was dried over anhydrous Na$_2$SO$_4$, filtered and evaporated in vacuo to afford a light tan viscous liquid which solidified to a light tan to cream foamy solid (618.0 mg, yield 98%). LC-MS analysis of the crude product showed the desired product with a purity >95% and the desired product's mass: m/z 331 (M+H-H$_2$O), m/z 349 (M+H) and m/z 371 (M+Na);

Calculated for $C_{21}H_{32}O_4$: 348.48. $^1$H NMR (400 MHz, CDCl$_3$): δ 1.14 (t, J=7.09 Hz, 3H, CH$_3$—CH$_2$—), 1.31 (s, 18H, 2×tert-C$_4$H$_9$—), 2.59-2.85 (m, 4H, —CH$_2$—CH—CH$_2$—), 3.64 (quin J=7.34 Hz, 1H, —CH$_2$—CH—CH$_2$—), 4.05 (q, J=7.09 Hz, 2H, —O—CH$_2$—CH$_3$), 7.05 (d, J=1.71 Hz, 2H, H-2, H-6), 7.28 (s, 1H, H-4), —COOH peak was hidden under baseline. $^1$H NMR spectrum of the product was consistent with the suggested structure of the product.

Step 5. Preparation of diethyl 3-(3,5-di-tert-butylphenyl)-5-oxo-heptanedioate

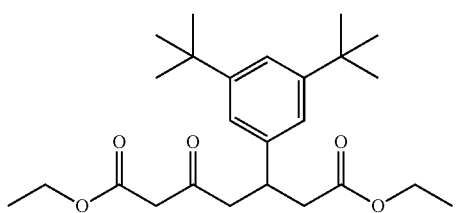 [SMILES: CCOC(=O)CC(=O)CC(CC(=O)OCC)c1cc(C(C)(C)C)cc(C(C)(C)C)c1]

To a solution of 3-(3,5-di-tert-butylphenyl)-5-ethoxy-1-oxo-pentanoic acid (618.0 mg, 1.773 mmol) from step 4 and Meldrum's acid (294.95 mg, 2.047 mmol) in anhydrous DMF under nitrogen atmosphere and at 0° C. (ice-bath) was slowly added diethyl cyanophosphonate (290 μL, 1.911 mmol), followed by triethylamine (900 μL, 6.457 mmol). The reaction mixture was stirred at 0° C. for 30 min to give a yellow-orange solution. After 30 min, the reaction mixture was warmed to room temperature and stirred at room temperature overnight under nitrogen atmosphere to give a dark orange solution. The reaction mixture was quenched into an ice cold 2 N HCl (10 mL) and stirred for 5 min to give a cream waxy residue. The mixture was diluted with water (20 mL) and extracted with ethyl acetate (2×25 mL). The organic layer were combined, washed with water (1×23 mL), brine (1×25 mL), dried over anhydrous Na$_2$SO$_4$, filtered and evaporated in vacuo to give a yellow-orange viscous liquid.

The viscous oil was dissolved in absolute ethanol (20.0 mL) and the reaction mixture was refluxed for 3 h to give an orange solution. LC-MS analysis of the reaction mixture after 3 h showed the desired product's mass: m/z 373 (M+H—C$_2$H$_5$O—), m/z 419 (M+H), and m/z 441 (M+Na). The solvent was evaporated in-vacuo to afford a yellow-orange viscous residue (696.3 mg). The crude product was dissolved in dichloromethane and applied to 24 g RediSep Silica column and was purified on a CombiFlashRf by silica-gel flash chromatography using 0 to 30% EtOAc in hexanes. The pure fractions were mixed together and the mixture was evaporated in vacuo to afford a colorless to a very pale yellow foamy solid (430.5 mg, yield 58%). LC-MS analysis of the solid showed the desired product with a purity >95% and the desired product's mass: m/z 373 (M+H-C$_2$H$_5$O—), m/z 419 (M+H), m/z 441 (M+Na); Calculated for $C_{25}H_{38}O_5$: 418.57. $^1$H NMR (400 MHz, CDCl$_3$): δ 1.15 (t, J=7.09 Hz, 3H, CH$_3$—CH$_2$—CO—), 1.25 (t, J=7.09 Hz, 3H, CH$_3$—CH$_2$—CO—), 1.31 (s, 18H, 2×tert-C$_4$H$_9$—), 2.59-2.74 (m, 2H, —CH$_2$—CH—CH$_2$—), 2.86-3.04 (m, 2H, —CH$_2$—CH—CH$_2$—), 3.33 (s, 2H, b-CO—CH$_2$—CO—), 3.70 (quin, J=7.21 Hz, 1H, —CH$_2$—CH—CH$_2$—), 4.04 (q, J=7.09 Hz, 2H, CH$_3$—CH$_2$—CO—), 4.16 (q, J=7.17 Hz, 2H, CH$_3$—CH$_2$—CO—), 7.02-7.06 (m, 2H, Ph-H-2, H-6), 7.25-7.28 (m, 1H, Ph-H-4). $^1$H NMR spectrum of the product was consistent with the suggested structure of the product Step 6. Preparation of ethyl 3-(3,5-di-tert-butylphenyl)-4-(5-hydroxy-1-methyl-pyrazol-3-yl)butanoate

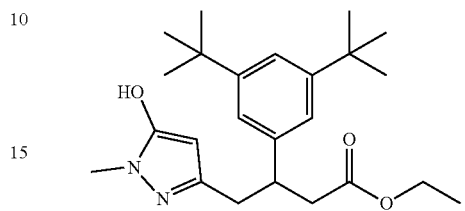

To a solution of diethyl 3-(3,5-di-tert-butylphenyl)-5-oxo-heptanedioate (430.50 mg, 1.028 mmol) from step 5 in absolute ethyl alcohol (5.0 mL) was added methylhydrazine (70 μL, 1.33 mmol) at room temperature to give a colorless solution. The reaction mixture was heated under refluxing conditions overnight to give a very pale yellow solution. The solvent was evaporated in vacuo to afford a dirty yellow foamy solid. The crude product was dissolved in ethyl acetate containing a trace of DCM and applied to 12 g RediSep Silica column and was purified by silica-gel flash chromatography using 0 to 20% methanol in EtOAc. The pure fractions were mixed together and the mixture was evaporated in vacuo to afford a very pale yellow viscous liquid, dried on a vacuum pump to afford a pale yellow to cream solid (355.5 mg, yield 86%). LC-MS analysis of the solid showed the desired product's mass: m/z 401 (M+H), m/z 423 (M+Na), and m/z 823 (2M+Na); Calculated for $C_{24}H_{36}N_2O_3$: 400.56. $^1$H NMR (400 MHz, CDCl$_3$): δ 1.18 (t, J=7.09 Hz, 3H, CH$_3$—CH$_2$—O—) 1.30 (s, 18H, 2×tert-C$_4$H$_9$—), 2.64-2.88 (m, 4H, —CH$_2$—CH—CH$_2$—, two diastereotopic —CH$_2$—), 2.81 (s, 1H, —OH), 3.24 (s, 3H, N—CH$_3$), 3.46 (quin, J=7.52 Hz, 1H, —CH$_2$—CH—CH$_2$—), 4.07 (q, J=7.10 Hz, 2H, —O—CH$_2$—CH$_3$), 7.02 (d, J=1.71 Hz, 2H, H-2, H-6), 7.25-7.29 (m, 2H, Py-H-4 and Ph-H$_4$). $^1$H NMR spectrum of the product was consistent with the suggested structure of the product.

Step 7. Preparation of ethyl 3-(3,5-di-tert-butylphenyl)-4-[1-methyl-5-[2-(5,6,7,8-tetrahydro-1,8-naphthyridin-2-yl)ethoxyl]pyrazol-3-yl]butanoate

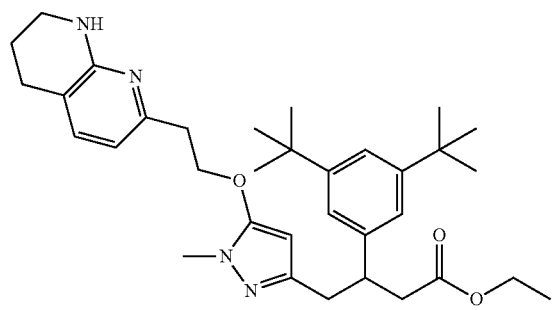 [SMILES: CCOC(=O)CC(Cc1cc(OCCc2ccc3c(n2)NCCC3)n(C)n1)c1cc(C(C)(C)C)cc(C(C)(C)C)c1]

To a solution of triphenylphosphine (262.5 mg, 1.00 mmol) in anhydrous THF (5 mL) at −10° C. (salt-ice bath) was added DIAD (200 μL, 1.02 mmol) drop wise to give a yellow suspension within 5 min. The reaction mixture was stirred at −10° C. for another 20 min. To the above reaction mixture was added drop wise a solution of 2-(5,6,7,8-tetrahydro-1,8-naphthyridin-2-yl)ethanol (155.7 mg, 0.874 mmol) in THF (4.0 mL). The reaction mixture was stirred at −10° C. for 20 min and then a solution of ethyl 3-(3,5-di-tert-butylphenyl)-4-(5-hydroxy-1-methyl-pyrazol-3-yl)butanoate (350.0 mg, 0.874 mmol) from step 6 in anhydrous THF (5.0 mL) was added in one portion to give an orange solution. The reaction mixture was warmed up to room temperature after stirring for 10 min at −10° C. and stirred overnight at room temperature. The reaction mixture was quenched with a saturated NH$_4$Cl solution (25 mL) and extracted with ethyl acetate (2×25 mL). The combined organic layer was washed with brine (1×25 mL), dried over anhydrous Na$_2$SO$_4$, filtered and evaporated in vacuo to afford a yellow foamy/gummy residue. The crude product was purified first by silica-gel flash chromatography using a RediSep 24 g silica column and elution with 0-2% methanol in ethyl acetate to afford the desired product as a yellow solid (1.092 g). LC-MS analysis of the product showed the desired product with a purity >70%. The second purification of the impure product by reverse-phase preparative HPLC using a RediSep C18 column and a gradient 10-60% acetonitrile in water containing 0.05% TFA afforded the desired product after lyophilization as a pale yellow foamy solid (244.3 mg; yield 50%). LC-MS analysis of the solid showed the desired product's mass: m/z 561 (M+H) and m/z 583 (M+Na); Calcd for $C_{34}H_{48}N_4O_3$: 560.78. $^1$H NMR (400 MHz, CDCl$_3$): δ 1.08 (t, J=7.09 Hz, 3H), 1.29 (s, 18H, 2×tert-C$_4$H$_9$—), 1.91-2.00 (m, 1H), 2.56-2.72 (m, 2H), 2.78 (t, I=6.24 Hz, 2H), 2.81-2.96 (m, 2H), 3.16 (t, J=5.99 Hz, 2H), 3.38-3.47 (m, 1H), 3.52 (t, J=4.65 Hz, 2H), 3.56 (s, 3H, N—CH$_3$), 3.97 (q, J=7.17 Hz, 2H), 4.29 (t, J=5.99 Hz, 2H), 5.36 (s, 1H), 6.38 (d, J=7.34 Hz, 1H), 7.04 (t, J=1.71 Hz, 2H), 7.24 (t, J=1.71 Hz, 2H), 7.27 (s, 1H), 7.33 (d, J=7.34 Hz, 1H), 10.39 (brs, 1H). $^1$H NMR spectrum of the product was consistent with the suggested structure of the product.

Step 8. Preparation of 3-(3,5-di-tert-butylphenyl)-4-[1-methyl-5-[2-(5,6,7,8-tetrahydro-1,8-naphthyridin-2-yl)ethoxy]pyrazol-3-yl]butanoic Acid Example 18

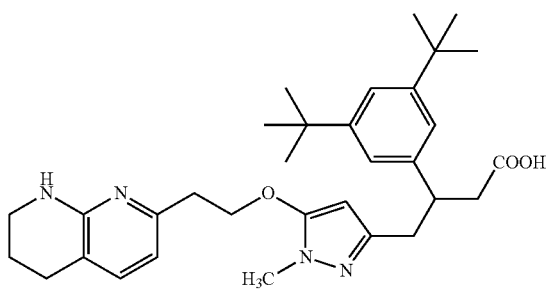 [SMILES: Cn1nc(CC(CC(=O)O)c2cc(C(C)(C)C)cc(C(C)(C)C)c2)cc1OCCc1ccc2c(n1)NCCC2]

To a solution of ethyl 3-(3,5-di-tert-butylphenyl)-4-[1-methyl-5-[2-(5,6,7,8-tetrahydro-1,8-naphthyridin-2-yl)ethoxy]pyrazol-3-yl]butanoate (235.0 mg, 0.419 mmol) from step 7 in anhydrous THF (3 mL) was added 1 N aqueous NaOH solution (4.0 mL) and the resulting solution was stirred at 50° C. overnight. The reaction mixture was acidified with 2 N HCl and the solvent was evaporated in-vacuo to afford a very pale yellow crystalline/gummy residue. The crude residue was purified by reverse-phase preparative HPLC using a RediSep C18 column and a gradient 10-60% acetonitrile in water containing 0.05% TFA. The pure fractions were mixed together and the mixture was evaporated in vacuo to afford a colorless gummy residue. The residue was dissolved in a mixture of water and acetonitrile and the solution was lyophilized to afford the desired product, Example 18, as a colorless lyophilized powder (240 mg).

LC-MS analysis of the solid showed the desired product's mass: m/z 533 (M+H) and m/z 555 (M+Na). Calculated for $C_{32}H_{44}N_4O_3$: 532.73. $^1$H NMR (400 MHz, DMSO-d$_6$): δ 1.24 (s, 18H, 2×tert-C$_4$H$_9$—), 1.78-1.87 (m, 2H), 2.58 (d, J=5.62 Hz, 1H), 2.60-2.69 (m, 3H), 2.74 (t, J=6.11 Hz, 2H), 3.09 (t, J=5.99 Hz, 2H), 3.24-3.34 (m, 1H), 3.39 (s, 3H), 3.40-3.44 (m, 1H), 4.23 (t, J=5.99 Hz, 2H), 5.40 (s, 2H), 6.69 (d, J=7.34 Hz, 1H), 7.02 (d, J=1.71 Hz, 1H), 7.11-7.22 (m, 1H), 7.64 (d, J=7.34 Hz, 1H), 8.12 (brs, 1H), 13.67 (brs; 1H). $^1$H NMR spectrum of the product was consistent with the suggested structure of the product.

Example 19

Preparation of 3-(3-bromo-5-(1-(difluoromethyl)cyclopropyl)phenyl)-4-(1-methyl-5-(2-(5,6,7,8-tetrahydro-1,8-naphthyridin-2-yl)ethoxy)-1H-pyrazol-3-yl)butanoic Acid

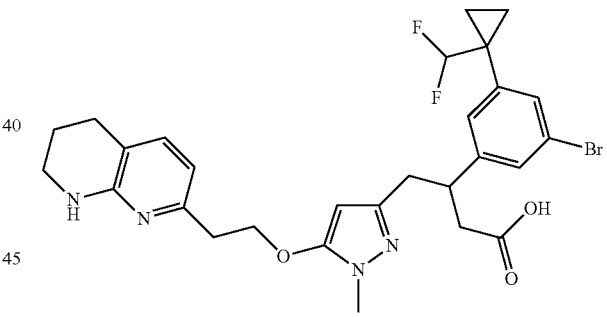

Example 19 was prepared in analogous manner to Example 1, using 3-bromo-5-(1-(difluoromethyl)cyclopropyl)benzaldehyde (synthesized according to Scheme 8) as the required benzaldehyde in the reaction Scheme 3. The crude product was purified by prep-HPLC (column: Phenomenex Gemini C18 250*50 10μ; mobile phase: [water (0.225% FA)-ACN]; B %: 23%-53%, 11.2 min). The HPLC effluent was lyophilized to give the title compound as a white solid (200 mg). LC-MS analysis of the solid showed the desired product's mass: m/z 589 (M+H); Calcd for $C_{28}H_{31}BrF_2N_4O_3$: 589.47. $^1$H NMR (400 MHz, CD$_3$OD): δ ppm 0.91 (br d, J=2.21 Hz, 2H) 1.08-1.15 (m, 2H) 1.84-1.96 (m, 2H) 2.51-2.61 (m, 1H) 2.62-2.85 (m, 5H) 2.94-3.10 (m, 2H) 3.34-3.47 (m, 6H) 4.28 (t, J=6.28 Hz, 2H) 5.40 (s, 1H) 5.45-5.80 (m, 1H) 6.52 (d, J=7.28 Hz, 1H) 7.20 (s, 1H) 7.34-7.39 (m, 2H). $^{19}$FNMR (400 MHz, CD$_3$OD): δ ppm −117.89-118.04.

Scheme 8

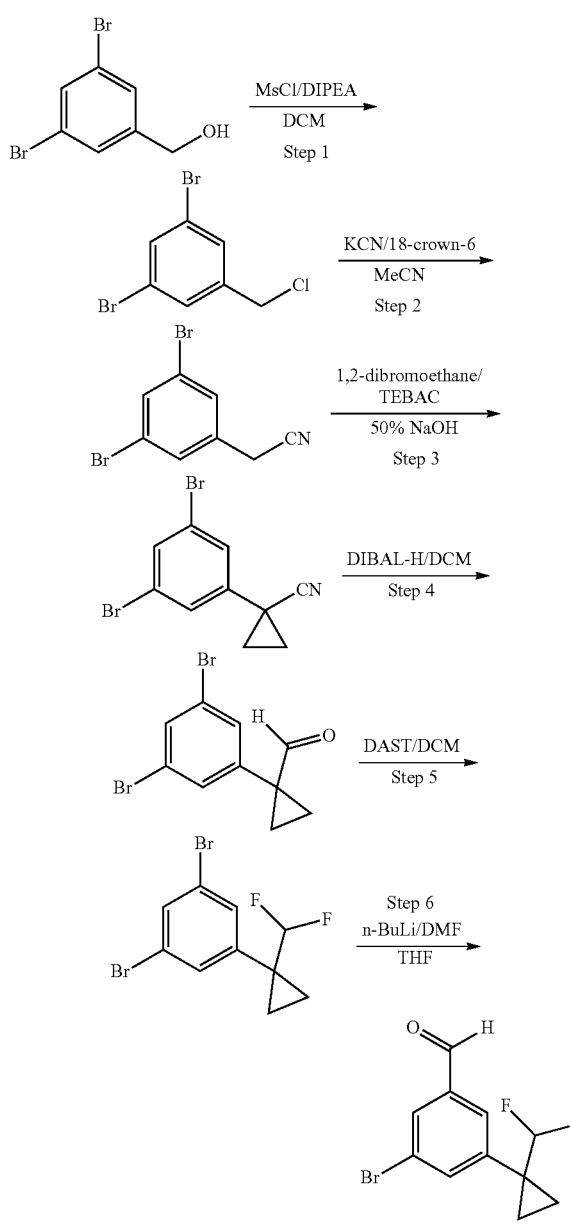

Step 1. Preparation of
1,3-dibromo-5-(chloromethyl)benzene

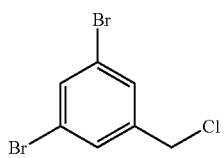

(3,5-Dibromophenyl)methanol (10 g, 37.60 mmol, 1 eq) was dissolved in anhydrous DCM (100 mL) in a dried flask under nitrogen. The reaction mixture was cooled to 0° C. and stirred under nitrogen atmosphere. DIEA (9.72 g, 75.21 mmol, 13.10 mL, 2 eq) was added drop wise to the above solution, after 10 minutes of stirring at 0° C., MsCl (6.46 g, 56.41 mmol, 4.37 mL, 1.5 eq) was added drop-wise to the above reaction mixture. Finally, the reaction mixture was allowed to stir at 26° C. for 2 hrs. TLC (Petroleum ehter: EtOAc=5:1, uv & stained by KMnO$_4$) showed starting alcohol was consumed up and two new spots were formed. Reaction mixture was washed with water (80 mL) followed by NaHCO$_3$ (80 mL) solution and brine (80 mL), dried over anhydrous Na$_2$SO$_4$, filtered and evaporated to dryness to give the desired product as a brown liquid (12.11 g). The above liquid was used directly for the next step without further purification. $^1$H NMR (400 MHz, CHLOROFORM-d) δ ppm 3.04 (s, 3H) 4.49 (s, 2H) 5.16 (s, 2H) 7.48 (d, J=1.76 Hz, 2H) 7.50 (d, J=1.76 Hz, 2H) 7.63 (t, J=1.76 Hz, 1H) 7.70 (t, J=1.76 Hz, 1H).

Step 2. Preparation of
2-(3,5-dibromophenyl)acetonitrile

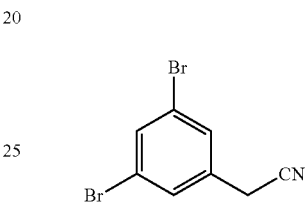

A suspension of 1,3-dibromo-5-(chloromethyl)benzene (12.11 g, 42.58 mmol, 1 eq), KCN (13.86 g, 212.92 mmol, 9.12 mL, 5 eq) and 1,4,7,10,13,16-hexaoxacyclooctadecane (1.13 g, 4.26 mmol, 0.1 eq) in CH$_3$CN (150 mL) was stirred for 12 hr at 28° C. A brown suspension was observed. TLC (petroleum ether: ethyl acetate=7:1, uv & stained by I$_2$) showed starting material was consumed up and one main new spot was formed. The reaction mixture was concentrated under reduced pressure. The resulting residue was taken up in water (100 mL) and extracted with Ethyl acetate (3×80 mL), organic layer was dried over sodium sulfate concentrated under reduced pressure to afford crude product as a brown residue. The residue was purified by flash silica gel chromatography (ISCO®; 80 g SepaFlash® Silica Flash Column, Eluent of 0~9% Ethyl acetate/Petroleum ethergradient @ 30 mL/min) to give the desired product as a light yellow solid (7.58 g, 27.57 mmol, 65% yield). $^1$H NMR (400 MHz, CHLOROFORM-d) δ ppm 3.73 (d, J=0.66 Hz, 2H) 7.36-7.55 (m, 2H) 7.67 (t, J=1.65 Hz, 1H).

Step 3. Preparation of
1-(3,5-dibromophenyl)cyclopropanecarbonitrile

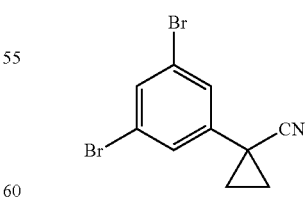

To a stirred solution of benzyl(triethyl)ammonium; chloride (303.21 mg, 1.33 mmol, 0.05 eq) in NaOH (43 mL, 50%) was added to a 2-(3,5-dibromophenyl)acetonitrile (7.32 g, 26.62 mmol, 1 eq), 1,2-dibromoethane (15 g, 79.87 mmol, 6.03 mL, 3 eq) solution at 0° C. The resulting mixture was stirred for 12 hrs at 26° C. TLC (petroleum ether: ethyl acetate=15:1) showed starting material was consumed up and one main new spot was formed above. The reaction mixture was poured into ice water (60 mL) and extracted with ethyl acetate (3×80 mL). Organic layer was dried over sodium sulfate and concentrated under reduced pressure to give a brown crude product. The residue was purified by flash silica gel chromatography (ISCO®; 80 g SepaFlash® Silica Flash Column, Eluent of 0~5% Ethyl acetate/Petroleum ether gradient @ 40 mL/min) to give the desired product as a yellow solid (7.1 g, 23.59 mmol, 88.60% yield). $^1$H NMR (400 MHz, CHLOROFORM-d) δ ppm 1.39-1.47 (m, 2H) 1.75-1.83 (m, 2H) 7.37 (d, J=1.76 Hz, 2H) 7.61 (t, J=1.76 Hz, 1H).

Step 4. Preparation of 1-(3,5-dibromophenyl)cyclopropanecarbaldehyde

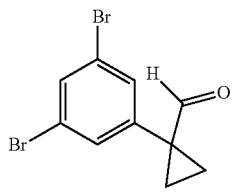

To a stirred solution of 1-(3,5-dibromophenyl)cyclopropanecarbonitrile (8.3 g, 27.58 mmol, 1 eq) in DCM (305 mL) was added DIBAL-H (1 M, 38.61 mL, 1.4 eq) at −78° C. The resulting mixture was stirred for 2 hr at −78° C. TLC (Petroleum ether: ethyl acetate=4:0.2 mL, stained by KMnO$_4$ & UV) showed a new spot was formed below starting material and starting material was consumed up. The reaction mixture was quenched with 2N HCl (100 mL) and stirred for 6 min, diluted with H$_2$O (60 mL), then extracted with ethyl acetate (3×150 mL). Organic layer was washed with saturated NaHCO$_3$ solution (150 mL), followed by brine (150 mL), dried over sodium sulfate and concentrated under reduced pressure to afford 8.9 g of crude product as yellow solid. The crude was used directly for the next step without further purification. $^1$H NMR (400 MHz, CHLOROFORM-d) δ ppm 1.37-1.47 (m, 2H) 1.55-1.69 (m, 2H) 7.40 (d, J=1.76 Hz, 2H) 7.63 (t, J=1.76 Hz, 1H) 9.10 (s, 1H).

Step 5. Preparation of 1,3-dibromo-5-(1-(difluoromethyl)cyclopropyl)benzene

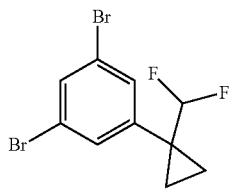 [SMILES: FC(F)C1(c2cc(Br)cc(Br)c2)CC1]

To a stirred solution of 1-(3,5-dibromophenyl)cyclopropanecarbaldehyde (8.9 g, 29.28 mmol, 1 eq) in DCM (126 mL), DAST (18.88 g, 117.11 mmol, 15.5 mL, 4 eq) was added slowly at 0° C. The resulting mixture was stirred for 12 hrs at 26° C. TLC (Petroleum ether: ethyl acetate=20:1, UV & stained by 12) showed starting material was consumed up and a new main spot with low polarity was formed above. The reaction mixture was washed with water (80 mL*2). Organic layer was dried over sodium sulfate and concentrated under reduced pressure to afford a brown residue. The residue was purified by flash silica gel chromatography (ISCO®; 20 g SepaFlash® Silica Flash Column, Eluent of 0~5% Ethyl acetate/Petroleum ether gradient @ 30 mL/min) to give the desired product as an off-white solid (5.92 g, 18.15 mmol, 61.990/% yield). $^1$HNMR (400 MHz, CHLOROFORM-d) δ ppm 0.93-1.04 (m, 2H) 1.13-1.22 (m, 2H) 5.40-5.75 (m, 1H) 7.49 (d, J=1.51 Hz, 2H) 7.61 (t, J=1.63 Hz, 1H); $^{19F}$NMR (400 MHz, CHLOROFORM-d) δ ppm −116.73.

Step 6. 3-bromo-5-(1-(difluoromethyl)cyclopropyl)benzaldehyde

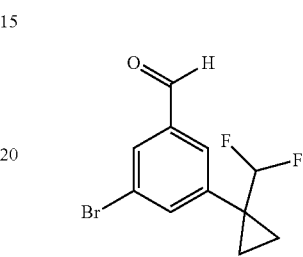

To a stirred solution of 1,3-dibromo-5-[1-(difluoromethyl)cyclopropyl]benzene (5.52 g, 16.93 mmol, 1 eq) in THF (82 mL) was added n-BuLi (2.5 M, 6.77 mL, 1.0 eq) drop wise at −78° C. The resulting mixture was stirred for 10 min at −78° C. and quenched with DMF (1.86 g, 25.4 mmol, 1.95 mL, 1.5 eq) at −78° C., and stirred for 1 hr −78° C. TLC (Petroleum ether: ethyl acetae=10:1, uv and KMnO$_4$) showed starting material was consumed up and one main new spot was formed below. Sat. NH$_4$Cl (15 mL) was added to the reaction mixture and diluted with H$_2$O (70 mL), then extracted with ethyl acetate (3×60 mL). Organic layer was dried over sodium sulfate and concentrated under reduced pressure to afford light yellow residue. The residue was purified by flash silica gel chromatography (ISCO®; 12 g SepaFlash® Silica Flash Column, Eluent of 0~10% Ethyl acetate/Petroleum ether gradient @ 30 mL/min) to give the desired product as an off-white solid (1.5 g, 5.45 mmol, 32.20% yield). $^1$H NMR (400 MHz, CHLOROFORM-d) δ ppm 1.01-1.08 (m, 2H) 1.21-1.28 (m, 2H) 5.43-5.74 (m, 1H) 7.83 (dt, J=11.30, 1.63 Hz, 2H) 7.94-7.98 (m, 1H) 9.96 (s, 1H).

Example 20

Preparation of 3-(3-cyano-5-(1-(difluoromethyl)cyclopropyl)phenyl)-4-(1-methyl-5-(2-(5,6,7,8-tetrahydro-1,8-naphthyridin-2-yl)ethoxy)-1H-pyrazol-3-yl)butanoic Acid Scheme 9

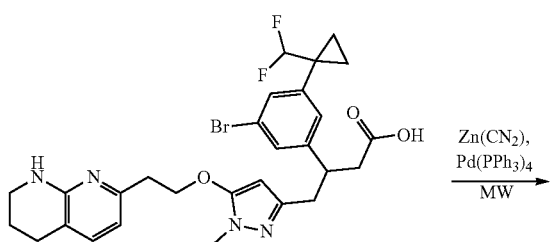

Example 19

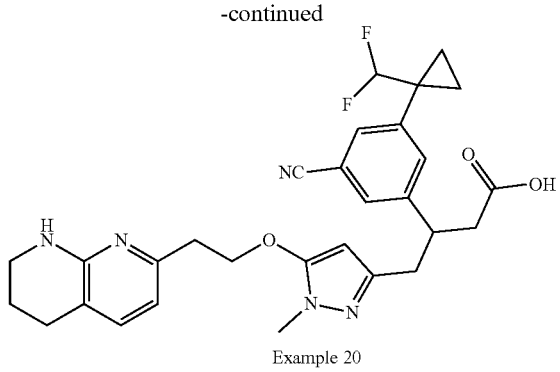

Example 20

A mixture of 3-[3-bromo-5-[1-(difluoromethyl)cyclopropyl]phenyl]-4-[1-methyl-5-[2-(5,6,7,8-tetrahydro-1,8-naphthyridin-2-yl)ethoxy]pyrazol-3-yl]butanoic acid (100 mg, 155.11 μmol, 1 eq, FA) and dicyanozinc (54.6 mg, 465.3 μmol, 29.5 μL, 3 eq) in DMF (6 mL) in a 25 mL microwave vial was evacuated and back-filled with $N_2$ (3×). Palladium triphenylphosphane (17.9 mg, 15.5 μmol, 0.1 eq) was added. The reaction vial was sealed, and the reaction mixture was again degassed and back-filled with $N_2$ (3×), and then stirred at 120° C. for 90 min under micro-wave irradiation. LCMS showed starting bromide was consumed up and the desired product was the main peak. HPLC showed 66% of the desired product was formed. The filtrate was purified by Pre-HPLC (column: Boston Green ODS 150*30 5μ; mobile phase: [water (0.1%/TFA)-ACN]; B %: 20%-50%, 7 min). After lyophilization, 85 mg of desired product was obtained a white solid (85 mg, 129.28 μmol, 83% yield, 98.8% purity, TFA). LC-MS analysis of the solid shows the desired product's mass: m/z 536 (M+H); Calcd for $C_{29}H_{31}F_2N_5O_3$: 535.24. $^1$H NMR (400 MHz, $CD_3OD$) δ ppm 0.92-1.01 (m, 2H) 1.13-1.20 (m, 2H) 1.90-2.00 (m, 2H) 2.62-2.94 (m, 6H) 3.11-3.19 (m, 2H) 3.42-3.53 (m, 6H) 4.29 (td, J=6.06, 2.20 Hz, 2H) 5.39 (s, 1H) 5.45-5.78 (m, 1H) 6.68 (d, J=7.50 Hz, 1H) 7.48-7.53 (m, 2H) 7.54-7.58 (m, 1H) 7.60 (d, J=7.28 Hz, 1H); $^{19}$FNMR (400 MHz, $CD_3OD$) δ ppm −77.3, −117.4.

Example 21

Preparation of 3-(3-(1-(difluoromethyl)cyclopropyl)-5-fluorophenyl)-4-(1-methyl-5-(2-(5,6,7,8-tetrahydro-1,8-naphthyridin-2-yl)ethoxy)-1H-pyrazol-3-yl)butanoic Acid

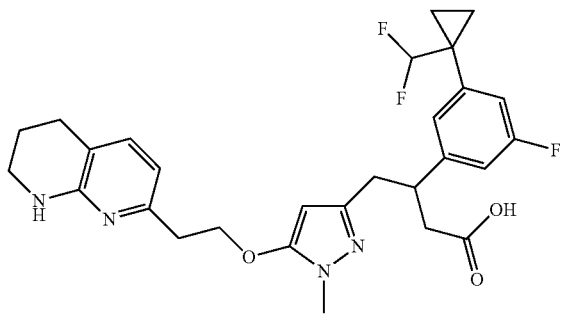 [SMILES: Cn1nc(CC(CC(=O)O)c2cc(F)cc(C3(C(F)F)CC3)c2)cc1OCCc1ccc2c(n1)NCCC2]

Example 21 was prepared in analogous manner to Example 19, using (3-bromo-5-fluorophenyl)methanol in place of 3,5-dibromophenyl)methanol in the reaction Scheme 8. The crude product was purified by prep-HPLC (Condition: column: Boston pH-lex 150*25 10 μm; mobile phase: [water (0.1% TFA)-ACN]; B %: 31%-61%, 8 min) to give desired compound (118.6 mg, yield 45%, purity 97.2%) as a white solid. LC-MS analysis of the solid showed the desired product's mass: m/z 529.1 (M+H); Calcd for $C_{21}H_{31}F_3N_4O_3$: 528.57. $^1$H NMR (400 MHz, $CD_3OD$): δ ppm=7.60 (d. J=7.5 Hz, 1H), 7.01 (s, 1H), 6.96-6.87 (m, 2H), 6.67 (d, J=7.3 Hz, 1H), 5.78-5.45 (m, 1H), 5.39 (s, 1H), 3.52-3.47 (m, 2H), 3.46-3.40 (m, 3H), 3.14 (t, J=5.8 Hz, 2H), 2.89-2.57 (m, 7H), 1.98-1.90 (m, 2H), 1.14-1.07 (m, 2H), 0.92 (br d, J=2.2 Hz, 2H). 19F NMR (376 MHz, $CD_3OD$): δ ppm=−77.39 (br s, 1F), −115.84 (t, J=9.5 Hz, 1F), −117.83--117.96 (m, 1F), −117.97--118.09 (m, 1F).

Example 22

Preparation of 3-(3-chloro-5-(1-(difluoromethyl)cyclopropyl)phenyl)-4-(1-methyl-5-(2-(5,6,7,8-tetrahydro-1,8-naphthyridin-2-yl)ethoxy)-1H-pyrazol-3-yl)butanoic Acid

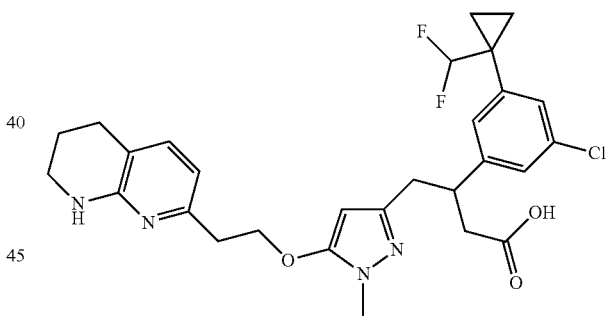

Example 22 was prepared in analogous manner to Example 19, using (3-bromo-5-chlorophenyl)methanol in place of 3,5-dibromophenyl)methanol in the reaction Scheme 8. The crude product was purified by prep-HPLC Condition: column: Boston Green ODS 150*30 5μ; mobile phase: [water (0.1% TFA)-ACN]; B %: 25%-55%, 8 min) to give the title compound (88 mg, 133 μmol, 44% yield, 100% purity, TFA) was obtained as a white solid. LC-MS analysis of the liquid shows the desired product's mass: m/z 545 (M+H) $^1$H NMR (400 MHz, $CD_3OD$): δ ppm=7.57 (d, J=7.3 Hz, 1H), 7.20 (t, J=1.7 Hz, 1H), 7.16 (t, J=1.7 Hz, 1H), 7.10 (s, 1H), 6.64 (d, J=7.3 Hz, 1H), 5.74-5.55 (m, 1H), 5.43 (s, 1H), 4.35-4.23 (m, 2H), 3.51-3.46 (m, 2H), 3.42-3.33 (m, 1H), 3.29 (td, J=1.6, 3.3 Hz, 3H), 3.17-3.08 (m, 2H), 2.91-2.60 (m, 6H), 1.93 (td, J=6.1, 11.9 Hz, 2H), 1.14-1.06 (m, 2H), 0.95-0.85 (m, 2H).

Example 23

Preparation of 3-(3-(1-(difluoromethyl)cyclopropyl)-5-(trifluoromethyl)phenyl)-4-(1-methyl-5-(2-(5,6,7,8-tetrahydro-1,8-naphthyridin-2-yl)ethoxy)-1H-pyrazol-3-yl)butanoic Acid

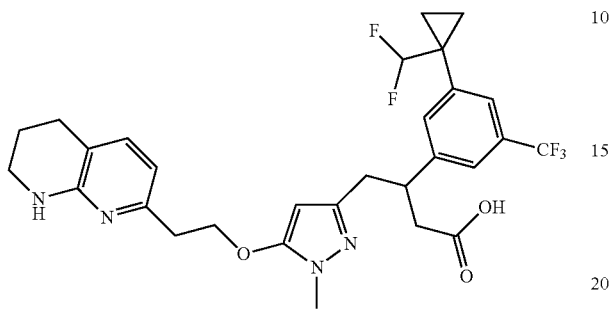

Example 23 was prepared in analogous manner to Example 19, using (3-bromo-5-(trifluoromethyl)phenyl)methanol in place of 3,5-dibromophenyl)methanol in the reaction Scheme 8. The crude product was purified by prep-HPLC (TFA condition: column: Boston Green ODS 150*30 5μ; mobile phase: [water (0.1% TFA)-ACN]; B %: 20%-50%, 8 min). The title compound (55 mg, 95 μmol, 60% yield, 100% purity) was obtained as a white solid. $^1$H NMR, $^{19}$F NMR, LC-MS, and HMBC were consistent with the title compound structure. $^1$H NMR (400 MHz, CD$_3$OD) δ ppm 7.60 (d, J=7.5 Hz, 1H), 7.49 (s, 1H), 7.46 (s, 1H), 7.42 (s, 1H), 6.67 (d, J=7.3 Hz, 1H), 5.80-5.45 (m, 1H), 5.42 (s, 1H), 4.34-4.24 (m, 2H), 3.53-3.47 (m, 3H), 3.45 (s, 3H), 3.14 (t, J=6.1 Hz, 2H), 2.94-2.64 (m, 6H), 1.95 (quin, J=6.0 Hz, 2H), 1.20-1.14 (m, 2H), 1.00-0.93 (m, 2H); $^{19}$F NMR (376 MHz, CD$_3$OD) −63.9, −77.4, −117.4, −117.6.

Example 24

Preparation of 3-(3-fluoro-5-(1,1,1-trifluoro-2-methylpropan-2-yl)phenyl)-4-(1-methyl-5-(2-(5,6,7,8-tetrahydro-1,8-naphthyridin-2-yl)ethoxy)-1H-pyrazol-3-yl)butanoic Acid

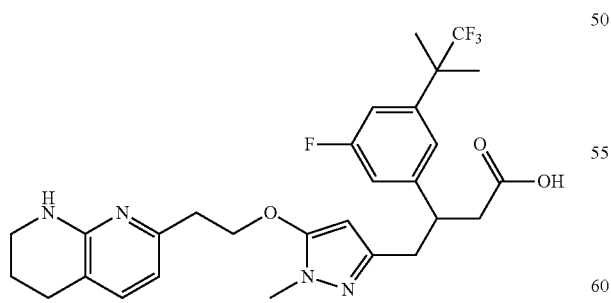

Example 24 was prepared in analogous manner to Example 1, using 3-fluoro-5-(1,1,1-trifluoro-2-methylpropan-2-yl)benzaldehyde (synthesized according to Scheme 10) as the required benzaldehyde in the reaction Scheme 3. The crude product was purified by prep-HPLC (column: Boston Green ODS 150*30 5μ; mobile phase: [water (0.1% TFA)-ACN]; B %: 30%-56%, 7 min). The HPLC effluent was lyophilized to give the desired product as a white solid (350 mg, 528 μmol, 65% yield, 100% purity, TFA). LC-MS analysis of the solid showed the desired product's mass: m/z 549 (M+H); Calcd for C$_{28}$H$_{32}$F$_4$N$_4$O$_3$: 548.24. $^1$H NMR (400 MHz, CD$_3$OD) ppm 1.52 (s, 6H) 1.95 (dd, J=6.50, 5.18 Hz, 2H) 2.59-2.93 (m, 6H) 3.15 (t, J=5.95 Hz, 2H) 3.41-3.54 (m, 6H) 4.30 (td, J=6.01, 1.87 Hz, 2H) 5.45 (s, 1H) 6.67 (d, J=7.50 Hz, 1H) 6.98 (dt, J=9.48, 1.76 Hz, 1H) 7.04-7.09 (m, 1H) 7.04-7.13 (m, 1H) 7.59 (d, J=7.28 Hz, 1H); $^{19}$F NMR (400 MHz, CD$_3$OD) ppm −77.3, −115.1.

Scheme 10

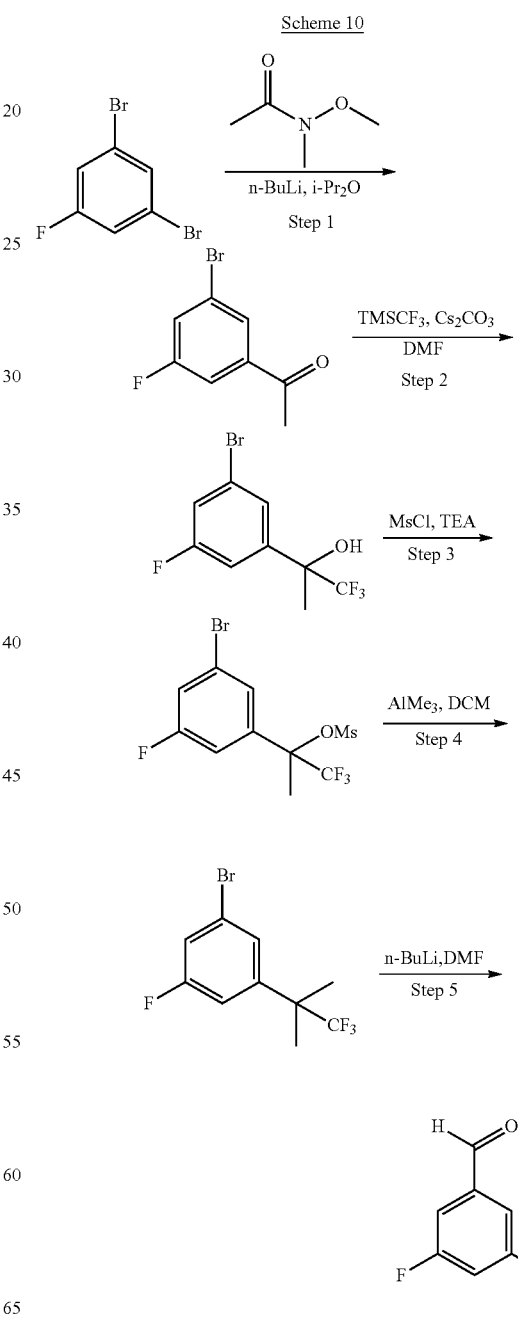

Step 1. Preparation of 1-(3-bromo-5-fluorophenyl)ethanone

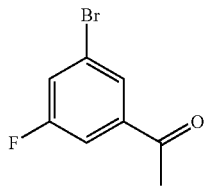

1,3-Dibromo-5-fluoro-benzene (20 g, 78.77 mmol, 1 eq) was dissolved in i-Pr$_2$O (200 mL) in a dried flask under nitrogen. The reaction mixture was cooled to −78° C. and stirred under nitrogen atmosphere. n-BuLi (2.5 M, 31.5 mL, 1 eq) was added drop wise to the above solution and the reaction mixture was stirred at −78° C. for 30 min. After complete addition of n-BuLi, N-methoxy-N-methyl-acetamide (9.75 g, 94.5 mmol, 10.05 mL, 1.2 eq) dropped to the above reaction mixture, while keeping the reaction mixture below −78° C. After addition, the reaction mixture was warmed slowly to 30° C. for 30 min. The reaction mixture was poured into water (150 mL) and the reaction mixture was stirred for 15 min. The organic phase was separated and the aqueous phase was extracted with ethyl acetate (150 mL), combined organic phase, dried over anhydrous Na$_2$SO$_4$, filtered and evaporated in vacuum to give residue (16 g crude). The residue was purified by flash silica gel chromatography (ISCO®; 120 g CombiFlash® Silica Flash Column, Eluent of 0~10% Ethyl acetate/Petroleum ether gradient @ 85 mL/min). Compound was obtained as off-white solid (11.3 g, yield 66%/). $^1$H NMR (400 MHz, CDCl$_3$) δ ppm 7.91-7.84 (m, 1H), 7.63-7.54 (m, 1H), 7.45 (td, J=2.0, 7.8 Hz, 1H), 2.63-2.55 (m, 3H).

Step 2. Preparation of 2-(3-bromo-5-fluorophenyl)-1,1,1-trifluoropropan-2-ol

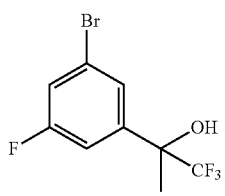

To a stirred solution of 1-(3-bromo-5-fluoro-phenyl)ethanone (11.2 g, 51.60 mmol, 1 eq) and TMSCF$_3$ (14.68 g, 103.2 mmol, 2 eq) in DMF (100 mL) was added Cs$_2$CO$_3$ (33.63 g, 103.2 mmol, 2 eq) portion wise at 0° C. resulting in a brown suspension. The reaction mixture was then stirred at 30° C. for 4 hr. The reaction mixture was quenched by water (100 mL) and separated and extracted with Ethyl acetate (200 mL*2), the organic layer was washed with water (200 mL*2), and brine (200 mL). The mixture reaction dried over anhydrous Na$_2$SO$_4$, filtered and evaporated in vacuum to give residue. The residue was purified by flash silica gel chromatography (ISCO®; 220 g CombiFlash® Silica Flash Column, Eluent of 0~30% Ethyl acetate/Petroleum ether gradient @ 100 mL/min). Compound was obtained as black brown liquid (18.4 g, crude). $^1$H NMR (400 MHz, CDCl$_3$) δ ppm 7.37 (s, 1H), 7.16-7.03 (m, 2H), 1.60 (s, 3H).

Step 3. Preparation of 2-(3-bromo-5-fluorophenyl)-1,1,1-trifluoropropan-2-yl methanesulfonate

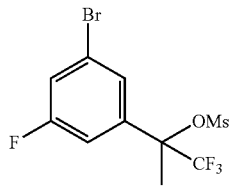 [SMILES: CC(OS(C)(=O)=O)(c1cc(F)cc(Br)c1)C(F)(F)F]

A mixture of 2-(3-bromo-5-fluoro-phenyl)-1,1,1-trifluoro-propan-2-ol (18 g, 62.71 mmol, 1 eq) and TEA (19.04 g, 188.1 mmol, 26.2 mL, 3 eq) was dissolved in DCM (180 mL) in a dried flask under nitrogen. The reaction mixture was cooled to 0° C. and stirred under a nitrogen atmosphere. MsCl (8.9 g, 77.7 mmol, 6 mL, 1.24 eq) was added drop wise to the above solution and the reaction mixture was stirred at 30° C. for 3 h. The reaction mixture was quenched by addition H$_2$O (100 mL), and then separated and extracted with DCM (250 mL). Combined organic layers and dried over Na$_2$SO$_4$, filtered and concentrated under reduced pressure to give a residue (15.6 g). The residue was purified by flash silica gel chromatography (ISCO®; 120 g CombiFlash® Silica Flash Column, Eluent of 0~10% Ethyl acetate/Petroleum ether gradient @ 85 mL/min). Compound was obtained as a yellow solid (11.6 g, yield 50.66%). $^1$H NMR (400 MHz, CDCl$_3$) ppm 7.48 (s, 1H), 7.38-7.32 (m, 1H), 7.30-7.22 (m, 1H), 3.22-3.17 (m, 3H), 2.28 (d, J=1.1 Hz, 3H).

Step 4. Preparation of 1-bromo-3-fluoro-5-(1,1,1-trifluoro-2-methylpropan-2-yl)benzene

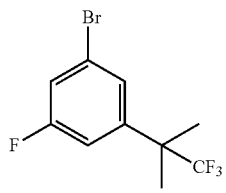

To a stirred solution of [1-(3-bromo-5-fluoro-phenyl)-2,2,2-trifluoro-1-methyl-ethyl] methanesulfonate (1000 mg, 2.74 mmol, 1 eq) in dry DCM (10 mL) was added dropwise trimethylaluminum (1 M, 5.48 mL, 2 eq) at −78° C. under N$_2$. The reaction mixture was warmed slowly to ambient temperature (26° C.) over 1 hr and stirred at this temperature for 1 hr. TLC (petroleum ether) showed the starting material was consumed up and two new spots was formed above. The mixture was poured into sat. NH$_4$Cl (30 mL) slowly, then stirred for 15 min. The un-dissolved sediment was filtered off through a pad of celite. The filtrate and washings were washed with brine (15 mL), dried over sodium sulfate, and concentrated in vacuum to give crude product. The residue was purified by flash silica gel chromatography (ISCO®; 12 g SepaFlash® Silica Flash Column, Eluent of 100%/o Petroleum ether gradient @ 32 mL/min) to give the desired product as a colorless oil (649 mg, 2.28 mmol, 83% yield). $^{1}$H NMR (400 MHz, CDCl$_3$) δ ppm 1.56 (s, 6H) 7.13-7.20 (m, 1H) 7.23 (dt, J=7.83, 1.93 Hz, 1H) 7.42 (s, 1H); $^{19}$F NMR (400 MHz, CHLOROFORM-d)) ppm −76.1, −110.5.

Step 5. Preparation of 3-fluoro-5-(1,1,1-trifluoro-2-methylpropan-2-yl)benzaldehyde

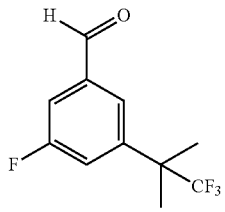 [SMILES: CC(C)(c1cc(F)cc(C=O)c1)C(F)(F)F]

To a stirred solution of 1-bromo-3-fluoro-5-(2,2,2-trifluoro-1,1-dimethyl-ethyl)benzene (3900 mg, 13.68 mmol, 1 eq) in diisopropyl ether (45 mL) was added n-BuLi (2.5 M, 10.94 mL, 2 eq) drop wise at −78° C. resulting in a yellow suspension. The resulting mixture was stirred for 30 mins at −78° C. and quenched with DMF (2 g, 27.36 mmol, 2.11 mL, 2 eq) at −78° C. resulting in a yellow clear solution, then warmed slowly to room temperature (26° C.) for 30 min. TLC (Petroleum ether, stained by KMnO$_4$) showed starting material was consumed and one major new spot was found below. Sat. NH$_4$Cl (50 mL) was added to the reaction mixture and diluted with H$_2$O (15 mL), stirred for 15 min, then extracted with ethyl acetate (3×40 mL). Organic layer was dried over sodium sulfate and concentrated under reduced pressure to afford light yellow residue. The residue was purified by flash silica gel chromatography (ISCO®; 24 g SepaFlash® Silica Flash Column, Eluent of 0~5% Ethyl acetate/Petroleum ether gradient @ 30 mL/min) to give the desired product as a light yellow oil (1.0 g, 4.27 mmol, 31% yield). $^{1}$H NMR (400 MHz, CDCl$_3$) ppm 1.63 (s, 7H) 7.46-7.51 (m, 1H) 7.51-7.57 (m, 1H) 7.82 (s, 1H) 10.01 (d, J=1.76 Hz, 1H); $^{19}$F NMR (400 MHz, CDCl$_3$) ppm −76.1, −110.8.

Example 25

Preparation of 4-[1-methyl-5-[2-(5,6,7,8-tetrahydro-1,8-naphthyridin-2-yl)ethoxy]pyrazol-3-yl]-3-[3-(2,2,2-trifluoro-1,1-dimethylethyl)-5-(trifluoromethyl)phenyl]butanoic Acid

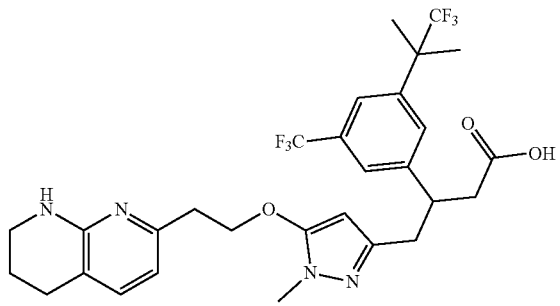 [SMILES: Cn1nc(CC(CC(=O)O)c2cc(C(F)(F)F)cc(C(C)(C)C(F)(F)F)c2)cc1OCCc1ccc2c(n1)NCCC2]

Example 25 was prepared in analogous manner to Example 24, using 1,3-dibromo-5-(trifluoromethyl)benzene in place of 1,3-dibromo-5-fluoro-benzene in the reaction Scheme 10. The crude product was purified by prep-HPLC (column: Xbridge 150*30 mm*10 μm; mobile phase: [water (0.05% ammonia hydroxide v/v)-ACN]; B %: 11%-51%, 12 min). The title compound (4.9 mg, 8.19 μmol, 3.42% yield, 100% purity) was obtained as a white solid. $^{1}$H NMR (400 MHz, DMSO-d$_6$) δ ppm 1.55 (d, J=2.5 Hz, 6H), 1.70-1.78 (m, 2H), 2.61-2.66 (m, 2H), 2.69-2.79 (m, 2H), 2.82 (t, J=6.5 Hz, 2H), 3.24 (br s, 2H), 3.35 (s, 3H), 3.44-3.55 (m, 1H), 4.19 (t, J=6.8 Hz, 2H), 5.37 (s, 1H), 6.25-6.36 (m, 2H), 7.05 (d, J=7.3 Hz, 1H), 7.59 (br d, J=5.0 Hz, 2H), 7.66 (s, 1H). LC-MS analysis of the solid shows the desired product's mass: m/z 599 (M+H).

Example 26

Preparation of 3-[3-bromo-5-(2,2,2-trifluoro-1,1-dimethyl-ethyl)phenyl]-4-[1-methyl-5-[2-(5,6,7,8-tetrahydro-1,8-naphthyridin-2-yl)ethoxy]pyrazol-3-yl]butanoic Acid

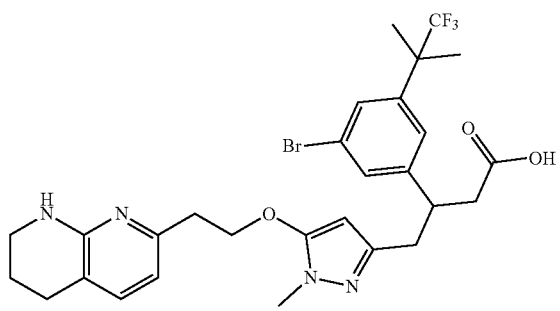 [SMILES: Cn1nc(CC(CC(=O)O)c2cc(Br)cc(C(C)(C)C(F)(F)F)c2)cc1OCCc1ccc2c(n1)NCCC2]

Example 26 was prepared in analogous manner to Example 24, using 1,3,5-tribromobenzene in place of 1,3-dibromo-5-fluoro-benzene in the reaction Scheme 10. The crude product was purified by prep-HPLC (column: Boston Green ODS 150*30 5μ; mobile phase: [water (0.1% TFA)-ACN]; B %: 25%-55%, 8 min). The title compound (20 mg, 33 μmol, 52% yield) was obtained as a white solid. LC-MS analysis of the liquid shows the desired product's mass: m/z 611 (M+H). $^{1}$H NMR (400 MHz, CD$_3$OD) 7.59 (d, J=7.5 Hz, 1H), 7.46 (s, 1H), 7.37-7.36 (m, 1H), 7.25 (s, 1H), 6.67 (d, J=7.3 Hz, 1H), 5.41 (s, 1H), 4.32-4.26 (m, 2H), 3.51-3.48 (m, 2H), 3.44 (s, 3H), 3.42-3.37 (m, 1H), 3.14 (t, J=6.0 Hz, 2H), 2.86-2.62 (m, 6H), 1.98-1.92 (m, 2H), 1.50 (s, 6H); $^{19}$F NMR (376 MHz, CD$_3$OD) −77.32, −77.36.

Example 27

Preparation of 3-(3-chloro-5-(1,1,1-trifluoro-2-methylpropan-2-yl)phenyl)-4-(1-methyl-5-(2-(5,6,7,8-tetrahydro-1,8-naphthyridin-2-yl)ethoxy)-1H-pyrazol-3-yl)butanoic Acid

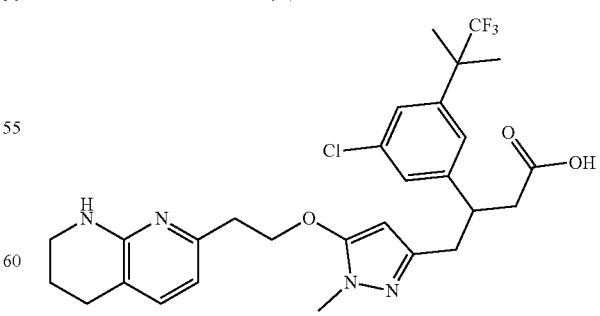

Example 27 was prepared in analogous manner to Example 24, using 1,3-dibromo-5-chloro-benzene in place of 1,3-dibromo-5-fluoro-benzene in the reaction Scheme 10. The crude product was purified by prep-HPLC (TFA condition: column: Boston Green ODS 150*30 5μ; mobile phase: [water (0.1% TFA)-ACN]; B %: 15%-45%, 8 min). The title compound (128 mg, 226 μmol, 80% yield, 100% purity) was obtained as a white solid. ¹H NMR (400 MHz, CD₃OD) 7.60 (d, J=7.3 Hz, 1H), 7.33 (s, 1H), 7.26-7.19 (m, 2H), 6.68 (d, J=7.3 Hz, 1H), 5.44 (s, 1H), 4.34-4.26 (m, 2H), 3.52-3.48 (m, 2H), 3.46 (s, 3H), 3.45-3.38 (m, 1H), 3.15 (t, J=5.9 Hz, 2H), 2.92-2.85 (m, 1H), 2.83 (t, J=6.3 Hz, 2H), 2.78-2.70 (m, 2H), 2.69-2.60 (m, 1H), 1.99-1.91 (m, 2H), 1.52 (s, 6H); ¹⁹F NMR (376 MHz, CD₃OD) −77.36. LCMS (mass: m/z 565.1 (M+H)).

Example 28

Preparation of 3-[3-cyano-5-(2,2,2-trifluoro-1,1-dimethyl-ethyl)phenyl]-4-[1-methyl-5-[2-(5,6,7,8-tetrahydro-1,8-naphthyridin-2-yl)ethoxy]pyrazol-3-yl]butanoic Acid Trifluoroacetate Scheme 11

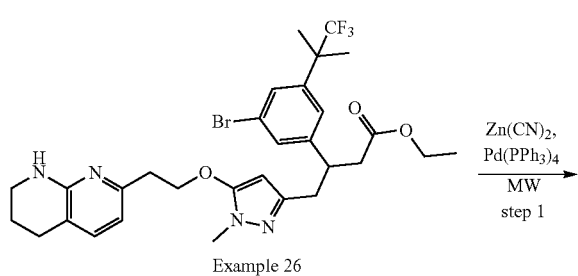

Example 26

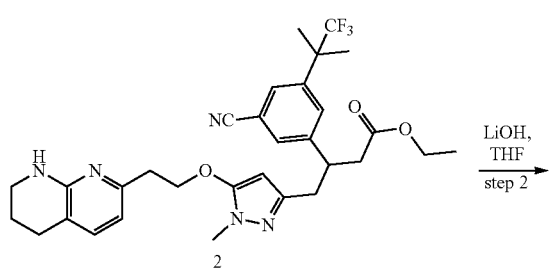

2

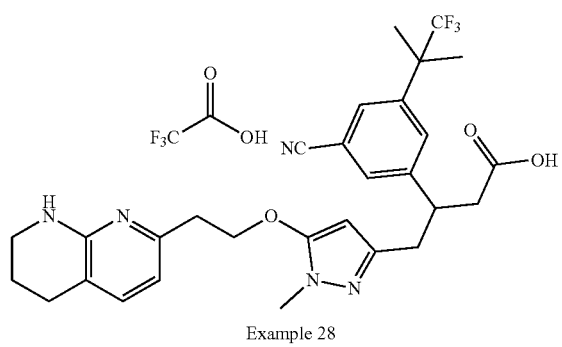

Example 28

Step 1. Preparation of ethyl 3-[3-cyano-5-(2,2,2-trifluoro-1,1-dimethyl-ethyl)phenyl]-4-[1-methyl-5-[2-(5,6,7,8-tetrahydro-1,8-naphthyridin-2-yl)ethoxy]pyrazol-3-yl]butanoate

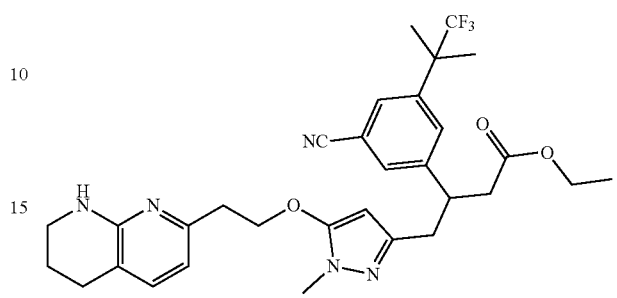

A mixture of ethyl 3-[3-bromo-5-(2,2,2-trifluoro-1,1-dimethyl-ethyl)phenyl]-4-[1-methyl-5-[2-(5,6,7,8-tetrahydro-1,8-naphthyridin-2-yl)ethoxy]pyrazol-3-yl]butanoate (50 mg, 78 μmol, 1 eq) and Zn(CN)₂ (27.6 mg, 235 umol, 14.93 μL, 3 eq) in DMF (3 mL) in a 25 mL microwave vial was evacuated and back-filled with N₂ for three times. Pd(PPh₃)₄ (9.06 mg, 7.8 μmol, 0.1 eq) was added. The reaction vial was sealed, and the reaction mixture was again degassed and back-filled with N₂ (3 times), and then stirred at 120° C. for 1.5 hr under microwave irradiation. LC-MS showed most of ethyl 3-[3-bromo-5-(2,2,2-trifluoro-1,1-dimethyl-ethyl)phenyl]-4-[1-methyl-5-[2-(5,6,7,8-tetrahydro-1,8-naphthyridin-2-yl)ethoxy]pyrazol-3-yl]butanoate was consumed and desired mass (m/z 584.2 (M+H)) was detected. The reaction mixture was concentrated under reduced pressure to give a residue. The residue was purified by prep-HPLC (column: Phenomenex Gemini C18 250*50 mm*10 μm; mobile phase: [water (0.05% HCl)-ACN]; B %: 30%-60%, 10 min). The title compound (40 mg, 69 μmol, 87% yield) was obtained as a white solid. LC-MS analysis of the liquid shows the desired product's mass: m/z 584.2 (M+H).

Step 2. Preparation of 3-[3-cyano-5-(2,2,2-trifluoro-1,1-dim ethyl)phenyl]-4-[1-methyl-5-[2-(5,6,7,8-tetrahydro-1,8-naphthyridin-2-yl)ethoxy]pyrazol-3-yl]butanoic Acid Trifluoroacetate

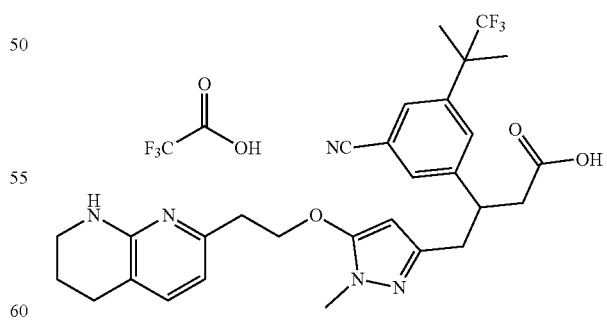

To a solution of ethyl 3-[3-cyano-5-(2,2,2-trifluoro-1,1-dimethyl-ethyl)phenyl]-4-[1-methyl-5-[2-(5,6,7,8-tetrahydro-1,8-naphthyridin-2-yl)ethoxy]pyrazol-3-yl]butanoate (40 mg, 68.54 umol, 1 eq) in THF (2 mL) was added LiOH.H₂O (1 M, 2.06 mL, 30 eq). The mixture was stirred at 60° C. for 16 hr. LC-MS showed ethyl ethyl 3-[3-cyano- 5-(2,2,2-trifluoro-1,1-dimethyl-ethyl)phenyl]-4-[1-methyl-5-[2-(5,6,7,8-tetrahydro-1,8-naphthyridin-2-yl)ethoxy]pyrazol-3-yl]butanoate was consumed completely and desired mass (m/z 556.1 (M+H)) was detected. The reaction mixture was concentrated under reduced pressure to remove THF. The residue was diluted with AcOH to pH (~5) and extracted with EtOAc 50 mL (25 mL*2). The combined organic layers were concentrated under reduced pressure to give a residue. The residue was purified by prep-HPLC (column: Boston Green ODS 150*30 5μ; mobile phase: [water (0.1% TFA)-ACN]; B %: 30%-56.25%, 7 min). The title compound (8.8 mg, 15.5 μmol, 23% yield, 98% purity) was obtained as a white solid. LC-MS analysis of the liquid shows the desired product's mass: m/z 556.1 (M+H). $^1$H NMR (400 MHz, CD$_3$OD) 7.71 (s, 1H), 7.64-7.60 (m, 3H), 6.71 (d, J=7.5 Hz, 1H), 5.42 (s, 1H), 4.33-4.26 (m, 2H), 3.54 (br s, 1H), 3.52 (br d, J=6.0 Hz, 2H), 3.45 (s, 3H), 3.16 (t, J=5.9 Hz, 2H), 2.95-2.71 (m, 1H), 2.95-2.71 (m, 5H), 2.00-1.94 (m, 2H), 1.57 (s, 6H). $^{19}$F NMR (376 MHz, CD$_3$OD) −77.37 (s, 1F), −77.41 (s, 1F).

Example 29

Preparation of 3-(3-chloro-5-(4-(methoxymethyl)tetrahydro-2H-pyran-4-yl)phenyl)-4-(1-methyl-5-(2-(5,6,7,8-tetrahydro-1,8-naphthyridin-2-yl)ethoxy)-1H-pyrazol-3-yl)butanoic Acid

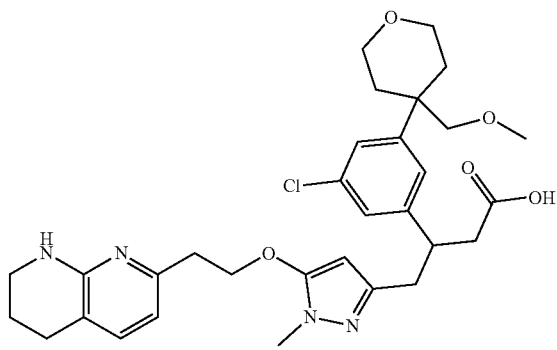 [SMILES: COCC1(c2cc(Cl)cc(C(CC(=O)O)Cc3cc(OCCc4ccc5c(n4)NCCC5)n(C)n3)c2)CCOCC1]

Example 29 was prepared in analogous manner to Example 1, using 3-chloro-5-(4-(methoxymethyl)tetrahydro-2H-pyran-4-yl)benzaldehyde (synthesized according to Scheme 12) as the required benzaldehyde in the reaction Scheme 3. The crude product was purified by prep-HPLC (column: Boston Green ODS 150*30 5μ; mobile phase: [water (0.1% TFA)-ACN]; B %: 15%-45%, 8 min). The title compound was obtained as light yellow solid (112.5 mg, yield 83%). LC-MS analysis of the compound showed the desired product's mass: m/z 583 (M+1); $^1$H NMR (400 MHz, CD$_3$OD) δ=7.61 (d, J=7.5 Hz, 1H), 7.18 (t, 0.1=1.8 Hz, 1H), 7.13 (s, 1H), 7.05 (s, 1H), 6.70 (d, J=7.5 Hz, 1H), 5.43 (s, 1H), 4.30 (t, J=6.1 Hz, 2H), 3.75-3.62 (m, 2H), 3.53-3.47 (m, 2H), 3.47-3.32 (m, 6H), 3.29-3.12 (m, 5H), 2.92-2.80 (m, 3H), 2.77-2.60 (m, 3H), 2.07-1.84 (m, 6H).

Scheme 12

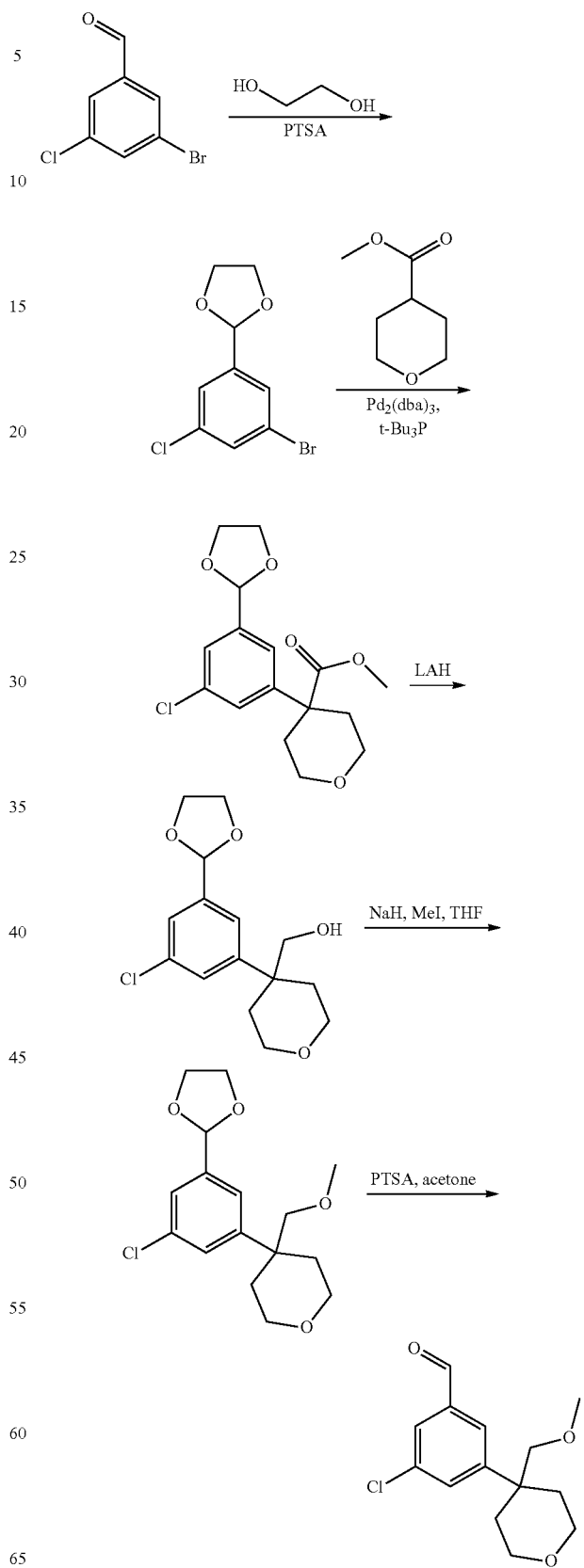

Step 1. Preparation of 2-(3-bromo-5-chlorophenyl)-1,3-dioxolane

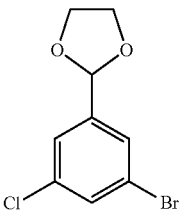 [SMILES: Clc1cc(Br)cc(C2OCCO2)c1]

A mixture of 3-bromo-5-chloro-benzaldehyde (10 g, 45.57 mmol, 1 eq) and ethylene glycol (8.48 g, 136.70 mmol, 7.64 mL, 3 eq), PTSA (156.93 mg, 911.32 umol, 0.02 eq) were dissolved in anhydrous toluene (100 mL) in a dried flask under nitrogen. The reaction mixture was refluxed at 140° C. for 2 hr. A saturated NaHCO$_3$ solution (100 mL) was added. The toluene layer was separated, washed with NaCl solution (150 mL) dried over anhydrous Na$_2$SO$_4$, filtered and evaporated in vacuo. The title compound was obtained as light yellow liquid (12.8 g, crude). $^1$H NMR (400 MHz, CD$_3$OD) δ=7.59-7.48 (m, 2H), 7.42 (d, J=1.3 Hz, 1H), 5.77 (s, 1H), 4.19-3.97 (m, 4H).

Step 2. Preparation of methyl 4-(3-chloro-5-(1,3-dioxolan-2-yl)phenyl)tetrahydro-2H-pyran-4-carboxylate

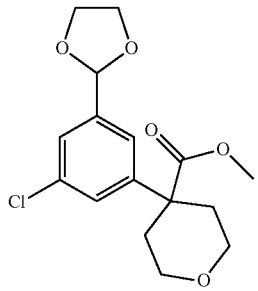 [SMILES: COC(=O)C1(c2cc(Cl)cc(C3OCCO3)c2)CCOCC1]

To a mixture of N-cyclohexylcyclohexanamine (6.26 g, 34.53 mmol, 6.88 mL, 1.3 eq) in toluene (70 mL) was added n-BuLi (2.5 M, 13.8 mL, 1.3 eq) at −20° C. under N$_2$. The mixture warmed to 0° C. and stirred for 20 min, methyl tetrahydropyran-4-carboxylate (3.83 g, 26.56 mmol, 3.55 mL, 1 eq) was added and stirred at 28° C. for 10 min. Then 2-(3-bromo-5-chloro-phenyl)-1,3-dioxolane (7 g, 26.56 mmol, 1 eq), Pd(dba)$_2$ (458 mg, 797 μmol, 0.03 eq) and t-Bu$_3$P (1.61 g, 796.92 μmol, 1.87 mL, 10% purity, 0.03 eq) was added. The mixture was stirred at 28° C. for 12 hr. The mixture was quenched by addition sat.NH$_4$Cl (50 mL) at 28° C., and then diluted with EtOAc (50 mL) and extracted with EtOAc (1500 mL*2). The combined organic layers were washed with brine (150 mL), dried over Na$_2$SO$_4$, filtered and concentrated under reduced pressure to give a residue. The residue was purified by flash silica gel chromatography (ISCO®; 80 g CombiFlash® Silica Flash Column, Eluent of 0~50% Ethylacetate/Petroleum ethergradient @ 65 mL/min). Compound was obtained as light yellow liquid (3.7 g, yield 43%). $^1$H NMR (400 MHz, CD$_3$OD) δ=7.41-7.39 (m, 1H), 7.35 (d, J=1.8 Hz, 2H), 5.77 (s, 1H), 4.15-4.09 (m, 2H), 4.08-4.01 (m, 2H), 3.94 (td, J=3.6, 12.0 Hz, 2H), 3.68 (s, 3H), 3.55 (dt, J=2.0, 11.7 Hz, 2H), 2.52 (dd, J=2.3, 13.6 Hz, 2H), 2.02-1.90 (m, 2H).

Step 3. Preparation of (4-(3-chloro-5-(1,3-dioxolan-2-yl)phenyl)tetrahydro-2H-pyran-4-yl)methanol

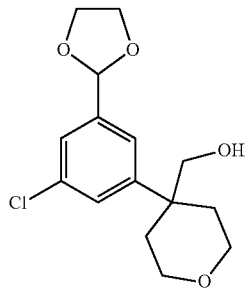 [SMILES: OCC1(c2cc(Cl)cc(C3OCCO3)c2)CCOCC1]

To a mixture of LAH (859.5 mg, 22.7 mmol, 2 eq) in THF (20 mL). A mixture of methyl 4-[3-chloro-5-(1,3-dioxolan-2-yl)phenyl]tetrahydropyran-4-carboxylate (3.7 g, 11.32 mmol, 1 eq) was dissolved in THF (40 mL) and added at 25° C. under N$_2$. The reaction mixture was stirred at 25° C. for 8 hr. The reaction mixture was quenched with H$_2$O (50 mL) and extracted with ethyl acetate (2*100 mL). The combined organic phase was washed with brine solution (120 mL), dried with anhydrous Na$_2$SO$_4$, filtered and evaporated in vacuo. The residue was purified by flash silica gel chromatography (ISCO®; 40 g CombiFlash® Silica Flash Column, Eluent of 0~50% Ethylacetate/Petroleum ethergradient @ 35 mL/min). Compound was obtained as white solid (2.4 g, yield 71%). $^1$H NMR (400 MHz, CD$_3$OD) &=7.41 (t, J=1.5 Hz, 1H), 7.33 (d, J=1.5 Hz, 2H), 5.78 (s, 1H), 4.16-4.09 (m, 2H), 4.08-4.02 (m, 2H), 3.80 (ddd, J=3.9, 5.7, 11.8 Hz, 2H), 3.63 (s, 2H), 3.57 (ddd, J=3.0, 8.8, 11.8 Hz, 2H), 2.15-2.06 (m, 2H), 1.98-1.90 (m, 2H).

Step 4. Preparation of 4-(3-chloro-5-(1,3-dioxolan-2-yl)phenyl)-4-(methoxymethyl)tetrahydro-2H-pyran

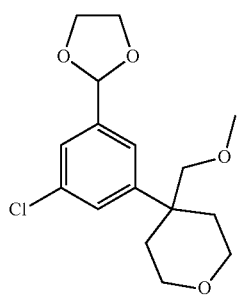 [SMILES: COCC1(c2cc(Cl)cc(C3OCCO3)c2)CCOCC1]

Under an argon atmosphere, NaH (803 mg, 20.1 mmol, 60% purity, 2.5 eq) was added to a solution of [4-[3-chloro-5-(1,3-dioxolan-2-yl)phenyl]tetrahydropyran-4-yl]methanol (2.4 g, 8.03 mmol, 1 eq) was dissolved in anhydrous THF (30 mL), and the resulting mixture was stirred at 0° C. for 30 min. CH$_3$I (6.9 g, 48.61 mmol, 3.03 mL, 6.05 eq) was added dropwise to the reaction solution, and the resulting mixture was stirred at 25° C. for 2 hr. The reaction mixture was quenched with brine (20 mL) slowly and then extracted with ethyl acetate (50 mL*3). The combined organic phase was washed with brine (100 mL), dried over anhydrous Na$_2$SO$_4$, filtered and concentrated in vacuo. The residue was purified by flash silica gel chromatography (ISCO®; 40 g CombiFlash® Silica Flash Column, Eluent of 0~50% Ethylacetate/Petroleum ethergradient @ 35 mL/min). The title compound was obtained as light yellow liquid (2.3 g, yield 92%). $^1$H NMR (400 MHz, CHLOROFORM-d) δ=7.37 (d, J=1.5 Hz, 1H), 7.31 (s, 2H), 5.79 (s, 1H), 4.16-4.10 (m, 2H), 4.09-4.02 (m, 2H), 3.82-3.74 (m, 2H), 3.55 (ddd, J=3.0, 8.7, 11.7 Hz, 2H), 3.36 (s, 2H), 3.21 (s, 3H), 2.07-2.03 (m, 2H), 2.03-1.95 (m, 2H).

Step 5. Preparation of 3-chloro-5-(4-(methoxymethyl)tetrahydro-2H-pyran-4-yl)benzaldehyde

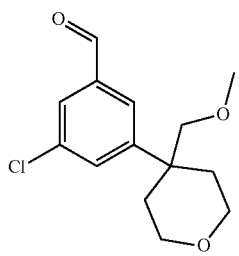 [SMILES: COCC1(c2cc(Cl)cc(C=O)c2)CCOCC1]

4-[3-Chloro-5-(1,3-dioxolan-2-yl)phenyl]-4-(methoxymethyl)tetrahydropyran (2.3 g, 7.35 mmol, 1 eq) and PTSA (253 mg, 1.47 mmol, 0.2 eq) were dissolved in acetone (30 mL) in a dried flask under nitrogen and stirred at 25° C. for 12 hrs. Saturated NaHCO$_3$ (30 mL*2) was added, the mixture was extracted with EtOAc (50 mL×2), dried over anhydrous Na$_2$SO$_4$, filtered and evaporated in vacuo to give the residue. The title compound was obtained as light yellow liquid (1.9 g, yield 96%). $^1$H NMR (400 MHz, CD$_3$OD) δ=10.01-9.94 (m, 1H), 7.74 (td, J=1.5, 8.0 Hz, 2H), 7.58 (t, J=1.9 Hz, 1H), 3.80 (ddd, J=3.8, 6.3, 11.8 Hz, 2H), 3.62-3.53 (m, 2H), 3.42 (s, 2H), 3.26-3.19 (m, 3H), 2.14-2.07 (m, 2H), 2.04-1.97 (m, 2H).

Example 30

Preparation of 3-(3-fluoro-5-(4-(methoxymethyl)tetrahydro-2H-pyran-4-yl)phenyl)-4-(1-methyl-5-(2-(5,6,7,8-tetrahydro-1,8-naphthyridin-2-yl)ethoxy)-1H-pyrazol-3-yl)butanoic Acid

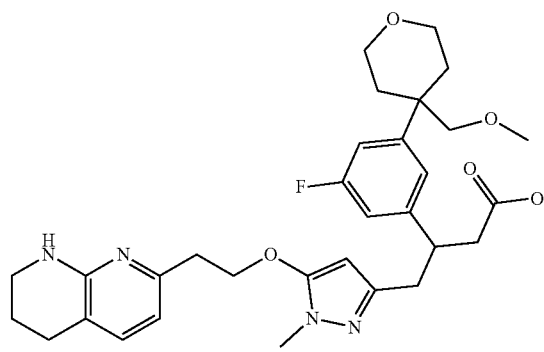

Example 30 was prepared in analogous manner to Example 29, using 3-bromo-5-fluorobenzaldehyde in place of 3-bromo-5-chloro-benzaldehyde in the reaction Scheme 12. The crude product was purified by prep-HPLC (column: Boston Green ODS 150*30 5μ; mobile phase: [water (0.1% TFA)-ACN]; B %: 15%-45%, 8 min). The title compound (6.7 mg, 9.8 μmol, 37% yield, 100° % purity, TFA) was obtained as a white solid. LC-MS analysis of the solid showed the desired product's mass: m/z 567.1 (M+H); Calcd for C$_{31}$H$_{39}$FN$_4$O$_5$: 566.66. $^1$H NMR (CD$_3$OD, 400 MHz) 7.60 (d, J=7.2 Hz, 1H), 6.90-6.96 (m, 2H), 6.85-6.90 (m, 1H), 6.69 (d, J=7.2 Hz, 1H), 5.46 (s, 1H), 4.30 (t, J=6.0 Hz, 2H), 3.61-3.75 (m, 2H), 3.46-3.55 (m, 3H), 3.45 (s, 3H), 3.32-3.44 (m, 4H), 3.12-3.19 (m, 5H), 2.60-2.91 (m, 6H), 1.85-2.06 (m, 6H).

Example 31

Preparation of 3-(3-(4-(methoxymethyl)tetrahydro-2H-pyran-4-yl)-5-(trifluoromethyl)phenyl)-4-(1-methyl-5-(2-(5,6,7,8-tetrahydro-1,8-naphthyridin-2-yl)ethoxy)-1H-pyrazol-3-yl)butanoic Acid

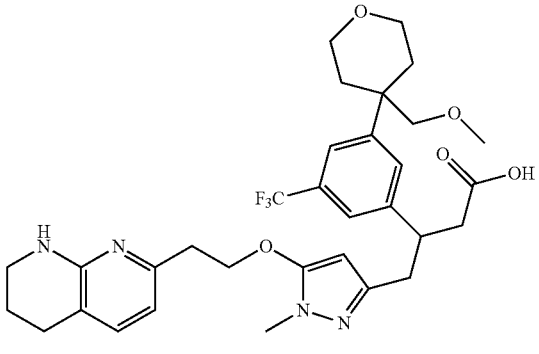 [SMILES: COCC1(c2cc(C(CC(=O)O)Cc3cc(OCCc4ccc5c(n4)NCCC5)n(C)n3)cc(C(F)(F)F)c2)CCOCC1]

Example 31 was prepared in analogous manner to Example 29, using 3-bromo-5-(trifluoromethyl)benzaldehyde in place of 3-bromo-5-chloro-benzaldehyde in the reaction Scheme 12. The crude product was purified by prep-HPLC (column: Boston Green ODS 150*30 5μ; mobile phase: [water (0.1% TFA)-ACN]; B %: 25%-51.25%). The title compound (19 mg, 26 μmol, 15% yield, 100% purity, TFA) was obtained as a yellow solid. $^1$H NMR (400 MHz, CD$_3$OD): δ ppm=7.58 (d, J=7.3 Hz, 1H), 7.43 (s, 1H), 7.37 (br d, J=4.2 Hz, 2H), 6.66 (d, J=7.5 Hz, 1H), 5.45 (s, 1H), 4.28 (t, J=6.0 Hz, 2H), 3.75-3.61 (m, 2H), 3.53-3.46 (m, 3H), 3.43 (s, 3H), 3.33 (s, 1H), 3.29 (d, J=1.3 Hz, 3H), 3.21-3.07 (m, 5H), 2.90 (dd, J=6.6, 14.3 Hz, 1H), 2.84-2.62 (m, 5H), 2.11-1.99 (m, 2H), 1.99-1.86 (m, 4H).

Example 32

Preparation of 3-(5-(tert-butyl)-2-methoxyphenyl)-4-(1-methyl-5-(2-(5,6,7,8-tetrahydro-1,8-naphthyridin-2-yl)ethoxy)-1H-pyrazol-3-yl)butanoic Acid

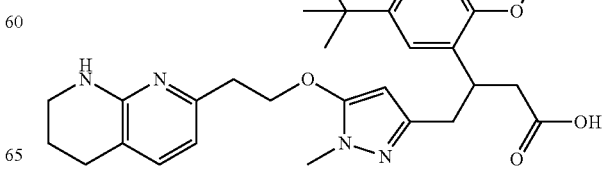

119

Example 32 was prepared in analogous manner to Example 1, using 5-(tert-butyl)-2-methoxybenzaldehyde (synthesized according to Scheme 13) as the required benzaldehyde in the reaction Scheme 3. The crude product was purified by prep-HPLC (column: Boston Green ODS 150*30 5μ; mobile phase: [water (0.1% TFA)-ACN]; B %: 25%-55%, 8 min). The title compound (93 mg, 149 μmol, 27% yield, 100% purity, TFA) was obtained as a white solid. LC-MS analysis of the liquid shows the desired product's mass: m/z 507 (M+H) $^1$H NMR (400 MHz, DMSO-$d_6$) δ ppm 1.16 (s, 9H), 1.74-1.83 (m, 2H), 2.51 (br dd, J=7.5, 4.6 Hz, 2H), 2.55-2.67 (m, 2H), 2.69-2.74 (m, 2H), 3.05 (t, J=6.1 Hz, 2H), 3.34 (s, 3H), 3.36-3.42 (m, 2H), 3.52-3.63 (m, 2H), 3.72 (s, 3H), 4.19 (t, J=6.1 Hz, 2H), 5.29 (s, 1H), 6.65 (d, J=7.3 Hz, 1H), 6.79 (d, J=9.3 Hz, 1H), 7.05-7.11 (m, 2H), 7.59 (d, J=7.3 Hz, 1H), 8.43 (br s, 1H).

Scheme 13

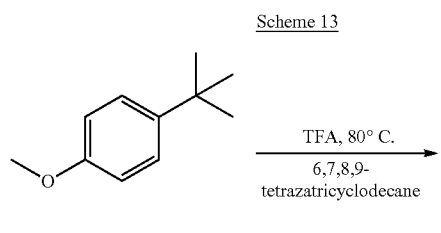

Preparation of 5-(tert-butyl)-2-methoxybenzaldehyde

To a solution of 1-tert-butyl-4-methoxy-benzene (3 g, 18.27 mmol, 1 eq) in TFA (30 mL) was added methenamine (5.12 g, 36.53 mmol, 6.83 mL, 2 eq). The mixture was stirred at 80° C. for 16 hr. LC-MS showed desired compound was detected. The reaction mixture was concentrated under reduced pressure to give a residue. The residue was purified by flash silica gel chromatography (ISCO®; 40 g SepaFlash® Silica Flash Column, Eluent of 0~3% Ethyl acetate/Petroleum ethergradient @ 30 mL/min). 5-Tert-butyl-2-methoxy-benzaldehyde (2.4 g, 12.5 mmol, 68% yield) was obtained as a yellow liquid. LC-MS analysis of the liquid shows the desired product's mass: m/z 193 (M+H) $^1$H NMR (400 MHz, DMSO-$d_6$) δ ppm 1.26 (s, 9H), 2.43-2.57 (m, 3H), 3.89 (s, 3H), 7.16 (d, J=8.8 Hz, 1H), 7.63-7.73 (m, 2H), 10.28-10.38 (m, 1H).

120

Example 33

Preparation of 3-(3-(tert-butyl)-2-methoxyphenyl)-4-(1-methyl-5-(2-(5,6,7,8-tetrahydro-1,8-naphthyridin-2-yl)ethoxy)-1H-pyrazol-3-yl)butanoic Acid

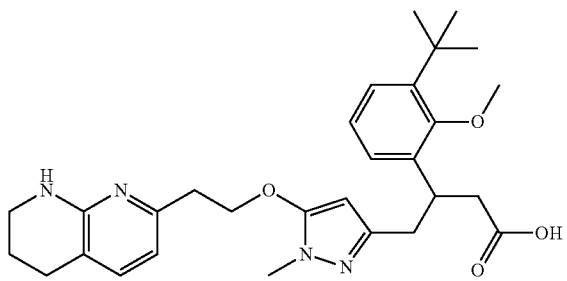 [SMILES: COc1c(C(CC(=O)O)Cc2cc(OCCc3ccc4c(n3)NCCC4)n(C)n2)cccc1C(C)(C)C]

Example 33 was prepared in analogous manner to Example 1, using 3-(tert-butyl)-2-methoxybenzaldehyde (synthesized according to Scheme 14) as the required benzaldehyde in the reaction Scheme 3. The crude product was purified by prep-HPLC (column: Boston Green ODS 150*30 5μ; mobile phase: [water (0.1% TFA)-ACN]; B %: 25%-55%, 8 min). The title compound (136.3 mg, 219.25 μmol, 66% yield, 99.8% purity, TFA) was obtained as a white solid. LC-MS analysis of the oil showed the desired product's mass: m/z 507.1 (M+H); Calcd for $C_{29}H_{38}N_4O_4$: 506.64. $^1$H NMR (CD$_3$OD, 400 MHz) δ ppm 7.59 (d, J=7.2 Hz, 1H), 7.17 (d, J=7.6 Hz, 2H), 7.00-7.05 (m, 1H), 6.67 (d. J=7.2 Hz, 1H), 5.46 (s, 1H), 4.31 (t, J=6.0 Hz, 2H), 3.86-3.95 (m, 1H), 3.77 (s, 3H), 3.47-3.53 (m, 5H), 3.15 (t, J=6.0 Hz, 2H), 2.93 (dd, J=14.4, 6.4 Hz, 1H), 2.83 (t, J=6.4 Hz, 2H), 2.64-2.79 (m, 3H), 1.95 (quin, J=6.0 Hz, 2H), 1.30 (s, 9H).

Scheme 14

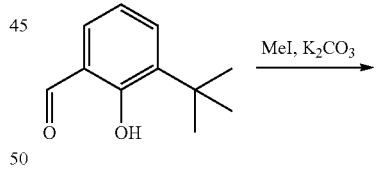

Preparation of 3-(tert-butyl)-2-methoxybenzaldehyde

3-Tert-butyl-2-hydroxy-benzaldehyde (5 g, 28.05 mmol, 1 eq) in anhydrous THF (75 mL) was treated with Cs$_2$CO$_3$ (18.28 g, 56.11 mmol, 2 eq) under an argon atmosphere, and the mixture was stirred at 20° C. for 30 min. Subsequently, CH₃I (17.9 g, 126.11 mmol, 7.85 mL, 4.50 eq) was added dropwise to the mixture, and the resulting mixture was stirred at 20° C. for 16 hr. TLC (Petroleum ether:Ethyl acetate=15:1, Rf=0.45) indicated 3-tert-butyl-2-hydroxy-benzaldehyde was consumed completely and one new spot formed. The mixture was poured into water (100 mL) and extracted with ethyl acetate (100 mL*3). The combined organic phase was washed with brine (150 mL), dried with anhydrous Na₂SO₄, filtered and concentrated in vacuum. The residue was purified by flash silica gel chromatography (ISCO®; 80 g SepaFlash® Silica Flash Column, Eluent of 0~5% Ethyl acetate/Petroleum ether gradient @ 60 mL/min). The title compound (4.2 g, 21.7 mmol, 77% yield, 99% purity) was obtained as yellow oil. LC-MS analysis of the oil showed the desired product's mass: m/z 193.0 (M+H); Calcd for $C_{12}H_{16}O_2$: 192.25. ¹H NMR (CDCl₃, 400 MHz) δ ppm 10.35 (s, 1H), 7.71 (dd, J=7.6, 2.0 Hz, 1H), 7.58 (dd, J=8.0, 1.6 Hz, 1H), 7.15 (t, J=7.6 Hz, H), 3.95 (s, 3H), 1.42 (s, 9H).

Example 34

Preparation of 3-(4-(tert-butyl)-2-methoxyphenyl)-4-(1-methyl-5-(2-(5,6,7,8-tetrahydro-1,8-naphthyridin-2-yl)ethoxy)-1H-pyrazol-3-yl)butanoic Acid

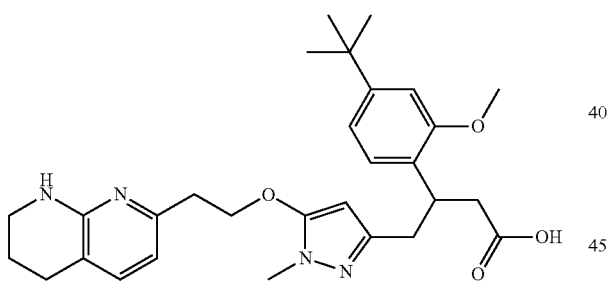

Example 34 was prepared in analogous manner to Example 33, using 4-tert-butyl-2-hydroxy-benzaldehyde in place of 3-tert-butyl-2-hydroxy-benzaldehyde in the reaction Scheme 14. The crude product was purified by prep-HPLC (TFA condition: column: Boston Green ODS 150*30 5μ; mobile phase: [water (0.1% TFA)-ACN]; B %: 30%-60%, 8 min). The title compound (88 mg, 138.6 μmol, 74% yield, 98% purity, TFA) was obtained as a white solid. LCMS analysis showed the desired product's mass: m/z 507.1 (M+H). ¹H NMR, ¹⁹F NMR and HMBC was consistent with the title compound. ¹H NMR (400 MHz, CD₃OD) δ ppm 7.60 (br d, J=6.8 Hz, 1H), 7.04 (d, J=8.0 Hz, 1H), 6.97-6.85 (m, 2H), 6.67 (br d, J=7.2 Hz, 1H), 5.49 (br s, 1H), 4.34 (br s, 2H), 3.84 (s, 3H), 3.71 (br t, J=7.2 Hz, 1H), 3.55-3.44 (m, 5H), 3.15 (br t, J=6.0 Hz, 2H), 2.83 (br t, J=6.0 Hz, 4H), 2.74-2.57 (m, 2H), 2.02-1.89 (m, 2H), 1.29 (s, 9H); ¹⁹F NMR (376 MHz, CD₃OD) −77.44 (s, 3F).

Example 35

Preparation of 3-(5-tert-butyl-2-isopropoxy-phenyl)-4-[1-methyl-5-[2-(5,6,7,8-tetrahydro-1,8-naphthyridin-2-yl)ethoxy]pyrazol-3-yl]butanoic Acid Trifluoroacetate

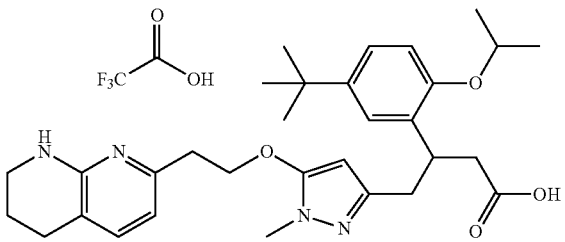 [SMILES: CC(C)Oc1ccc(C(C)(C)C)cc1C(CC(=O)O)Cc1cc(OCCc2ccc3c(n2)NCCC3)n(C)n1 ; O=C(O)C(F)(F)F]

Example 35 was prepared in analogous manner to Example 33, using 5-tert-butyl-2-hydroxy-benzaldehyde in place of 3-tert-butyl-2-hydroxy-benzaldehyde and 2-bromopropane in place of CH₃I in the reaction Scheme 14. The crude product was purified by prep-HPLC (column: Boston Green ODS 150*30 5μ; mobile phase: [water (0.1% TFA)-ACN]; B %: 30%-60%, 8 min). The title compound (78.5 mg, 119 μmol, 44% yield, 98% purity, TFA) was obtained as a white solid. LC-MS analysis of the liquid shows the desired product's mass: m/z 535.1 (M+H). ¹H NMR (400 MHz, CD₃OD) 7.58 (d, J=7.3 Hz, 1H), 7.13 (dd, J=2.4, 8.6 Hz, 1H), 7.09 (d, J=2.4 Hz, 1H), 6.81 (d, J=8.6 Hz, 1H), 6.66 (d, J=7.3 Hz, 1H), 5.40 (s, 1H), 4.63-4.54 (m, 1H), 4.29 (t, J=6.0 Hz, 2H), 3.69 (quin, J=7.4 Hz, 1H), 3.49 (d, J=5.6 Hz, 1H), 3.52-3.48 (m, 1H), 3.47 (s, 3H), 3.13 (t, J=6.0 Hz, 2H), 2.89-2.61 (m, 6H), 1.93 (quin, J=6.0 Hz, 2H), 1.32 (dd, J=6.0, 7.7 Hz, 6H), 1.22 (s, 9H), ¹⁹F NMR (376 MHz, CD₃OD) −77.36 (s, 1F).

Example 36

Preparation of 3-[3-tert-butyl-5-(trifluoromethoxy)phenyl]-4-[1-methyl-5-[2-(5,6,7,8-tetrahydro-1,8-naphthyridin-2-yl)ethoxy]pyrazol-3-yl]butanoic Acid

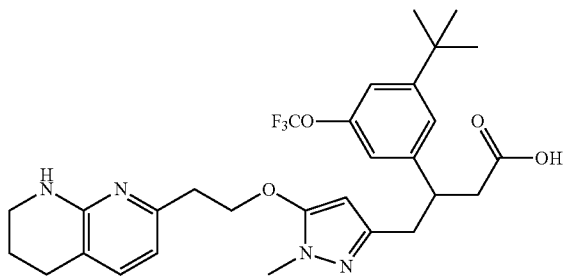 [SMILES: Cn1nc(CC(CC(=O)O)c2cc(OC(F)(F)F)cc(C(C)(C)C)c2)cc1OCCc1ccc2c(n1)NCCC2]

Example 36 was prepared in analogous manner to Example 1, using 3-tert-butyl-5-(trifluoromethoxy)benzaldehyde (synthesized according to Scheme 15) as the required benzaldehyde in the reaction Scheme 3. The crude product was purified by prep-HPLC (column: Boston pH-lex 150*25 10 μm; mobile phase: [water (0.1% TFA)-ACN]; B %: 35%-65%, 8 min). The title compound (14 mg, 25 μmol, 37% yield, 100% purity) was obtained as a white solid.

LC-MS analysis of the liquid shows the desired product's mass: m/z 561.3. $^1$H NMR (400 MHz, DMSO-$d_6$) δ ppm 1.20 (s, 9H), 1.72-1.84 (m, 2H), 2.58-2.76 (m, 6H), 3.06 (t, J=5.8 Hz, 2H), 4.18 (t, J=6.1 Hz, 2H), 5.36 (s, 1H), 6.66 (d, J=7.3 Hz, 1H), 6.96-7.01 (m, 1H), 7.05 (s, 1H), 7.20 (s, 1H), 7.61 (d, J=7.1 Hz, 1H).

Scheme 15

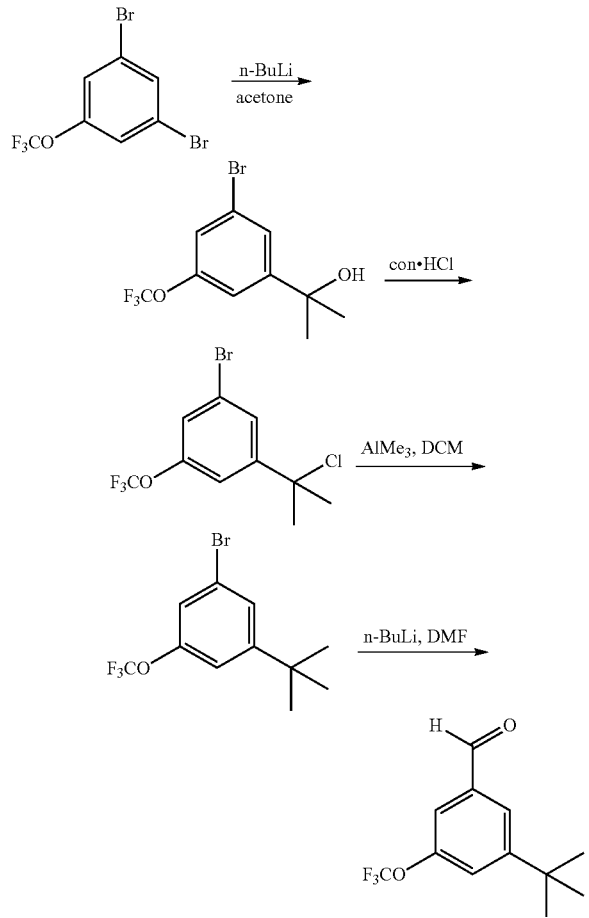

Step 1. Preparation of 2-[3-bromo-5-(trifluoromethoxy)phenyl]propan-2-ol

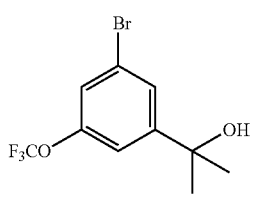 [SMILES: CC(C)(O)c1cc(Br)cc(OC(F)(F)F)c1]

To a solution of 1,3-dibromo-5-(trifluoromethoxy)benzene (25 g, 78.15 mmol, 1 eq) in i-Pr$_2$O (50 mL) was added n-BuLi (2.5 M, 32 mL, 1.02 eq) at −78° C. for 0.5 h, then acetone (7.9 g, 136 mmol, 10 mL, 1.74 eq) was added. The mixture was stirred at 20° C. for 2 h. The reaction mixture was poured into 100 mL of aqueous NH$_4$Cl and the resulting mixture was stirred for 15 min. The organic phase was separated, dried over anhydrous Na$_2$SO$_4$, filtered and evaporated in vacuo to give a residue. The residue was purified by flash silica gel chromatography (ISCO®; 80 g SepaFlash® Silica Flash Column, Eluent of 0~1% Ethylacetate/Petroleum ethergradient @ 50 mL/min). The title compound (8 g, 26.75 mmol, 34% yield) was obtained as a yellow liquid. $^1$H NMR (400 MHz, DMSO-$d_6$) δ ppm 1.94 (s, 6H), 5.90 (s, 1H), 7.91-8.01 (m, 2H), 8.19-8.25 (m, 1H).

Step 2. Preparation of 1-bromo-3-(1-chloro-1-methyl-ethyl)-5-(trifluoromethoxy)benzene

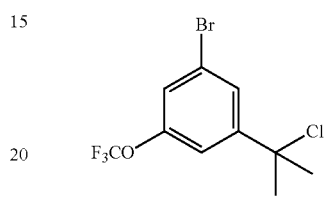

To a solution of 2-[3-bromo-5-(trifluoromethoxy)phenyl]propan-2-ol (8 g, 26.75 mmol, 1 eq) was added HCl (54.2 g, 535 mmol, 53.1 mL, 36% purity, 20 eq). The mixture was stirred at 20° C. for 2 hr. TLC (Petroleum ether:Ethyl acetate=20:1, UV) showed 2-[3-bromo-5-(trifluoromethoxy)phenyl]propan-2-ol was consumed completely and one spot was detected. The reaction mixture was poured into 100 mL of H$_2$O at 0° C. Then the mixture was extracted with DCM (50 mL*3). The combined organic layers were concentrated under reduced pressure to give a product without further purification. The title compound (7 g, 22 mmol, 82% yield) was obtained as a yellow liquid. $^1$H NMR (400 MHz, DMSO-$d_6$) δ ppm 1.84-2.01 (m, 6H), 7.59 (br d, J=12.8 Hz, 2H), 7.81 (t, J=1.5 Hz, 1H).

Step 3. Preparation of 1-bromo-3-tert-butyl-5-(trifluoromethoxy)benzene

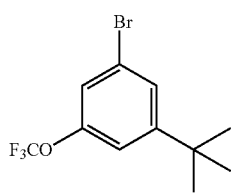 [SMILES: CC(C)(C)c1cc(Br)cc(OC(F)(F)F)c1]

To a solution of 1-bromo-3-(1-chloro-1-methyl-ethyl)-5-(trifluoromethoxy)benzene (6 g, 18.90 mmol, 1 eq) in DCM (60 mL) was added Al(CH$_3$)$_3$ (in hexane) (1 M, 37.79 mL, 2 eq) at −78° C. The mixture was stirred at 20° C. for 2 hr. TLC (Petroleum ether:Ethyl acetate=1:0, UV) indicated 1-bromo-3-(1-chloro-1-methyl-ethyl)-5-(trifluoromethoxy)benzene was consumed completely, and one new spot with lower polarity was detected. The reaction mixture was poured into 100 mL of aqueous NH$_4$Cl and the reaction mixture was stirred for 15 min. The organic phase was separated, dried over anhydrous Na$_2$SO$_4$, filtered and evaporated in vacuo to give a residue. The residue was purified by flash silica gel chromatography (ISCO®; 80 g SepaFlash® Silica Flash Column, Eluent of 0-1% Ethylacetate/Petroleum ethergradient @ 100 mL/min). The title compound (4.6 g, 15.5 mmol, 82% yield) was obtained as a yellow liquid 1H NMR (400 MHz, DMSO-$d_6$) δ ppm 1.27 (s, 9H), 7.36 (s, 1H), 7.47 (s, 1H), 7.61 (t, J=1.6 Hz, 1H).

Step 4. Preparation of 3-tert-butyl-5-(trifluoromethoxy)benzaldehyde

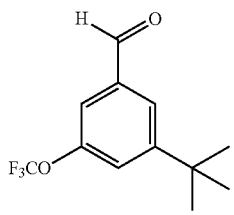 [SMILES: CC(C)(C)c1cc(C=O)cc(OC(F)(F)F)c1]

To a solution of 1-bromo-1-tert-butyl-5-(trifluoromethoxy)benzene (5.7 g, 19.18 mmol, 1 eq) in i-$Pr_2O$ (50 mL) was added n-BuLi (2.5 M, 10 mL, 1.30 eq) and stirred 0.5 h at −78° C., then DMF (2.1 g, 28.8 mmol, 2.21 mL, 1.5 eq) was added. The mixture was stirred at 20° C. for 2 hr. TLC (Petroleum ether:Ethyl acetate=20:1, UV) showed 1-bromo-3-tert-butyl-5-(trifluoromethoxy)benzene was consumed completely and one spot was detected. The reaction mixture was poured into 50 mL of $H_2O$ at 0° C. Then the mixture was extracted with DCM (50 mL*3). The combined organic layers were concentrated under reduced pressure to give a product residue. The residue was purified by flash silica gel chromatography (ISCO®; 40 g SepaFlash® Silica Flash Column, Eluent of 0~1.5% Ethylacetate/Petroleum ethergradient @ 60 mL/min). The title compound (1.95 g, 7.92 mmol, 41% yield) was obtained as a yellow liquid. $^1$H NMR (400 MHz, DMSO-$d_6$) δ ppm 1.29 (s, 9H), 7.63 (br d, J=6.4 Hz, 2H), 7.97 (t, J=1.4 Hz, 1H), 9.90-10.06 (m, 1H)

Example 37

Preparation of 3-[3-tert-butyl-5-(trifluoromethyl)phenyl]-4-[1-methyl-5-[2-(5,6,7,8-tetrahydro-1,8-naphthyridin-2-yl)ethoxy]pyrazol-3-yl]butanoic Acid

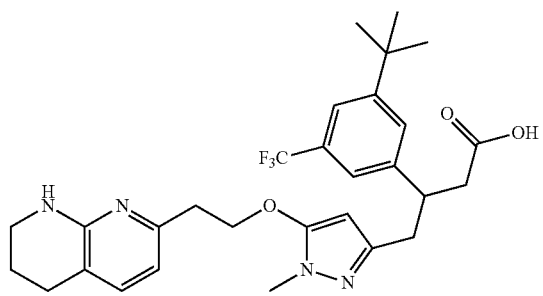 [SMILES: Cn1nc(CC(CC(=O)O)c2cc(C(C)(C)C)cc(C(F)(F)F)c2)cc1OCCc1ccc2c(n1)NCCC2]

Example 37 was prepared in analogous manner to Example 36, using 1,3-dibromo-5-(trifluoromethyl)benzene in place of 1,3-dibromo-5-(trifluoromethoxy)benzene in the reaction Scheme 15. The crude product was purified by prep-HPLC (column: Boston Green ODS 150*30 5μ; mobile phase: [water (0.1% TFA)-ACN]; B %: 35%-65%, 8 min). The title compound (12.4 mg, 22.25 μmol, 51% yield, 98% purity) was obtained as a white solid. LC-MS analysis of the liquid shows the desired product's mass: m/z 545.3.

$^1$H NMR (400 MHz, $CD_3OD$) δ ppm 1.28 (s, 9H), 1.87-1.97 (m, 2H), 2.65-2.88 (m, 6H), 3.13 (t, J=6.1 Hz, 2H), 3.43 (s, 3H), 3.44-3.55 (m, 4H), 4.28 (t, J=5.7 Hz, 2H), 5.42 (s, 1H), 6.68 (d, J=7.5 Hz, 1H), 7.27 (s, 1H), 7.44 (s, 2H), 7.59 (d, J=7.3 Hz, 1H)

Example 38

Preparation of 3-(3-(tert-butyl)-5-fluorophenyl)-4-(1-methyl-5-(2-(5,6,7,8-tetrahydro-1,8-naphthyridin-2-yl)ethoxy)-1H-pyrazol-3-yl)butanoic Acid

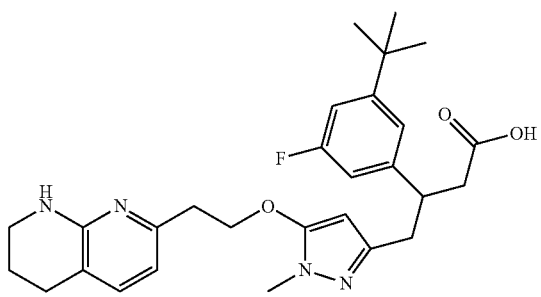 [SMILES: Cn1nc(CC(CC(=O)O)c2cc(F)cc(C(C)(C)C)c2)cc1OCCc1ccc2c(n1)NCCC2]

Example 38 was prepared in analogous manner to Example 1, using 3-tert-butyl-5-fluoro-benzaldehyde as the required benzaldehyde in the reaction Scheme 3. The crude product was purified by prep-HPLC (column: Boston Green ODS 150*30 5μ; mobile phase: [water (0.1% TFA)-ACN]; B %: 30%-56.25%, 7 min). The title compound was obtained as a white solid (57 mg, yield 41%). LC-MS analysis of the compound showed the desired product's mass: m/z 495 (M+H): $^1$H NMR (400 MHz, $CD_3OD$) δ=7.59 (d, J=7.3 Hz, 1H), 7.00 (s, 1H), 6.92 (br d, J=11.0 Hz, 1H), 6.79 (br d, J=9.8 Hz, 1H), 6.68 (d, J=7.3 Hz, 1H), 5.56 (s, 1H), 4.35 (t, J=6.0 Hz, 2H), 3.52-3.37 (m, 5H), 3.17 (t, J=5.9 Hz, 2H), 2.94-2.57 (m, 6H), 1.95 (quin, J=5.9 Hz, 2H), 1.25 (s, 9H).

Example 39

Preparation of 3-(5-isopropyl-2-methoxyphenyl)-4-(1-methyl-5-(2-(5,6,7,8-tetrahydro-1,8-naphthyridin-2-yl)ethoxy)-1H-pyrazol-3-yl)butanoic Acid Trifluoroacetate

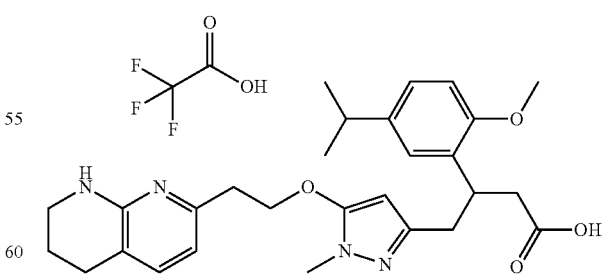

Example 39 was prepared in analogous manner to Example 1, using 5-isopropyl-2-methoxy-benzaldehyde as the required benzaldehyde in the reaction Scheme 3. The crude product was purified by prep-HPLC (column: Boston Green ODS 150*30 5μ; mobile phase: [water (0.1% TFA)-

ACN]; B %: 25%-55%, 8 min). The title compound (105 mg, 172 μmol, 55% yield, 99.1% purity, TFA) was obtained as a white solid, which was confirmed by LCMS (m/z 493.1 (M+H)), HPLC, ¹H NMR and ¹⁹F NMR. ¹H NMR (CD₃OD, 400 MHz) 7.59 (d, J=7.2 Hz, 1H), 7.02 (dd, J=8.4, 2.4 Hz, 1H), 6.96 (d, J=2.0 Hz, 1H), 6.84 (d, J=8.4 Hz, 1H), 6.67 (d, J=7.2 Hz, 1H), 5.50 (s, 1H), 4.34 (t, J=6.0 Hz, 2H), 3.80 (s, 3H), 3.73 (quin, J=7.6 Hz, 1H), 3.47-3.53 (m, 5H), 3.16 (t, J=6.0 Hz, 2H), 2.85-2.96 (m, 2H), 2.74-2.85 (m, 3H), 2.61-2.74 (m, 2H), 1.95 (quin, J=6.0 Hz, 2H), 1.16 (d, J=7.2 Hz, 6H); ¹⁹F NMR (CD₃OD, 376 MHz) -77.31 (s, 1F).

Example 40

Preparation of 3-(3-bromo-5-isopropyl-phenyl)-4-[1-methyl-5-[2-(5,6,7,8-tetrahydro-1,8-naphthyridin-2-yl)ethoxy]pyrazol-3-yl]butanoic acid trifluoroacetate

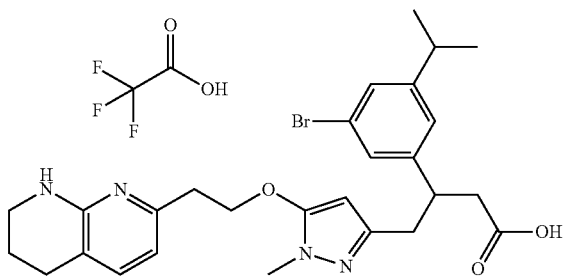

Example 40 was prepared in analogous manner to Example 1, using 3-bromo-5-isopropyl-benzaldehyde as the required benzaldehyde in the reaction Scheme 3. The crude product was purified by prep-HPLC (column: Boston Green ODS 150*30 5μ; mobile phase: [water (0.1% TFA)-ACN]; B %: 35%-59.4%, 6.5 min). The title compound was obtained as a white solid which was confirmed by LCMS (m/z 543.0 (M+H)), HPLC, ¹H NMR and ¹⁹F NMR. ¹H NMR (CD₃OD, 400 MHz) 7.60 (d, J=7.3 Hz, 1H), 7.19 (d, J=7.3 Hz, 2H), 7.04 (s, 1H), 6.68 (d, J=7.3 Hz, 1H), 5.57-5.42 (m, 1H), 4.45-4.26 (m, 2H), 3.54-3.33 (m, 5H), 3.17 (t, 0.1=6.0 Hz, 2H), 2.92-2.54 (m, 7H), 1.95 (quin, J=5.9 Hz, 2H), 1.19 (dd, J=1.4, 6.9 Hz, 6H). ¹⁹F NMR (CD₃OD, 376 MHz) -77.33 (s, 1F).

Example 41

Preparation of 3-(3-bromo-5-tert-butyl-phenyl)-4-[5-[2-(5,6,7,8-tetrahydro-1,8-naphthyridin-2-yl)ethoxy]-1-(2,2,2-trifluoroethyl)pyrazol-3-yl]butanoic Acid Trifluoroacetate

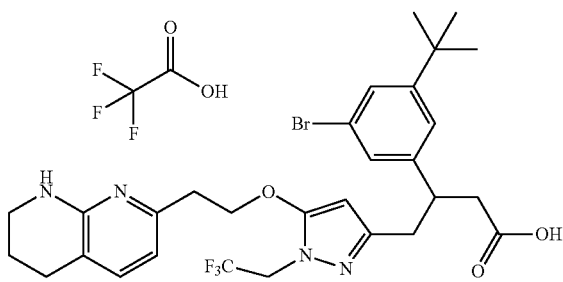

Example 41 was prepared in analogous manner to Example 1, using 3-bromo-5-tert-butylbenzaldehyde as the required benzaldehyde and (2,2,2-trifluoroethyl)hydrazine in place of methyl hydrazine in the reaction Scheme 3. The crude product was purified by prep-HPLC (TFA condition: column: Boston Green ODS 150*30 5μ; mobile phase: [water (0.1% TFA)-ACN]; B %: 38%-68%, 8 min). The title compound (105 mg, 134 μmol, 51% yield, 95% purity, TFA) was obtained as a white solid. ¹H NMR (400 MHz, CD₃OD) 7.60 (br d, J=7.6 Hz, 1H), 7.31 (s, 1H), 7.16 (dd, J=1.6, 4.0 Hz, 2H), 6.72-6.63 (m, 1H), 5.47 (s, 1H), 4.50 (q, J=8.8 Hz, 2H), 4.32 (t, J=6.0 Hz, 2H), 3.53-3.46 (m, 2H), 3.44-3.35 (m, 1H), 3.15 (t, J=6.0 Hz, 2H), 2.89-2.79 (m, 3H), 2.79-2.66 (m, 2H), 2.65-2.56 (m, 1H), 1.94 (quin, J=6.0 Hz, 2H), 1.24 (s, 9H). ¹⁹F NMR (376 MHz, CD₃OD) -72.69 (t, J=8.8 Hz, 3F), -77.33 (br s, 3F). LC-MS analysis shows the desired product's mass: m/z 625.1 (M+H), Calcd for: C₂₉H₃₄BrF₃N₄O₃: 624.17.

Example 42

Preparation of 3-(5-tert-butyl-2-hydroxy-phenyl)-4-[1-methyl-5-[2-(5,6,7,8-tetrahydro-1,8-naphthyridin-2-yl)ethoxy]pyrazol-3-yl]butanoic Acid Sodium Salt

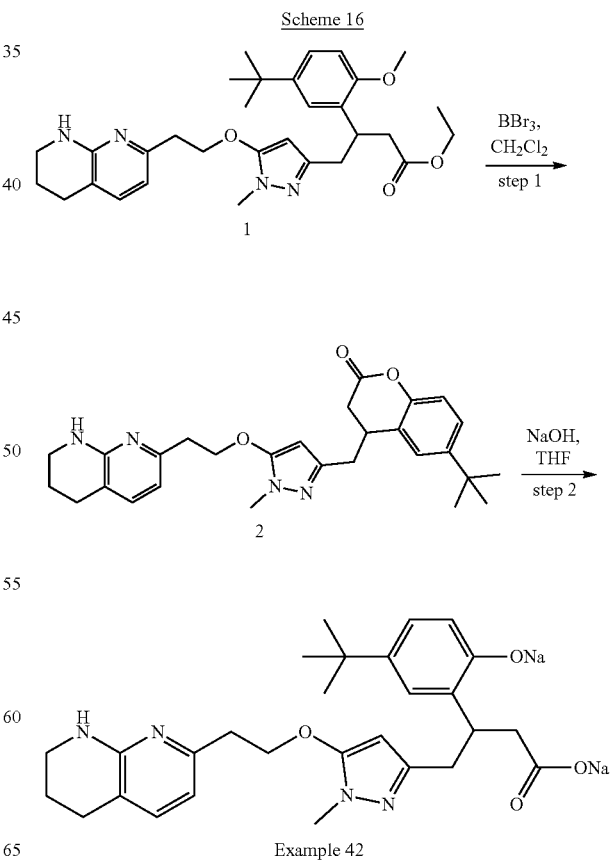

Step 1. Preparation of 6-tert-butyl-4-[[1-methyl-5-[2-(5,6,7,8-tetrahydro-1,8-naphthyridin-2-yl)ethoxy]pyrazol-3-yl]methyl]chroman-2-one

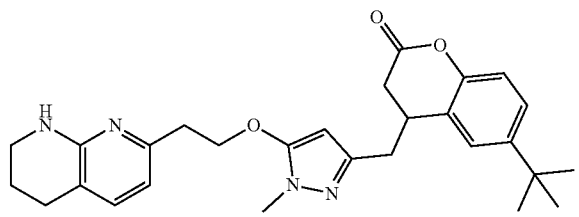 [SMILES: Cn1nc(CC2CC(=O)Oc3ccc(C(C)(C)C)cc32)cc1OCCc1ccc2c(n1)NCCC2]

To a solution of ethyl 3-(5-tert-butyl-2-methoxy-phenyl)-4-[1-methyl-5-[2-(5,6,7,8-tetrahydro-1,8-naphthyridin-2-yl)ethoxy]pyrazol-3-yl]butanoate (30 mg, 56 μmol, 1 eq) in CH$_2$Cl$_2$ (10 mL) was added BBr$_3$ (14.06 mg, 56 μmol, 5.4 μL, 1 eq) in CH$_2$Cl$_2$ (5 mL) at −78° C. The mixture was warmed to 25° C. and stirred at this temperature for 2 hr. LC-MS showed ethyl 3-(5-tert-butyl-2-methoxy-phenyl)-4-[1-methyl-5-[2-(5,6,7,8-tetrahydro-1,8-naphthyridin-2-yl)ethoxy]pyrazol-3-yl]butanoate was consumed completely and desired mass (m/z 475.1 (M+H)) was detected. The reaction mixture was poured into water (60 mL), and the resulting aqueous layer was extracted with CH$_2$Cl$_2$ (20 mL*3). The organic extracts were dried with anhydrous Na$_2$SO$_4$ and the solvent evaporated under vacuum to afford a residue without further purification. The title compound (25 mg, 53 μmol, 94% yield) was obtained as a yellow gum. LC-MS analysis of the liquid shows the desired product's mass: m/z 475.1 (M+H).

Step 2. Preparation of 3-(5-tert-butyl-2-hydroxy-phenyl)-4-[1-methyl-5-[2-(5,6,7,8-tetrahydro-1,8-naphthyridin-2-yl)ethoxy]pyrazol-3-yl]butanoic Acid Sodium Salt

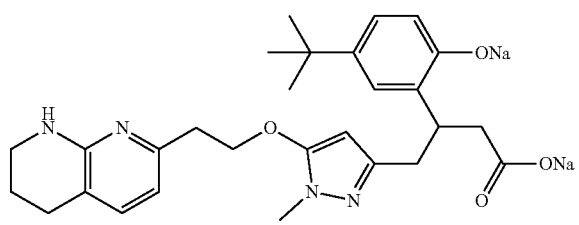

To a solution of 6-tert-butyl-4-[[1-methyl-5-[2-(5,6,7,8-tetrahydro-1,8-naphthyridin-2-yl)ethoxy]pyrazol-3-yl]methyl]chroman-2-one (25 mg, 53 μmol, 1 eq) in THF (1 mL) was added NaOH (1 M, 1.58 mL, 30 eq). The mixture was stirred at 60° C. for 16 hr. LC-MS showed 6-tert-butyl-4-[[1-methyl-5-[2-(5,6,7,8-tetrahydro-1,8-naphthyridin-2-yl)ethoxy]pyrazol-3-yl]methyl]chroman-2-one was consumed completely and desired mass (m/z 493.1 (M+H)) was detected. The reaction mixture was concentrated under reduced pressure to remove THF to give a residue. The residue was purified by prep-HPLC (column: Xbridge 150*30 mm*10 um; mobile phase: [water (0.05% ammonia hydroxide v/v)-ACN]; B %: 20%-60%, 7 min). The title compound was obtained as a white solid. LC-MS analysis of the liquid shows the desired product's mass: m/z 493.1 (M+H). $^1$H NMR (400 MHz, CD$_3$OD) 7.24 (d, J=7.3 Hz, 1H), 7.13 (d, J=2.3 Hz, 1H), 7.03 (dd, J=2.4, 8.4 Hz, 1H), 6.69 (d, J=8.5 Hz, 1H), 6.45 (d, J=7.3 Hz, 1H), 5.40 (s, 1H), 4.28 (t, J=6.4 Hz, 2H), 3.75 (quin, J=7.3 Hz, 1H), 3.42 (br s, 2H), 3.40 (s, 3H), 3.04-2.81 (m, 4H), 2.77-2.59 (m, 4H), 1.90 (quin, J=5.9 Hz, 2H), 1.25 (s, 9H).

Example 43

Preparation of 3-(5-(tert-butyl)-2-chlorophenyl)-4-(1-methyl-5-(2-(5,6,7,8-tetrahydro-1,8-naphthyridin-2-yl)ethoxy)-1H-pyrazol-3-yl)butanoic Acid Trifluoroacetate

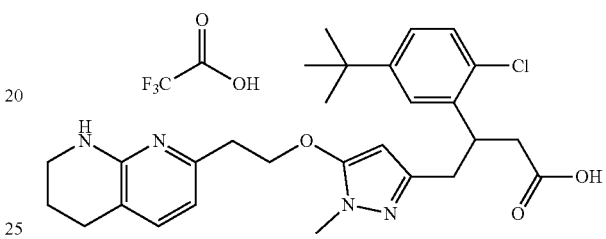

Example 43 was prepared in analogous manner to Example 1, using 5-(tert-butyl)-2-chlorobenzaldehyde (synthesized according to Scheme 17) as the required benzaldehyde in the reaction Scheme 3. The crude product was purified by Prep-HPLC (column: Boston Green ODS 150*30 5μ; mobile phase: [water (0.1% TFA)-ACN]; B %: 30%-60%, 8 min). The title compound (50.5 mg, 97.95 μmol, 41% yield, 99% purity) was obtained as a white solid which was confirmed by LCMS (m/z 511.1 (M+H)), HPLC, HMBC, $^1$H NMR and $^{19}$F NMR. $^1$H NMR (CD$_3$OD, 400 MHz) δ 7.61 (d, J=7.5 Hz, 1H), 7.30-7.23 (m, 2H), 7.22-7.18 (m, 1H), 6.69 (d, J=7.3 Hz, 1H), 5.40 (s, 1H), 4.31 (t, J=6.0 Hz, 2H), 3.96 (quin, J=7.4 Hz, 1H), 3.54-3.44 (m, 5H), 3.15 (t, J=6.0 Hz, 2H), 2.92-2.64 (m, 6H), 1.96 (quin, J=5.9 Hz, 2H), 1.27 (s, 9H). $^{19}$F NMR (CD$_3$OD, 376 MHz) −77.37 (br s, 1F).

Scheme 17

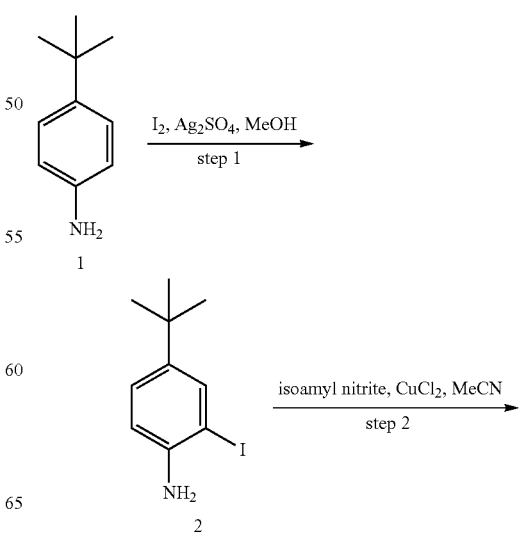

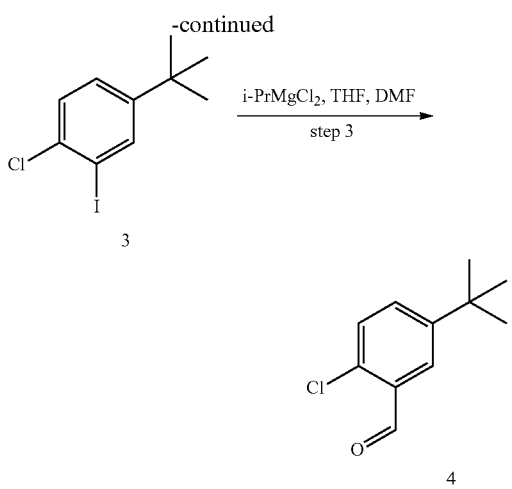

Step 1. Preparation of 4-(tert-butyl)-2-iodoaniline

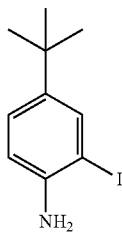

I₂ (17.01 g, 67.01 mmol, 13.5 mL, 1 eq) was added to a mixture of 4-tert-butylaniline (10 g, 67.01 mmol, 10.6 mL, 1 eq), Ag₂SO₄ (20.89 g, 67.01 mmol, 11.4 mL, 1 eq) in MeOH (300 mL). The resulting mixture was stirred at 15° C. for 2 h. The mixture was filtered, and the filtrate was concentrated. The concentrate partitioned between saturated Na₂SO₃ (150 mL) and Et₂O (200 mL). The aqueous layer was separated and extracted with Et₂O (2*150 mL). The combined organic extracts were washed with brine (200 mL), dried over Na₂SO₄ and concentrated in vacuo to give residue. The residue was purified by flash silica gel chromatography (ISCO®; 120 g CombiFlash® Silica Flash Column, Eluent of 0~10% Ethyl acetate/Petroleum ether gradient @ 80 mL/min). The title compound (14.6 g, 53.07 mmol, 79% yield) was obtained as a black brown liquid which was confirmed by ¹H NMR. ¹H NMR (CDCl₃, 400 MHz) 7.63 (d, J=2.0 Hz, 1H), 7.17 (dd, J=2.1, 8.4 Hz, 1H), 6.70 (d, J=8.3 Hz, 1H), 4.06-3.85 (m, 2H), 1.26 (s, 9H).

Step 2. Preparation of 4-(tert-butyl)-1-chloro-2-iodobenzene

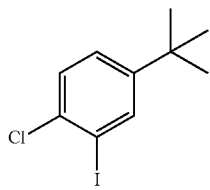

Tert-butyl nitrite (2.81 g, 27.26 mmol, 3.24 mL, 1.5 eq) was added to a mixture of CuCl₂ (2.93 g, 21.81 mmol, 1.2 eq) in CH₃CN (30 mL) under N₂. The resulting mixture was treated with a solution of 4-tert-butyl-2-iodo-aniline (5 g, 18.17 mmol, 1 eq) in CH₃CN (30 mL) and then the mixture was heated at 65° C. for 2 h. The mixture was diluted with EtOAC (50 mL) and washed with water (50 mL). The aqueous layer was extracted with EtOAC (100*2 mL). The combined organic was dried over Na₂SO₄ and concentrated in vacuo. The residue was purified by flash silica gel chromatography (ISCO®; 80 g CombiFlash® Silica Flash Column, Eluent of 0% Ethyl acetate/Petroleum ether gradient @ 65 mL/min). The title compound (3.9 g, 13.24 mmol, 73% yield) was obtained as a red liquid which was confirmed by ¹H NMR. ¹H NMR (CDCl₃, 400 MHz) 7.91-7.81 (m, 1H), 7.39-7.33 (m, 1H), 7.33-7.28 (m, 1H), 1.32-1.27 (m, 9H).

Step 3. Preparation of 5-(tert-butyl)-2-chlorobenzaldehyde

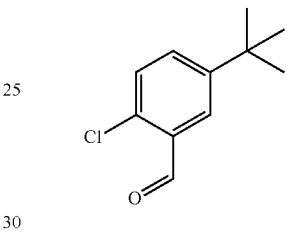

To a stirred solution of 4-tert-butyl-1-chloro-2-iodo-benzene (3.9 g, 13.24 mmol, 1 eq) in THF (20 mL) and EtOAc (20 mL) was added i-PrMgCl (2.0 M, 6.62 mL, 1 eq) drop wise at −78° C. The resulting mixture was stirred for 2 h at −78° C. and then treated with DMF (1.94 g, 26.48 mmol, 2.04 mL, 2 eq) dropwise at −78° C. After complete addition, the mixture was warmed slowly to 15° C. over 12 hr. The reaction mixture was quenched with water (20 mL), the organic layer was separated and the aqueous layer was extracted with EtOAc (30 mL*3), the combined organic layers were washed with brine (100 mL) and dried over Na₂SO₄, and evaporation. The residue was purified by flash silica gel chromatography (ISCO®; 40 g CombiFlash® Silica Flash Column, Eluent of 0% Ethyl acetate/Petroleum ether gradient @ 35 mL/min). The title compound (1.3 g, 6.61 mmol, 50% yield) was obtained as a colorless liquid which was confirmed by ¹H NMR. ¹H NMR (CDCl₃, 400 MHz) 10.52-10.44 (m, 1H), 7.95 (d, J=2.5 Hz, 1H), 7.57 (dd, J=2.5, 8.5 Hz, 1H), 7.38 (d, J=8.5 Hz, 1H), 1.38-1.31 (m, 9H).

Example 44

Preparation of 3-(5-tert-butyl-2-methyl-phenyl)-4-[1-methyl-5-[2-(5,6,7,8-tetrahydro-1,8-naphthyridin-2-yl)ethoxy]pyrazol-3-yl]butanoic Acid Trifluoroacetate

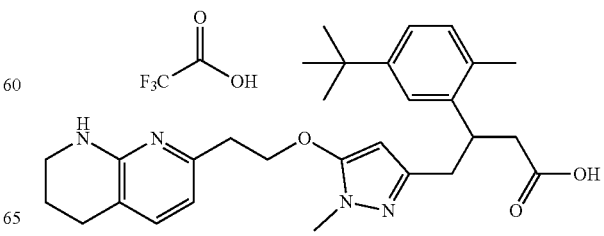

Example 44 was prepared in analogous manner to Example 1, using 5-tert-butyl-2-methyl-benzaldehyde (synthesized according to Scheme 18) as the required benzaldehyde in the reaction Scheme 3. The crude product was purified by Prep-HPLC (column: Xbridge BEH C18, 250*50 mm, 10 μm; mobile phase: [water (0.1% TFA)-ACN]; B %: 25%-41%, 9 min). The title compound 52 mg, 87 μmol, 15.5% yield, TFA) was obtained as a yellow solid. $^1$H NMR (400 MHz, CD$_3$OD): δ ppm=7.60 (d, J=7.3 Hz, 1H), 7.21 (d, J=2.0 Hz, 1H), 7.11-7.06 (m, 1H), 7.03-6.98 (m, 1H), 6.67 (d, J=7.3 Hz, 1H), 5.35 (s, 1H), 4.34-4.25 (m, 2H), 3.71 (quin, J=7.5 Hz, 1H), 3.57-3.45 (m, 5H), 3.14 (t, J=6.0 Hz, 2H), 2.83 (br t, J=6.1 Hz, 2H), 2.77 (dd, J=2.8, 7.5 Hz, 2H), 2.69-2.63 (m, 2H), 2.27 (s, 3H), 1.95 (td, J=6.0, 11.8 Hz, 2H), 1.31-1.23 (m, 9H). $^{19}$F NMR (376 MHz, CD$_3$OD)=−77.34 (s, 1F).

Scheme 18

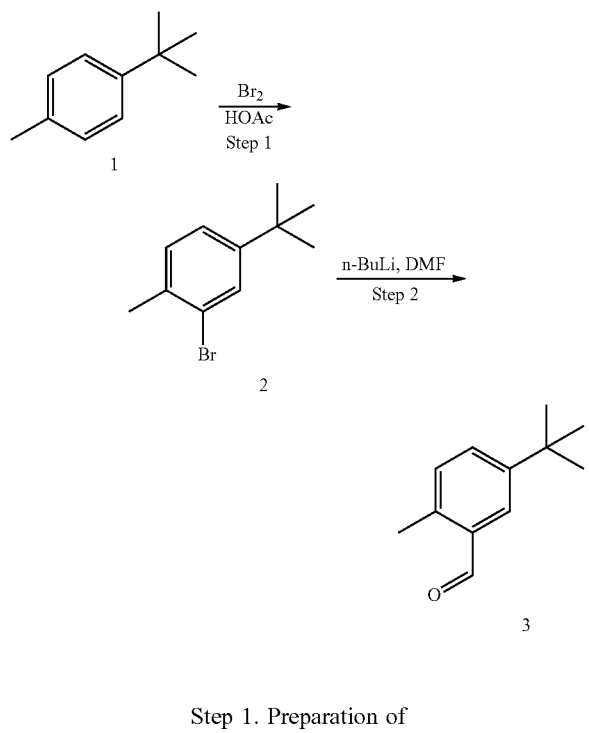

Step 1. Preparation of 2-bromo-4-tert-butyl-1-methyl-benzene

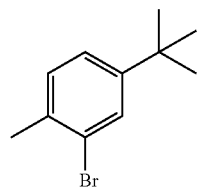

To a solution of Br$_2$ (12.94 g, 80.95 mmol, 4.17 mL, 1.2 eq) was added a solution of 1-tert-butyl-4-methyl-benzene (10 g, 67.46 mmol, 11.66 mL, 1 eq) in HOAc (30 mL) dropwise at 20° C. The resulting mixture was heated at 50° C. for 120 h. The mixture was allowed to cool to room temperature, and then water (100 mL) and aqueous sodium hydrogen sulfite were added. The mixture was extracted with Ethyl acetate (100 mL). The combined extracts were washed with water, dried over sodium sulfate, and filtered. Rotary evaporation of the filtrate gave a residue. The residue was purified by flash silica gel chromatography (ISCO®; 120 g SepaFlash® Silica Flash Column, Eluent of 100% Petroleum ether gradient @ 40 mL/min). The title compound (12.5 g, 54.9 mmol, 81% yield) was obtained as a colorless liquid.

Step 2. Preparation of 5-tert-butyl-2-methyl-benzaldehyde

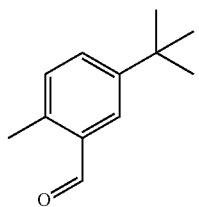

To a stirred solution of 2-bromo-4-tert-butyl-1-methyl-benzene (12.5 g, 54.9 mmol, 1 eq) in THF (170 mL) was added n-BuLi (2.5 M, 26.35 mL, 1.2 eq) dropwise at −78° C. The resulting mixture was stirred for 10 mins at −78° C. and quenched with DMF (6.02 g, 82.35 mmol, 6.34 mL, 1.5 eq) at −78° C., and stirred for 1 hr. After warming to rt, sat. NH$_4$Cl (100 mL) was added to the mixture. The resulting aqueous mixture was extracted with ethyl acetate (3×100 mL). The organic extract was dried over sodium sulfate and concentrated under reduced pressure. The residue was purified by flash silica gel chromatography (ISCO®; 40 g SepaFlash® Silica Flash Column, Eluent of 100% Petroleum ether gradient @ 35 mL/min). The title compound (4.09 g, 23.2 mmol, 42% yield) was obtained as a light yellow liquid.

Example 45

Preparation of 3-(3-bromo-5-tert-butyl-phenyl)-4-[1-tert-butyl-5-[2-(5,6,7,8-tetrahydro-1,8-naphthyridin-2-yl)ethoxy]pyrazol-3-yl]butanoic Acid Trifluoroacetate

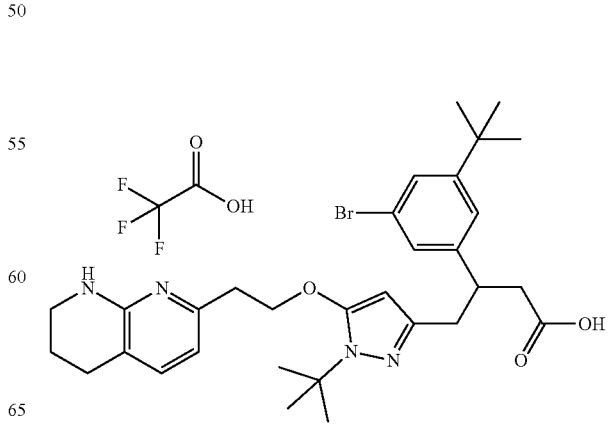

Example 45 was prepared in analogous manner to Example 1, using 3-bromo-5-tert-butylbenzaldehyde as the required benzaldehyde and tert-butylhydrazine in place of methyl hydrazine in the reaction Scheme 3. The crude product was purified by prep-HPLC (TFA condition: column: X bridge BEH C18, 250*50 mm, 10 μm; mobile phase: [water (0.1% TFA)-ACN]; B %: 25%-55%, 9 min). The title compound (0.016 g, 21.81 μmol, 44% yield, 97% purity, TFA) was obtained as a white solid. LC-MS analysis shows the desired product's mass: m/z 599.1 (M+3H); Calcd for: $C_{32}H_{43}BrN_4O_3$: 596.24. LCMS and HPLC, $^1H$ NMR and $^{19}F$ NMR, 2D NMR confirmed it was the target product. $^1H$ NMR (400 MHz, $CD_3OD$) δ 7.60 (d, J=7.2 Hz, 1H), 7.34-7.30 (m, 1H), 7.16 (d, J=12.0 Hz, 2H), 6.69 (d, J=7.6 Hz, 1H), 5.50 (s, 1H), 4.31 (t, J=6.0 Hz, 2H), 3.54-3.47 (m, 2H), 3.39 (quin, J=7.6 Hz, 1H), 3.19 (t, J=6.0 Hz, 2H), 2.89-2.56 (m, 6H), 1.94 (quin, J=6.0 Hz, 2H), 1.40 (s, 9H), 1.26 (s, 9H). $^{19}F$ NMR (376 MHz, $CD_3OD$) −77.24 (br s, 3F).

Examples 46, 47, and 48 are Prepared According to Scheme 19

Step 1. Preparation of ethyl 3-(5-cyano-2-methoxy-phenyl)-4-(1-methyl-5-(2-(5,6,7,8-tetrahydro-1,8-naphthyridin-2-yl)ethoxy)-1H-pyrazol-3-yl)butanoate

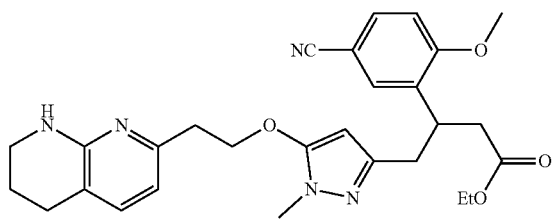 [SMILES: CCOC(=O)CC(Cc1cc(OCCc2ccc3c(n2)NCCC3)n(C)n1)c1cc(C#N)ccc1OC]

A mixture of ethyl 3-(5-bromo-2-methoxy-phenyl)-4-[1-methyl-5-[2-(5,6,7,8-tetrahydro-1,8-naphthyridin-2-yl)ethoxy]pyrazol-3-yl]butanoate (380 mg, 666 μmol, 1 eq), prepared during the synthesis of Example 14, and $Zn(CN)_2$ (234 mg, 2 mmol, 1267 μL, 3 eq) in DMF (5 mL) in a microwave vial was evacuated and back-filled with $N_2$ (3×). $Pd(PPh_3)_4$ (77 mg, 67 μmol, 0.1 eq) was added. The reaction vial was sealed, and the reaction mixture was again degassed and back-filled with $N_2$ (3×), and then stirred at 120° C. for 1.5 hr under micro-wave irradiation. The mixture was then Scheme 19

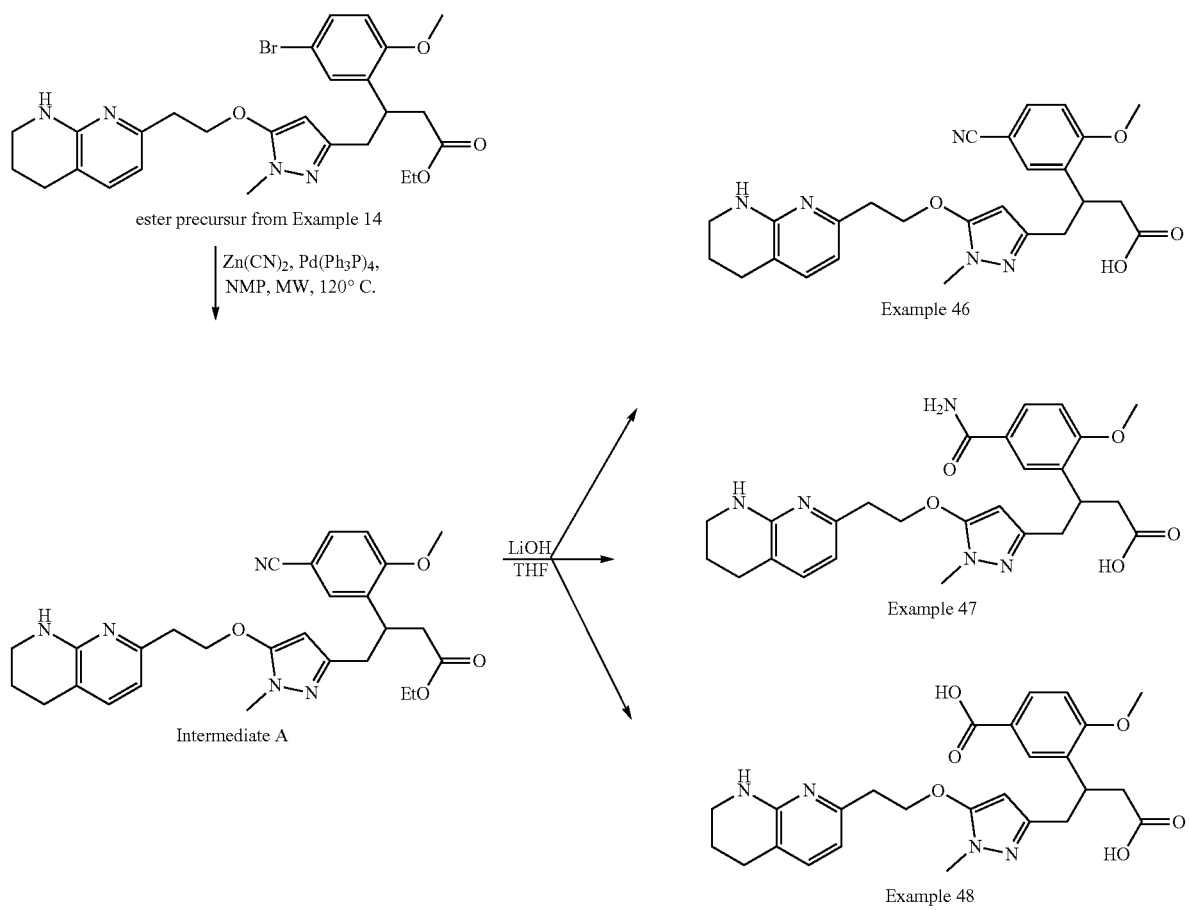

poured into water (80 mL), and extracted with EtOAc (3*50 mL). The combined organic layer was washed with brine (50 mL), dried over sodium sulfate, and evaporated to give the residue. The residue was purified by flash silica gel chromatography (ISCO®; 12 g SepaFlash® Silica Flash Column, Eluent of 0~100% Ethyl acetate/Petroleum ether gradient @ 30 mL/min). The title (135 mg, 245 µmol, 37% yield, 91% purity) was obtained as colorless oil, which was confirmed by LCMS (m/z 526.1 (M+Na))

Step 2. Preparation of Examples 46, 47 and 48

To a solution of ethyl 3-(5-cyano-2-methoxy-phenyl)-4-[1-methyl-5-[2-(5,6,7,8-tetrahydro-1,8-naphthyridin-2-yl)ethoxy]pyrazol-3-yl]butanoate, from Step 1 above, (135 mg, 245 µmol, 1 eq) in THF (5 mL) was added LiOH (1 M, 8 mL, 32.69 eq). The reaction mixture was stirred at 60° C. for 16 hr. LC-MS showed 13.8% of 3-(5-cyano-2-methoxy-phenyl)-4-[1-methyl-5-[2-(5,6,7,8-tetrahydro-1,8-naphthyridin-2-yl)ethoxy]pyrazol-3-yl]butanoic acid (Example 46), 54.2% of 3-(5-carbamoyl-2-methoxy-phenyl)-4-[1-methyl-5-[2-(5,6,7,8-tetrahydro-1,8-naphthyridin-2-yl)ethoxy]pyrazol-3-yl]butanoic acid (Example 47), 22.8% of 3-[1-(carboxymethyl)-2-[1-methyl-5-[2-(5,6,7,8-tetrahydro-1,8-naphthyridin-2-yl)ethoxy]pyrazol-3-yl]ethyl]-4-methoxybenzoic acid (Example 48). The mixture was concentrated under reduced pressure to give a residue, the residue was adjusted to pH=5 with AcOH and extracted with ethyl acetate (10 mL*2). The combined organic phase was concentrated in vacuo. The residue was purified by prep-HPLC (column: Xbridge BEH C18, 250*50 mm, 101 µm; mobile phase: [water (0.1% TFA)-ACN]; B %: 15%-45%, 9 min). The compound of Example 46 (16.2 mg, 27 µmol, 11%/0 yield, 98% purity, TFA) was obtained as a white solid; the compound of Example 47 (53 mg, 86 µmol, 35% yield, 99% purity, TFA) was obtained as a white solid; and the compound of Example 48 (20 mg, 30 µmol, 12% yield, 91% purity, TFA) was obtained as a white solid.

Example 46

Preparation of 3-(5-cyano-2-methoxyphenyl)-4-(1-methyl-5-(2-(5,6,7,8-tetrahydro-1,8-naphthyridin-2-yl)ethoxy)-1H-pyrazol-3-yl)butanoic Acid Trifluoroacetate

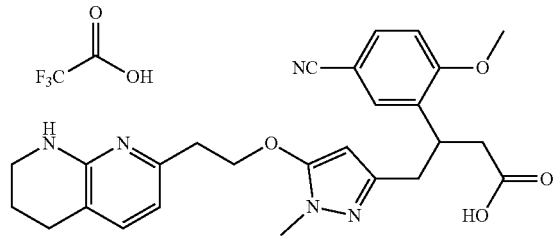 [SMILES: COc1ccc(C#N)cc1C(CC(=O)O)Cc1cc(OCCc2ccc3c(n2)NCCC3)n(C)n1 ; O=C(O)C(F)(F)F]

Example 46 was prepared using ethyl 3-(5-bromo-2-methoxy-phenyl)-4-[1-methyl-5-[2-(5,6,7,8-tetrahydro-1,8-naphthyridin-2-yl)ethoxy]pyrazol-3-yl]butanoate, prepared during the synthesis of Example 14, as shown in reaction Scheme 19, (16.2 mg, 27 µmol, 11% yield, 98% purity, TFA) was obtained as a white solid.

$^1$H NMR (CD$_3$OD, 400 MHz) δ 7.55-7.62 (m, 2H), 7.46 (d, J=2.0 Hz, 1H), 7.09 (d, J=8.4 Hz, 1H), 6.67 (d, J=7.6 Hz, 1H), 5.56 (s, 1H), 4.33-4.39 (m, 2H), 3.92 (s, 3H), 3.73-3.84 (m, 1H), 3.47-3.53 (m, 5H), 3.17 (t, J=6.0 Hz, 2H), 2.78-2.96 (m, 4H), 2.63-2.77 (m, 2H), 1.91-1.99 (m, 2H). (m/z 476.1 (M+H)).

Example 47

Preparation of 3-(5-carbamoyl-2-methoxyphenyl)-4-(1-methyl-5-(2-(5,6,7,8-tetrahydro-1,8-naphthyridin-2-yl)ethoxy)-1H-pyrazol-3-yl)butanoic Acid trifluoroacetate

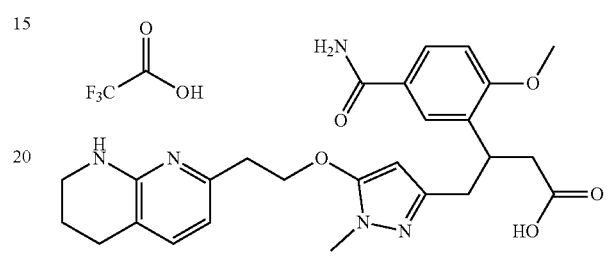

Example 47 was prepared using ethyl 3-(5-bromo-2-methoxy-phenyl)-4-[1-methyl-5-[2-(5,6,7,8-tetrahydro-1,8-naphthyridin-2-yl)ethoxy]pyrazol-3-yl]butanoate, prepared during the synthesis of Example 14, as shown in reaction Scheme 19, (53 mg, 86 µmol, 35% yield, 99% purity, TFA) was obtained as a white solid.

$^1$H NMR (DMSO-d$_6$, 400 MHz) 13.88 (br s, 1H), 8.40 (br s, 1H), 7.83 (br s, 1H), 7.70-7.77 (m, 2H), 7.62 (d, J=7.6 Hz, 1H), 7.16 (br s, 1H), 6.94-7.01 (m, 1H), 6.67 (d, J=7.2 Hz, 1H), 5.36 (s, 1H), 4.24 (br t, J=6.0 Hz, 2H), 3.82 (s, 3H), 3.68 (quin, J=7.6 Hz, 1H), 3.34-3.44 (m, 5H), 3.08 (br t, J=6.0 Hz, 2H), 2.52-2.78 (m, 6H), 1.77-1.86 (m, 2H) $^{19}$F NMR (DMSO-d$_6$, 376 MHz) −74.61 (s, 1F). LCMS (m/z 494.1 (M+H)).

Example 48

Preparation of 3-(1-carboxy-3-(1-methyl-5-(2-(5,6,7,8-tetrahydro-1,8-naphthyridin-2-yl)ethoxy)-1H-pyrazol-3-yl)propan-2-yl)-4-methoxybenzoic Acid Trifluoroacetate

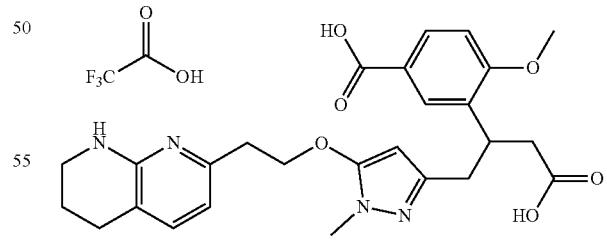

Example 48 was prepared using ethyl 3-(5-bromo-2-methoxy-phenyl)-4-[1-methyl-5-[2-(5,6,7,8-tetrahydro-1,8-naphthyridin-2-yl)ethoxy]pyrazol-3-yl]butanoate, prepared during the synthesis of Example 14, as shown in reaction Scheme 19, (20 mg, 30 µmol, 12% yield, 91% purity, TFA) was obtained as a white solid.

$^1$H NMR (DMSO-d$_6$, 400 MHz) δ 13.88 (br s, 1H), 8.38 (br s, 1H), 7.79 (dd, J=8.4, 2.0 Hz, 1H), 7.72 (d, J=2.0 Hz,

1H), 7.62 (d, J=7.2 Hz, 1H), 7.04 (d, J=8.4 Hz, 1H), 6.67 (d, J=7.6 Hz, 1H), 5.38 (s, 1H), 4.25 (t, J=6.0 Hz, 2H), 3.86 (s, 3H), 3.66 (quin, J=7.6 Hz, 1H), 3.36-3.44 (m, 5H), 3.08 (t, J=6.0 Hz, 2H), 2.54-2.77 (m, 6H), 1.77-1.86 (m, 2H) $^{19}$F NMR (DMSO-d$_6$, 376 MHz) −74.74 (s, 1F). LCMS (m/z 495.1 (M+H)).

Example 49

Preparation of 3-(3-tert-butylphenyl)-4-[1-methyl-5-[2-(5,6,7,8-tetrahydro-1,8-naphthyridin-2-yl)ethoxy]pyrazol-3-yl]butanoic Acid Trifluoroacetate

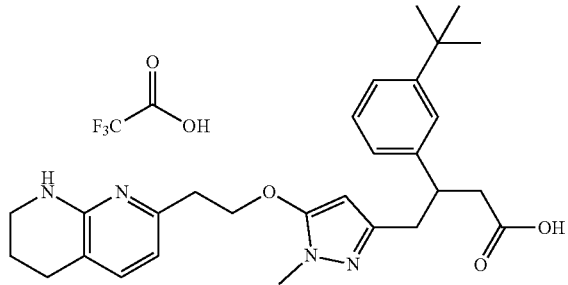 [SMILES: Cn1nc(CC(CC(=O)O)c2cccc(C(C)(C)C)c2)cc1OCCc1ccc2c(n1)NCCC2 ; O=C(O)C(F)(F)F]

Example 49 was prepared in analogous manner to Example 1, using 3-tert-butylbenzaldehyde as the required benzaldehyde in the reaction Scheme 3. The crude product was purified by Prep-HPLC (column: Boston Green ODS 150*30 5; mobile phase: [water (0.1% TFA)-ACN]; B %: 25%-500/%, 8 min). The title compound (21.7 mg, 45 μmol, 99.7% purity, TFA salt) was obtained as a white solid. $^1$H NMR (400 MHz, CD$_3$OD): δ 7.59 (br d, J=7.6 Hz, 1H), 7.24-7.13 (m, 3H), 7.04 (br d, J=6.4 Hz, 1H), 6.67 (d. J=7.2 Hz, 1H), 5.62-5.43 (m, 1H), 4.34 (br d, J=3.2 Hz, 2H), 3.54-3.45 (m, 5H), 3.44-3.34 (m, 1H), 3.16 (t, J=6.0 Hz, 2H), 2.96-2.75 (m, 4H), 2.75-2.56 (m, 2H), 2.02-1.88 (m, 2H), 1.31-1.19 (m, 9H). $^{19}$F NMR (376 MHz, CD$_3$OD) −77.33 (br d, J=5.6 Hz, 3F) LCMS (m/z 477.1 (M+H)).

Example 50

Preparation of 3-[2-methoxy-5-(4-methoxytetrahydropyran-4-yl)phenyl]-4-[1-methyl-5-[2-(5,6,7,8-tetrahydro-1,8-naphthyridin-2-yl)ethoxy]pyrazol-3-yl]butanoic Acid

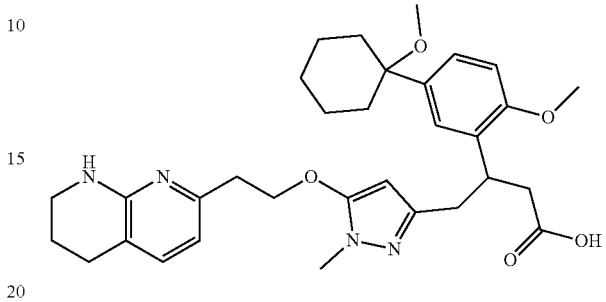

Example 50 was prepared in analogous manner to Example 1, using 2-methoxy-5-(4-methoxytetrahydro-2H-pyran-4-yl)benzaldehyde as the required benzaldehyde in the reaction Scheme 3. The crude product was purified by prep-HPLC (TFA condition: column: Boston Prime C18 150*30 mm 5 μm; mobile phase: [water (0.05% ammonia hydroxide v/v)-ACN]; B° %: 20%-50%, 7 min. The title compound (55.5 mg, 94.6 μmol, 97% purity, Sodium salt) was obtained as a white solid. $^1$H NMR (400 MHz, CD$_3$OD) δ 7.19 (d, J=7.3 Hz, 1H), 7.15 (dd, J=2.0, 8.5 Hz, 1H), 7.11 (d, J=2.0 Hz, 1H), 6.89 (d, J=8.5 Hz, 1H), 6.41 (d, J=7.3 Hz, 1H), 5.32 (s, 1H), 4.21 (t, J=−6.5 Hz, 2H), 3.82 (s, 3H), 3.80-3.78 (m, 1H), 3.77-3.64 (m, 4H), 3.38-3.34 (m, 2H), 3.33 (s, 3H), 2.99-2.80 (m, 4H), 2.79 (s, 3H), 2.70 (br t, J=6.1 Hz, 2H), 2.63 (d, J=7.3 Hz, 2H), 1.94-1.88 (m, 4H), 1.88-1.82 (m, 2H).

2-Methoxy-5-(4-methoxytetrahydro-2H-pyran-4-yl)benzaldehyde was synthesized in a manner similar to the benzaldehyde in Scheme 12, substituting 5-bromo-2-methoxybenzaldehyde for 3-bromo-5-chloro-benzaldehyde and tetrahydro-4H-pyran-4-one for methyl tetrahydropyran-4-carboxylate.

IX. BIOLOGICAL ASSAY RESULTS

The integrin inhibitory activities of the compounds of the present disclosure are shown in Table 5 along with data from a Comparator Compounds 1 and 2 (CC1 and CC2), which are depicted in Table 3.

The methods for conducting each assay are described below.

TABLE 5

| | Integrin Inhibition Assay Data | | | | | |
|---|---|---|---|---|---|---|
| Example | αvβ$_1$ SPRA IC$_{50}$ (nM) | αvβ$_3$ SPRA IC$_{50}$ (nM) | αvβ$_5$ SPRA IC$_{50}$ (nM) | αvβ$_6$ SPRA IC$_{50}$ (nM) | αvβ$_8$ SPRA IC$_{50}$ (nM) | α$_5$β$_1$ SPRA IC$_{50}$ (nM) |
| Example 1 | 6 | 5 | 0.9 | 35 | 52 | 229 |
| Example 2 | 5 | 4 | 0.3 | 43 | 32 | 192 |
| Example 3 | 5 | 3 | 0.4 | 99 | 114 | 114 |
| Example 4 | 5 | 3 | 0.5 | 189 | 79 | 343 |
| Example 5 | 11 | 6 | 0.4 | 73 | 16 | 140 |
| Example 6 | 10 | 5 | 0.4 | 8 | 19 | 158 |
| Example 7 | 7 | 7 | 0.6 | 50 | 23 | 224 |
| Example 8 | 12 | 6 | 1 | 52 | 48 | 166 |
| Example 9 | 9 | 6 | 0.2 | 12 | 62 | 110 |
| Example 10 | 17 | 3.6 | 1 | 25 | 12 | 120 |
| Example 11 | 11 | 6 | 0.8 | 60 | 42 | 150 |
| Example 12 | 4.5 | 4.3 | 0.1 | 27 | 14 | NT |
| Example 13 | 5.8 | 11 | 16 | 51 | 26 | 59 |

TABLE 5-continued

Integrin Inhibition Assay Data

| Example | αvβ$_1$ SPRA IC$_{50}$ (nM) | αvβ$_3$ SPRA IC$_{50}$ (nM) | αvβ$_5$ SPRA IC$_{50}$ (nM) | αvβ$_6$ SPRA IC$_{50}$ (nM) | αvβ$_8$ SPRA IC$_{50}$ (nM) | α$_5$β$_1$ SPRA IC$_{50}$ (nM) |
|---|---|---|---|---|---|---|
| Example 14 | 5 | 6.7 | 7.9 | 22 | 12 | 44 |
| Example 15 | 3.8 | 2.6 | 0.3 | 49 | 90 | 85 |
| Example 16 | 3 | 7.7 | 3.1 | 80 | 7.8 | 30 |
| Example 17 | 4.4 | 7.4 | 0.4 | 28 | 6.9 | 11 |
| Example 18 | 1.4 | 84 | 180 | 620 | 85 | 6.4 |
| Example 19 | 6.3 | 6.4 | 1.2 | 45 | 8.5 | 15 |
| Example 20 | 3.9 | 3.6 | 0.2 | 17 | 14 | 5.5 |
| Example 21 | 3.7 | 2.5 | 0.2 | 47 | 53 | 12 |
| Example 22 | 2.2 | 3.3 | 0.6 | 26 | 17 | 8.8 |
| Example 23 | 3.8 | 7.5 | 6.5 | 38 | 7.9 | 8.8 |
| Example 24 | 4.4 | 4.5 | 0.2 | 110 | 89 | 15 |
| Example 25 | 3.1 | 4.6 | 2.9 | 25 | 12 | 12 |
| Example 26 | 6.8 | 9.6 | 1.8 | 45 | 9.3 | 16 |
| Example 27 | 4.4 | 5.6 | 0.5 | 47 | 11 | 18 |
| Example 28 | 3.9 | 10 | 0.8 | 15 | 3.5 | 8.5 |
| Example 29 | 9.4 | 5.3 | 0.5 | 52 | 9.5 | 5.1 |
| Example 30 | 6.6 | 8.1 | 0.5 | 180 | 81 | 12 |
| Example 31 | 1.4 | 6.5 | 3.3 | 63 | 9.9 | 12 |
| Example 32 | 0.9 | 380 | 280 | 230 | 87 | 33 |
| Example 33 | 2400 | 150 | 3.1 | 2400 | 970 | 3900 |
| Example 34 | 47 | 4.6 | 2.3 | 130 | 42 | 550 |
| Example 35 | 7.6 | 10000 | 10000 | 1100 | 120 | 75 |
| Example 36 | 6.5 | 10 | 1.1 | 120 | 40 | 7.1 |
| Example 37 | 7.5 | 7.3 | 6.2 | 140 | 18 | 7.9 |
| Example 38 | 4.5 | 7.9 | 0.3 | 110 | 140 | 23 |
| Example 39 | 3.2 | 290 | 96 | 230 | 110 | 31 |
| Example 40 | 6.3 | 7.2 | 1.1 | 79 | 9 | 21 |
| Example 41 | 4.5 | 9 | 2.2 | 85 | 6.9 | 6.5 |
| Example 42 | 2.4 | 18 | 6.6 | 20 | 3.1 | 2.1 |
| Example 43 | 7.3 | 94.4 | 16.6 | 800 | 88 | 77 |
| Example 44 | 14 | 270 | 76 | 7100 | 360 | 230 |
| Example 45 | 3 | 7.7 | 3.1 | 80 | 7.8 | 30 |
| Example 46 | 8.1 | 9.9 | 1 | 30 | 31 | 51 |
| Example 47 | 4.9 | 4.9 | 0.3 | 77 | 3.6 | 13 |
| Example 48 | 19 | 5 | 0.7 | 680 | 92 | 230 |
| Example 49 | 4.4 | 7 | 0.4 | 94 | 73 | 12 |
| CC1 | 7 | 3 | 0.3 | 132 | 100 | 79 |
| CC2 | 19 | 3.1 | 0.2 | 54 | 680 | 770 |

NT = Not Tested

A. Solid Phase Receptor Assay (SPRA) for α5β1 Function

Purified human fibronectin (R&D Systems, 1918-FN) diluted to 2 μg/mL in TBS+ buffer (25 mM Tris pH 7.4, 137 mM NaCl, 2.7 mM KCl, 1 mM CaCl$_2$, 1 mM MgCl$_2$, 1 mM MnCl$_2$) was added to wells (50 μL/well) of a 96-well half-well transparent microtiter plate (Costar 3690) and incubated overnight at 4° C. Wells were washed 3 times with 150 μL TBS+ and then 150 μL of blocking buffer (TBS+ with 1% bovine serum albumin, Sigma A7906) was added. The plate was incubated for 1 hr at 37° C. and then washed 3× with TBS+ buffer. Recombinant human integrin α5β1 (R&D Systems, 3230-A5) was diluted to 0.1 μg/mL in TBS+/0.1% bovine serum albumin, and 49 μL was added to each well. Compounds were diluted to 20 μM and then 1 μL was added to each well of the plate according to a standard template with each sample repeated in triplicate. After incubation for two hours at room temperature, the plate was washed 3× with 150 μL of TBS+ buffer. To each well, 50 μL of biotinylated anti-α5 antibody (R&D Systems, BAF1864) at 0.5 μg/mL in TBS+/0.1% BSA were added and the plate covered and incubated for 1 hr at room temperature. After washing the plate 3× with 150 μL of TBS+ buffer, 50 μL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 μL of room temperature TMB substrate (Sigma, T4444) added to each well in the dark and the plate incubated for 25 min at room temperature. 25 μL of 1.0 M phosphoric acid was added as a stop solution and the plates were read at 450 nm using a Spectramax plate reader. Concentration-response curves were constructed by non-linear regression (best fit) analysis, and IC$_{50}$ values were calculated for each compound.

B. Solid Phase Receptor Assay (SPRA) for αvβ1 Function

Purified human fibronectin (R&D Systems, 1918-FN) diluted to 5 μg/mL in TBS+ buffer (25 mM Tris pH 7.4, 137 mM NaCl, 2.7 mM KCl, 1 mM CaCl$_2$), 1 mM MgCl$_2$, 1 mM MnCl$_2$) was added to wells (50 μL/well) of a 96-well half-well transparent microtiter plate (Costar 3690) and incubated overnight at 4° C. Wells were washed 3 times with 150 μL TBS+ and then 150 μL of blocking buffer (TBS+ with 1% bovine serum albumin, Sigma A7906) was added. The plate was incubated for 1 hr at 37° C. and then washed 3× with TBS+ buffer. Recombinant human integrin αvβ1 (R&D Systems. 6579-AV) was diluted to 2.0 μg/mL in TBS+/0.1% bovine serum albumin, and 49 μL was added to each well. Compounds were diluted to 20 μM and 1 μL was added to each well of the plate according to a standard template with each sample repeated in triplicate. After incubation for two hours at room temperature, the plate was washed 3 with 150 μL of TBS+ buffer. To each well, 50 μL of biotinylated anti-αv antibody (R&D Systems, BAF1219) at 1 μg/mL in TBS+/0.1% BSA were added and the plate covered and incubated for 1 hr at room temperature. After washing the plate 3× with 150 μL of TBS+ buffer, 50 μL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 μL of TMB substrate (Sigma, T4444) added to each well in the dark and the plate incubated for 25 min at room temperature. 25 μL of 1.0 M phosphoric acid was added as a stop solution and the plates were read at 450 nm using a Spectramax plate reader. Concentration-response curves were constructed by non-linear regression (best fit) analysis, and $IC_{50}$ values were calculated for each compound.

C. Solid Phase Receptor Assay (SPRA) for αvβ3 Function

Recombinant human vitronectin (R & D Systems, 2308-VN) diluted to 1 μg/mL in TBS+ buffer (25 mM Tris pH 7.4, 137 mM NaCl, 2.7 mM KCl, 1 mM $CaCl_2$), 1 mM $MgCl_2$, 1 mM $MnCl_2$) was added to wells (50 μL/well) of a 96-well half-well transparent microtiter plate (Costar 3690) and incubated overnight at 4° C. Wells were washed 3 times with 150 μL TBS+ and then 150 μL of blocking buffer (TBS+ with 1% bovine serum albumin, Sigma A7906) was added. The plate was incubated for 1 hr at 37° C. and then washed 3× with TBS+ buffer. Recombinant human integrin αvβ3 (R&D Systems, 3050-AV) was diluted to 1 pig/mL in TBS+/0.1% bovine serum albumin, and 49 μL was added to each well. Compounds were diluted to 20 μM and then 1 μL was added to each well of the plate according to a standard template with each sample repeated in triplicate. After incubation for two hours at room temperature, the plate was washed 3× with 150 μL of TBS+ buffer. To each well, 50 μL of biotinylated anti-αv antibody (R&D Systems, BAF1219) at 0.5 μg/mL in TBS+/0.1% BSA were added and the plate covered and incubated for 1 hr at room temperature. After washing the plate 3× with 150 μL of TBS+ buffer, 50 μL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 μL of TMB substrate (Sigma, T4444) added to each well in the dark and the plate was incubated for 25 min at room temperature. 25 μL of 1.0 M phosphoric acid was added as a stop solution and the plates were read at 450 nm using a Spectramax plate reader. Concentration-response curves were constructed by non-linear regression (best fit) analysis, and $IC_{50}$ values were calculated for each compound.

D. Solid Phase Receptor Assay (SPRA) for αvβ5 Function

Recombinant human vitronectin (R& D Systems, 2308-VN) at 0.25 μg/mL in TBS+ buffer (25 mM Tris pH 7.4, 137 mM NaCl, 2.7 mM KCl, 1 mM $CaCl_2$), 1 mM $MgCl_2$, 1 mM $MnCl_2$) was added to wells (50 μL/well) of a 96-well half-well transparent microtiter plate (Costar 3690) and incubated overnight at 4° C. Wells were washed 3 times with 150 μL TBS+ and then 150 μL of blocking buffer (TBS+ with 1% bovine serum albumin, Sigma A7906) was added. The plate was incubated for 1 hr at 37° C. and then washed 3× with TBS+ buffer. Recombinant human integrin αvβ5 (R&D Systems, 2528-AV) was diluted to 0.1 μg/mL in TBS+/0.1% bovine serum albumin, and 49 μL was added to each well. Compounds were diluted to 20 μM and then 1 μL was added to each well of the plate according to a standard template with each sample repeated in triplicate. After incubation for two hours at room temperature, the plate was washed 3× with 150 μL of TBS+ buffer. To each well, 50 μl of biotinylated anti-αv antibody (R&D Systems, BAF1219) at 0.5 μg/mL in TBS+/0.1% BSA at 0.5 μg/mL were added and the plate covered and incubated for 1 hr at room temperature. After washing the plate 3 with 150 μL of TBS+ buffer, 50 μL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 μL of TMB substrate (Sigma T4444) added to each well in the dark and the plate incubated for 5 min at room temperature. 25 μL of 1.0 M phosphoric acid was added as a stop solution and the plates were read at 450 nm using a Spectramax plate reader. Concentration-response curves were constructed by non-linear regression (best fit) analysis, and $IC_{50}$ values were calculated for each compound.

E. Solid Phase Receptor Assay (SPRA) for αvβ6 Function

Recombinant human LAP (R&D Systems, 246-LP) diluted to 0.25 μg/mL in TBS+ buffer (25 mM Tris pH 7.4, 137 mM NaCl, 2.7 mM KCl, 1 mM $CaCl_2$), 1 mM $MgCl_2$, 1 mM $MnCl_2$) was added to wells (50 μL/well) of a 96-well half-well transparent microtiter plate (Costar 3690) and incubated overnight at 4° C. Wells were washed 3 times with 150 μL TBS+, and then 150 μL of blocking buffer (TBS+ with 1% bovine serum albumin, Sigma A7906) was added. The plate was incubated for 1 hr at 37° C., and then washed 3× with TBS+ buffer. Recombinant human integrin αvβ6 (R&D Systems, 3817-AV) was diluted to 0.1 μg/mL in TBS+/0.1% bovine serum albumin, and 49 μL was added to each well. Compounds were diluted to 20 μM and then 1 μL was added to each well of the plate according to a standard template with each sample repeated in triplicate. After incubation for two hours at room temperature, the plate was washed 3× with 150 μL of TBS+ buffer. To each well, 50 μL of biotinylated anti-αv antibody (R&D Systems, BAF1219) at 0.5 μg/mL in TBS+/0.1% BSA were added and the plate was covered and incubated for 1 hr at room temperature. After washing the plate 3× with 150 μL of TBS+ buffer, 50 μL of streptavidin-conjugated horseradish peroxidase (R&D Systems, DY998) diluted in TBS+ blocking buffer were added to the wells and the plate incubated for 20 min at room temperature. The plate was washed 3× with TBS+ buffer followed by 50 μL of TMB substrate (Sigma T4444) added to each well in the dark and the plate incubated for 10 min at room temperature. 25 μL of 1.0 M phosphoric acid was added as a stop solution and the plates were read at 450 nm using a Spectramax plate reader. Concentration-response curves were constructed by non-linear regression (best fit) analysis, and $IC_{50}$ values were calculated for each compound.

F. Solid Phase Receptor Assay (SPRA) for αvβ8 Function

Recombinant human LAP protein (R&D Systems, Inc, 246-LP) diluted to 0.5 μg/mL in TBS+ buffer (25 mM Tris pH 7.4, 137 mM NaCl, 2.7 mM KCl, 1 mM $CaCl_2$), 1 mM $MgCl_2$, 1 mM $MnCl_2$) was added to wells (50 μl/well) of a 96-well half-well transparent microtiter plate (Costar 3690), and incubated overnight at 4° C. Wells were washed 3 times with 150 μL TBS+ and then 150 μL of blocking buffer (TBS+ with 1% bovine serum albumin, Sigma A7906) was added. The plate was incubated for 1 hr at 37° C. and then washed 3× with TBS+. Recombinant human integrin αvβ8 (R&D Systems, 4135-AV) was diluted to 0.1 μg/mL in TBS+/0.1% bovine serum albumin, and 49 µL was added to each well. Compounds were diluted to 20 µM and 1 µL was added to each well of the plate according to a standard template with each sample repeated in triplicate. After incubation for two hours at room temperature, the plate was washed 3× with 150 µL of TBS+. To each well, 50 µL of biotinylated anti-αv antibody (R&D Systems, BAF1219) at 1 µg/mL in TBS+/0.1% BSA were added and the plate was covered and incubated for 1 hr at room temperature. After washing the plate 3× with 150 µL of TBS+ buffer, 50 µL of streptavidin-conjugated horseradish peroxidase (R&D Systems, DY998) diluted in TBS+ blocking buffer were added to the wells and the plate incubated for 20 min at room temperature. The plate was washed 3× with TBS+ followed by 50 µL of TMB substrate (Sigma T4444) added to each well in the dark and the plate incubated for 10 min at room temperature. 25 µL of 1.0 M phosphoric acid was added as a stop solution and the plates were read at 450 nm using a Spectramax plate reader. Concentration-response curves were constructed by non-linear regression (best fit) analysis, and $IC_{50}$ values were calculated for each compound.

While the disclosure may have focused on several embodiments or may have been described in terms of preferred embodiments, it will be apparent to those of skill in the art that variations and modifications may be applied to the compounds, compositions, and methods without departing from the spirit, scope, and concept of the invention. All variations and modifications apparent to those skilled in the art are deemed to be within the spirit, scope, and concept of the invention as defined by the appended claims.

X. REFERENCES

The following references to the extent that they provide exemplary procedural or other details supplementary to those set forth herein, are specifically incorporated herein by reference.

U.S. Pat. Pub. 2005/0004200
PCT Pub. WO 2004/058761
Adachi et al., *Clin. Cancer Res.*, 6(1):96-101, 2000.
Asano et al., *J. Immunol.*, 175(11):7708-7718, 2005a.
Asano, et al., *Arthritis Rheum.*, 52(9):2897-2905, 2005b.
Avraamides et al., *Nat. Rev. Cancer,* 8(8):604-617, 2008.
Bax et al., *J. Biol. Chem.*, 278(36):34605-34616, 2003.
Becker et al., *Tetrahedron,* 39:4189-4192, 1983.
Bennet, *J. Clin. Invest.*, 115(12):3363-69, 2005.
Bhaskar et al., *J. Transl. Med.*, 5:61, 2007.
Blase et al., *Int. J. Cancer,* 60(6):860-866, 1995.
Bouzeghrane, et al., *J. Mol. Cell. Cardiology,* 36:343-353, 2004.
Clark, et al., *Organic Process Research & Development,* 8:51-61, 2004.
Clark, et al., *Organic Process Research & Development,* 8:571-575, 2004.
Collo, *J. Cell Sci.,* 112(Pt 4):569-578, 1999.
Cook et al., *JPET* 281:677-89, 1997.
Danen et al., *Histopathology,* 24(3):249-256, 1994.
Edward, *Curr. Opin. Oncol.,* 7(2):185-191, 1995.
Engleman et al., *J. Clin. Invest.,* 99(9):2284-2292, 1997.
Faulconbridge et al., *Tetrahedron Lett.,* 41:2679-2681, 2000.
Ferrari et al., *Proc. Natl. Acad. Sci. USA,* 103(46):17260-17265, 2006.
Gao and Brigstock, *Gut,* 55:856-862, 2006.
Gerber, et al., *Nature,* 503(7474):126-130, 2013.
Girsch et al., *J. Med. Chem.,* 50:1658-1667, 2007.
Girsch et al., *J. Med. Chem.,* 51:6752-6760, 2008.
Giordano et al., *Curr. Drug Metab.,* 17(2):194-203, 2016.
Greene & Wuts, *Protective Groups in Organic Synthesis,* 3rd Ed., John Wiley, 1999. *Handbook of Pharmaceutical Salts: Properties, and Use,* Stahl and Wermuth (Eds.), Verlag Helvetica Chimica Acta, 2002.
Henderson, et al., *Nat. Med.,* 19(12):1617-1624, 2013.
Herlt, et al., *Austr. J. Chem.,* 34(6):1319-1324, 1981.
Horan et al., *Am. J. Respir. Crit. Care Med.,* 177(1):56-65, 2008.
Huang, et al., *J. Cell. Biol.,* 133(4):921-928, 1996.
Jorgensen, et al., *J. Am. Chem. Soc.,* 124(42):12557-12565, 2002.
Kim et al., *Am. J. Pathol.,* 156(4):1345-1362, 2000.
King et al., *Vascular Pharmacology,* 78:10-16, 2016.
Lacy-Hulbert, et al., *Proc. Natl. Acad. Sci. USA,* 104(40): 15823-15828, 2007.
Landis et al., *Organic Process Research & Development.* 6:539-546, 2002.
Levine, et al., *Am. J. Pathol.,* 156:1927-1935, 2000.
Li et al., *Invest. Ophthalmol. Vis. Sci.,* 50(12):5988-5996, 2009.
Livant et al., *J. Clin. Invest.,* 105(11):1537-1545, 2000.
Lobert et al., *Dev. Cell,* 19(1):148-159, 2010.
Lu, et al., *J. Cell Sci.,* 115:4641-4648, 2002.
Luzina, et al., *Arthritis Rheum.,* 60(5): 1530-1539, 2009.
*March's Advanced Organic Chemistry: Reactions, Mechanisms, and Structure,* 2007.
Melton et al., *J. Clin. Invest.,* 120(12):4436-4444, 2010.
Millard et al., *Theranostics,* 1:154-88, 2011.
Mu et al., *Cell Biol.,* 157(3):493-507, 2002.
Munger et al., *Cell.,* 96(3):319-328, 1999.
Munger et al., *Mol. Biol. Cell,* 9:2627-2638, 1998.
Nakamura, et al., *J. Bone Miner. Metab.,* 25(6):337-334, 2007.
Nishimura, *Am. J. Pathol.,* 175(4):1362-1370, 2009.
Patsenker, et al., *J. Hepatol.,* 46(5):878-887, 2007.
Penning, et al., *Bioorg. Med Chem. Lett.,* 16:3156-3161, 2006.
Perdih, *Curr. Med. Chem.,* 17(22):2371-2392, 2010.
Popov et al., *J. Hepatol.,* 48(3):453-464, 2008.
Reagan-Shaw et al., *FASEB J.,* 22(3):659-661, 2008
Reed, et al., *Sci. Transl. Med.,* 7(288):288ra79, 2015.
Schneider, et al., *Bone,* 48(1):54-65, 2011.
Scotton et al., *J. Clin. Invest.,* 119(9):2550-2563, 2009.
Suehiro et al., *J. Biochem.,* 128(4):705-710, 2000.
Sun, et al., *Am. J. Therapeutics,* 2014.
Tatler, et al, *J. Immunol.,* 187(11):6094-6107, 2011.
Travis, et al., *Nature,* 449(7160):361-365, 2007.
Wipff et al., *J. Cell Biol.,* 179(6): 1311-1323, 2007.
Worthington, et al., *Immunity,* 42(5):903-915, 2015.
Yang et al., *Development,* 119(4): 1093-1105, 1993.
Yoshimura, *Curr. Top. Microbiol. Immunol.,* 350:127-147, 2011.
Zahn et al., *Arch. Ophthalmol.,* 127(10):1329-1335, 2009.
Zahn et al., *Invest. Ophthalmol. Vis. Sci.,* 51(2):1028-1035, 2010.

What is claimed is:

1. A compound of the formula:

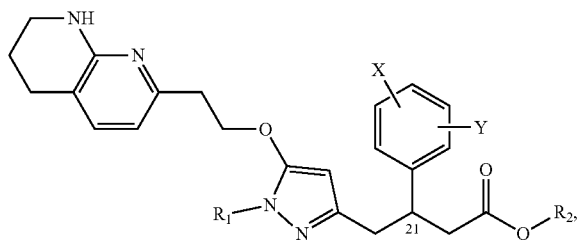

(I)

or a pharmaceutically acceptable salt or tautomer thereof, wherein:

$R_1$ is hydrogen, unsubstituted $C_{1-8}$alkyl, substituted $C_{1-8}$alkyl;

$R_2$ is hydrogen, unsubstituted $C_{1-8}$alkyl, or substituted $C_{1-8}$alkyl;

X is hydrogen, halo, cyano, unsubstituted $C_{1-12}$alkyl, substituted $C_{1-12}$alkyl, unsubstituted $C_{1-12}$alkoxy, substituted $C_{1-12}$alkoxy, unsubstituted 3-10 membered heterocycloalkyl, substituted 3-10 membered heterocycloalkyl, unsubstituted $C_{2-12}$acyloxy, substituted $C_{2-12}$acyloxy, or

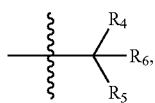

where $R_4$ and $R_5$ are each independently unsubstituted $C_{1-8}$alkyl or substituted $C_{1-8}$alkyl, and $R_6$ is hydrogen, —OH, —CN, —NH$_2$, —CF$_3$, —CF$_2$H, —CH$_2$F, —CO$_2$H, —CO$_2$—C$_{1-8}$alkyl, —C(=O)NH$_2$, —CH$_2$OH, —CH$_2$O—C$_{1-8}$alkyl, or C$_{1-8}$alkoxy, or X is

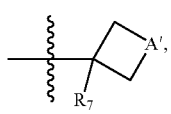

where A' is —CF$_2$—, —O—, C$_{1-6}$alkanediyl, C$_{1-8}$alkoxydiyl, or a covalent bond, thereby forming a cyclopropane ring, and $R_7$ is —OH, —CN, —NH$_2$, —CO$_2$H, —CO$_2$—C$_{1-8}$alkyl, —C(=O)NH$_2$, —CF$_3$, —CF$_2$H, —CH$_2$F, —CH$_2$OH, —CH$_2$O—C$_{1-8}$alkyl, C$_{1-8}$alkyl or C$_{1-8}$alkoxy;

Y is t-butyl, or

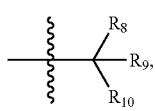

where $R_8$ and $R_9$ are each independently unsubstituted $C_{1-8}$alkyl or substituted $C_{1-8}$alkyl, and $R_{10}$ is hydrogen, —OH, —CN, —NH$_2$, —CF$_3$, —CF$_2$H, —CFH$_2$, —CO$_2$H, —CO$_2$—C$_{1-8}$alkyl, —C(=O)NH$_2$, —CH$_2$OH, CH$_2$O—C$_{1-8}$alkyl, or C$_{1-8}$alkoxy, or Y is

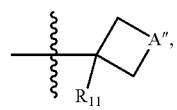

where A" is —CF$_2$—, —O—, C$_{1-6}$alkanediyl, C$_{1-8}$alkoxydiyl, or a covalent bond, thereby forming a cyclopropane ring; and $R_{11}$ is —OH, —CN, —NH$_2$, —CO$_2$H, —CO$_2$—C$_{1-8}$alkyl, —C(=O)NH$_2$, —CF$_3$, —CF$_2$H, —CH$_2$F, —CH$_2$OH, —CH$_2$O—C$_{1-8}$alkyl, C$_{1-8}$alkyl or C$_{1-8}$alkoxy.

2. The compound of claim 1 further defined as:

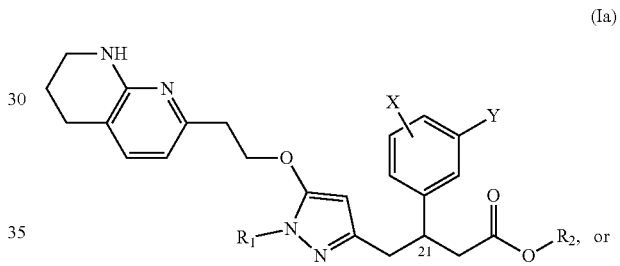

(Ia)

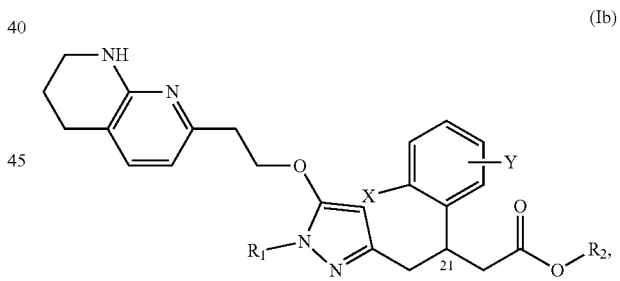

(Ib)

or a pharmaceutically acceptable salt or tautomer thereof.

3. The compound of claim 1 further defined as:

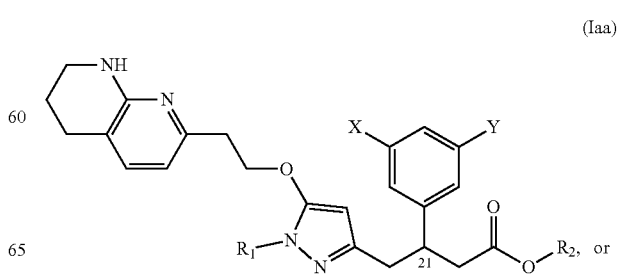

(Iaa)

-continued (Iba)

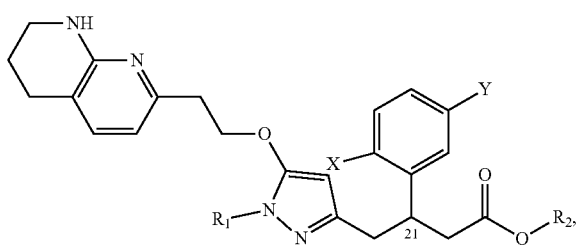

or a pharmaceutically acceptable salt or tautomer thereof, wherein:

$R_1$ is unsubstituted $C_{1-8}$alkyl, substituted $C_{1-8}$alkyl;

$R_2$ is hydrogen, unsubstituted $C_{1-6}$alkyl, or substituted $C_{1-6}$alkyl;

X is halo, cyano, unsubstituted $C_{1-12}$alkyl, substituted $C_{1-12}$alkyl, unsubstituted $C_{1-12}$alkoxy, substituted $C_{1-12}$alkoxy, unsubstituted 3-10 membered heterocycloalkyl, substituted 3-10 membered heterocycloalkyl, unsubstituted $C_{2-12}$acyloxy, substituted $C_{2-12}$acyloxy, or

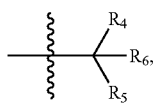

or
X is

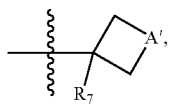

where A' is —CF$_2$—, —O—, $C_{1-6}$alkanediyl, $C_{1-8}$alkoxydiyl, or a covalent bond, thereby forming a cyclopropane ring;

$R_8$ and $R_9$ are each independently are each independently unsubstituted $C_{1-6}$alkyl or substituted $C_{1-6}$alkyl; and and $R_{10}$ is hydrogen, —OH, —CN, —NH$_2$, —CF$_3$, —CF$_2$H, —CFH$_2$, —CO$_2$H, —CO$_2$—C$_{1-6}$alkyl, —C(=O)NH$_2$, —CH$_2$OH, CH$_2$O—C$_{1-6}$alkyl, or $C_{1-6}$alkoxy.

4. The compound of claim 1 further defined as:

(Iaa)

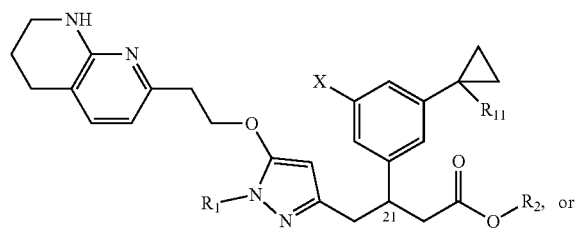

or

-continued (Iab)

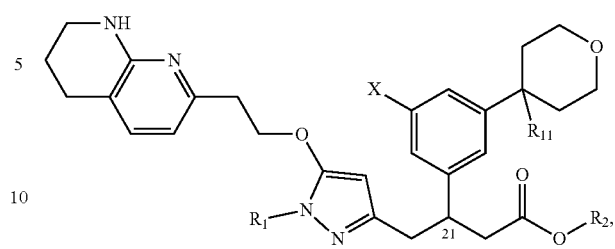

or a pharmaceutically acceptable salt or tautomer thereof.

5. The compound according to claim 1, wherein $R_2$ is hydrogen and $R_1$ is selected from the group consisting of unsubstituted $C_{1-8}$alkyl and methyl.

6. The compound according to claim 1, wherein X is hydrogen, halo, cyano, unsubstituted $C_{1-12}$alkyl, substituted $C_{1-12}$alkyl, unsubstituted $C_{1-12}$alkoxy, substituted $C_{1-12}$alkoxy, unsubstituted 3-10 membered heterocycloalkyl, substituted 3-10 membered heterocycloalkyl, unsubstituted $C_{2-12}$acyloxy, or substituted $C_{2-12}$acyloxy or

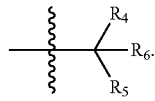

7. The compound of claim 1, wherein X is bromo, fluoro, or chloro.

8. The compound according to claim 1, wherein X is selected from the group consisting of —CF$_3$, —OH, cyano, unsubstituted $C_{1-8}$alkyl, unsubstituted $C_{3-6}$alkyl, t-butyl, unsubstituted $C_{1-8}$alkoxy, methoxy, and isopropoxy.

9. The compound according to claim 1, wherein Y is t-butyl or

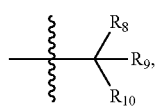

10. The compound of claim 1, wherein $R_8$ and $R_9$ are each independently unsubstituted $C_{1-8}$alkyl.

11. The compound according to claim 1, wherein $R_{10}$ is hydrogen, —CH$_3$, —CF$_3$, —CF$_2$H, or —CFH$_2$.

12. The compound according to claim 1 wherein Y is

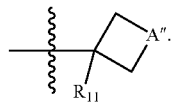

13. The compound of claim 8, wherein A" is $C_{1-3}$alkanediyl, $C_{1-4}$alkoxydiyl, or a covalent bond, thereby forming a cyclopropane ring.

14. The compound according to claim 8, wherein $R_{11}$ is —CF$_3$, —CF$_2$H, —CH$_2$F, methoxy, —CH$_2$O—CH$_3$, —CH$_2$O—C$_{1-6}$alkyl, $C_{1-6}$alkyl or $C_{1-8}$alkoxy.

15. The compound according to claim 1, wherein the carbon atom 21 is in the S configuration.

16. The compound according to claim 1, wherein X is in the 3 position.

17. The compound according to claim 1, wherein Y is in the 4 or 5 position.

18. The compound according to claim 1, wherein the compound is an integrin antagonist.

19. The compound of claim 18, wherein the integrin is an $\alpha_5\beta_1$ integrin or $\alpha v\beta_1$ integrin.

20. The compound of claim 9, wherein the compound exhibits an $IC_{50}$ value for the $\alpha_5\beta_1$ integrin of less than 50 nM, 40 nM, 30 nM, 20 nM, 15 nm or 1 nM, or a range defined by any of the preceding as measured by a solid phase receptor assay for $\alpha_5\beta_1$ integrin function.

21. The compound according to claim 1, wherein the compound exhibits an $IC_{50}$ value for the $\alpha v\beta_1$ integrin of less than 15 nM as measured by a solid phase receptor assay for $\alpha v\beta_1$ integrin function.

22. The compound according to claim 1 wherein the compound exhibits an $IC_{50}$ value for an $\alpha v\beta_3$ integrin of less than 10 nM as measured by a solid phase receptor assay for $\alpha v\beta_3$ integrin function.

23. The compound according to claim 1, wherein the compound exhibits an $IC_{50}$ value for an $\alpha v\beta_5$ integrin of less than 10 nM as measured by a solid phase receptor assay for $\alpha v\beta_5$ integrin function.

24. The compound according to claim 1, wherein the compound exhibits an $IC_{50}$ value for the $\alpha v\beta_1$, $\alpha v\beta_3$, and $\alpha v\beta_5$ integrins of less than 10 nM as measured by a solid phase receptor assays for $\alpha v\beta_1$, $\alpha v\beta_3$, and $\alpha v\beta_5$ integrin function.

25. The compound according to claim 1, wherein the compound exhibits an $IC_{50}$ value for the $\alpha v\beta_6$ and $\alpha v\beta_8$ integrins of greater than 10 nM as measured by solid phase receptor assays for $\alpha v\beta_6$ and $\alpha v\beta_8$ integrin function.

26. The compound of claim 1, wherein the compound is further defined as:

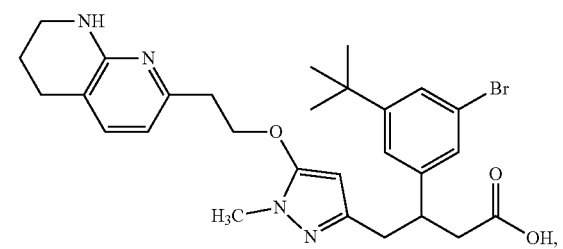

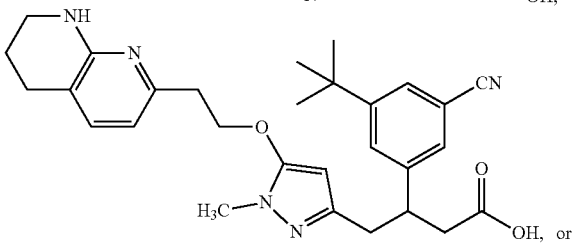

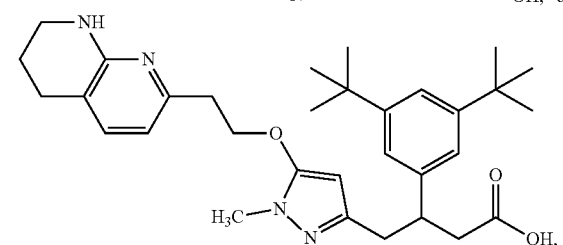

or a pharmaceutically acceptable salt thereof.

27. The compound of claim 1 further defined as:

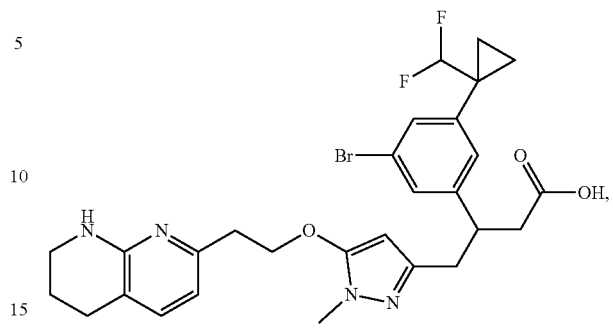

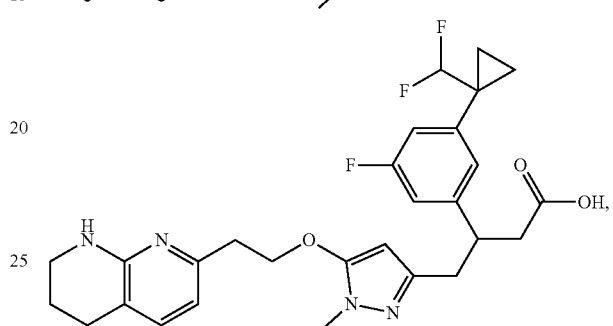

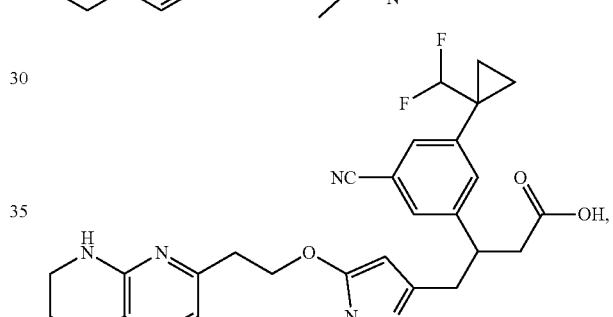

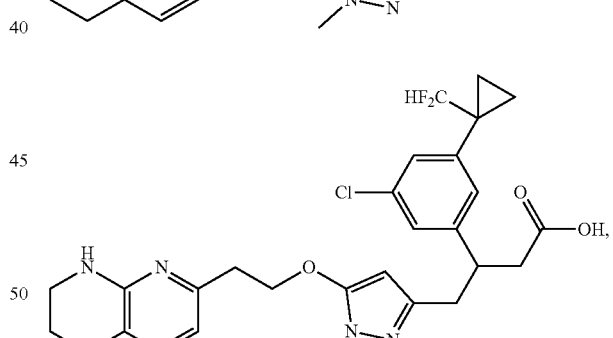

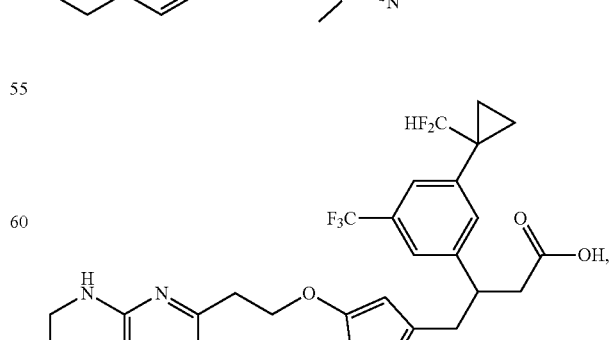

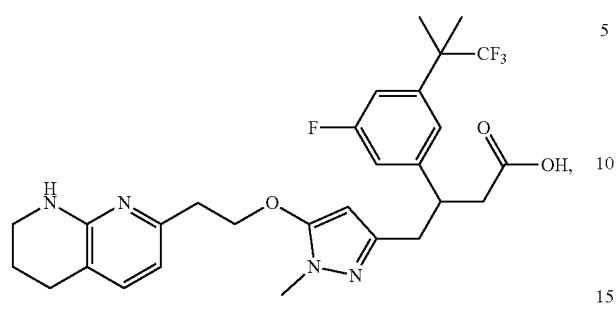
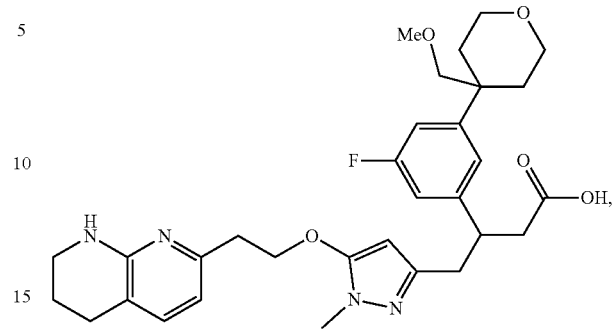
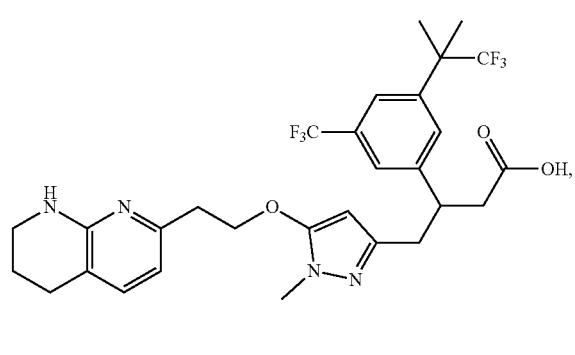
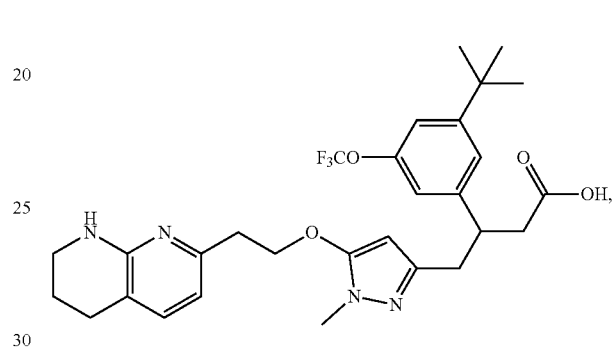
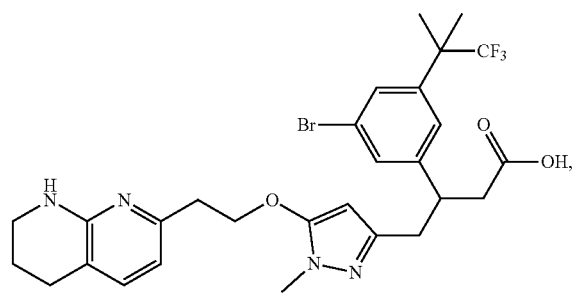
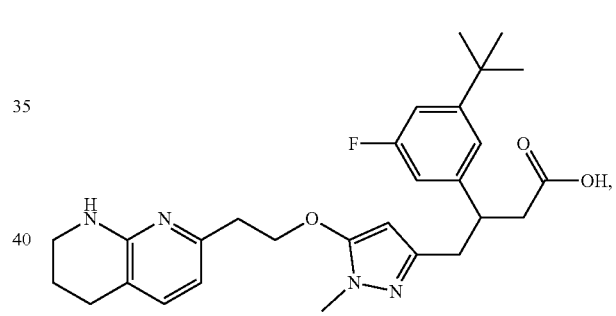
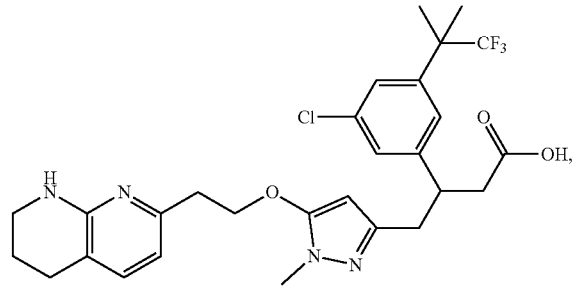
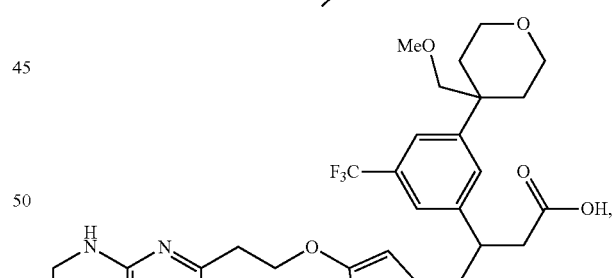
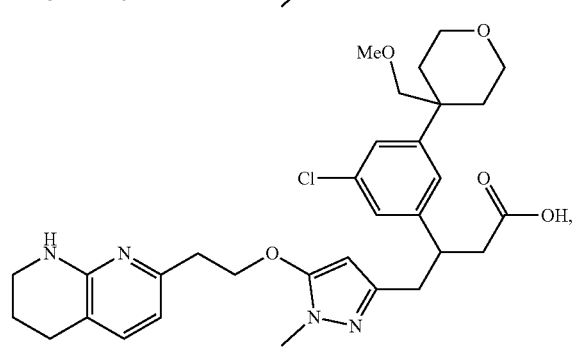
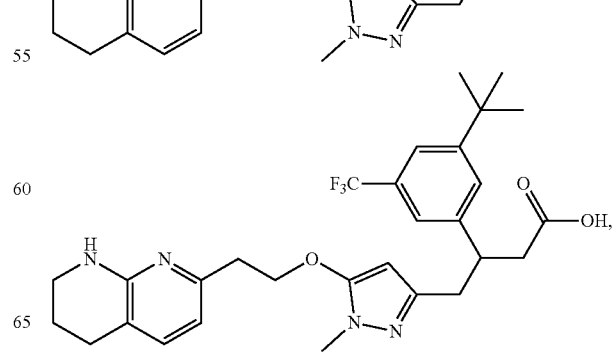

155
-continued
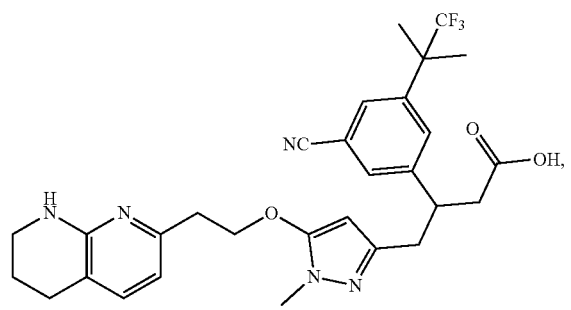
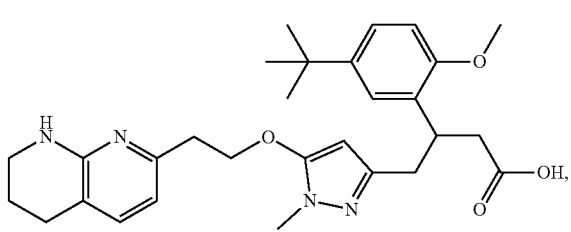
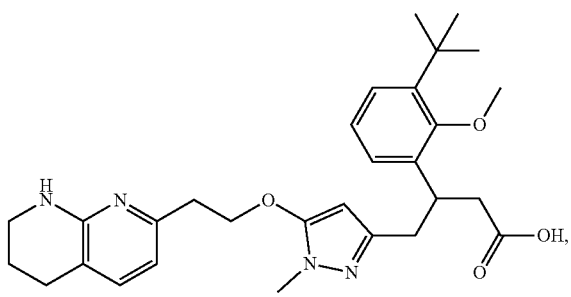
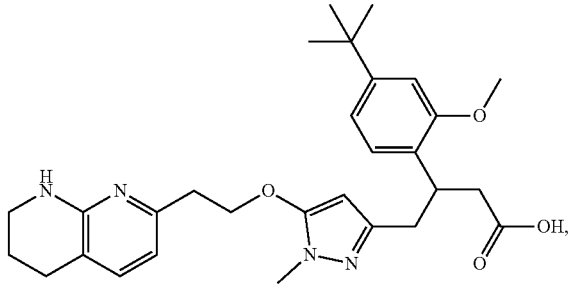
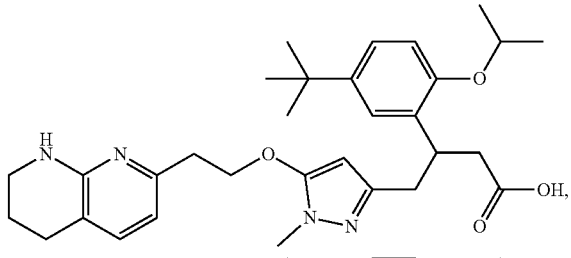
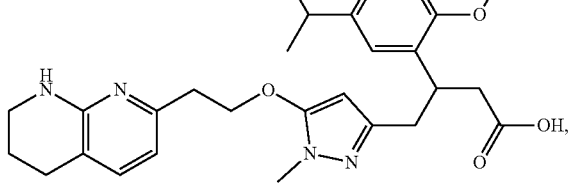
156
-continued
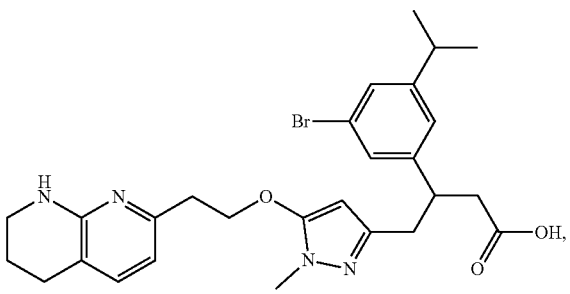
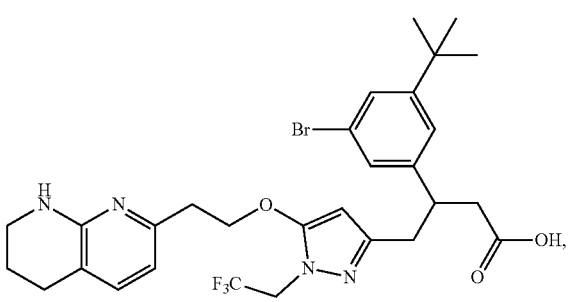
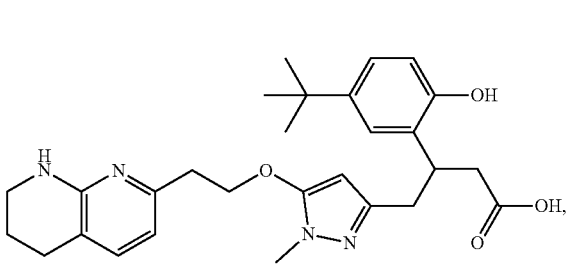
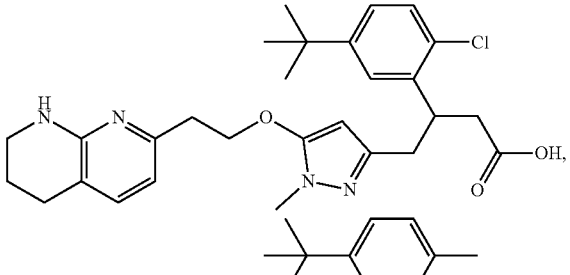
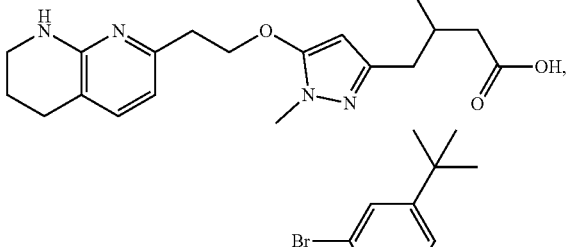
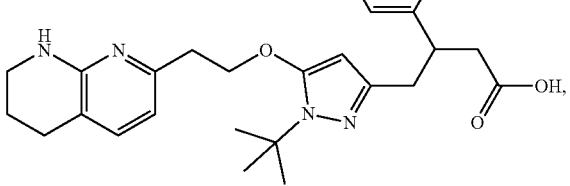

-continued

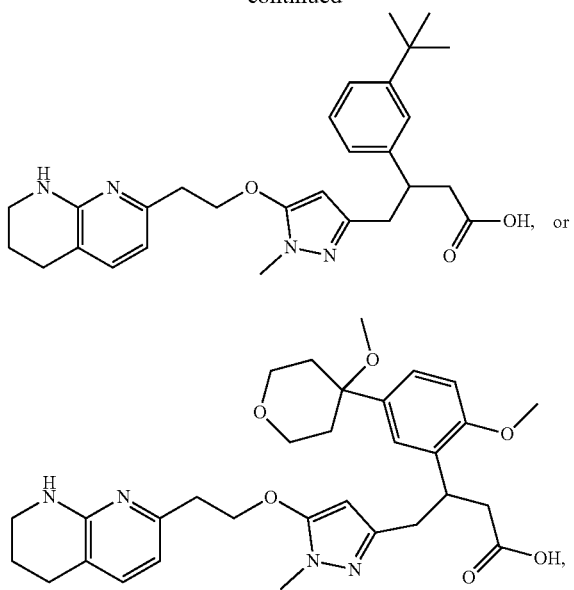

or a pharmaceutically acceptable salt thereof.

28. A pharmaceutical composition comprising:
a) the compound according to claim 1; and
b) an excipient.

29. The pharmaceutical composition of claim 13, wherein the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crémes, in lipid compositions, via a catheter, via a lavage, via continuous infusion, via infusion, via inhalation, via injection, via local delivery, or via localized perfusion.

* * * * *